(12) United States Patent
Jang et al.

(10) Patent No.: US 10,914,619 B2
(45) Date of Patent: *Feb. 9, 2021

(54) ELECTRONIC DEVICE AND HARDWARE DIAGNOSIS RESULT-BASED PROCESS EXECUTION METHOD THEREOF

(71) Applicant: Samsung Electronics Co., Ltd., Gyeonggi-do (KR)

(72) Inventors: Minsuk Jang, Gyeonggi-do (KR); Gyoseung Koo, Gyeonggi-do (KR); Seokhee Na, Incheon (KR); Kyuok Choi, Seoul (KR)

(73) Assignee: Samsung Electronics Co., Ltd

( * ) Notice: Subject to any disclaimer, the term of this patent is extended or adjusted under 35 U.S.C. 154(b) by 0 days.

This patent is subject to a terminal disclaimer.

(21) Appl. No.: 16/819,680

(22) Filed: Mar. 16, 2020

(65) Prior Publication Data

US 2020/0217695 A1 Jul. 9, 2020

Related U.S. Application Data

(63) Continuation of application No. 15/408,147, filed on Jan. 17, 2017, now Pat. No. 10,591,324.

(30) Foreign Application Priority Data

Jan. 15, 2016 (KR) .......................... 10-2016-0005637

(51) Int. Cl.
*G01D 18/00* (2006.01)
*G06Q 10/00* (2012.01)
(Continued)

(52) U.S. Cl.
CPC ......... *G01D 18/00* (2013.01); *A61B 5/02055* (2013.01); *A61B 5/1172* (2013.01);
(Continued)

(58) Field of Classification Search
CPC ...... G01D 18/00; G06F 3/0482; G06F 3/0418; G06F 3/04817; G06F 3/0417;
(Continued)

(56) References Cited

U.S. PATENT DOCUMENTS 7,209,737 B2 4/2007 Cho
7,886,189 B2 2/2011 Mori et al.
(Continued)

FOREIGN PATENT DOCUMENTS

JP 2003-124866 4/2003
JP 2014-215843 11/2014
(Continued)

OTHER PUBLICATIONS

Feng et al., Continuous Remote Mobile Identity Management Using Biometric Integrated Touch-Display, 2012 IEEE/ACM 45th International Symposium on Microarchitecture Workshops, pp. 55-62 (Year: 2012).*

(Continued)

*Primary Examiner* — Toan M Le
(74) *Attorney, Agent, or Firm* — The Farrell Law Firm, P.C.

(57) ABSTRACT

A process execution method and apparatus of an electronic device are provided for performing hardware diagnosis and executing a process based on the hardware diagnosis result. The electronic device includes a plurality of hardware components; a display configured to display information on the hardware components; and a processor configured to diagnose a hardware component selected as a diagnosis target among the hardware components, determine, based on a diagnosis result, whether the diagnosis target is operating normally, and display information indicating whether the diagnosis target is operating normally and a link for providing a service related to the diagnosis target.

18 Claims, 114 Drawing Sheets

(51) Int. Cl.
| | |
|---|---|
| *A61B 5/0205* | (2006.01) |
| *A61B 5/1172* | (2016.01) |
| *G06F 3/0354* | (2013.01) |
| G06F 3/041 | (2006.01) |
| G06F 11/22 | (2006.01) |
| A61B 5/021 | (2006.01) |
| A61B 5/024 | (2006.01) |
| G06F 3/0481 | (2013.01) |
| G06F 3/0482 | (2013.01) |

(52) U.S. Cl.
CPC ......... *G06F 3/03545* (2013.01); *G06Q 10/20* (2013.01); *A61B 5/021* (2013.01); *A61B 5/024* (2013.01); *A61B 2560/0276* (2013.01); *G06F 3/0416* (2013.01); *G06F 3/0418* (2013.01); *G06F 3/0482* (2013.01); *G06F 3/04817* (2013.01); *G06F 11/2221* (2013.01)

(58) Field of Classification Search
CPC .... G06F 3/0416; G06F 3/03545; G06F 11/22; G06F 11/2221; G06Q 10/20; A61B 5/1172; A61B 5/024; A61B 5/021; A61B 5/02055; A61B 2560/0276
See application file for complete search history.

(56) References Cited

U.S. PATENT DOCUMENTS

| | | | |
|---|---|---|---|
| 8,006,121 | B1 | 8/2011 | Samoilova et al. |
| 8,996,919 | B2 | 3/2015 | Gao et al. |
| 10,591,324 | B2 * | 3/2020 | Jang ................... A61B 5/02055 |
| 2009/0150819 | A1 | 6/2009 | Cheong et al. |
| 2009/0164849 | A1 | 6/2009 | Sugaya |
| 2014/0066015 | A1 | 3/2014 | Aissi |
| 2014/0068332 | A1 | 3/2014 | Choi et al. |
| 2015/0161057 | A1 | 6/2015 | Zeng et al. |
| 2017/0068935 | A1 * | 3/2017 | Cohen ................... G06Q 10/20 |

FOREIGN PATENT DOCUMENTS

| | | |
|---|---|---|
| KR | 1020130064859 | 6/2013 |
| KR | 10-1481510 | 1/2015 |

OTHER PUBLICATIONS

International Search Report dated Mar. 29, 2017 issued in counterpart application No. PCT/KR2017/000538, 3 pages.
European Search Report dated Aug. 23, 2018 issued in counterpart application No. 17738706.5-1222, 23 pages.
Weiss et al., Trust Evaluation in Mobile Devices: An Empirical Study, 2015 IEEE Trustcom/BigDataSE/ISPA, pp. 25-32.
Fang et al., Continuous Remote Mobile Identity Management Using Biometric Integrated Touch-Display, 2012 IEEE/ACM 45th International Symposium on Microarchitecture Workshops, pp. 55-62.
Yang et al., Efficient and Secure Fingerprint Verification for Embedded Devices, 2006, EURASIP Journal on Applied Signal Processing, vol. 2006, Article ID 58263, pp. 1-11.
Ratha et al., Enhancing Security and Privacy in Biometrics-Based Authentication Systems, 2001, IBM Systems Journal, vol. 40, No. 3, pp. 614-634.

* cited by examiner

ELECTRONIC DEVICE AND HARDWARE DIAGNOSIS RESULT-BASED PROCESS EXECUTION METHOD THEREOF

PRIORITY

This application is a Continuation of U.S. patent application Ser. No. 15/408,147, which was filed with the U.S. Patent and Trademark Office on Jan. 17, 2017, and claims priority under 35 U.S.C. § 119(a) to Korean Patent Application Serial No. 10-2016-0005637, which was filed in the Korean Intellectual Property Office on Jan. 15, 2016, the entire disclosure of each of which is incorporated herein by reference.

BACKGROUND

1. Field of the Disclosure

The present disclosure relates generally to a process execution method, and more particularly, to an electronic device for performing hardware diagnosis and executing a process based on the hardware diagnosis result.

2. Description of the Related Art

An electronic device (e.g., smartphone) may be equipped with various types of hardware components, such as various sensors (e.g., an image sensor, a fingerprint sensor, an acceleration sensor, a heart rate sensor, a proximity sensor, and a light sensor), various short range communication modules (e.g., a near field communication (NFC) module, a Wi-Fi module, and a Bluetooth module), etc. Typically, such electronic devices are configured to diagnose hardware problems and provide the user with the diagnosis result. However, even when provided with the diagnosis result, it is often still difficult for the user to correct any diagnosed hardware problems.

SUMMARY

Accordingly, aspects of the present disclosure are directed to an electronic device and method thereof, which allow a user to easily and conveniently access services based on a hardware diagnosis result.

In accordance with an aspect of the present disclosure, an electronic device is provided that includes a plurality of hardware components, a display configured to display information on at least one component of the plurality of hardware components and a processor configured to diagnose a hardware component selected as a diagnosis target among the plurality of hardware components, and display information related to a result of the diagnosis and a link for providing a service related to the diagnosis target, wherein the displayed information indicates that the diagnosis target is operating normally or abnormally.

In accordance with another aspect of the present disclosure, a method is provided for operating an electronic device equipped with a plurality of hardware components. The method includes diagnosing a hardware component selected as a diagnosis target among the plurality of hardware components and displaying information related to a result of the diagnosis and a link for providing a service related to the diagnosis target, wherein the displayed information indicates that the diagnosis target is operating normally.

BRIEF DESCRIPTION OF THE DRAWINGS

The above and other aspects, advantages, and features of certain embodiments of the present disclosure will become apparent to those skilled in the art from the following detailed description, when taken in conjunction with the accompanying drawings, in which.

DETAILED DESCRIPTION

Figure 1:
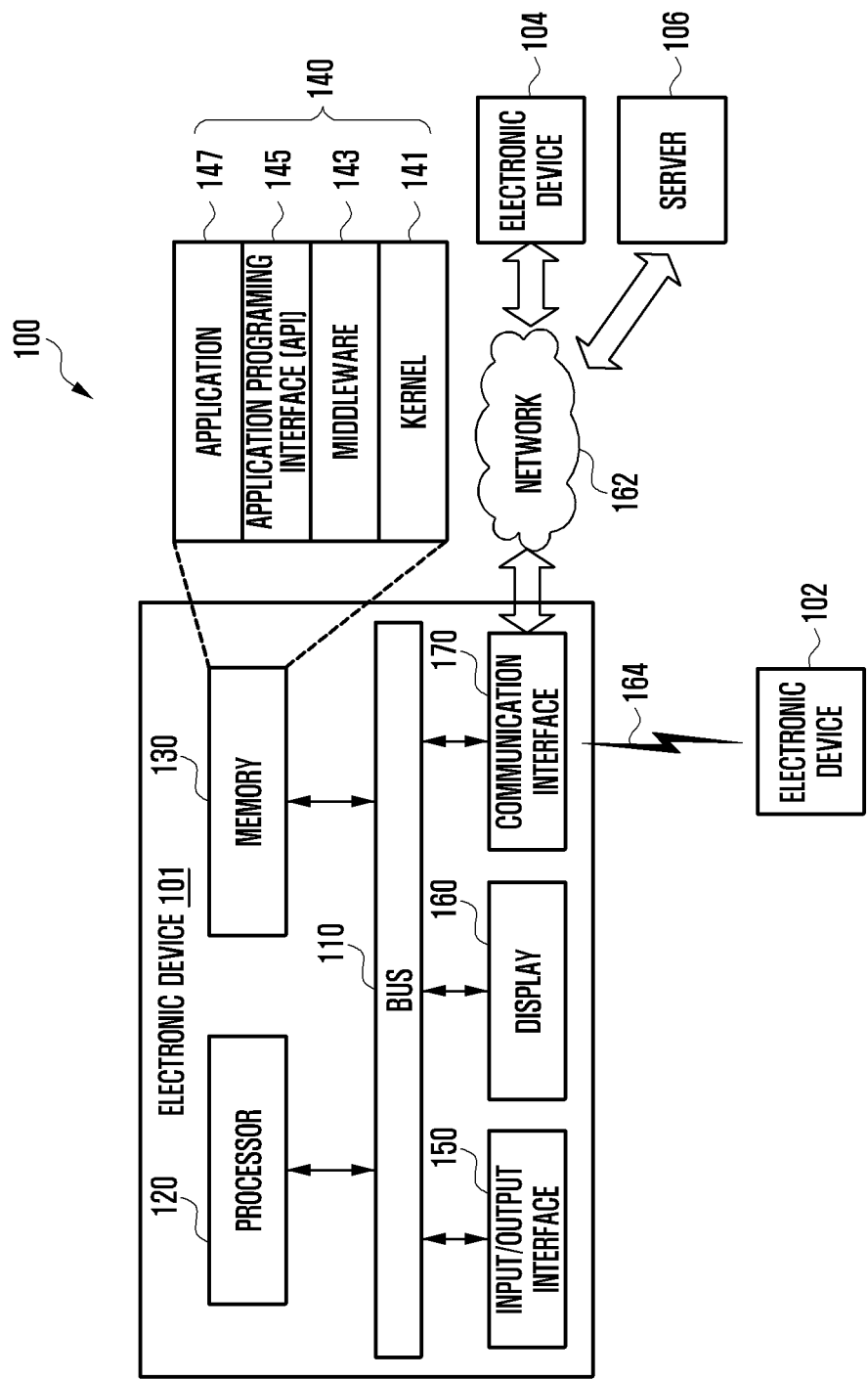
FIG. 1 illustrates a network environment including electronic devices according to an embodiment of the present disclosure.

The present disclosure is described below with reference to the accompanying drawings. Although specific embodiments are illustrated in the drawings and related detailed descriptions are discussed, the present disclosure may have various modifications and several embodiments. However, the present disclosure is not limited to a specific implementation form and it should be understood that the present disclosure includes all changes and/or equivalents and substitutes included in the spirit and scope of various embodiments of the present disclosure.

In the drawings, similar components are designated by the same reference numeral.

The terms used in describing various embodiments of the present disclosure are only examples for describing a specific embodiment, but do not limit the various embodiments of the present disclosure.

Singular forms are intended to include plural forms unless the context clearly indicates otherwise.

Unless defined differently, all terms used herein, which include technical terminologies or scientific terminologies, have the same meanings as would be understood by a person skilled in the art to which the present disclosure belongs. Terms defined in a commonly used dictionary are to be defined using meanings that are consistent with the contextual meanings in the relevant field of art, and are not to be defined using ideal or excessively formal meanings unless clearly defined as such in the present description.

Herein, the term have", "include", or "may include" refer to the existence of a corresponding disclosed function, characteristic, number, step, operation, constituent element, component, or a combination thereof, but may not be construed to exclude the existence of or a possibility of the addition of one or more other functions, characteristics, numbers, steps, operations, constituent elements, components, or combinations thereof.

The expression "or" or "at least one of A or/and B" includes any or all of combinations of words listed together. For example, the expression "A or B" or "at least A or/and B" may include A, B, or both A and B.

Expressions, such as "1st", "2nd", "first", and "second" may modify various components but do not limit the corresponding components. These types of expressions do not limit the sequence and/or importance of the components, but may be used to distinguish one component from another component. For example, a first user device and a second user device may indicate different user devices, although both of them are user devices. Similarly, a first structural element may be referred to as a second structural element, and the second structural element may be referred to as the first structural element.

A component "coupled to" or "connected to" another component may be directly coupled or connected to another component or may be directly coupled or connected to another component, such that an additional component may exist between the component and another component. However, when a component is "directly coupled to" or "directly connected to" another component, an additional component does not exist between the component and another component.

An electronic device according to an embodiment of the present disclosure may be a device including a communication function, such as a smart phone, a tablet personal computer (PC), a mobile phone, a video phone, an e-book reader, a desktop PC, a laptop PC, a netbook computer, a personal digital assistant (PDA), a camera, and a wearable device (e.g., a head-mounted-device (HMD) such as electronic glasses, electronic clothes, an electronic bracelet, an electronic necklace, an electronic accessary, an electronic tattoo, and a smart watch).

The electronic device may be a smart home appliance having a communication function, such as a television (TV), a digital video disk (DVD) player, an audio player, an air conditioner, a cleaner, an oven, a microwave oven, a washing machine, an air cleaner, a set-top box, a TV box (e.g., Samsung HomeSync™, Apple TV™, or Google TV™), a game console, an electronic dictionary, an electronic key, a camcorder, and an electronic frame.

The electronic device may also include a medical device (e.g., a magnetic resonance angiography (MRA) device, a magnetic resonance Imaging (MRI) device, a computed tomography (CT) device, a scanner, an ultrasonic device, etc.), a navigation device, a GNSS receiver, an event data recorder (EDR), a flight data recorder (FDR), a vehicle infotainment device, electronic equipment for a ship (e.g., a navigation device for ship, a gyro compass, etc.), avionics equipment, a security device, a head unit for a vehicle, an industrial or home robot, an automatic teller machine (ATM), a point of sale (POS) device of shops, and an Internet of things (IoT) device (e.g., a fire alarm, a sensor, an electric or gas meter, a sprinkler, a thermostat, a streetlamp, a toaster, a sports outfit, a hot-water tank, a heater, a boiler, etc.).

The electronic device may include furniture or a part of a building/structure, an electronic board, an electronic signature receiving device, a projector, and various types of measuring devices (e.g., a water meter, an electricity meter, a gas meter, a radio wave meter, etc.).

Further, the electronic device may be a flexible device.

An electronic device according to an embodiment of the present disclosure may also be any combination of the above-described devices. However, an electronic device according to an embodiment of the present disclosure is not limited to the above-described devices.

Herein, the term "user" may refer to a person who uses an electronic device or a device (e.g., an artificial intelligence electronic device) that uses an electronic device.

FIG. 1 illustrates a network environment including electronic devices according to an embodiment of the present disclosure.

Referring to FIG. 1, an electronic device 101 includes a bus 110, a processor 120, a memory 130, an input/output interface 150, a display 160, and a communication interface 170.

The bus 110 may be a circuit connecting the above-described components and transmitting communication signals (e.g., a control message) between the components.

The processor 120 may receive commands from other components (e.g., the memory 130, the input/output interface 150, the display 160, or the communication interface 170) through the bus 110, analyze the received commands, and execute calculation or data processing according to the analyzed commands.

The memory 130 stores commands or data received from the processor 120 or other components (e.g., the input/output interface 150, the display 160, or the communication interface 170) or generated by the processor 120 or other components.

The memory 130 may store a software and/or a program 140. For example, the program 140 includes a kernel 141, middleware 143, an application programming interface (API) 145, and an application program (or an application) 147. At least part of the kernel 141, the middleware 143 or the API 145 may refer to as "an operating system (OS)".

The kernel 141 controls or manages system resources (e.g., the bus 110, the processor 120, or the memory 130) used for executing an operation or function implemented by the remaining other programming modules, for example, the middleware 143, the API 145, or the application 147. Further, the kernel 141 provides an interface for accessing individual components of the electronic device 101 by the middleware 143, the API 145, or the application 147, to control or manage the components.

The middleware 143 performs a relay function for the API 145 or the application 147 to communicate with the kernel 141 to exchange data. Further, in operation requests received from the application 147, the middleware 143 performs a control for the operation requests (e.g., scheduling or load balancing) by assigning a priority, by which system resources (e.g., the bus 110, the processor 120, the memory 130, etc.) of the electronic device 101 can be used, to the application 147.

The API 145 is an interface by which the application 147 can control a function provided by the kernel 141 or the middleware 143 and includes, for example, at least one interface or function (e.g., command) for a file control, a window control, image processing, or a character control.

The application 147 may include a short message service (SMS)/multimedia messaging service (MMS) application, an email application, a calendar application, an alarm application, a health care application (e.g., application measuring quantity of exercise or blood sugar level) or an environment information application (e.g., application providing information on barometric pressure, humidity or temperature). Additionally or alternatively, the application 147 may be related to an information exchange between the electronic device 101 and an electronic device 104. The application 147 related to the information exchange may include, for example, a notification relay application for transferring particular information to the external electronic device or a device management application for managing the external electronic device.

For example, the notification relay application may include a function of transmitting notification information generated by another application (e.g., an SMS/MMS application, an email application, a health care application or an environment information application) of the electronic device 101 to the electronic device 104. Additionally or alternatively, the notification relay application may receive notification information from the external electronic device 104, and provide the received notification information to the user. The device management application may manage (e.g., install, remove, or update) at least a part of functions of the electronic device. For example, the device management application may turn on/off the external electronic device (or some components of the external electronic device), control a brightness of the display of the external electronic device or communicate with the electronic device 101, an application executed in the external electronic device 104, or a service (e.g., call service or message service) provided by the external electronic device 104.

The application 147 may include an application designated according to an attribute (e.g., type of electronic device) of the external electronic device 104. For example, when the external electronic device 104 is an MP3 player, the application 147 may include an application related to music reproduction. Similarly, when the external electronic device 104 is a mobile medical device, the application 147 may include an application related to health care.

The application 147 may include at least one of an application designated to the electronic device 101 and an application received from a server 106 or the electronic device 104.

The input/output interface 150 transmits a command or data input from the user through an input/output device 140 (e.g., a sensor, a keyboard, or a touch screen) to the processor 120, the memory 130, the communication interface 170, or the display control module 150 through the bus 110. The input/output interface 150 may provide data on a user's touch input through a touch screen to the processor 120. Further, the input/output interface 150 may output a command or data received, through the bus 110, from the processor 120, the memory 130, or the communication interface 170 through the input/output device (e.g., a speaker or a display). For example, the input/output interface 150 may output voice data processed through the processor 120 to the user through the speaker.

The display 160 may include a liquid crystal display (LCD), a flexible display, a transparent display, a light-emitting diode (LED) display, an organic light-emitting diode (OLED) display, a microelectromechanical systems (MEMS) display, or an electronic paper display. The display 160 may visually offer various content (e.g., text, image, video, icon, symbol, etc.) to users. The display 160 may include a touch screen that receives a touch, gesture, proximity, and/or hovering input using an electronic pen or a user's body. The display 160 may be one or more displays. The display 160 may be included in the electronic device 101 or included in the electronic device 102 or 104 having a wired or wireless connection with the electronic device 101, thus outputting information offered by the electronic device 101 to users.

The display 160 may be attachable to or detachable from the electronic device 101. For example, the display 160 may include an interface that can be mechanically or physically connected with the electronic device 101. When the display 160 is detached (e.g., separated) from the electronic device 101 by a user's selection, the display 160 may receive various control signals or image data from the processor 120, e.g., through wireless communication.

The communication interface 170 may establish communication between the electronic device 101 and the first external electronic device 102, the second external electronic device 104, and/or the server 106. For example, the communication interface 170 may be connected with a network 162 through wired or wireless communication and thereby communicate with the external electronic device 104, and/or the server 106. The electronic device 101 may be connected with the external electronic device 102 and the external electronic device 104 without using the communication interface 170. For example, based on at least one of a magnetic sensor, a contact sensor, a light sensor, etc., that is equipped in the electronic device 101, the electronic device 101 may sense whether at least one of the external electronic devices 102 and 104 is contacted with at least part of the electronic device 101, or whether at least one of the external electronic devices 102 and 104, respectively, is attached to at least part of the electronic device 101.

Wireless communication may use a cellular communication protocol, such as long-term evolution (LTE), LTE Advance (LTE-A), code division multiple access (CDMA), wideband CDMA (WCDMA), universal mobile telecommunications system (UMTS), wireless broadband (WiBro), global system for mobile communications (GSM), etc. A short-range communication 164 may include at least one of Wi-Fi, Bluetooth, NFC, magnetic secure transmission or near field magnetic data stripe transmission (MST), GNSS, etc. The GNSS may include at least one of a global positioning system (GPS), a global navigation satellite system (Glonass), a Beidou navigation satellite system (Beidou), and Galileo (the European global satellite-based navigation system). Hereinafter, "GPS" may be interchangeably used with "GNSS".

Wired communication may include at least one of universal serial bus (USB), high definition multimedia interface (HDMI), recommended standard-232 (RE-232), plain old telephone service (POTS), etc.

The network 162 may include a telecommunication network, a computer network (e.g., a local area network (LAN) or a wide area network (WAN)), the Internet, and a telephone network.

The external electronic devices 102 and 104 may be identical to, or different from, the electronic device 101. The external electronic devices 102 and 104 may include a plurality of electronic devices.

The server 106 may include a single server or a group of servers. All or part of operations executed in the electronic device 101 may be executed in the electronic device 102, the electronic device 104, and/or the server 106.

When the electronic device 101 is required to perform a certain function or service automatically or by request, the electronic device 101 may request the electronic device 102, the electronic device 104, and/or the server 106 to execute instead, or additionally at least part, of at least one or more functions associated with the required function or service. The requested device may execute the requested function and deliver the result of execution to the electronic device 101. The electronic device 101 may offer the required function or service, based on the received result or by processing the received result. For the above, cloud computing technology, distributed computing technology, or client-server computing technology may be used, for example.

Figure 2:
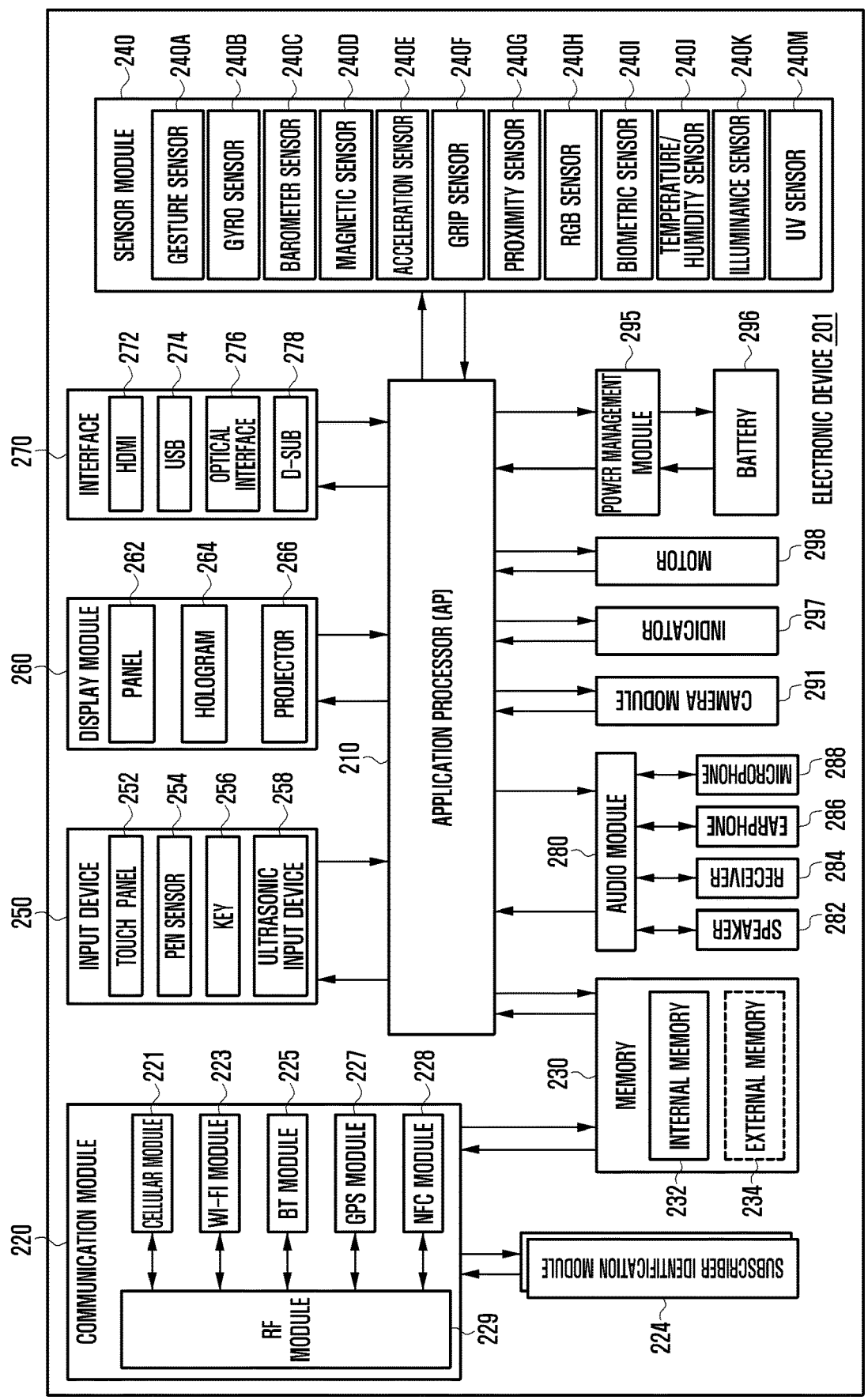
FIG. 2 illustrates an electronic device according to an embodiment of the present disclosure.

FIG. 2 illustrates an electronic device 201 according to an embodiment of the present disclosure.

Referring to FIG. 2, the electronic device 201 includes an application processor (AP) 210, a communication module 220, a SIM 224, a memory 230, a sensor module 240, an input device 250, a display 260, an interface 270, an audio module 280, a camera module 291, a power management module 295, a battery 296, an indicator 297, and a motor 298.

The AP 210 is capable of driving an OS or an application program to control a plurality of hardware or software components connected to the AP 210, processing various data, and performing operations. The AP 210 may be implemented as a system on chip (SoC). The AP 210 may further include a graphic processing unit (GPU) and/or an image signal processor. The AP 210 may also include at least part of the components separately illustrated in FIG. 2, e.g., a cellular module 221. The AP 210 is capable of loading commands or data received from at least one of other components (e.g., a non-volatile memory) on a volatile memory, processing the loaded commands or data. The AP 210 is capable of storing various data in a non-volatile memory.

The communication module 220 includes the cellular module 221, a Wi-Fi module 223, a Bluetooth (BT) module 225, a GPS module 226, an NFC module 227, and a radio frequency (RF) module 229. The communication module 220 may also include an MST module.

The cellular module 221 is capable of providing a voice call, a video call, an SMS service, an Internet service, etc., through a communication network. The cellular module 221 is capable of identifying and authenticating an electronic device 201 in a communication network by using the SIM 224 (e.g., a SIM card). The cellular module 221 is capable of performing at least part of the functions provided by the AP 210. The cellular module 221 may also a communication processor (CP).

Each of the Wi-Fi module 223, the BT module 225, the GPS module 226, and the NFC module 227 may include a processor for processing data transmitted or received through the corresponding module. The MST module may include a processor for processing data transmitted or received through the corresponding module. At least part of the cellular module 221, the Wi-Fi module 223, the BT module 225, the GPS module 226, the NFC module 227, and the MST module (e.g., two or more of the modules) may be included in an integrated chip (IC) or an IC package.

The RF module 229 is capable of transmission/reception of communication signals, e.g., RF signals. The RF module 229 may include a transceiver, a power amp module (PAM), a frequency filter, a low noise amplifier (LNA), an antenna, etc. At least one of the cellular module 221, the Wi-Fi module 223, the BT module 225, the GPS module 226, the NFC module 227, and the MST module may transmit and receive RF signals through a separate RF module.

The SIM 224 may be a SIM card and/or an embedded SIM. The SIM 224 may include unique identification information, e.g., an integrated circuit card identifier (ICCID) or subscriber information, e.g., an international mobile subscriber identity (IMSI).

The memory 230 includes an internal memory 232 and an external memory 234. The internal memory 232 may include a volatile memory, e.g., a dynamic random access memory (DRAM), a static random access memory (SRAM), a synchronous dynamic random access memory (SDRAM), etc., and a non-volatile memory, e.g., a one-time programmable read only memory (OTPROM), a programmable read only memory (PROM), an erasable and programmable read only memory (EPROM), an electrically erasable and programmable read only memory (EEPROM), a mask read only memory, a flash read only memory, a flash memory (e.g., a NAND flash memory, an NOR flash memory, etc.), a hard drive, a solid state drive (SSD), etc.

The external memory 234 may include a flash drive, e.g., a compact flash (CF), a secure digital (SD), a micro secure digital (Micro-SD), a mini secure digital (Mini-SD), an extreme digital (xD), a multi-media card (MMC), a memory stick, etc. The external memory 234 is capable of being connected to the electronic device 201, functionally and/or physically, through various interfaces.

The memory 230 may store payment information and a payment application as one of the application programs. The payment information may refer to credit card numbers and personal identification numbers (PINs), corresponding to a credit card. The payment information may also include user authentication information, e.g., fingerprints, facial features, voice information, etc.

When the payment application is executed by the AP 210, the payment application may enable the AP 210 to perform an interaction with the user to make payment (e.g., displaying a screen to select a card (or a card image) and obtaining information (e.g., a card number) corresponding to a selected card (e.g., a pre-specified card) from payment information), and an operation to control magnetic field communication (e.g., transmitting the card information to an external device (e.g., a card reading apparatus) through the NFC module 227 or MST module).

The sensor module 240 is capable of measuring/detecting a physical quantity or an operation state of the electronic device 201, and converting the measured or detected information into an electronic signal. The sensor module 240 includes a gesture sensor 240A, a gyro sensor 240B, an atmospheric pressure (barometer) sensor 240C, a magnetic sensor 240D, an acceleration sensor 240E, a grip sensor 240F, a proximity sensor 240G, a color sensor 240H (e.g., a red, green and blue (RGB) sensor), a biometric sensor 240I, a temperature/humidity sensor 240J, an illuminance sensor 240K, and a ultraviolet (UV) sensor 240M. Additionally or alternatively, the sensor module 240 may include an E-nose sensor, an electromyography (EMG) sensor, an electroencephalogram (EEG) sensor, an electrocardiogram (ECG) sensor, an infrared (IR) sensor, an iris sensor and/or a fingerprint sensor. The sensor module 240 may also include a control circuit for controlling one or more sensors included therein.

Alternatively, the electronic device 201 may include a processor, configured as part of the AP 210 or a separate component, for controlling the sensor module 240. In this case, while the AP 210 is operating in sleep mode, the processor is capable of controlling the sensor module 240.

The input unit 250 includes a touch panel 252, a digital pen sensor 254, a key 256, and an ultrasonic input unit 258. The touch panel 252 may be a capacitive type, a resistive type, an infrared type, and/or an ultrasonic type. The touch panel 252 may also include a control circuit. The touch panel 252 may also include a tactile layer to offer a tactile feedback to a user. The touch panel 252 may include a pressure sensor (or a force sensor) capable of measuring the strength or pressure of a user's touch. The pressure sensor may be formed integrally with or separately from the touch panel 252.

The digital pen sensor 254 may be a part of the touch panel or include a separate sheet for recognition.

The key 256 may include a physical button, an optical key, and/or a keypad.

The ultrasonic input unit 258 may detect ultrasonic waves occurring at an input tool through a microphone 288 and thereby identify data corresponding to the detected ultrasonic waves.

The display 260 includes a panel 262, a hologram unit 264, and a projector 266. The panel 262 may be flexible, transparent, and/or wearable. The panel 262 may also be incorporated with the touch panel 252 into a single module.

The hologram unit 264 is capable of showing a stereoscopic image in the air by using light interference.

The projector 266 is capable of displaying an image by projecting light onto a screen. The screen may be located inside or outside of the electronic device 201.

The display 260 may also include a control circuit for controlling the panel 262, the hologram unit 264, and/or the projector 266.

The interface 270 includes an HDMI 272, a USB 274, an optical interface 276, and a D-subminiature (D-sub) 278. Additionally or alternatively, the interface 270 may include a mobile high-definition link (MHL) interface, an SD card/MMC interface, and/or an infrared data association (IrDA) standard interface.

The audio module 280 is capable of providing bidirectional conversion between a sound and an electronic signal. The audio module 280 is capable of processing sound information input or output through a speaker 282, a receiver 284, earphones 286, the microphone 288, etc.

The camera module 291 may capture still and moving images. The camera module 291 may include one or more image sensors (e.g., a front image sensor or a rear image sensor), a lens, an image signal processor (ISP), a flash (e.g., an LED or xenon lamp), etc.

The power management module 295 is capable of managing power of the electronic device 201. The power management module 295 may include a power management integrated circuit (PMIC), a charger IC, and/or a battery gauge. The PMIC may employ wired charging and/or wireless charging methods. Examples of the wireless charging method are magnetic resonance charging, magnetic induction charging, and electromagnetic charging. Accordingly, the PMIC may further include an additional circuit for wireless charging, such as a coil loop, a resonance circuit, a rectifier, etc. The battery gauge is capable of measuring the residual capacity, charge in voltage, current, or temperature of the battery 296. The battery 296 may be a rechargeable battery and/or a solar battery.

The indicator 297 is capable of displaying a specific status of the electronic device 201 or a part thereof (e.g., the AP 210), e.g., a boot-up status, a message status, a charging status, etc.

The motor 298 is capable of converting an electrical signal into mechanical vibrations, such as, a vibration effect, a haptic effect, etc.

Although not illustrated, the electronic device 201 may also include a processing unit (e.g., a GPU) for supporting a mobile TV, which is capable of processing media data pursuant to various standards, e.g., digital multimedia broadcasting (DMB), digital video broadcasting (DVB), mediaFlo™, etc.

Each of the elements described in the present disclosure may be formed with one or more components, and the names of the corresponding elements may vary according to the type of the electronic device. The electronic device may include at least one of the above-described elements described in the present disclosure, and may exclude some of the elements or further include other additional elements. Further, some of the elements of the electronic device according to various embodiments may be combined to form a single entity while performing the same functions as those of the corresponding elements before the coupling.

Figure 3:
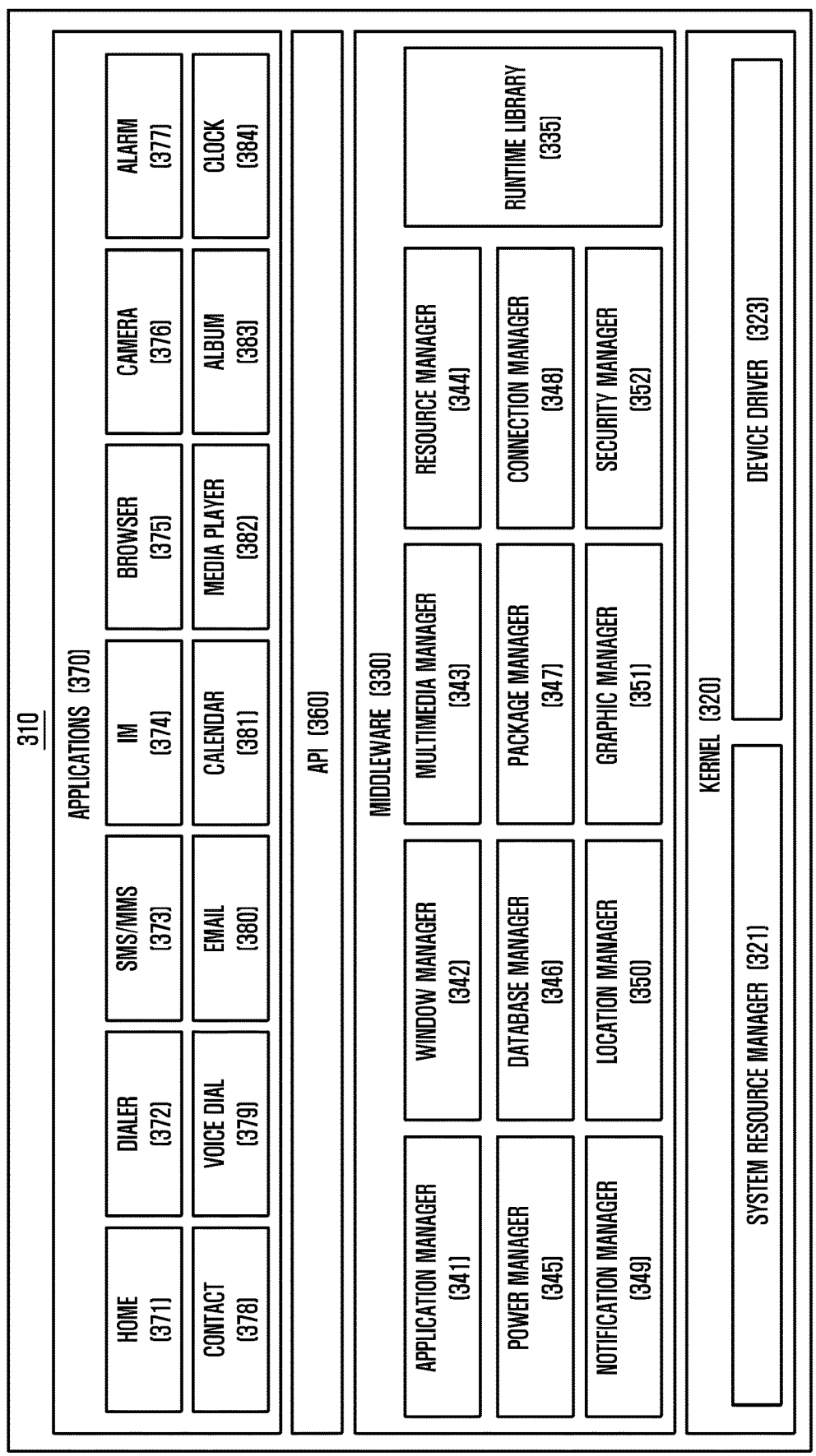
FIG. 3 illustrates a program module according to an embodiment of the present disclosure.

FIG. 3 illustrates a programming module according to an embodiment of the present disclosure.

Referring to FIG. 3, the program module 310 may include an OS for controlling resources related to an electronic device and/or various applications running on the OS. For example, the OS may be Android®, iOS®, Windows®, Symbian®, Tizen®, Bada®, etc.

The program module 310 includes a kernel 320, middleware 330, an API 360 and applications 370. At least part of the program module 310 may be preloaded on the electronic device or downloaded from a server.

The kernel 320 includes a system resource manager 321 and a device driver 323. The system resource manager 321 may include a process manager, a memory manager, and a file system manager. The system resource manager 321 may perform a system resource control, allocation, and recall. The device driver 323 may include a display driver, a camera driver, a Bluetooth driver, a shared memory driver, a USB driver, a keypad driver, a Wi-Fi driver, and an audio driver. Further, the device driver 312 may include an Inter-Process Communication (IPC) driver.

The middleware 330 may provide a function required in common by the applications 370. Further, the middleware 330 may provide a function through the API 360 to allow the applications 370 to efficiently use limited system resources within the electronic device. The middleware 330 includes a runtime library 335, an application manager 341, a window manager 342, a multimedia manager 343, a resource manager 344, a power manager 345, a database manager 346, a package manager 347, a connection manager 348, a notification manager 349, a location manager 350, a graphic manager 351, and a security manager 352.

The runtime library 335 may include a library module used by a complier to add a new function through a programming language while the applications 370 are executed.

The runtime library 335 executes input and output, management of a memory, a function associated with an arithmetic function, etc.

The application manager 341 may manage a life cycle of at least one of the applications 370.

The window manager 342 may manage graphic user interface (GUI) resources used on the screen.

The multimedia manager 343 may detect a format required for reproducing various media files and perform an encoding or a decoding of a media file by using a codec suitable for the corresponding format.

The resource manager 344 manages resources such as a source code, a memory, or a storage space of at least one of the applications 370.

The power manager 345 may operate together with a basic input/output system (BIOS) to manage a battery or power and provides power information required for the operation.

The database manager 346 may manage generation, search, and change of a database to be used by at least one of the applications 370.

The package manager 347 may manage an installation or an update of an application distributed in a form of a package file.

The connection manager 348 may manage a wireless connection such as Wi-Fi or Bluetooth.

The notification manager 349 may display or notify a user of an event such as an arrival message, an appointment, a proximity alarm, etc.

The location manager 350 may manage location information of the electronic device.

The graphic manager 351 may manage a graphic effect provided to the user or a user interface related to the graphic effect.

The security manager 352 provides a general security function required for system security or user authentication.

When the electronic device has a call function, the middleware 330 may further include a telephony manager for managing a voice of the electronic device or a video call function.

The middleware 330 may include modules configuring various combinations of functions of the above-described components. The middleware 330 is capable of providing modules that are specialized according to types of operation systems to provide distinct functions. The middleware 330 may be adaptively configured in such a way as to remove part of the existing components or to include new components.

The API 360 may be a set of API programming functions, and may be provided with a different configuration according to an OS. For example, in Android® or iOS®, a single API set may be provided for each platform. In Tizen®, two or more API sets may be provided.

The applications 370 include a home application 371, a dialer application 372, an SMS/MMS application 373, an instant message (IM) application 374, a browser application 375, a camera application 376, an alarm application 377, a contact application 378, a voice dial application 379, an email application 380, a calendar application 381, a media player application 382, an album application 383, and a clock application 384. Additionally or alternatively, the applications 370 may include a health care application (e.g., an application for measuring amount of exercise, blood sugar level, etc.), and an environment information application (e.g., an application for providing atmospheric pressure, humidity, temperature, etc.).

The applications 370 may include an information exchange application for supporting information exchange between an electronic device and an external device. The information exchange application may include a notification relay application for relaying specific information to external devices or a device management application for managing external devices.

For example, the notification relay application may include a function for relaying notification information, created in other applications of the electronic device (e.g., SMS/MMS application, email application, health care application, environment information application, etc.) to external devices. In addition, the notification relay application is capable of receiving notification information from external devices to provide the received information to the user.

The device management application is capable of managing (e.g., installing, removing or updating) at least one function of an external device communicating with the electronic device. Examples of the function include turning-on/off the external device or part of the external device, controlling the brightness (or resolution) of the display, applications running on the external device, services provided by the external device, etc. Examples of the services are a call service, messaging service, etc.

The applications 370 may include an application (e.g., a health care application of a mobile medical device, etc.) specified by attributes of an external device.

The applications 370 may include applications received from an external device. The applications 370 may also include a preloaded application or third party applications that can be downloaded from a server. It should be understood that the components of the program module 310 may be called different names according to the type of OS being used.

At least part of the program module 310 can be implemented with software, firmware, hardware, or any combination of two or more of them. At least part of the program module 310 can be implemented (e.g., executed) by a processor. At least part of the programing module 310 may include modules, programs, routines, sets of instructions or processes, etc., in order to perform one or more functions.

In accordance with an embodiment of the present disclosure, a handheld electronic device is provided, which is capable of transmitting, to a card reading apparatus, card information carried by magnetic field signals, and thus making payment for costs. The handheld electronic device may still be capable of making payments, through communication with a card reading apparatus, although the apparatus is not equipped with an NFC module, without modifying the existing solution, as if a magnetic card is used against the apparatus. Therefore, the present disclosure is capable of leading to activating offline mobile payments.

Herein, the term "module" may indicate a unit including one of hardware, software, firmware, or any combination thereof. The term "module" may be interchangeable with the terms "unit," "logic," "logical block," "component," and "circuit." A module may be the smallest unit of an integrated component or a part thereof. A module may be the smallest unit that performs one or more functions or a part thereof.

A module may be mechanically or electronically implemented. For example, a module according to an embodiment of the present disclosure may include at least one of application-specific integrated circuit (ASIC) chips, field-programmable gate arrays (FPGAs), and programmable-logic devices for performing certain operations, which are now known or will be developed in the future.

At least part of the method (e.g., operations) or system (e.g., modules or functions) according to various embodiments can be implemented with instructions as programming modules that are stored in computer-readable storage media. One or more processors can execute instructions, thereby performing the functions. An example of the computer-readable storage media may be a memory 130. At least part of the programming modules can be implemented (executed) by a processor. At least part of the programing module may include modules, programs, routines, sets of instructions or processes, etc., in order to perform one or more functions.

Examples of computer-readable media include magnetic media, such as hard disks, floppy disks, and magnetic tape, optical media such as compact disc ROM (CD-ROM) disks and DVDs, magneto-optical media, such as floptical disks, and hardware devices that are specially configured to store and perform program instructions (e.g., programming modules), such as ROM, RAM, flash memory, etc.

Examples of program instructions include machine code instructions created by assembly languages, such as a compiler, and code instructions created by a high-level programming language executable in computers using an interpreter, etc. The described hardware devices may be configured to act as one or more software modules in order to perform the operations and methods described above, or vice versa.

Modules or programming modules according to various embodiments may include one or more components, remove part of them described above, or include new components. The operations performed by modules, programming modules, or the other components, according to various embodiments, may be executed in serial, parallel, repetitive, or heuristic fashion. Part of the operations can be executed in any other order, skipped, or executed with additional operations.

Figure 4:
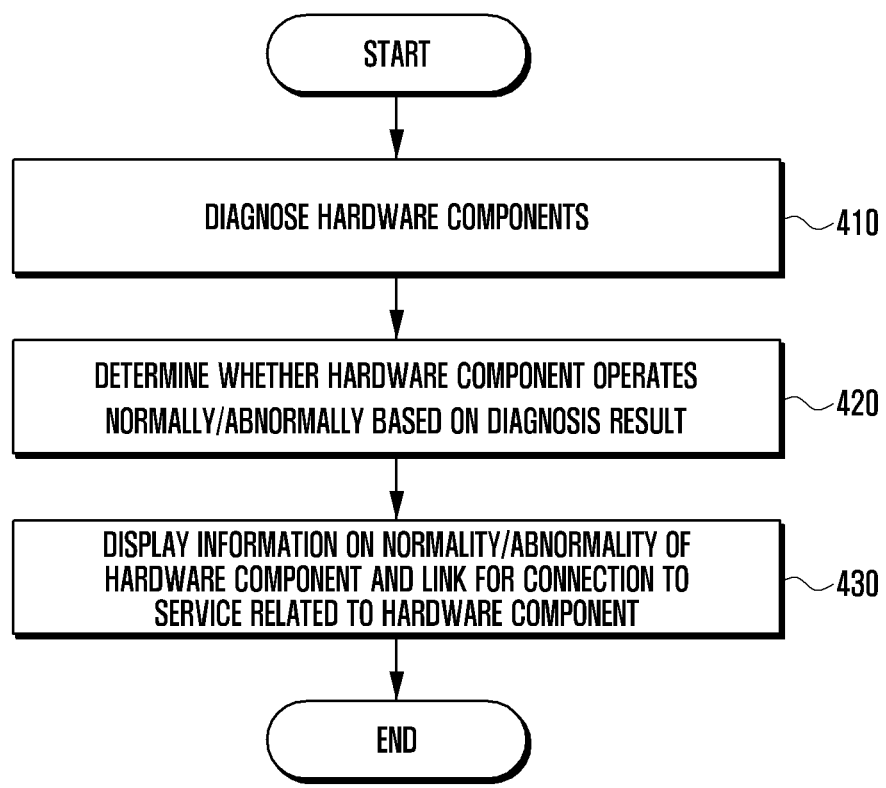
FIG. 4 is a flowchart illustrating a hardware diagnosis and diagnosis-based information provision method according to an embodiment of the present disclosure.

FIG. 4 is a flowchart illustrating a hardware diagnosis and diagnosis result-based information provision method according to an embodiment of the present disclosure. Although the method of FIG. 4 is described below as being performed by the electronic device illustrated FIG. 2, it is not limited thereto.

Referring to FIG. 4, the AP 210 performs hardware diagnosis in step 410. For example, the AP 210 may control the display 260 to display an icon corresponding to a hardware care application. When the icon is selected (e.g., by a tap on icon) on the touch panel 252, the AP 210 may execute the hardware care application.

The AP 210 may control the display unit 260 to display a menu for accessing answers to frequently asked questions, a menu for receiving an inquiry to the electronic device 201 and transmitting the inquiry to a designated external device (e.g., the server 106), a menu for transmitting a user's opinion (about function required to be improved or added, idea, or error) to an external device (e.g., the server 106), and a diagnosis menu for hardware analysis. If the user selects the diagnosis menu, the AP 210 may control the display 260 to display a list of items (e.g., battery, sensor, vibration, Wi-Fi, Bluetooth, microphone, speaker, touch & drag, electronic pen, button, SIM card, plug, and camera) and performs hardware diagnosis on the item selected by the user.

The AP 210 may perform hardware diagnosis periodically, or may perform hardware diagnosis upon receipt of a hardware function execution command (e.g. stress measurement), before executing the corresponding function.

In step 420, the AP 210 may determine whether there is a hardware error based on the diagnosis result.

The AP 210 performs hardware diagnosis to check the presence/absence of a hardware error based on the diagnosis result or by comparing the diagnosis result with data of a predetermined diagnosis test. For example, the AP 210 may write the diagnosis test data to the memory 230, read the diagnosis test data to determine whether a diagnosis result matches any of the diagnosis test data, and if so, determine that the memory 230 operates normally.

The AP 210 may diagnose the condition of the battery 296. For example, the AP 210 may acquire an internal resistance value of the battery 296 from the power management module 295 or calculate the internal resistance value of the battery 296 using predetermined factors indicative of battery condition (e.g., temperature, voltage, and current). The AP 210 may compare the internal resistance value with the previously stored diagnosis test data to determine whether the battery condition is normal.

The AP 210 may control the operations of other hardware components (e.g., the sensor module 240, the speaker 282, the receiver 284, the earphones 286, the microphone 288, the camera module 291, the motor 298, the Wi-Fi module 223, the BT module 225, the GPS module 227, the NFC module 228, the USB 274, the touch panel 252, the SIM 224), receive data generated under such control from the corresponding hardware components, compare the received data with the diagnosis test data, and determine whether there is a hardware error based on the comparison result or presence/absence of received data.

In step 430, the AP 210 displays, on the display 260, the information indicating presence/absence of a hardware error and a link for providing services associated with the hardware components.

At least one of the aforementioned information and link may be transmitted to an external device using a short-range communication module (e.g., the BT module 225 and the NFC module 228) in order to be displayed on the external device.

The link may be information provided based on the determination result. For example, the diagnosis target may be biometric sensor 240I. If it is determined that the biometric sensor 240I is operating normally, the link may be connected to an application related to the biometric sensor 240I. However, if it is determined that the biometric sensor 240I is operating abnormally, the link may be connected to a menu for transmitting a user's opinion about an error report or AS request service to an external device (e.g., the server 106).

Herein, the term "link" is used in the sense of "interface for providing users with a certain function or service," but it is not limited thereto. Accordingly, the term "link" should be construed broadly, as including all changes, equivalents, and substitutes. For example, a link may be expressed in the form of an icon, an item, or an object.

Figure 5:
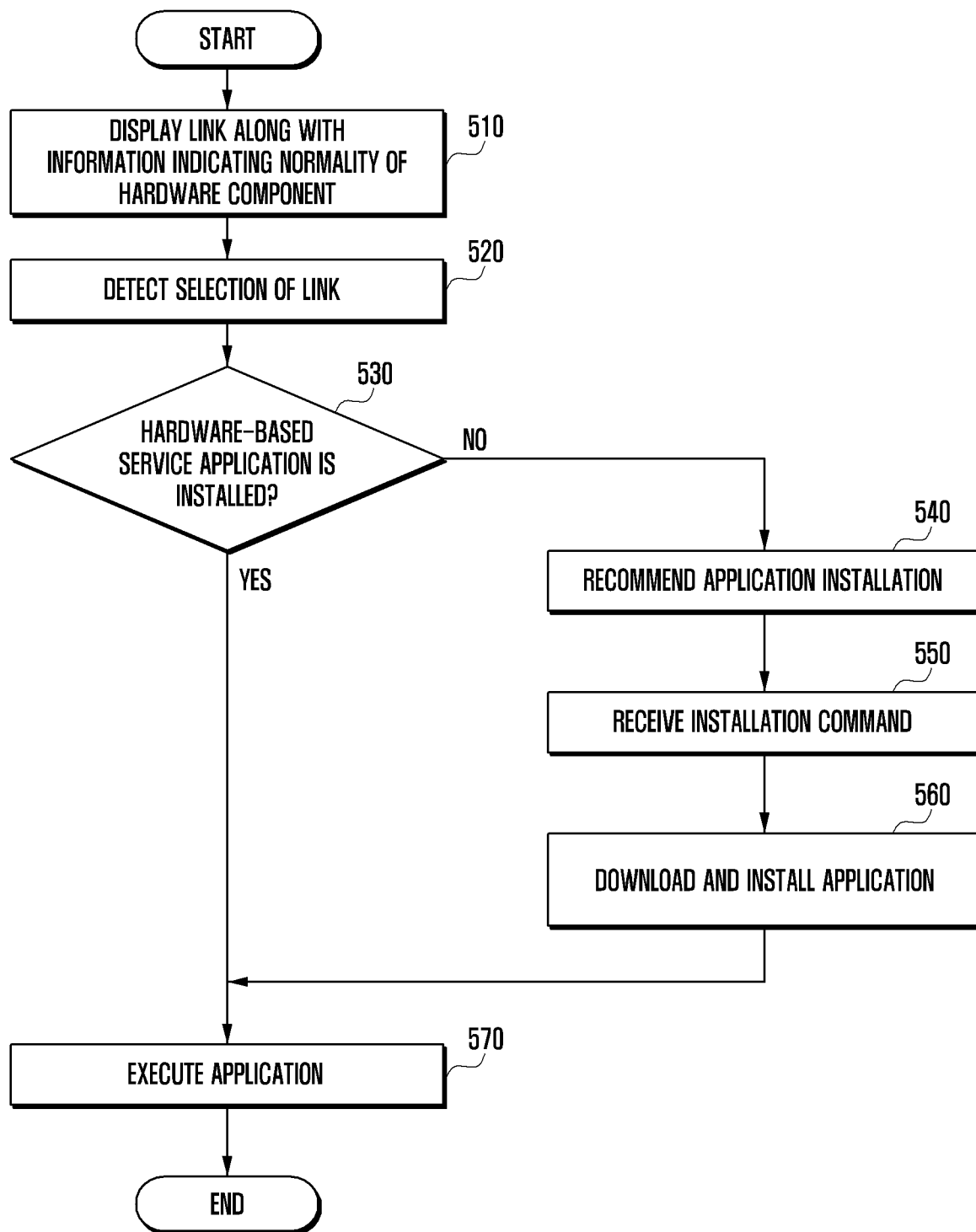
FIG. 5 is a flowchart illustrating a procedure based on a hardware diagnosis result according to an embodiment of the present disclosure.

FIG. 5 is a flowchart illustrating a procedure based on a hardware diagnosis result according to an embodiment of the present disclosure. Although the method of FIG. 5 is described below as being performed by the electronic device illustrated FIG. 2, it is not limited thereto.

Referring to FIG. 5, in step 510, the AP 210 displays, on the display 260, a link and information indicating that a hardware component is operating normally. For example, the information may be generated based on a determination made in step 420 of FIG. 4.

In step 520, the AP 210 receives an input for selecting the link. The AP 210 may receive the link selection input as a touch input, in the form of a voice command made through the audio module 280, or from an external device using the BT module 225 or the NFC module 228.

In response to selection of the link in step 520, in step 530, the AP 210 determines whether an application capable of providing a hardware-based service is present in the electronic device 201.

If the hardware-based service application is not present in the electronic device 201 in step 530, the processor recommends installation of an application in step 540. For example, the AP 210 may display information of the application (e.g., application name and icon).

In step 550, the AP 210 receives an installation command. The AP 210 may receive the installation command as a touch input, as a voice command, or from an external device.

Upon receipt of the installation command, in step 560, the AP 210 downloads and installs the application. For example, the AP 210 accesses an external device via the communication module 220 to download the corresponding application and install the downloaded application in the electronic device.

After installing the application in step 560 or if the hardware-based service application is present in the electronic device 201 in step 530, the AP 210 executes the application in step 570. For example, the AP 210 executes the application to provide the user with a hardware-related service. Alternatively, the AP 210 may also control the display 260 to display a pop-up window asking the user whether or not to execute the application. If the user makes an input to execute the application, the AP 210 executes the application.

Figure 6:
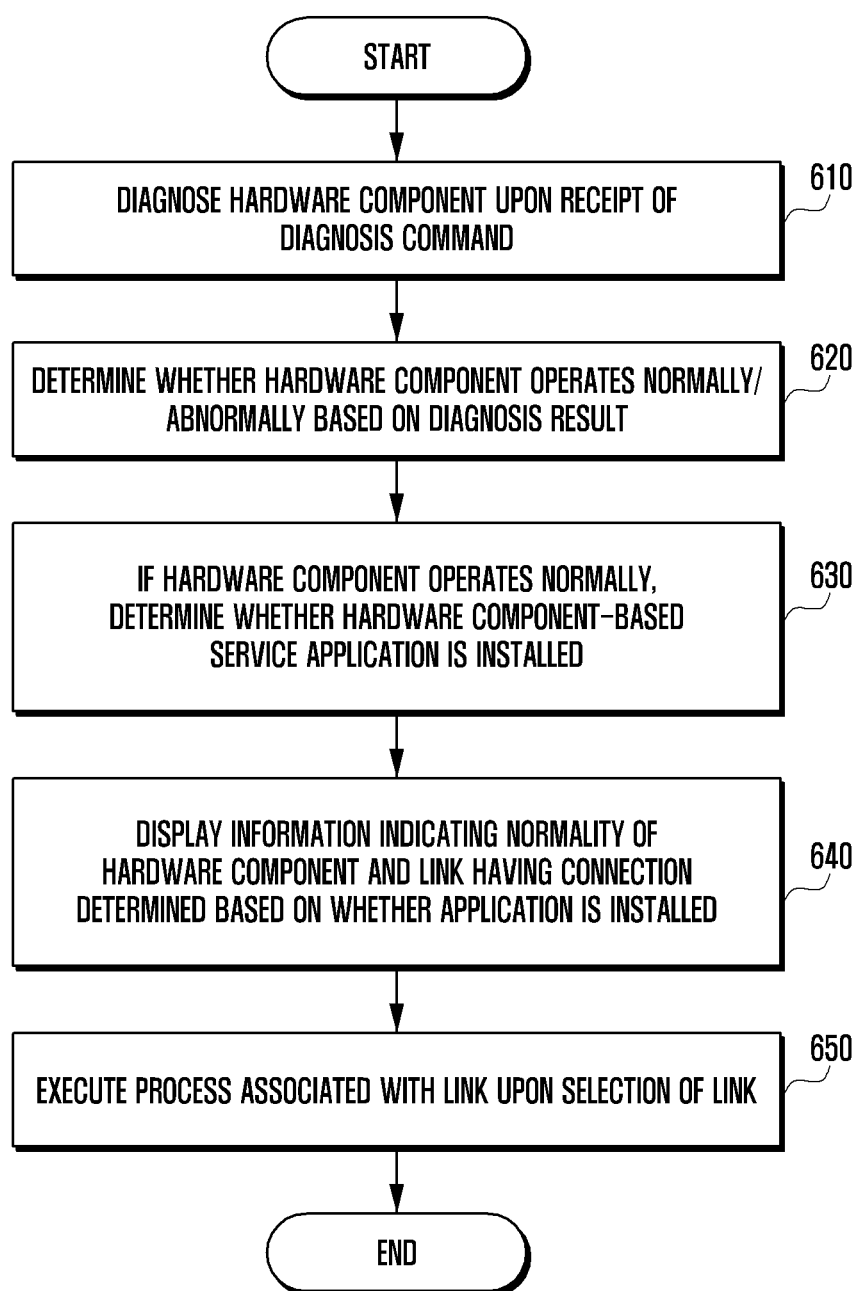
FIG. 6 is a flowchart illustrating a procedure based on a hardware diagnosis result according to an embodiment of the present disclosure.

FIG. 6 is a flowchart illustrating a procedure based on a hardware diagnosis result according to an embodiment of the present disclosure. Although the method of FIG. 6 is described below as being performed by the electronic device illustrated FIG. 2, it is not limited thereto.

Referring to FIG. 6, in step 610, the AP 210 performs hardware diagnosis, in response to a diagnosis command.

In step 620, the AP 210 determines that no hardware error is detected based on the diagnosis result.

In step 630, the AP 210 determines whether a hardware-based service application is installed in the electronic device 201.

In step 640, the AP 210 controls the display 260 to display a link based on whether the hardware-based service application is installed and information indicating that no hardware error is detected. For example, if it is determined that the hardware-based service application is installed in step 630, the link may include the hardware-related application information (e.g., an application name). However, if it is determined that no hardware-based service application is installed in step 630, the link may include the application installation information (e.g., an application store).

In step 650, the AP 210 executes a process associated with the link. For example, the AP 210 may execute the corresponding application, in response to selecting the link including the application name, or install and then execute the application, in response to the selection of the link including the application installation information, e.g., a link to the application store.

Figure 7:
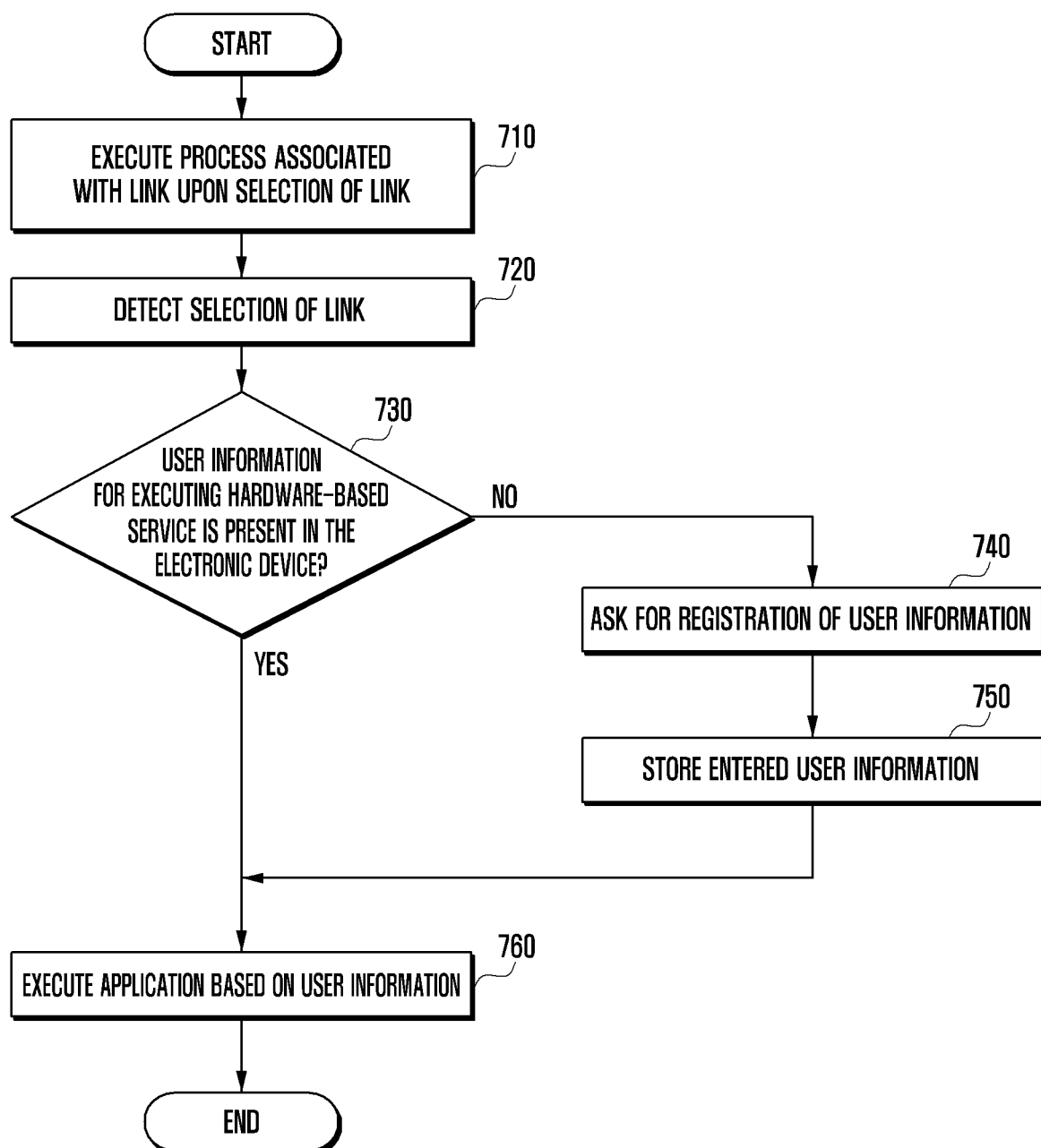
FIG. 7 is a flowchart illustrating a procedure based on a hardware diagnosis result according to an embodiment of the present disclosure.

FIG. 7 is a flowchart illustrating a procedure based on a hardware diagnosis result according to an embodiment of the present disclosure. Although the method of FIG. 7 is described below as being performed by the electronic device illustrated FIG. 2, it is not limited thereto.

Referring to FIG. 7, in step 710, the AP 210 controls the display 260 to display a link and information indicating that the hardware component is operating normally. For example, the information may be generated based on the determination made in step 420 of FIG. 4.

In step 720, the AP 210 receives the link selection input as a touch input, in the form of a voice command made through the audio module 280, or from an external device via a short-range communication module (e.g., the BT module 225 or the NFC module 228).

If the link is selected in step 720, in step 730, the AP 210 determines user information for executing a hardware-based service exists in the electronic device 201.

For example, the service may be an electronic transaction, touchscreen unlock, or internet banking service using a sensor for collecting biometric information (e.g., fingerprint and iris data). The service may be a health care service (for measuring heart rate, stress, oxygen saturation, and running speed) based on the information collected via a physical quantity sensor (e.g., acceleration sensor and direction sensor) and a biometric sensor (e.g., heart rate sensor, temperature sensor, and blood pressure sensor).

If it is determined that the user information (e.g., fingerprint information, iris information, and password) does not exist in step 730, the AP 210 requests to the user to register user information in step 740. For example, the AP 210 may control the display 260 to display a page for the user to enter user information.

In step 750, the AP 210 stores the entered user information in the memory 230.

After storing the user information in step 750 or if it is determined that the user information exists in the electronic device 201 in step 730, the AP 210 executes the application based on the user information in step 760. For example, the AP 210 compares the user information input via the input device 250 with the user information stored in the memory 230, and if they match, executes the application.

Figure 8:
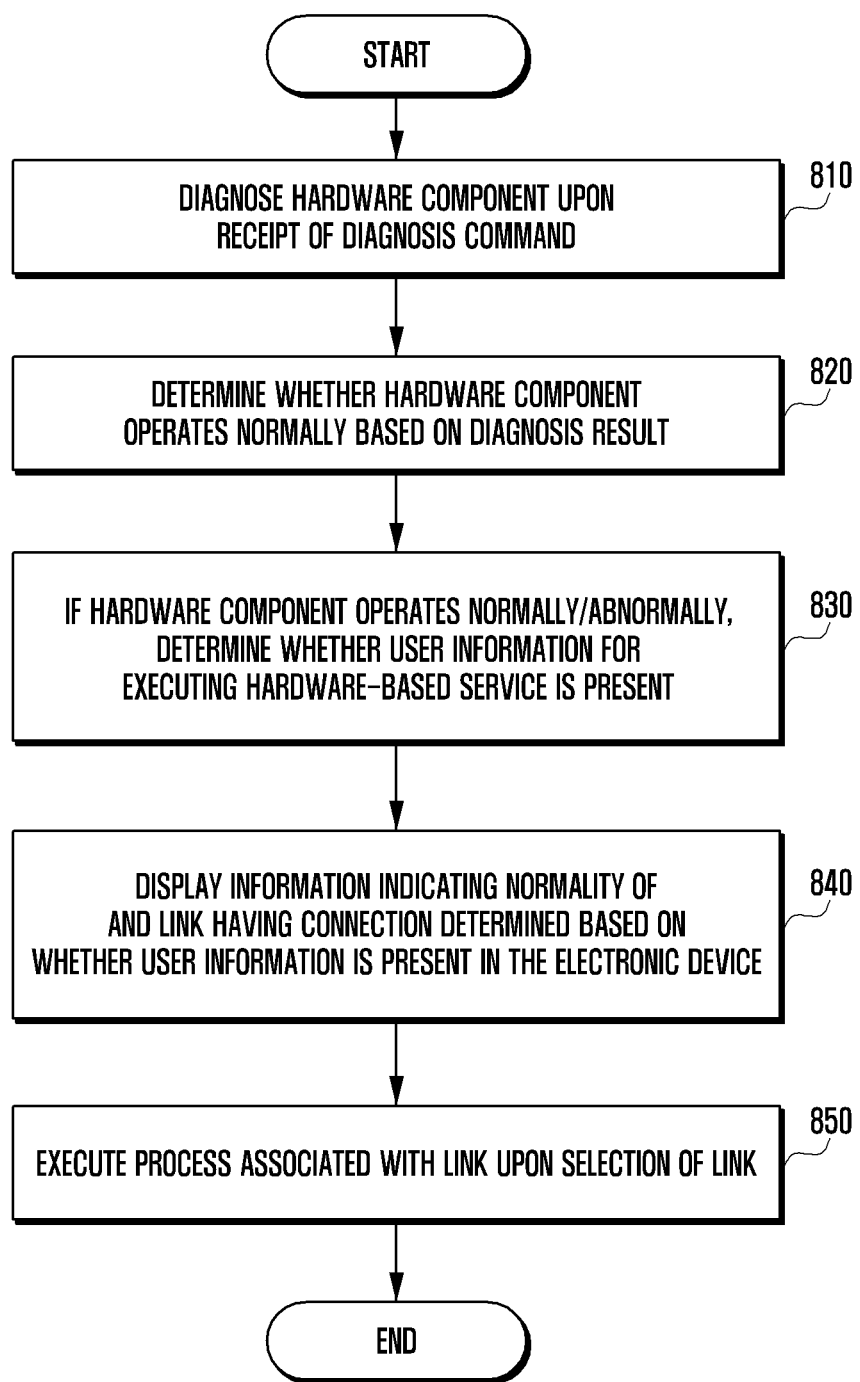
FIG. 8 is a flowchart illustrating a procedure based on a hardware diagnosis result according to an embodiment of the present disclosure.

FIG. 8 is a flowchart illustrating a procedure based on a hardware diagnosis result according to an embodiment of the present disclosure. Although the method of FIG. 8 is described below as being performed by the electronic device illustrated FIG. 2, it is not limited thereto.

Referring to FIG. 8, in step 810, the AP 210 performs hardware diagnosis, in response to a diagnosis command.

In step 820, the AP 210 determines whether a hardware error is detected based on the diagnosis result.

In step 830, the AP 210 determines whether user information for executing a hardware-based service is present.

In step 840, the AP 210 controls the display unit 260 to display information indicating that the no hardware error is detected and a link based on the determination as to whether user information for executing a hardware-based service is present.

If the link is selected, the AP 210 may execute a process associated with the link in step 850.

For example, if the user information exists in the electronic device 201, the link may include the application information (e.g., the application name). If the application information is selected, the AP 210 may execute the application based on the user information.

However, if no user information exists in the electronic device 201, the link may include information for requesting the user to register the user information. If the registration request information is selected, the AP 210 may execute a user information registration process.

Alternatively, if no user information exists in the electronic device 201, the link may include application installation information (e.g., the application store). If the application installation information is selected, the AP 210 may execute an application installation process and a user information-based execution process.

Figure 9:
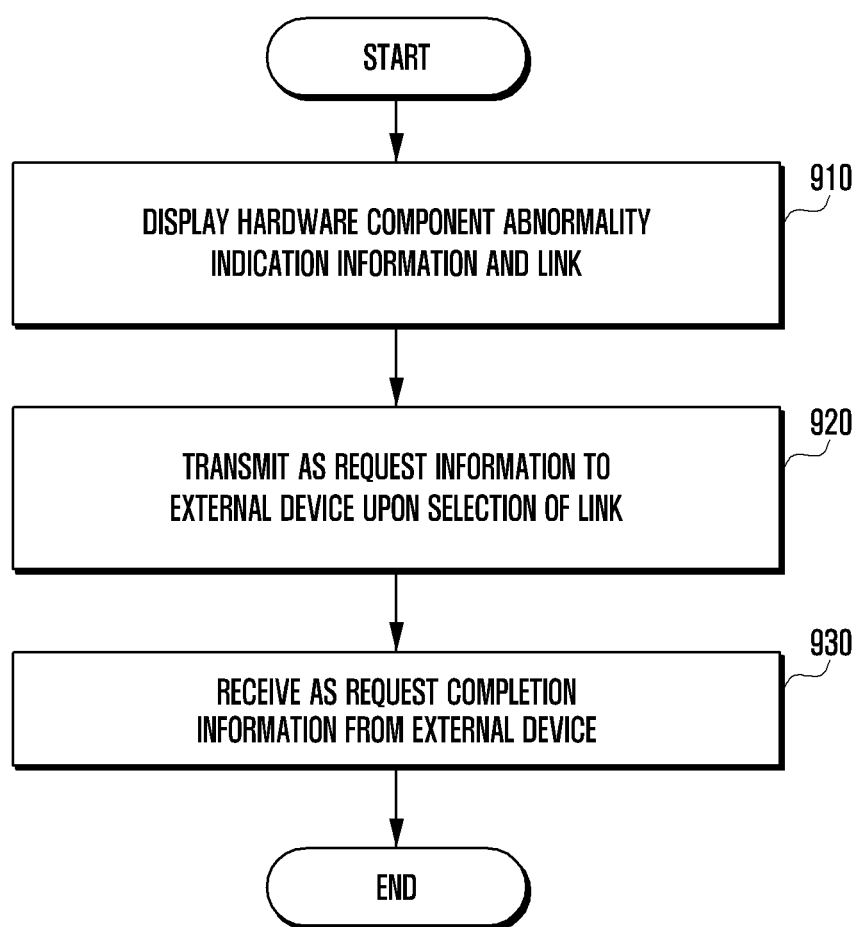
FIG. 9 is a flowchart illustrating an after service (AS) request procedure based on a hardware error determination according to an embodiment of the present disclosure.

FIG. 9 is a flowchart illustrating an AS request procedure based on a hardware error determination according to an embodiment of the present disclosure. Although the method of FIG. 9 is described below as being performed by the electronic device illustrated FIG. 2, it is not limited thereto.

Referring to FIG. 9, in step 910, the AP 210 controls the display 260 to display a link and information indicating a hardware error. For example, the information may be configured based on the determination result of step 420 in FIG. 4.

If the link is selected, the AP 210 transmits AS request information to an external device via the communication module 220 in step 920.

For example, if the link is selected, the AP 210 may transmit, to the external device, the information including device model of the electronic device 201, information on the erroneous hardware component, and system log data. The system log data may include the accumulated use history of the electronic device 201, and whether to transmit the system log data may be determined by the user. The AP 210 may further transmit the user information (e.g., name, address, and phone number).

Alternatively, if the link is selected, the AP 210 may download an AS request page from an external device via the communication module 220 and control the display unit 260 to display the AS request page. The user may enter a user's opinion on the page. For example, the user's opinion may include a user's recommended reservation time and local service center. The AP 210 may transmit to the external device the user's opinion and the device model, hardware information, and system log data.

In step 930, the AP 210 receives AS reservation completion information from the external device via the communication module 220. For example, the reservation completion information may include the location of the AS service center and reservation time.

Figure 10:
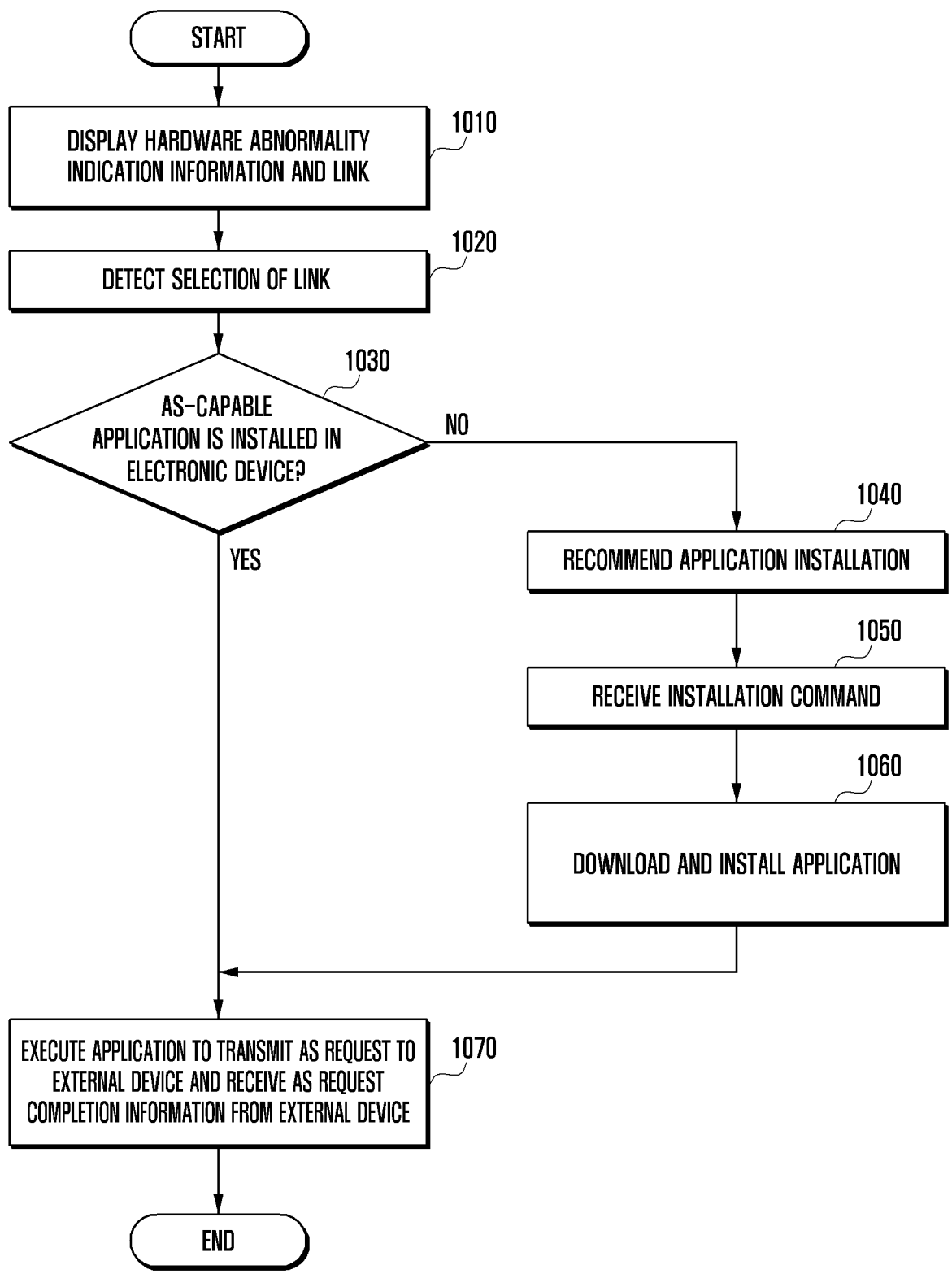
FIG. 10 is a flowchart illustrating an AS request procedure based on a hardware error determination according to an embodiment of the present disclosure.

FIG. 10 is a flowchart illustrating an AS request procedure based on a hardware error determination according to an embodiment of the present disclosure. Although the method of FIG. 10 is described below as being performed by the electronic device illustrated FIG. 2, it is not limited thereto.

Referring to FIG. 10, in step 1010, the AP 210 controls the display unit 260 to display a link and information indicating a hardware error. For example, the hardware error information may be generated based on the determination result in step 420 of FIG. 4.

In step 1020, the AP 210 receives a link selection signal input through the input device 250, the microphone 288, the BT module 225, or the NFC module 228.

If the link is selected in step 1030, the processor determines whether any application capable of providing an AS request service is installed.

If it is determined that no application capable of providing the AS request service is installed in step 1030, the AP 210 recommends to install an application in step 1040. For example, the AP 210 may control the display 260 to display application information (e.g., name and icon).

In step 1050, the AP 210 receives an installation command input through the input device 250 or the microphone 288 in step 1050. The AP 210 may also receive the installation command from an external device via a short-range communication module.

If the installation command is received in step 1050, the AP 210 accesses the external deice via the communication module 220 in order to download and install an application in the electronic device 201 in step 1060.

After downloading and installing the application in step 1060 or if it is determined that an application capable of providing the AS service is installed in step 1030, the AP 210 executes the application in order to transmit an AS request information to the external device and receive an AS request complete information from the external device in step 1070.

Figure 11:
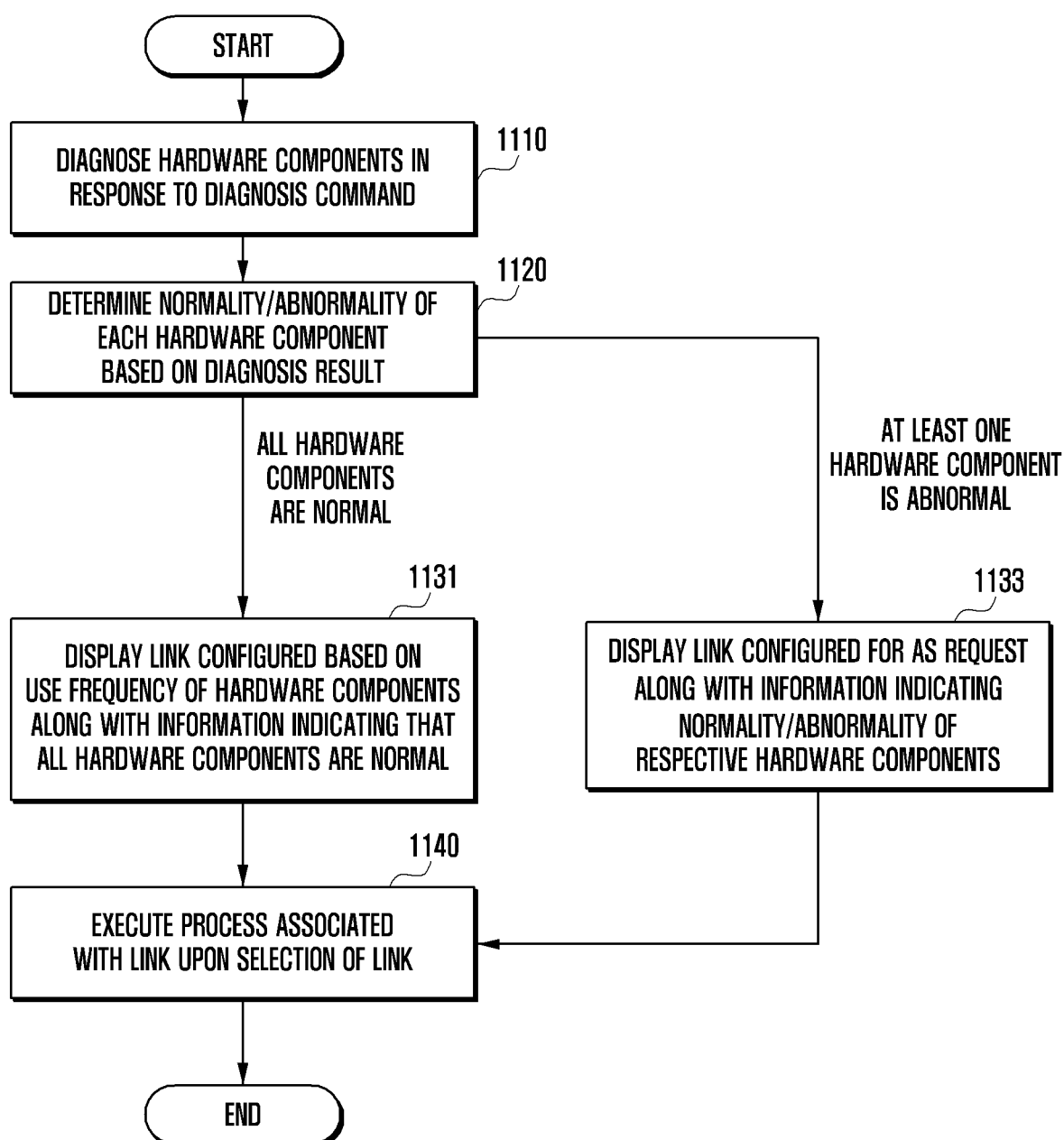
FIG. 11 is a flowchart illustrating a procedure based on a sensor diagnosis result according to an embodiment of the present disclosure.

FIG. 11 is a flowchart illustrating a procedure based on a sensor diagnosis result according to an embodiment of the present disclosure. Although the method of FIG. 11 is described below as being performed by the electronic device illustrated FIG. 2, it is not limited thereto.

Referring to FIG. 11, in step 1110, the AP 210 performs hardware diagnosis, in response to a diagnosis command.

In step 1120, the AP 210 determines whether there is an erroneous hardware component based on the diagnosis.

If all hardware components are operating normally in step 1120, the AP 210 controls the display 260 to display information indicating that all hardware components are operating normally and a link based on use frequencies of the hardware components in step 1131.

For example, if the acceleration sensor 240E has a use frequency equal to or greater than a predetermined threshold value, the AP 210 may control the display 260 to display the information (e.g., name and icon) representing a workout application (e.g., pedometer). If the acceleration sensor 240E has a use frequency less than the predetermined threshold value, the AP 210 may control the display 260 to display information representing a health care application to the user.

If at least one hardware component is operating abnormally in step 1120, the AP 210 controls the display 260 to display information indicating how each hardware component is operating and an AS request link in step 1133.

If the link is selected, the AP 210 executes a process associated with the selected link in step 1140.

For example, the AP 210 may execute an application associated with the link selected based on the use frequencies of the hardware components. If it is determined that the corresponding application is not installed in the electronic device 201, the AP 210 may execute the application installation process (e.g., steps 540, 550, and 560 of FIG. 5). If the AS request link is selected, the AP 210 may transmit AS request information to the external device and receive AS request completion information from the external device.

FIGS. 12A to 12G illustrate a user interface for displaying a heart rate/fingerprint sensor diagnosis operation and diagnosis result according to an embodiment of the present disclosure. Although the user interface of FIGS. 12A to 12G is described below as being displayed by the electronic device illustrated FIG. 2, it is not limited thereto.

Figure 12A:
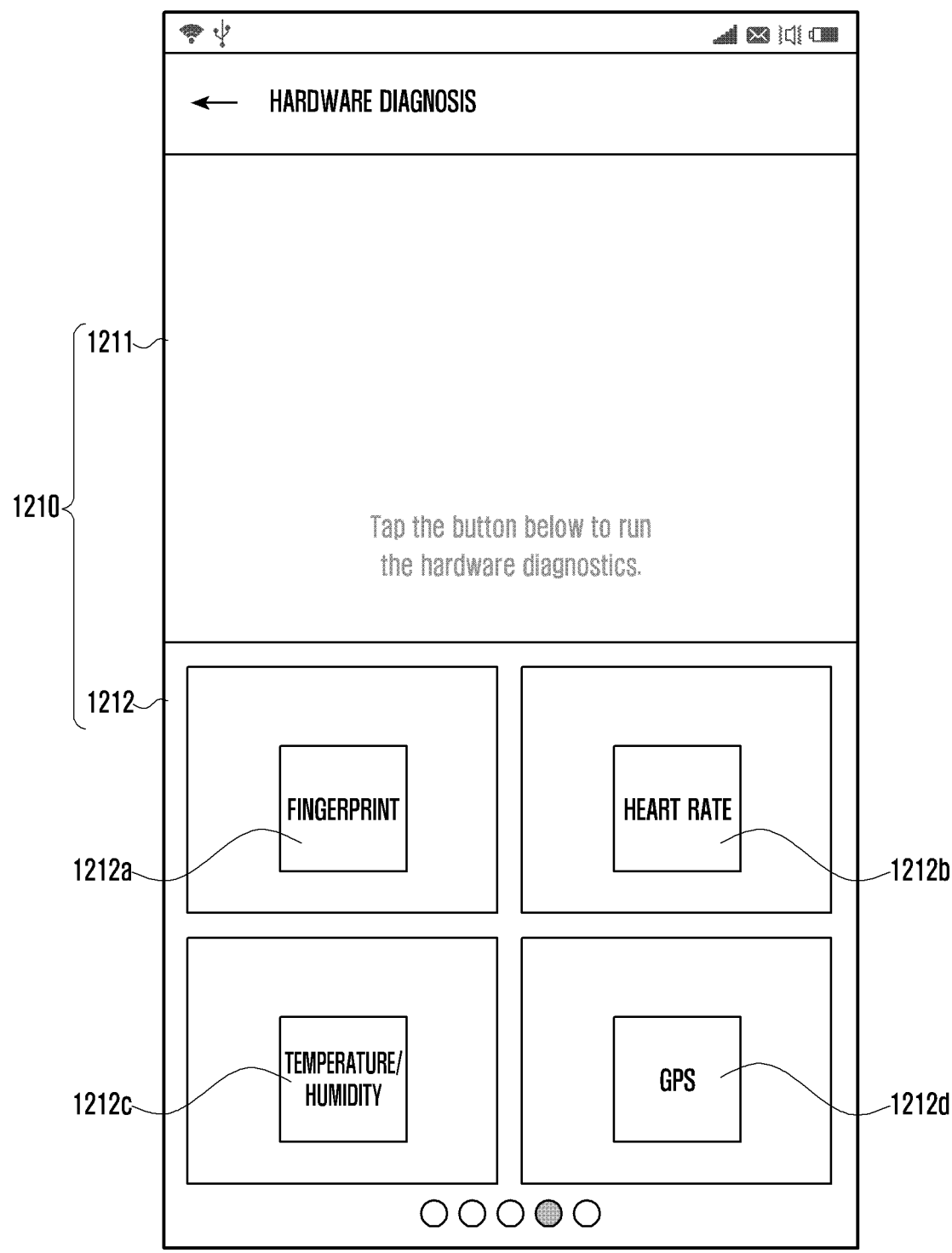
FIGS. 12A to 12G illustrate a user interface for displaying a heart rate/fingerprint sensor diagnosis operation and diagnosis result according to an embodiment of the present disclosure.

Referring to FIG. 12A, the AP 210 controls the display 260 to display a page 1210 for hardware diagnosis. The page 1210 is divided into two parts; the top for hardware diagnosis guidance as denoted by reference number 1211 and the bottom for a user's diagnosis target selection as denoted by reference number 1212. The hardware components that may be diagnosed are displayed as icons in the diagnosis target selection window 1212. Specifically, the diagnosis target selection window 1212 displays a fingerprint icon 1212*a*, a heart rate icon 1212*b*, a temperature/humidity icon 1212*c*, and a GPS icon 1212*d* that respectively represent the fingerprint sensor, heart rate sensor, temperature/humidity sensor, and GPS module. The objects displayed in the diagnosis target selection window 1212 may vary. For example, if the user swipes left or right on the diagnosis target selection window 1212 with a finger (or a touch input device such as an electronic pen), the AP 210 may control the display 260 to display other icons (e.g., battery icon, Bluetooth icon, Wi-Fi icon, sensor icon, SIM card icon, etc.) in response to the swipe gesture.

If the user selects one of the icons displayed in the diagnosis target selection window 1212, this may trigger starting a diagnosis on the hardware component represented by the selected icon. For example, if the heart rate icon 1212*b* is selected, the AP 210 controls the display unit 260 to display the heart rate sensor diagnosis information in the diagnosis guidance window 1211, as illustrated in FIG. 12B.

Figure 12B:
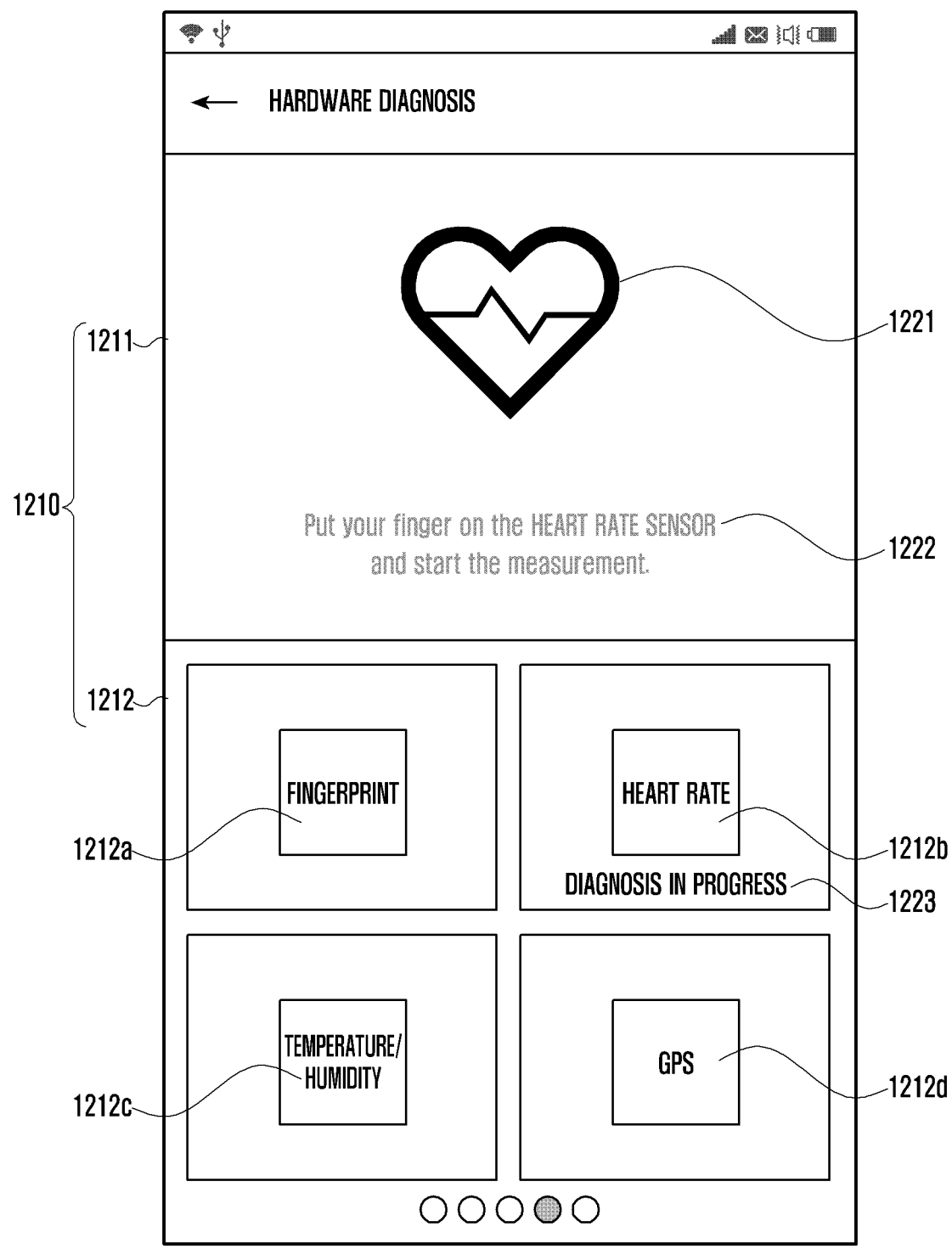
Figure 12C:
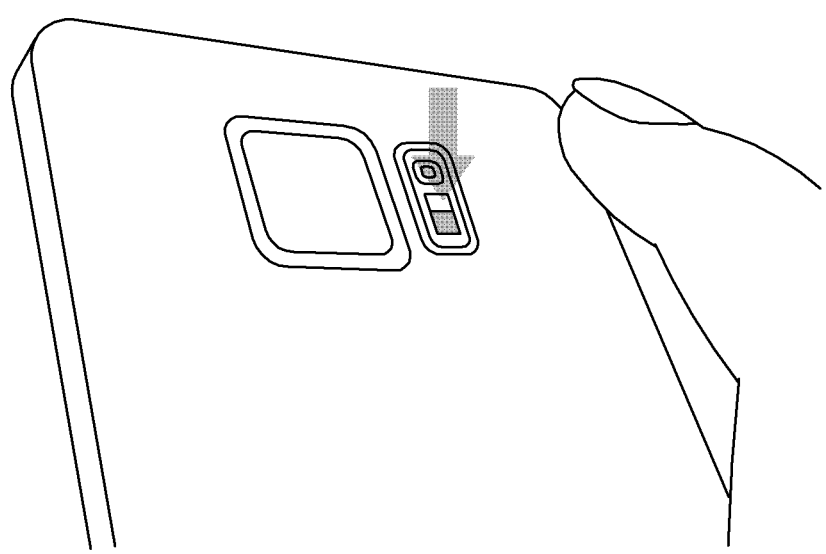

Referring to FIG. 12B, the diagnosis guidance window 1211 includes a heart rate sensor image 1221 and text guidance 1222. The AP 210 may also control the display 260 to display another image in the diagnosis guidance window 1211 to notify the user of the position of the heart rate sensor, as illustrated in FIG. 12 C.

If the user places a finger on the heart rate sensor according to the guidance image, the AP 210 detects the contact on the heart rate sensor and performs diagnosis on the heart rate sensor using the measurement data received from the heart rate sensor. When the diagnosis starts, the AP 210 controls the display unit 260 to display, below the heart rate icon 1212*b*, the information 1223 indicating that the heart rate sensor diagnosis is in progress.

Figure 12D:
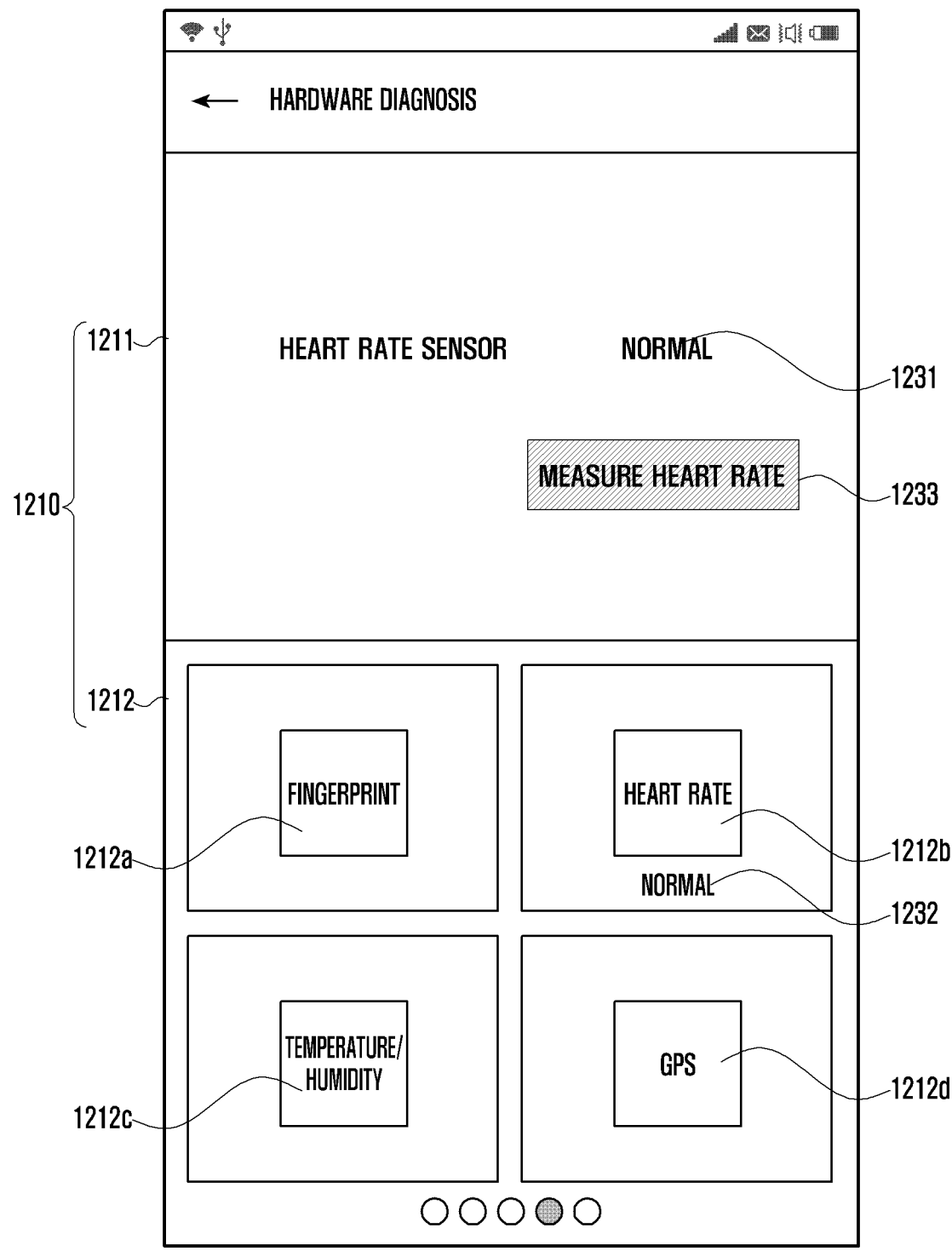

When the hardware diagnosis is complete, the AP 210 controls the display 260 to display the diagnosis result in the diagnosis guidance window 1211, as illustrated in FIG. 12D. The AP 210 also controls the display 260 to display a link for providing a hardware-related service in the diagnosis guidance window 1211. For example, the processor controls the display 260 to display diagnosis result information 1231 indicating that the corresponding hardware component is normal and to display the diagnosis result information 1232 near the heart rate icon 1212*b*. The AP 210 also controls the display 260 to display the text link 1233 with the wording "heart rate measurement" in the diagnosis guidance window 1211.

Figure 12E:
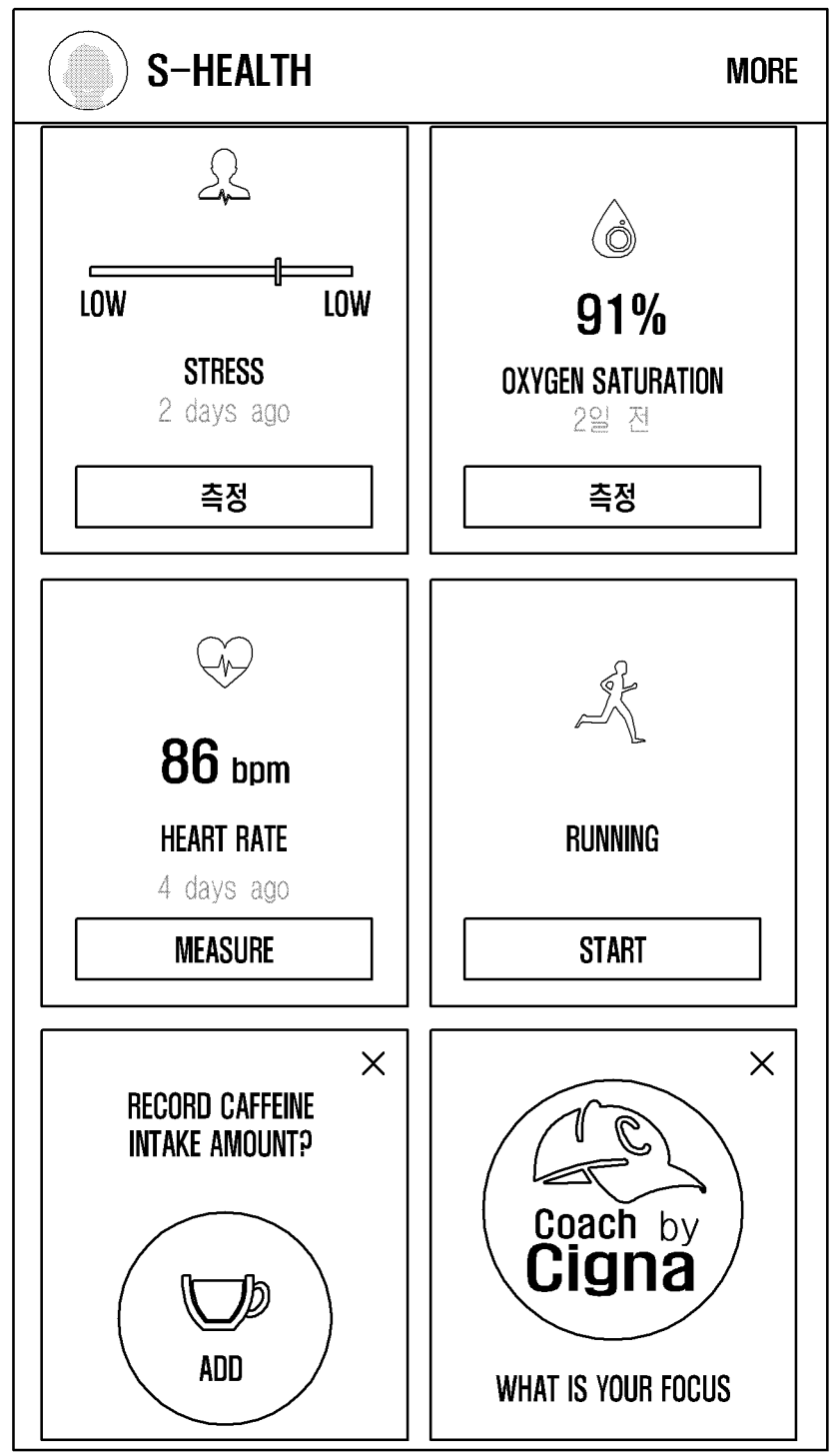

If the text link 1233 is selected, the AP 210 executes a corresponding application (e.g., a health care application) and controls the display 260 to display a health care application execution page including an oxygen saturation section, a stress section, a heart rate section, and a running section, as illustrated in FIG. 12E. If the corresponding application is not installed, the AP 210 may execute an app store program and control the display unit 260 to display an application downlink page.

Figure 12F:
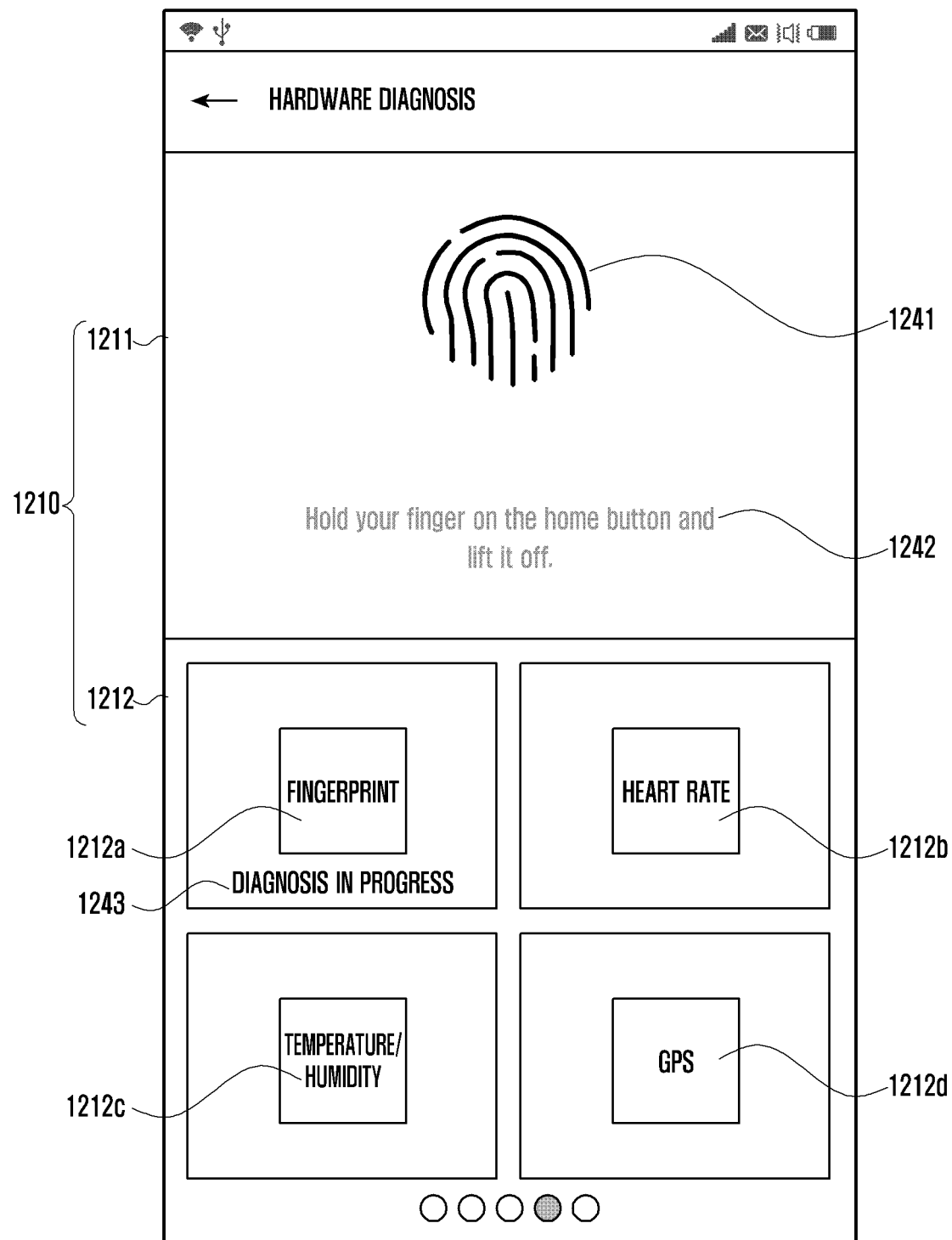

Referring again to FIG. 12B, if the user selects the fingerprint icon 1212*a* in the diagnosis target selection window 1212, the AP 210 controls the display 260 to display a fingerprint sensor diagnosis indication in the diagnosis guidance window 1211 in response to the selection of the fingerprint icon 1212*a*, as illustrated in FIG. 12F.

Referring to FIG. 12F, the diagnosis guidance window 1211 includes a fingerprint image 1241 and a text guidance 1242. If the user places a finger on the fingerprint sensor, the AP 210 detects the contact on the fingerprint sensor and performs diagnosis on the fingerprint sensor using the measurement data from the fingerprint sensor. When the diagnosis is started, the AP 210 controls the display 260 to display the information 1243 indicating that that the fingerprint sensor diagnosis is in progress below the fingerprint icon 1212*a*.

Figure 12G:
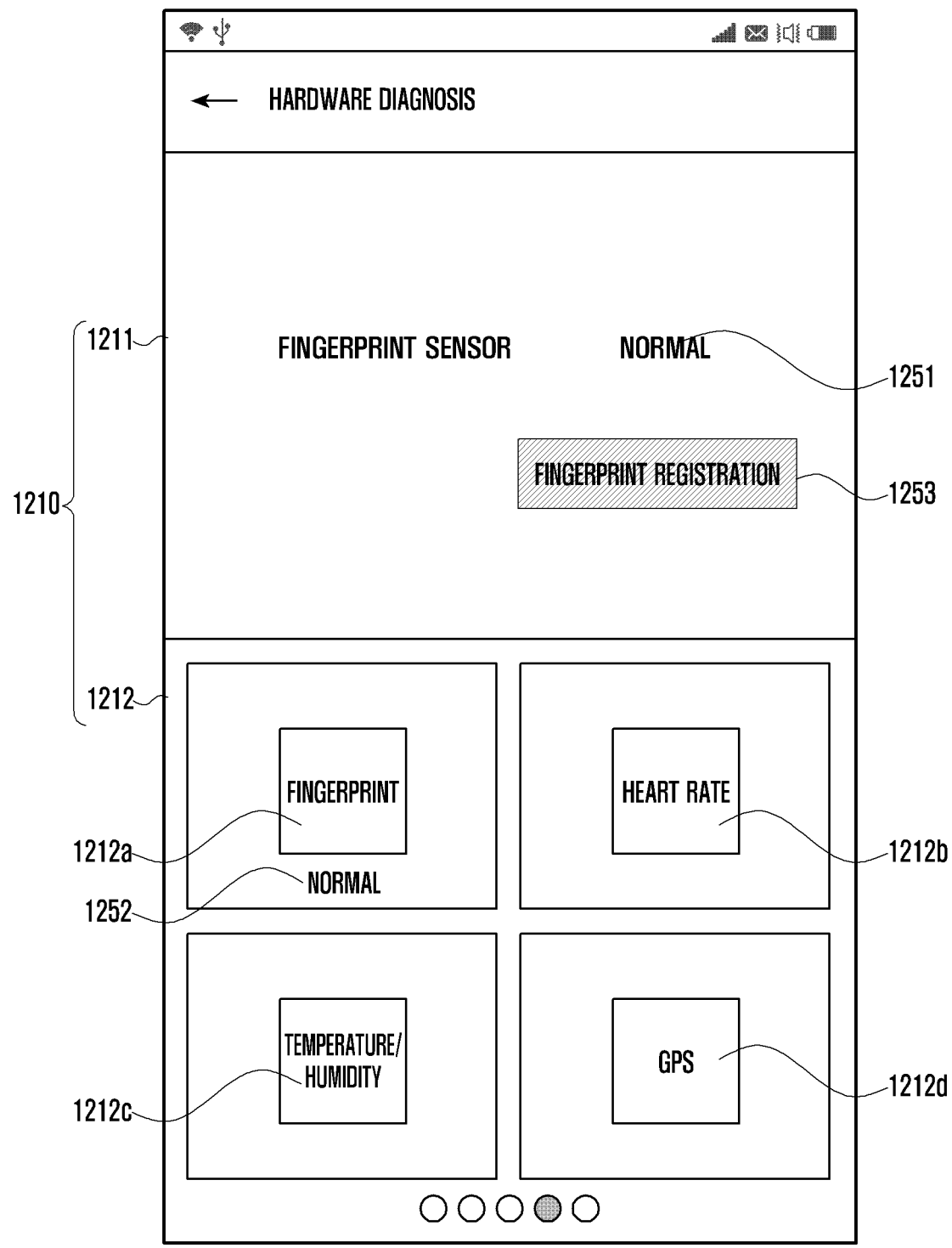

Referring to FIG. 12G, the AP 210 controls the display 260 to display the fingerprint sensor diagnosis result, e.g., the information 1251, notifying that the fingerprint sensor is operating normally, in the diagnosis guidance window 1211. The AP 210 also controls the display 260 to display the diagnosis result information 1252 indicating that the fingerprint sensor is operating normally near the fingerprint icon 1212*a*.

If there is no registered fingerprint of the user, the processor may control the display 260 to display the text link 1253 with the wording "fingerprint registration" in the diagnosis guidance window 1211. If the text link 1253 is selected, the processor may control the display 260 to display a fingerprint registration page.

FIGS. 13A to 13F illustrate a user interface for displaying a sensor module diagnosis operation and diagnosis result according to an embodiment of the present disclosure. Although the user interface of FIGS. 13A to 13F is described below as being displayed by the electronic device illustrated FIG. 2, it is not limited thereto.

Figure 13A:
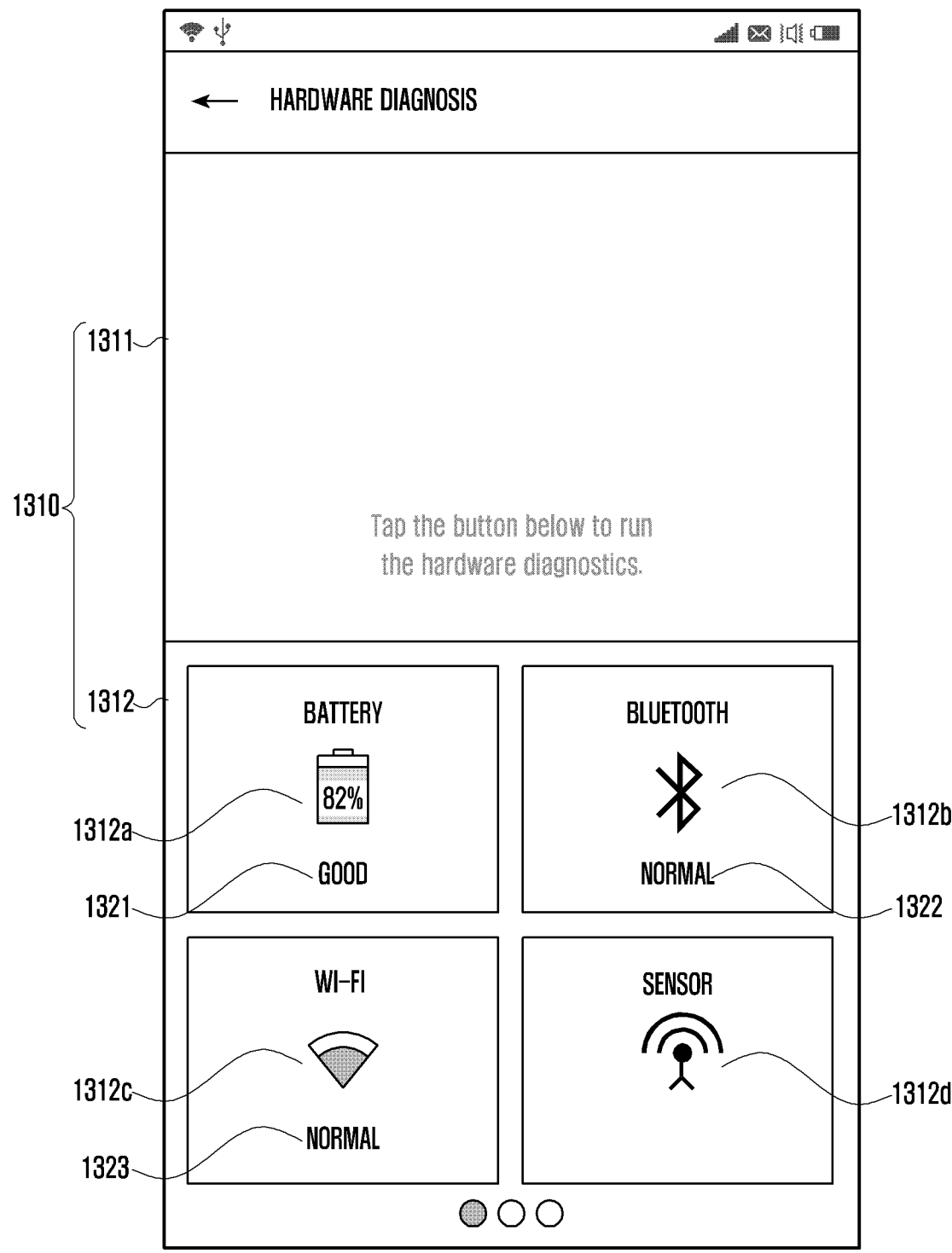
FIGS. 13A to 13F illustrate a user interface for displaying a sensor module diagnosis operation and diagnosis result according to an embodiment of the present disclosure.

Referring to FIG. 13A, the processor controls the display 260 to display a page 1310 for hardware diagnosis. The page 1310 is divided into two parts; the top for hardware diagnosis guidance is denoted by reference number 1311 and the bottom for a user's diagnosis target selection is denoted by reference number 1312. For example, the diagnosis target selection window 1312 includes a battery icon 1312*a*, a Bluetooth icon 1312*b*, a Wi-Fi icon 1312*c*, and a sensor icon 1312*d* that respectively represent the battery, the Bluetooth module, the Wi-Fi module, and the sensor module. The battery, the Bluetooth module, and the Wi-Fi module may be diagnosed already, such that the diagnosis results of the respective modules are displayed in the diagnosis target selection window 1312. For example, the battery icon 1312*a*, the Bluetooth icon 1312*b*, and the Wi-Fi icon 1312*c* are displayed with the text, respectively, "good" 1321, "normal" 1322, and "normal" 1323. The sensor module may not be diagnosed yet, such that no text is displayed below the sensor icon 1312*d*. The sensor icon 1312*d* may also be displayed with the information indicating that the sensor module is not diagnosed yet (or should be diagnosed).

Figure 13B:
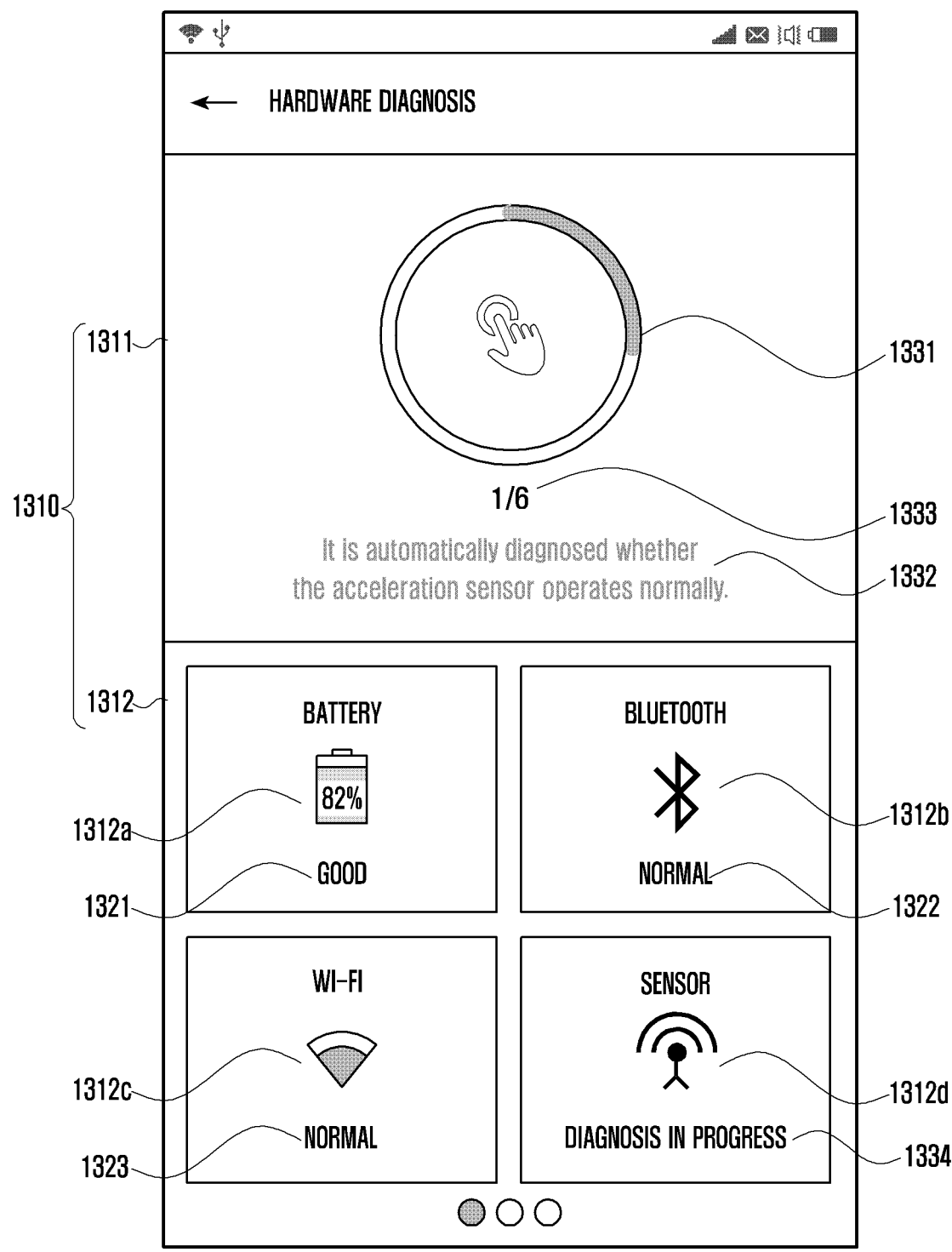

If the user selects the sensor icon 1312*d* in the diagnosis target selection window 1312, the processor controls the display 260 to display sensor module diagnosis-related information in the diagnosis guidance window 1311 as illustrated in FIG. 13B.

Referring to FIG. 13B, the diagnosis guidance window 1311 includes a diagnosis process image 1331, the diagnosis target device information 1332, and the diagnosis order information 1333. Information indicating that the diagnosis is in progress is displayed below the sensor icon 1312*d*, as denoted by reference number 1334.

Figure 13C:
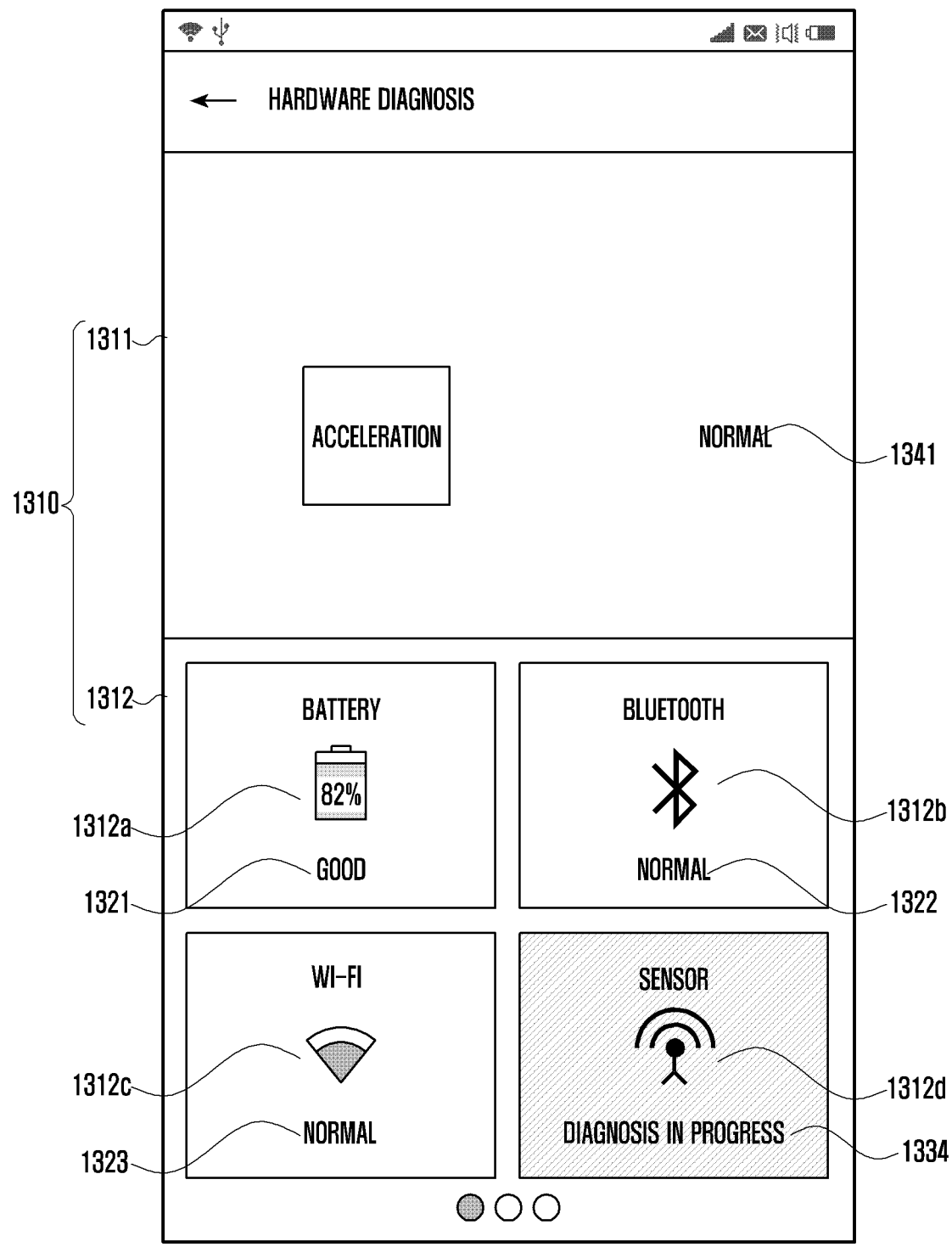

If the diagnosis on the sensor is completed, the diagnosis result is displayed in the diagnosis guidance window 1311, as illustrated in FIG. 13C. For example, if the diagnosis on the acceleration sensor is completed, the AP 210 controls the display 260 to display the diagnosis result 1341 indicating that the acceleration sensor is operating normally.

Figure 13D:
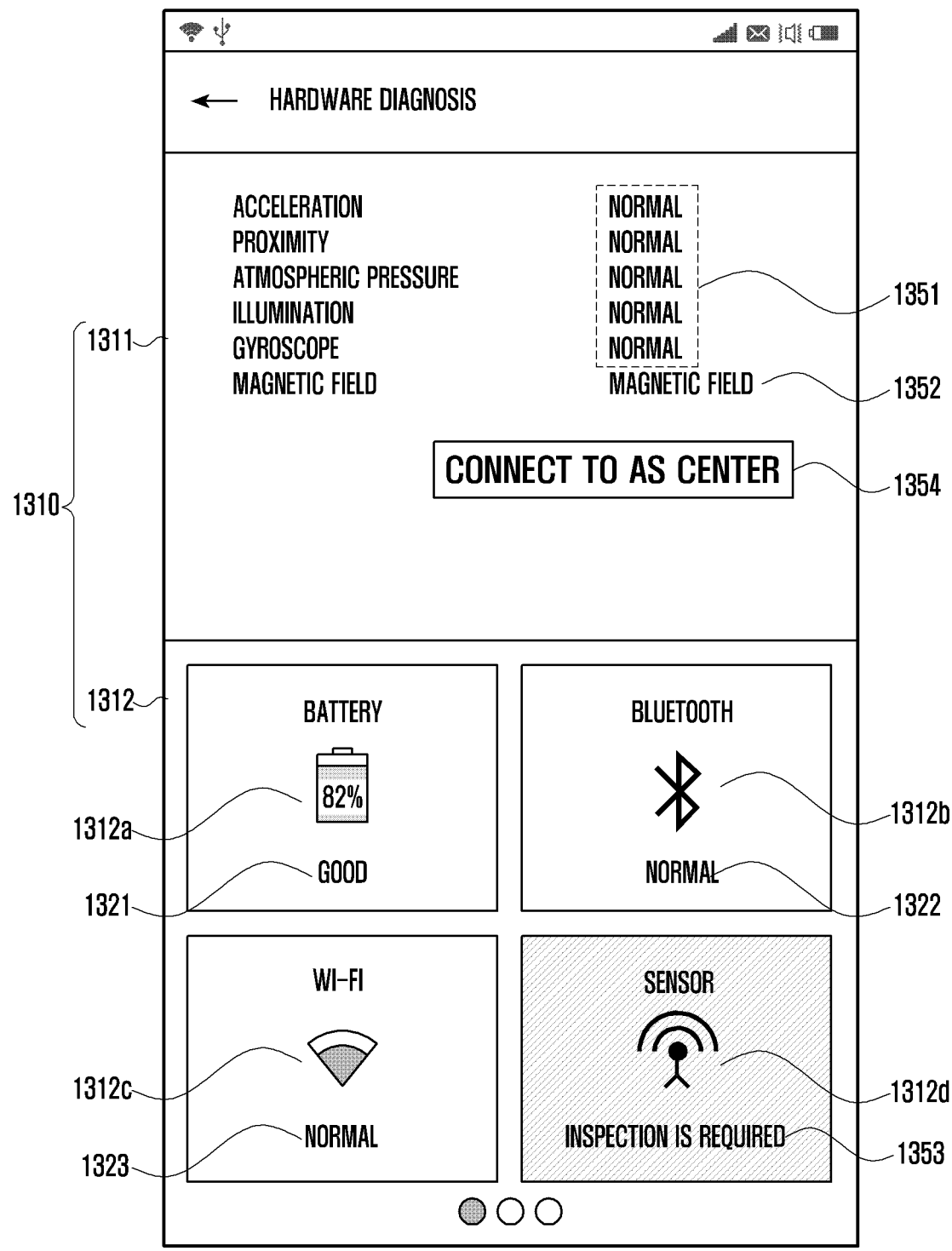

If diagnosis of all of the sensors is completed, the AP 210 controls the display 260 to display the diagnosis results of the respective sensors and a link in the diagnosis guidance window 1311, as illustrated in FIG. 13D.

Referring to FIG. 13D, the acceleration sensor, the proximity sensor, the barometer, the light sensor, and the gyroscope sensor are diagnosed as normal, and thus, normal status indication information 1351 is displayed in the guidance window 1311. However, the magnetic sensor is diagnosed as abnormal, and thus, abnormal status indication information 1352 may be displayed in the diagnosis guidance window 1311.

The diagnosis result may also be displayed below the corresponding sensor icon 1312*d*. For example, if the sensor is diagnosed as abnormal, the text "inspection is required" 1353 is displayed below the sensor icon 1312*d*. As the sensor is diagnosed as abnormal, a link associated with AS is provided by the AP 210 controlling the display 260 to display the text link "Connect to AS Center" 1354 in the diagnosis guidance window 1311.

If the link 1354 is selected, the AP 210 acquires AS request information (e.g., a model number of the electronic device 201, hardware component diagnosed as abnormal, and system log data) and transmits the AS request information to an external device via the communication module 220. Alternatively, the AP 210 may display, on the display 260, a page for an AS request and transmit a user opinion and AS request information input in the page to an external device.

A diagnosis may be paused and then resumed.

Figure 13E:
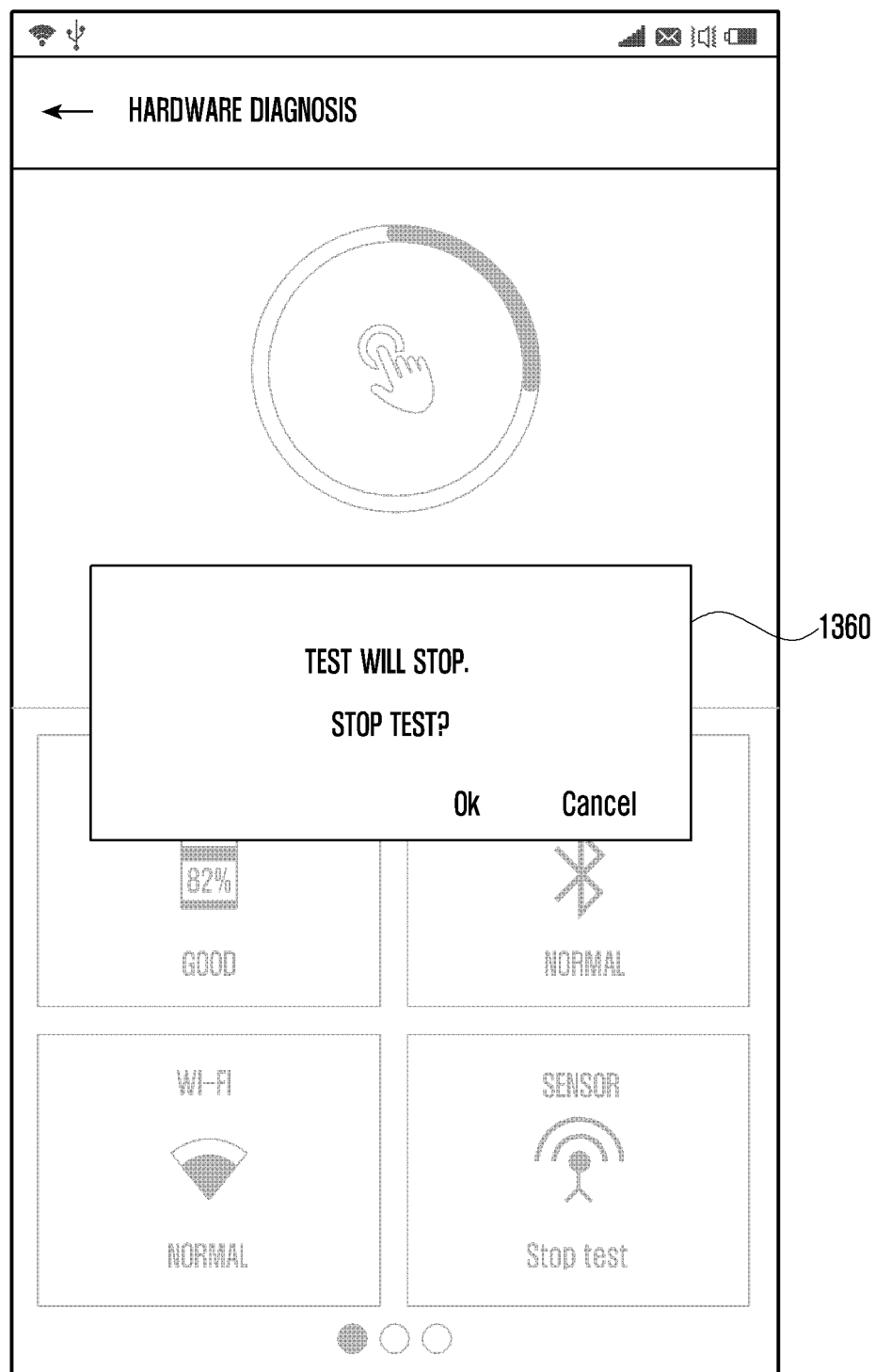
Figure 13F:
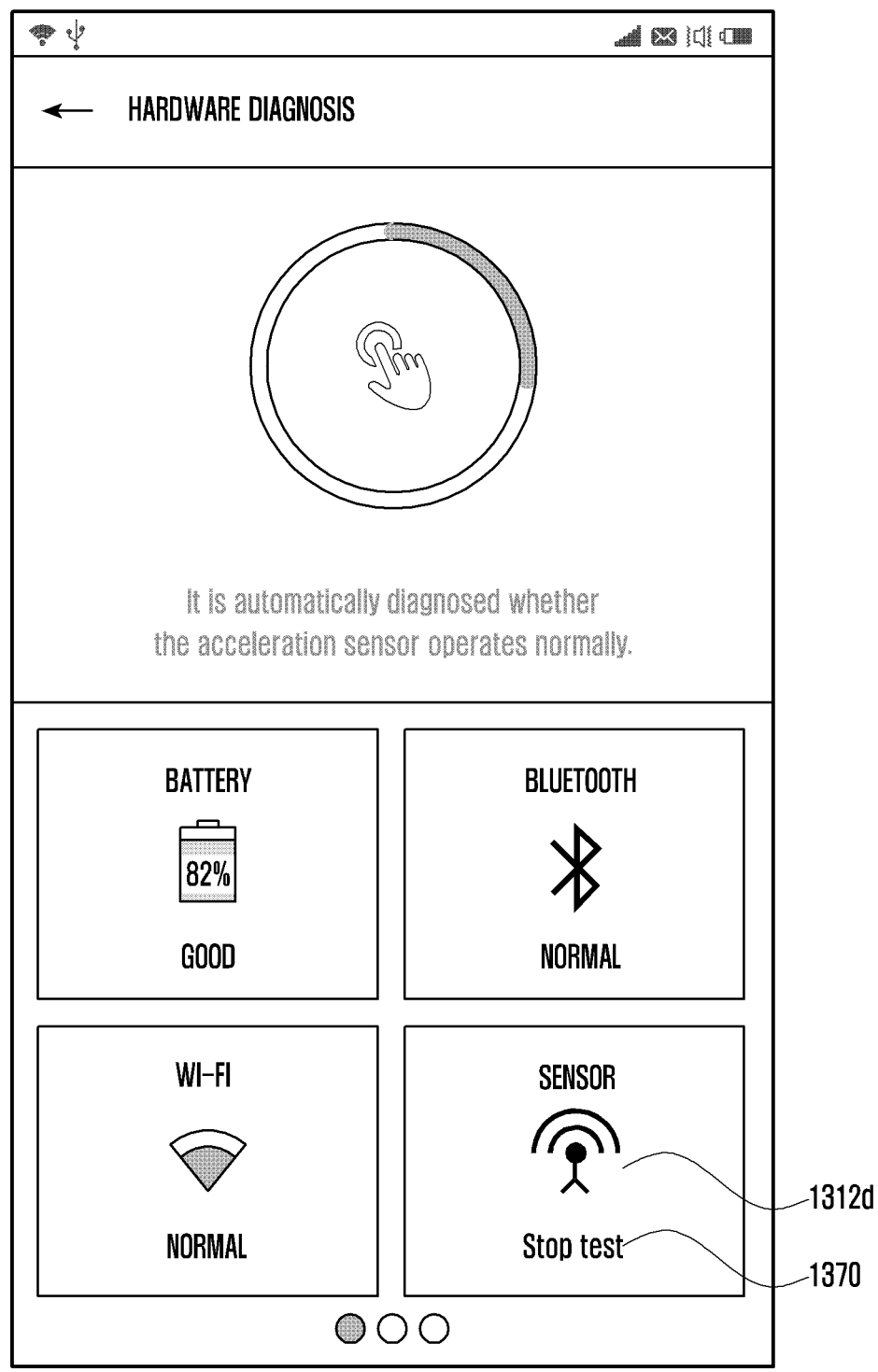

Referring to FIG. 13E, the AP 210 may detect an interrupt (generated by another component such as input device 250, communication module 220, and interface 270) during the diagnosis of the acceleration sensor and suspend the diagnosis upon detection of the interrupt. The AP 210 may control the display 1260 to display a popup window 1360 for asking whether to stop the diagnosis. If the user selects a cancel button in the popup window, the AP 210 may hide the popup window 1360 and resume the diagnosis. If the user selects an OK button in the popup window, the AP 210 may hide the popup window 1360 and control the display 260 to display the information indicating that the diagnosis is stopped below the sensor icon 1312*d*, as illustrated in FIG. 13F. If the user selects the sensor icon 1312*d* again, the AP 210 may resume the diagnosis.

FIGS. 14A to 14D illustrate a user interface for displaying a battery diagnosis operation and diagnosis result according to an embodiment of the present disclosure. Although the user interface of FIGS. 14A to 14D is described below as being displayed by the electronic device illustrated FIG. 2, it is not limited thereto.

Figure 14A:
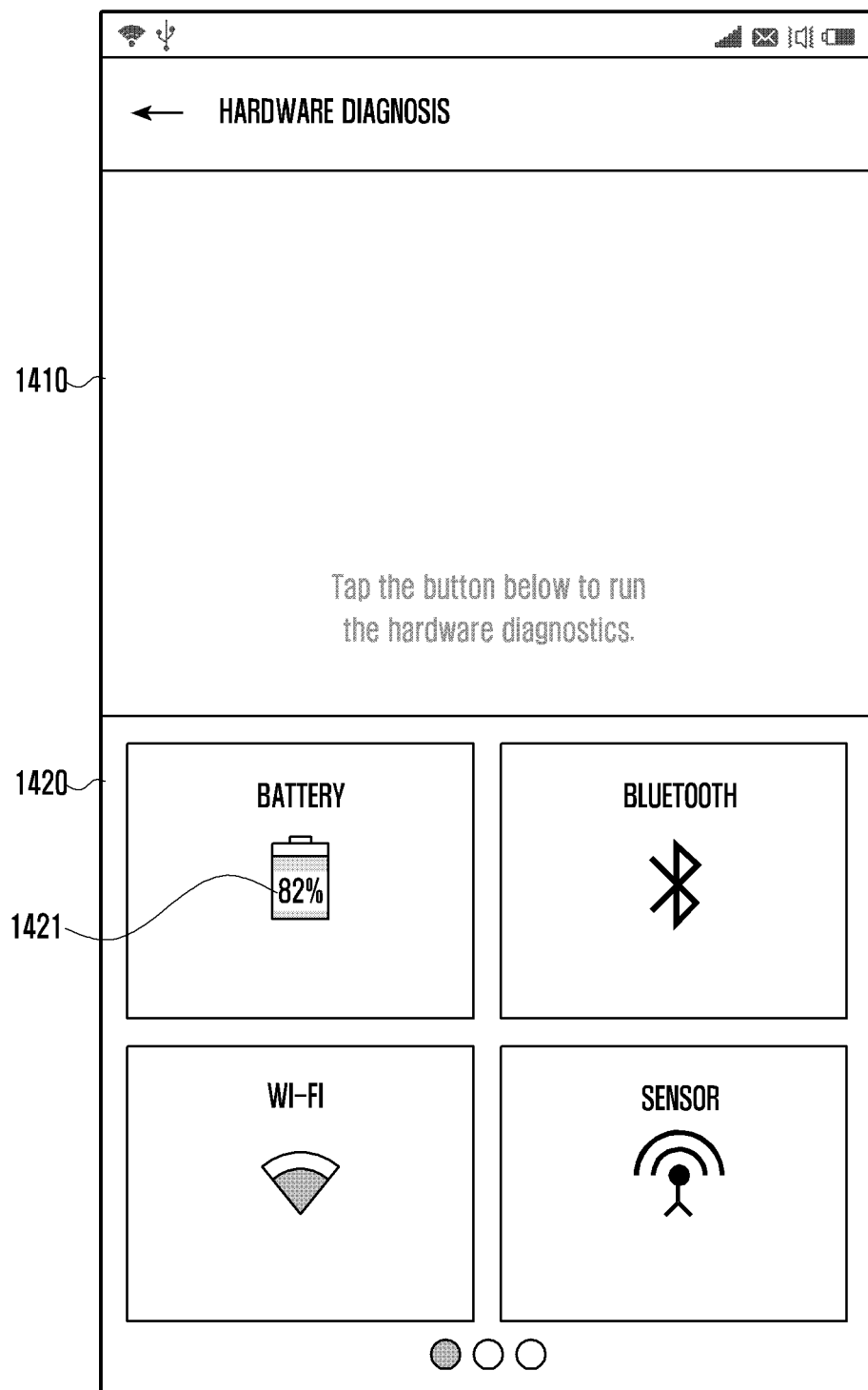
FIGS. 14A to 14D illustrate a user interface for displaying a battery diagnosis operation and diagnosis result according to an embodiment of the present disclosure.
Figure 14B:
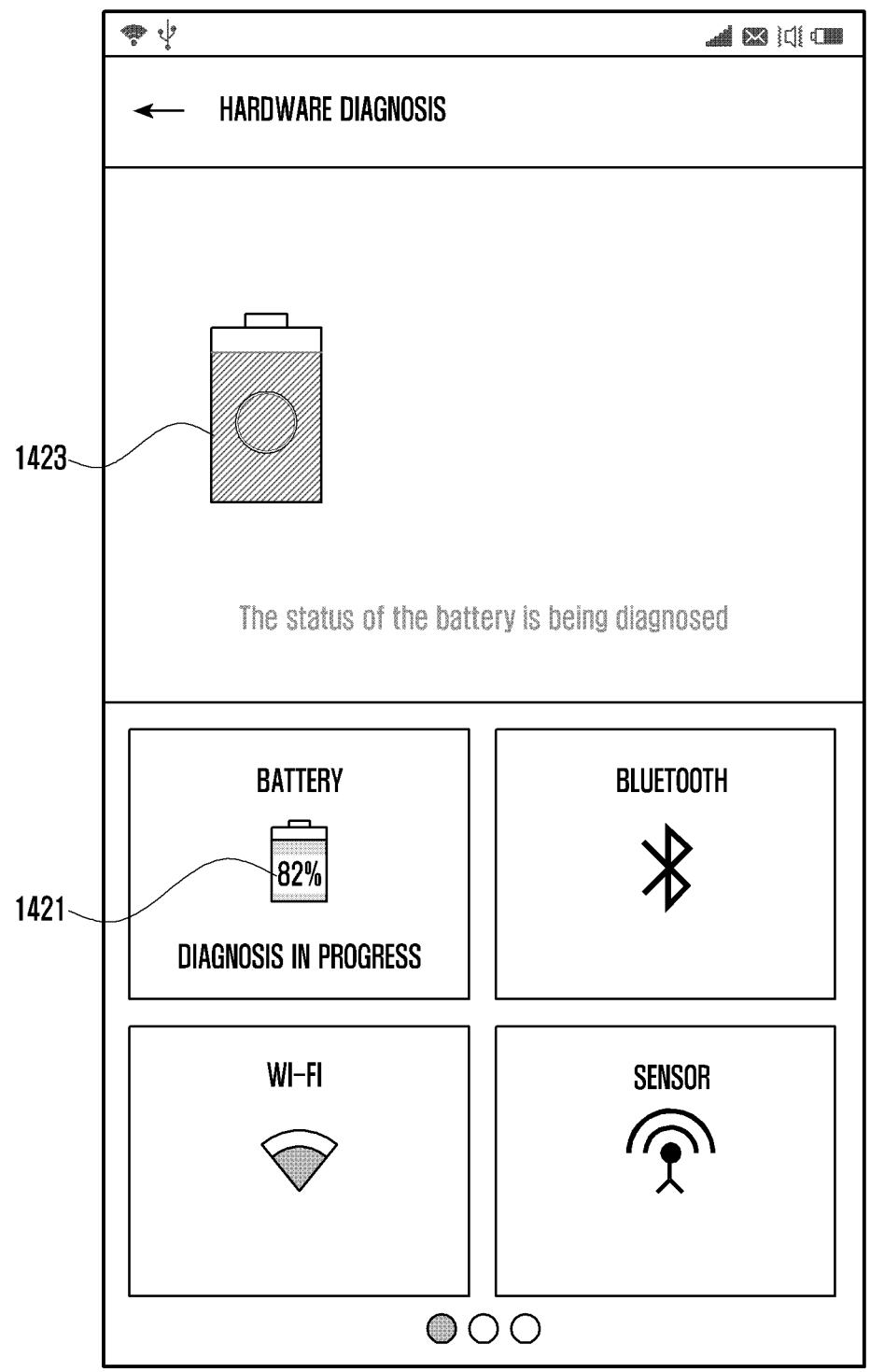

Referring to FIGS. 14A and 14B, the AP 210 controls the display 260 to display a guidance window 1410 and a diagnosis target selection window 1420. The diagnosis target selection window 1420 includes a battery icon 1421 indicating battery status (e.g., residual battery capacity). If the battery icon 1421 is selected, the AP 210 starts diagnosing the battery 296 and controls the display 260 to display the battery diagnosis information in the guidance window 1410. For example, the guidance window 1410 shows a battery image (e.g., animation) 1423. The battery icon 1421 may be displayed along with the information indicating that battery diagnosis is in progress.

Figure 14C:
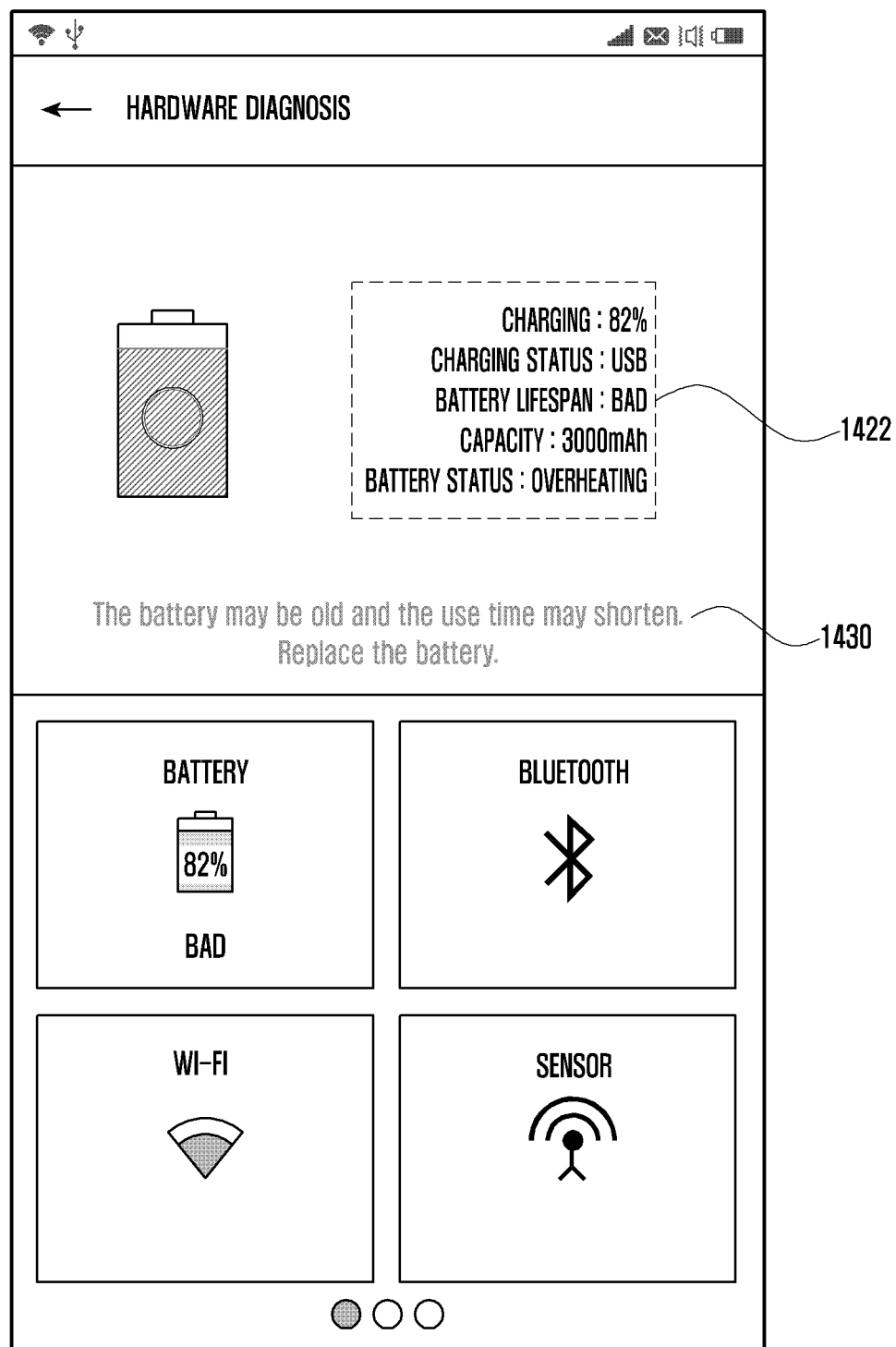

When the battery diagnosis is completed, the AP 210 controls the display 260 to display the diagnosis result, as illustrated in FIG. 14C.

Referring to FIG. 14C, the AP 210 controls the display 260 to display, in the guidance window 1410, as the diagnosis result, a residual battery capacity, a charging status (e.g., "USB" when charging the battery through USB 274 and "wireless" when charging the battery through a wireless charging module), a battery lifespan (e.g., "bad", "good", and "normal" according to battery lifespan), a battery capacity, and battery status (e.g., unknown, overheated, dead, overvoltage, failure (status check failure) according to the battery status). The AP 210 controls the display 260 to display advice 1430 in the guidance window 1410 based on the diagnosis result 1422.

Figure 14D:
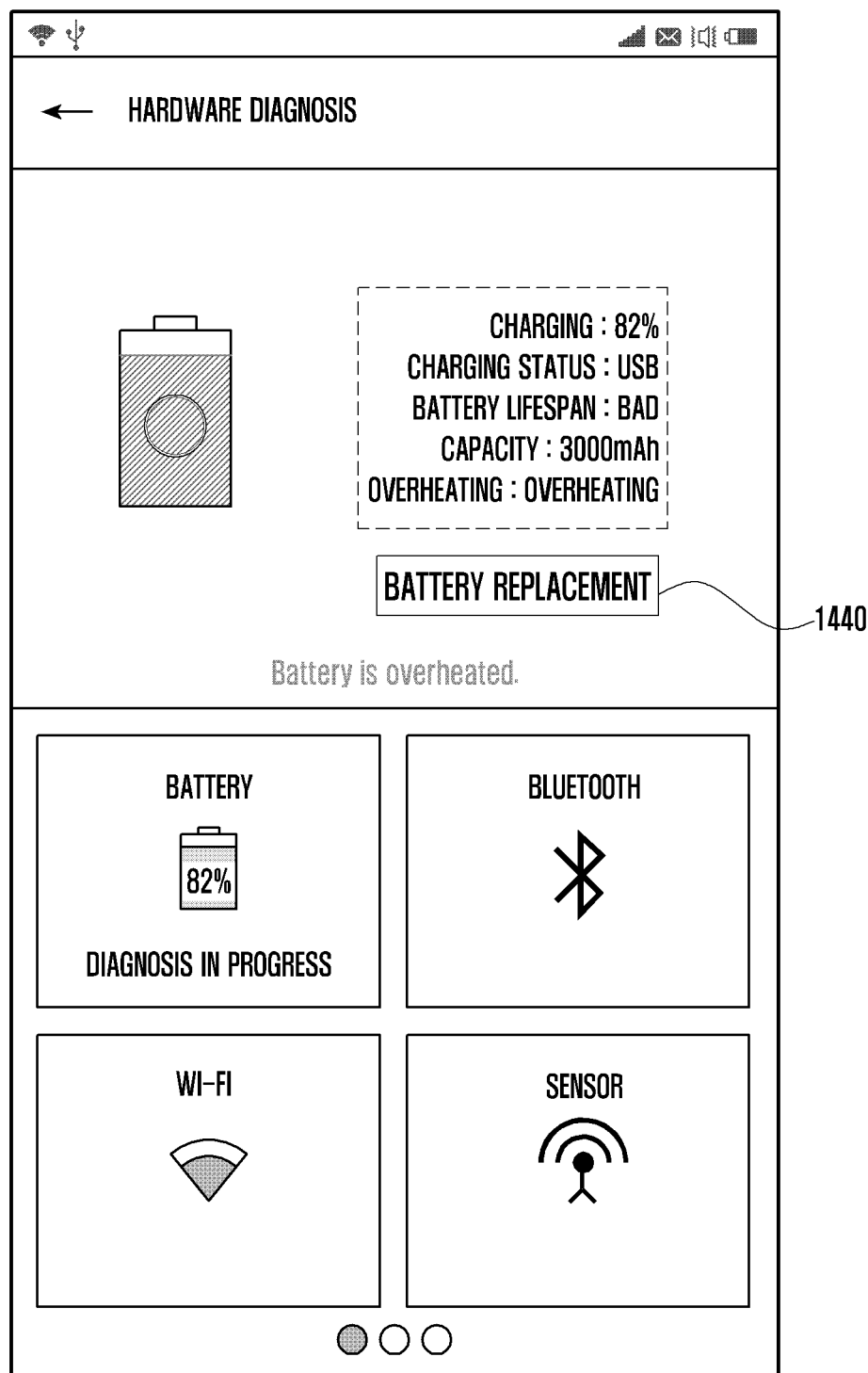

Referring to FIG. 14D, if it is determined that the battery 296 is abnormal, the AP 210 controls the display 260 to display in the guidance window 1410 the text link "battery change" 1440, which is associated with the AS request service.

FIGS. 15A to 15E illustrate a user interface for displaying a Bluetooth module diagnosis operation and diagnosis result according to an embodiment of the present disclosure. Although the user interface of FIGS. 15A to 15E is described below as being displayed by the electronic device illustrated FIG. 2, it is not limited thereto.

Figure 15A:
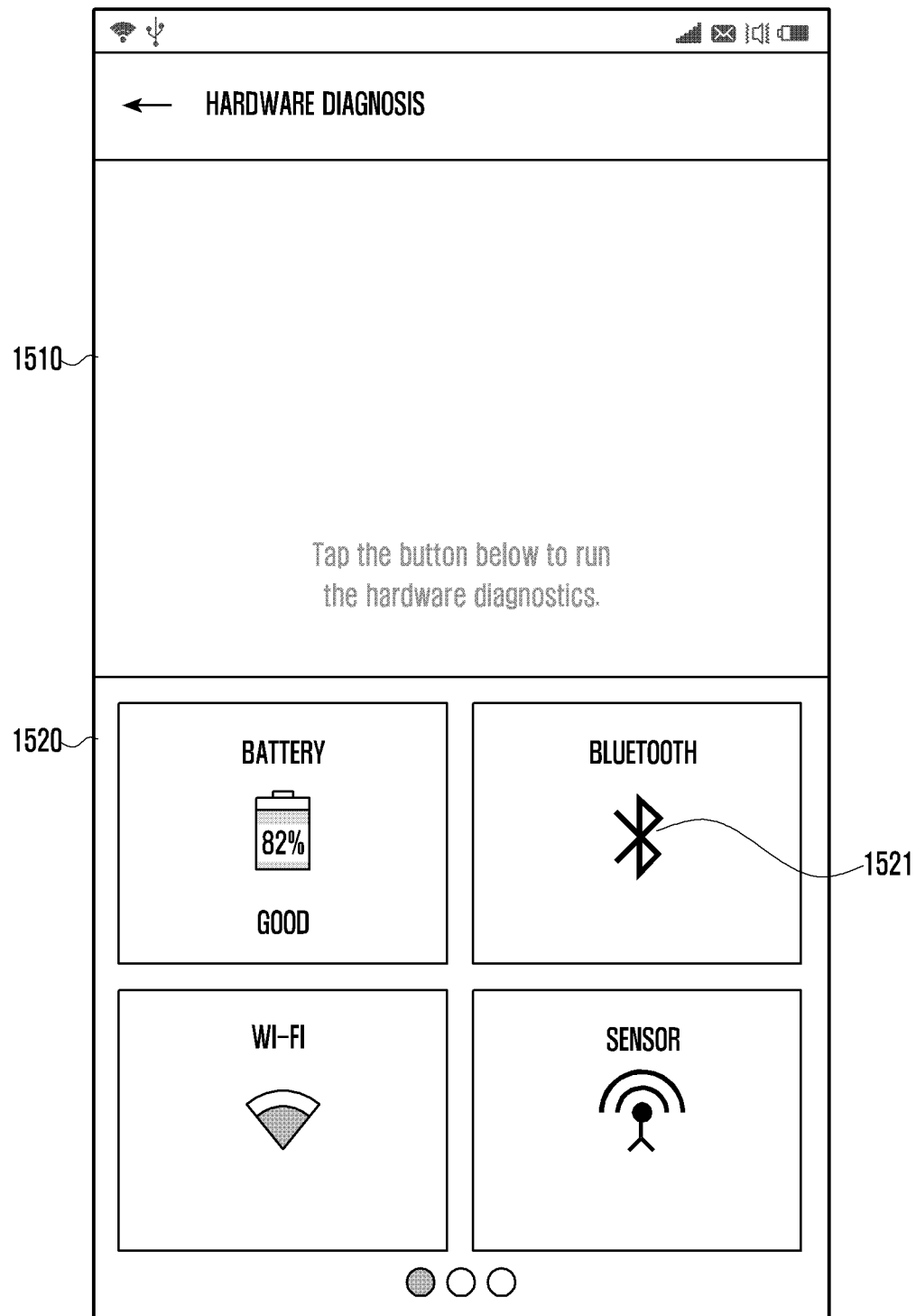
FIGS. 15A to 15E illustrate a user interface for displaying a Bluetooth module diagnosis operation and diagnosis result according to an embodiment of the present disclosure.
Figure 15B:
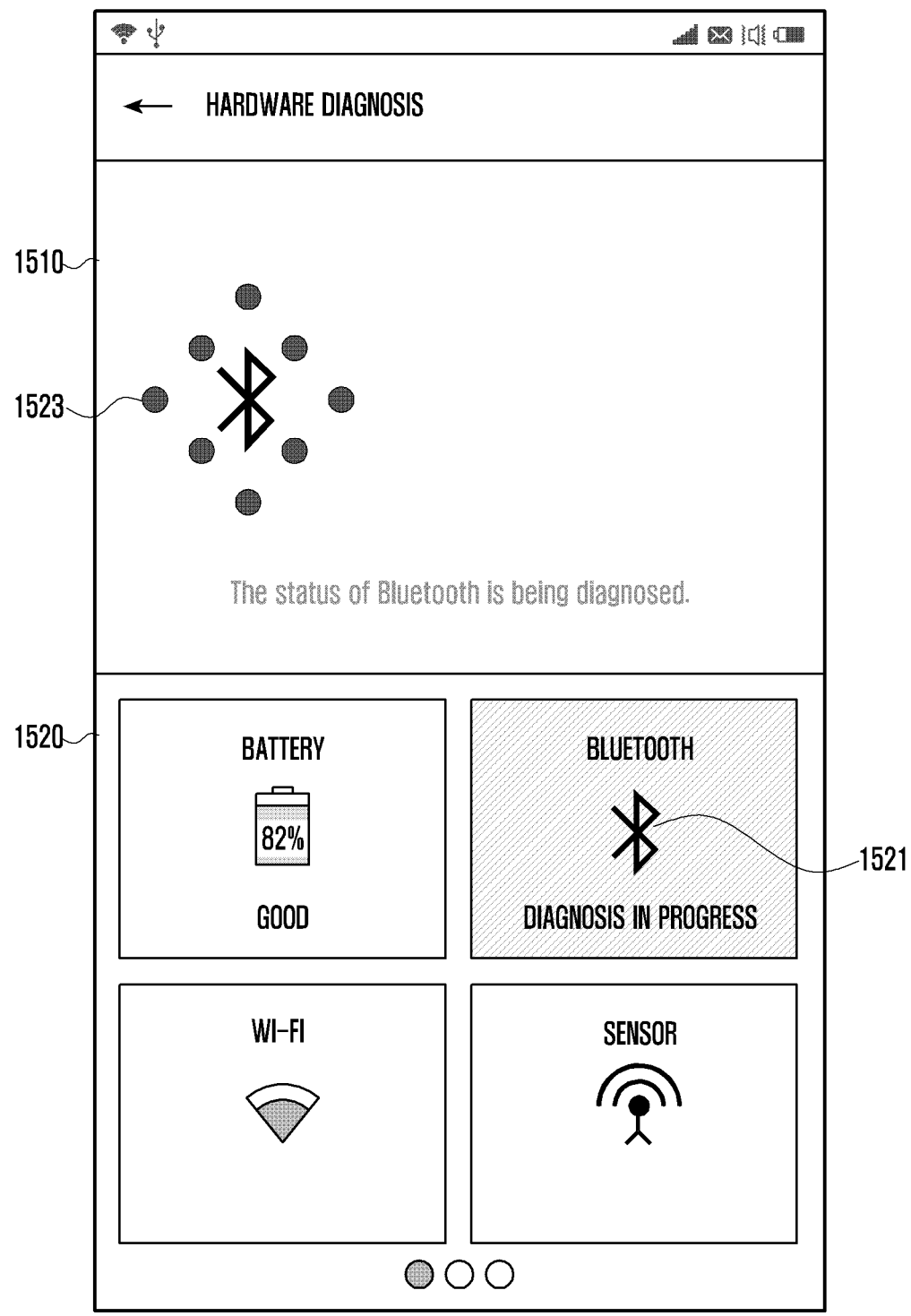

Referring to FIGS. 15A and 15B, the AP 210 controls the display 260 to display a guidance window 1510 and a diagnosis target selection window 1520. If the Bluetooth icon 1521 is selected in the diagnosis target selection window 1520, the AP 210 starts diagnosis on the BT module 225 and controls the display 260 to display the diagnosis-related data upon selection of the Bluetooth icon 1521. For example, the guidance window 1510 may show a Bluetooth image 1523 (or animation). The processor also controls the display 260 to display the information indicating that the Bluetooth diagnosis is in progress under the Bluetooth icon 1521. If the BT module 225 is on and an external device is connected to the BT module 225 and it is recognized, the AP 210 determines that the BT module 225 is normal. If an external device is either not connected to the BT module 225 or not recognized, the AP 210 determines that the BT module 225 should be checked.

Figure 15C:
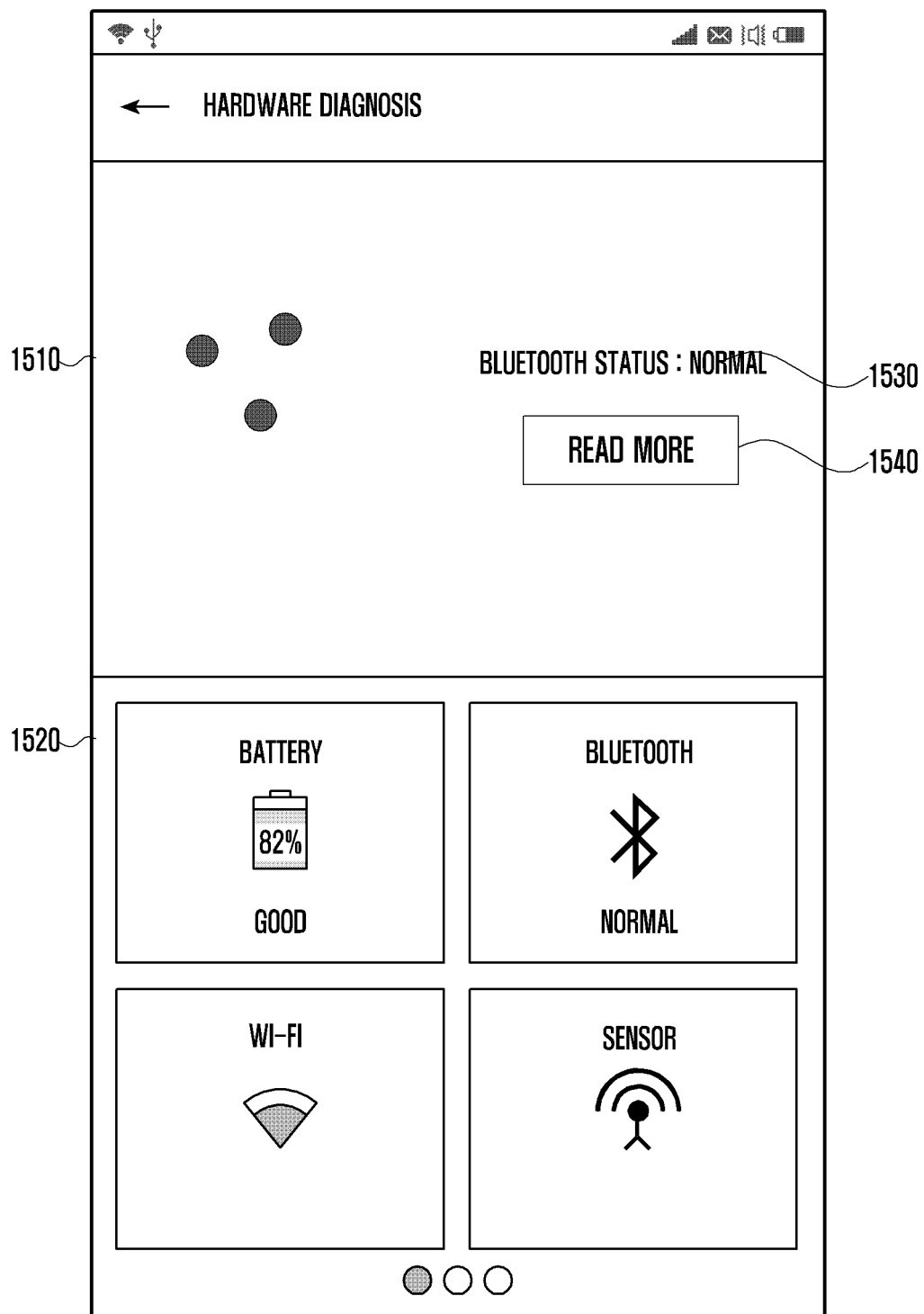

Referring to FIG. 15C, if another device is connected to the BT module 225, the AP 210 controls the display 260 to display, in the guidance window 1510, the text link "read more" 1540 for providing the diagnosis result and the information indicating the normal operation status.

Figure 15D:
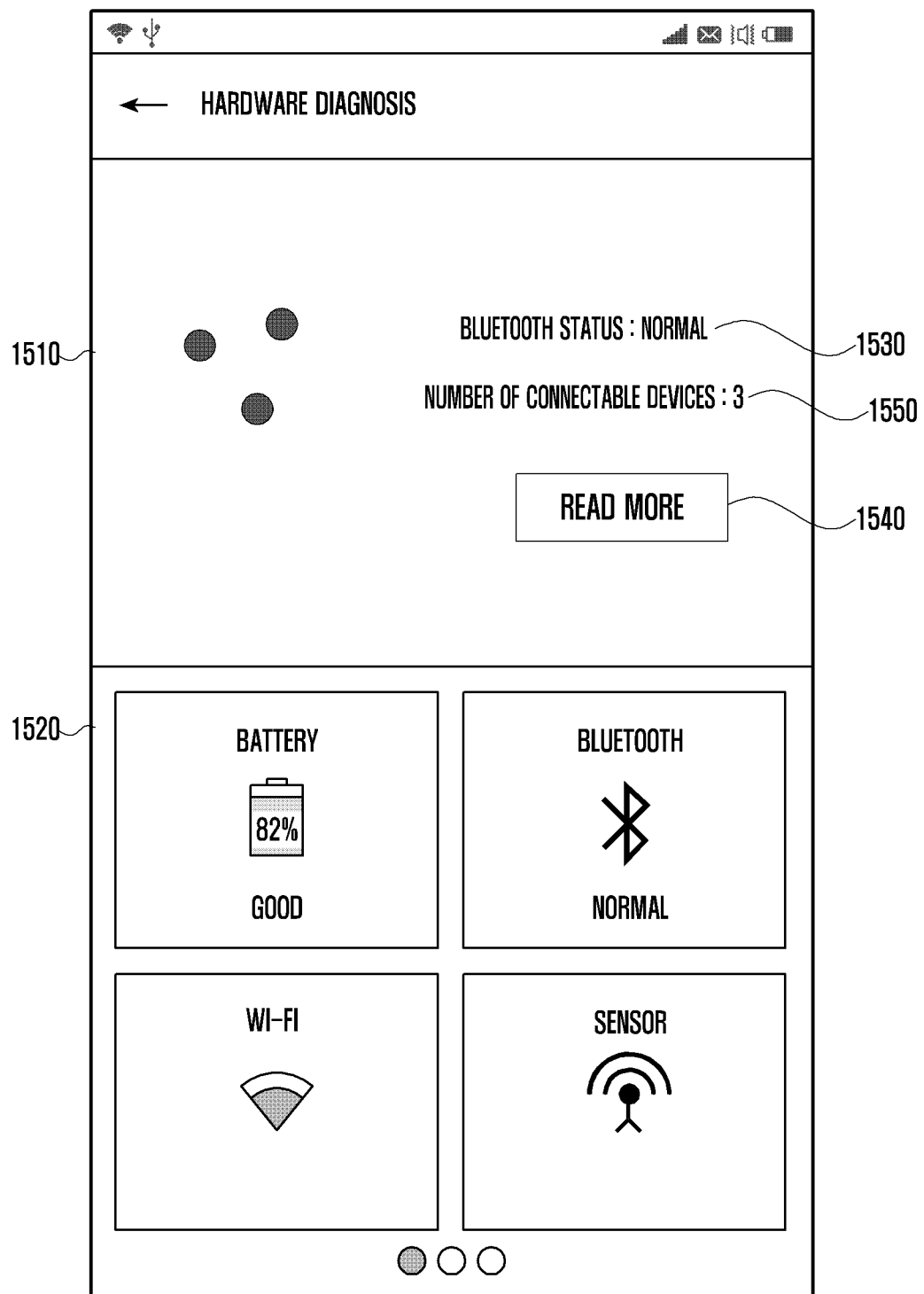

Referring to FIG. 15D, if an external device is recognized using the BT module 225, the AP 210 controls the display 260 to display, in the guidance window 1510, the normal operation status indication information 1530, the link 1540, and the information 1550 indicating the number of devices recognized nearby.

Figure 15E:
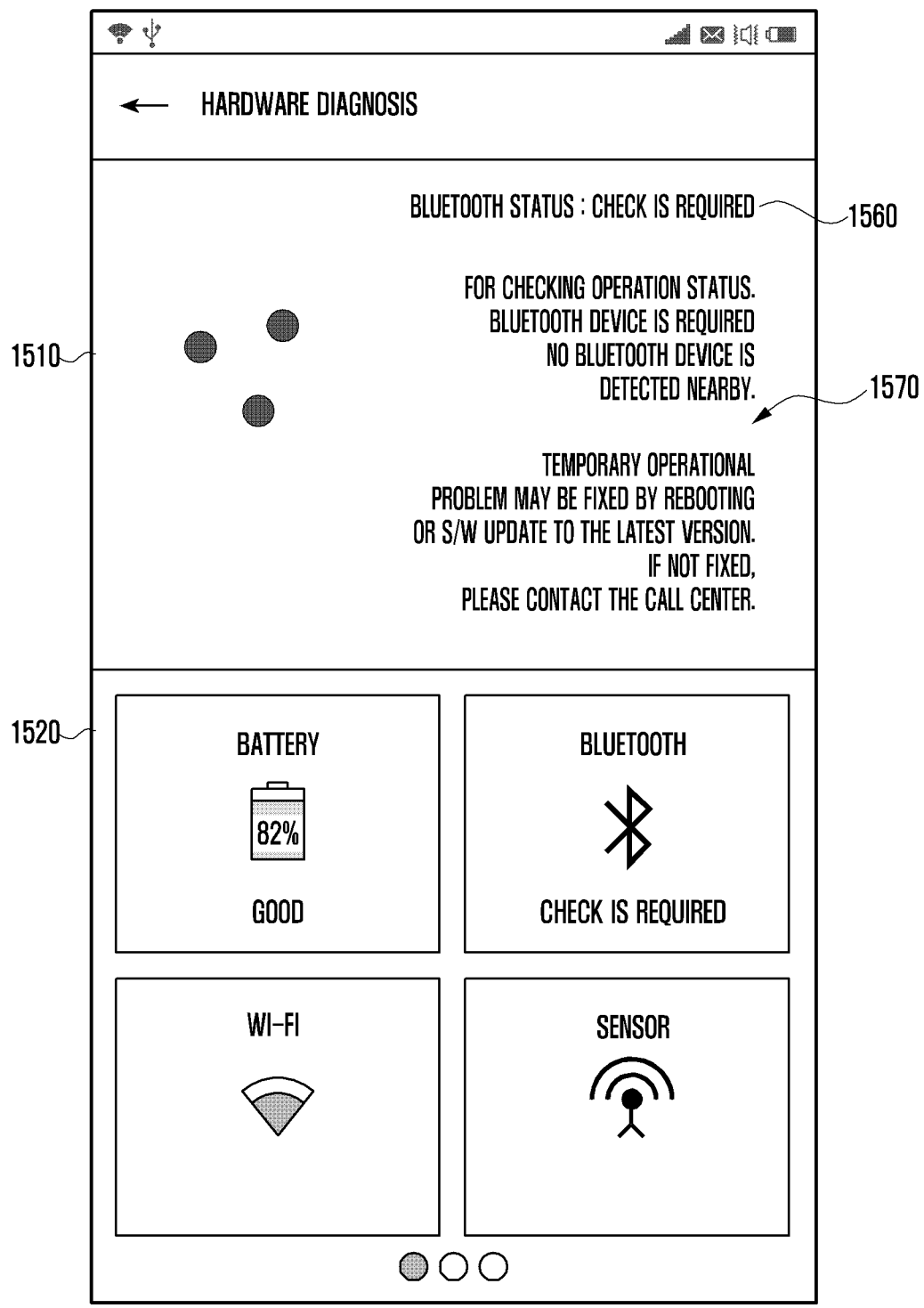

Referring to FIG. 15E, if no devices are connected to the BT module 225 or recognized, the AP 210 determines that the BT module should be checked and controls the display 260 to display a recommendation 1570 based on the "check requirement status" along with the diagnosis result 1560 indicating as such.

Although the diagnosis operation and interface described with reference to FIGS. 15A to 15E uses Bluetooth, the diagnosis operation and interface may be implemented in the same manner using other short-range communication modules (e.g., the Wi-Fi module 223).

FIGS. 16A to 16E illustrate a user interface for displaying a touch panel diagnosis operation and diagnosis result according to an embodiment of the present disclosure. Although the user interface of FIGS. 16A to 16E is described below as being displayed by the electronic device illustrated FIG. 2, it is not limited thereto.

Figure 16A:
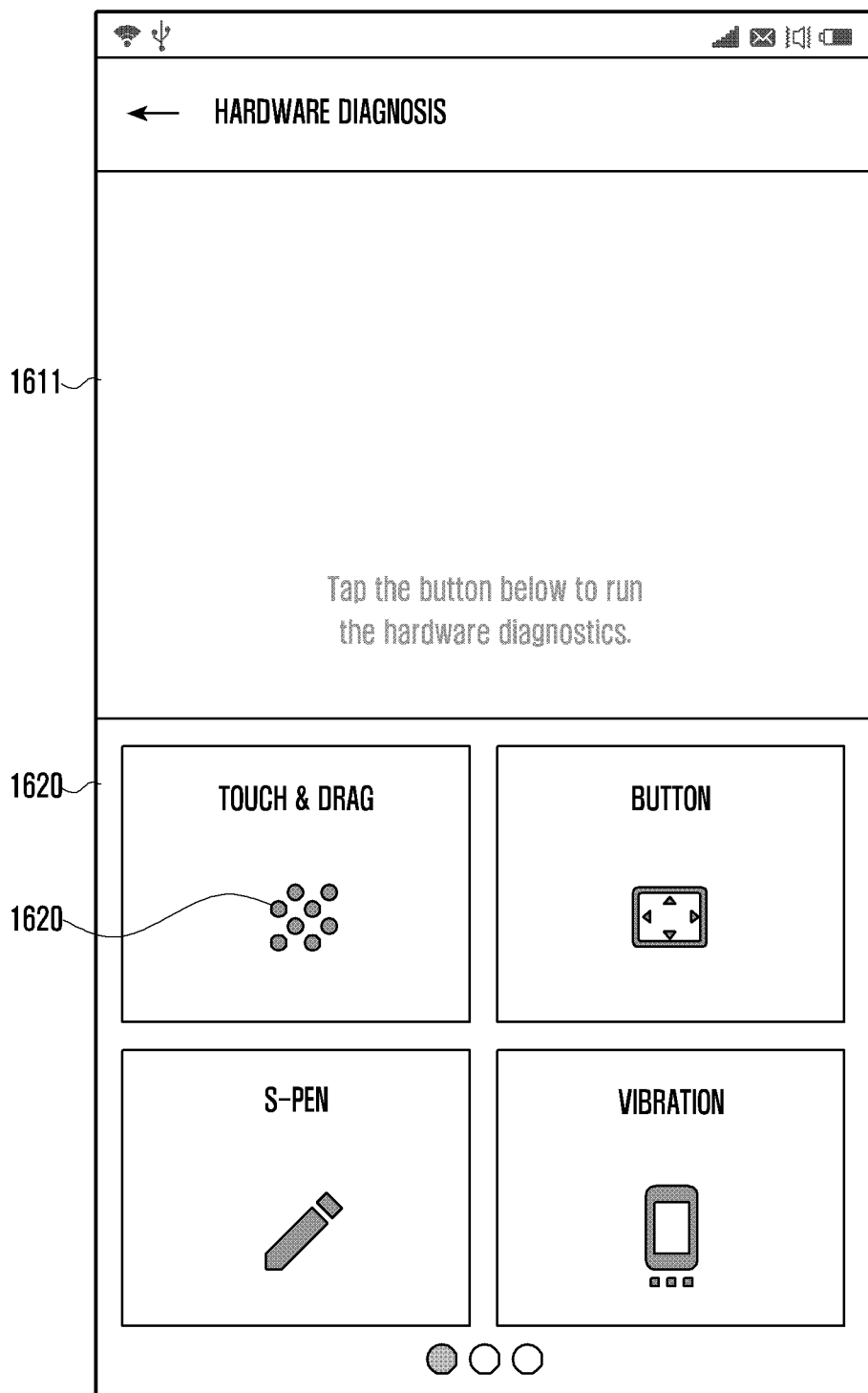
FIGS. 16A to 16E illustrate a user interface for displaying a touch panel diagnosis operation and diagnosis result according to an embodiment of the present disclosure.

Referring to FIG. 16A, the AP 210 controls the display 260 to display a guidance window 1610 and a diagnosis target selection window 1620. If a touch & drag icon 1621 is selected in the diagnosis target selection window 1620, the AP 210 may control the display 260 to display an image as illustrated in FIG. 16B.

Figure 16B:
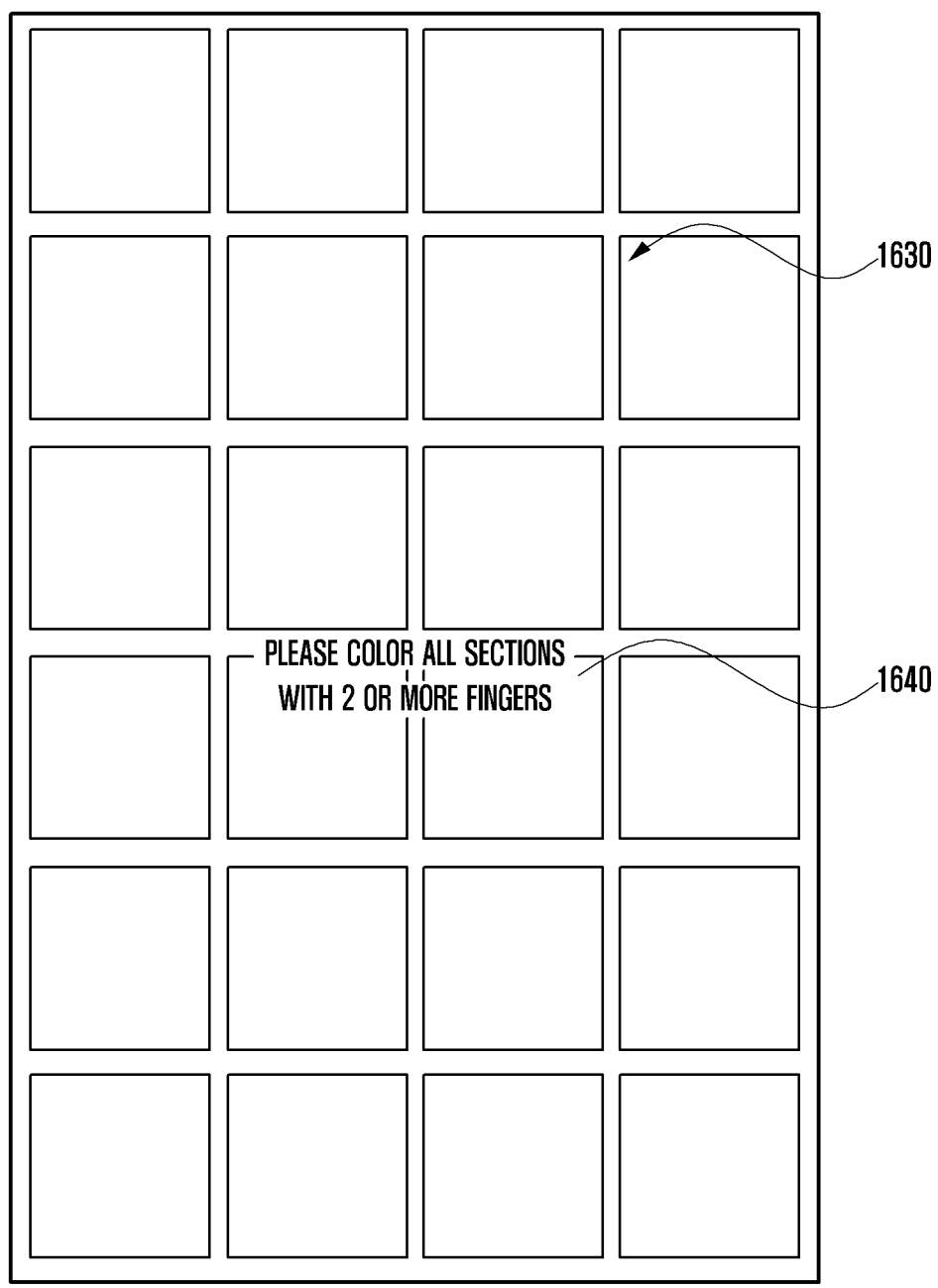

Referring to FIG. 16B, the AP 210 controls the display 260 to display a grid image 1630 for diagnosis of the touch panel 252. The AP 210 also controls the display 260 to display a text 1640 prompting the user to make a touch input on the image 1630.

Figure 16C:
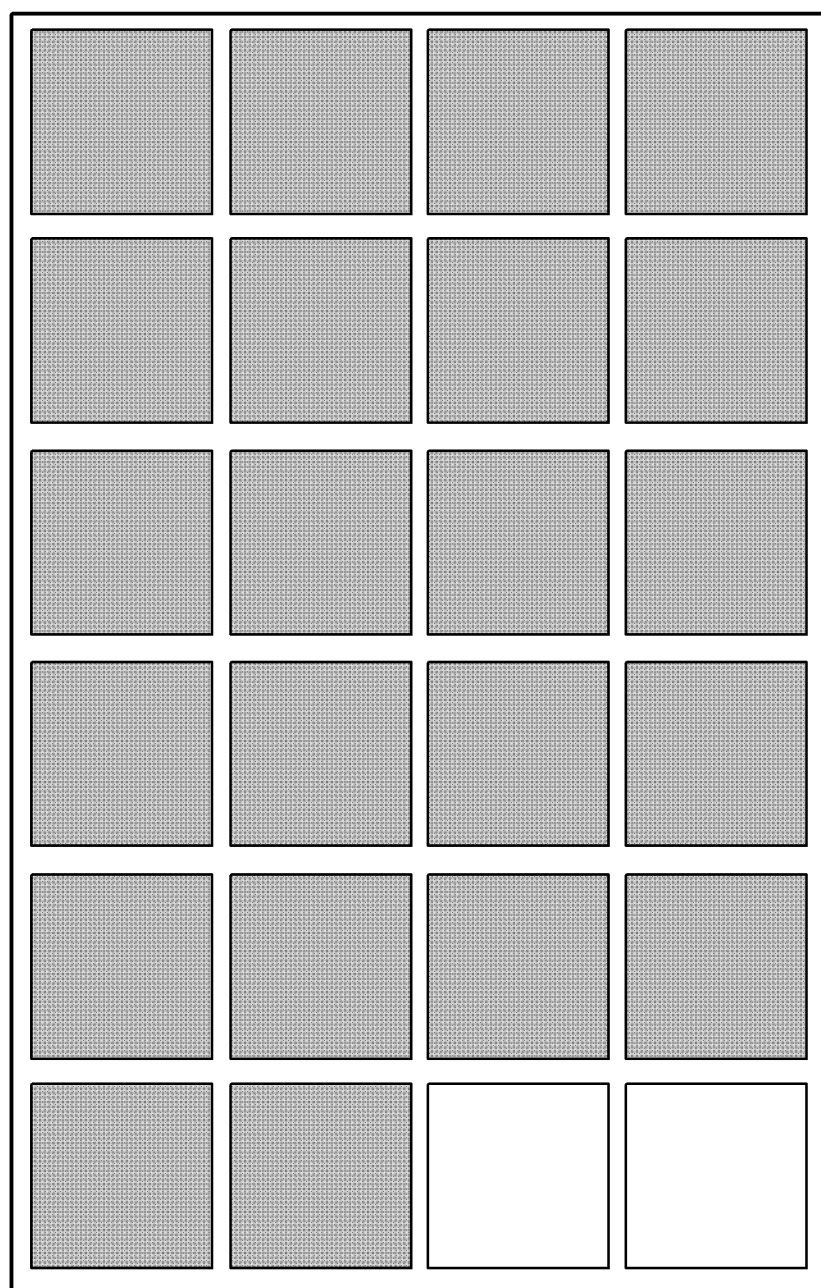

Referring to FIG. 16C, if a touch input is detected at the individual sections of the grid image 130 on the touch panel 152, the AP 210 may change the sections (e.g., color) to notify the user that the input has been made normally.

Figure 16D:
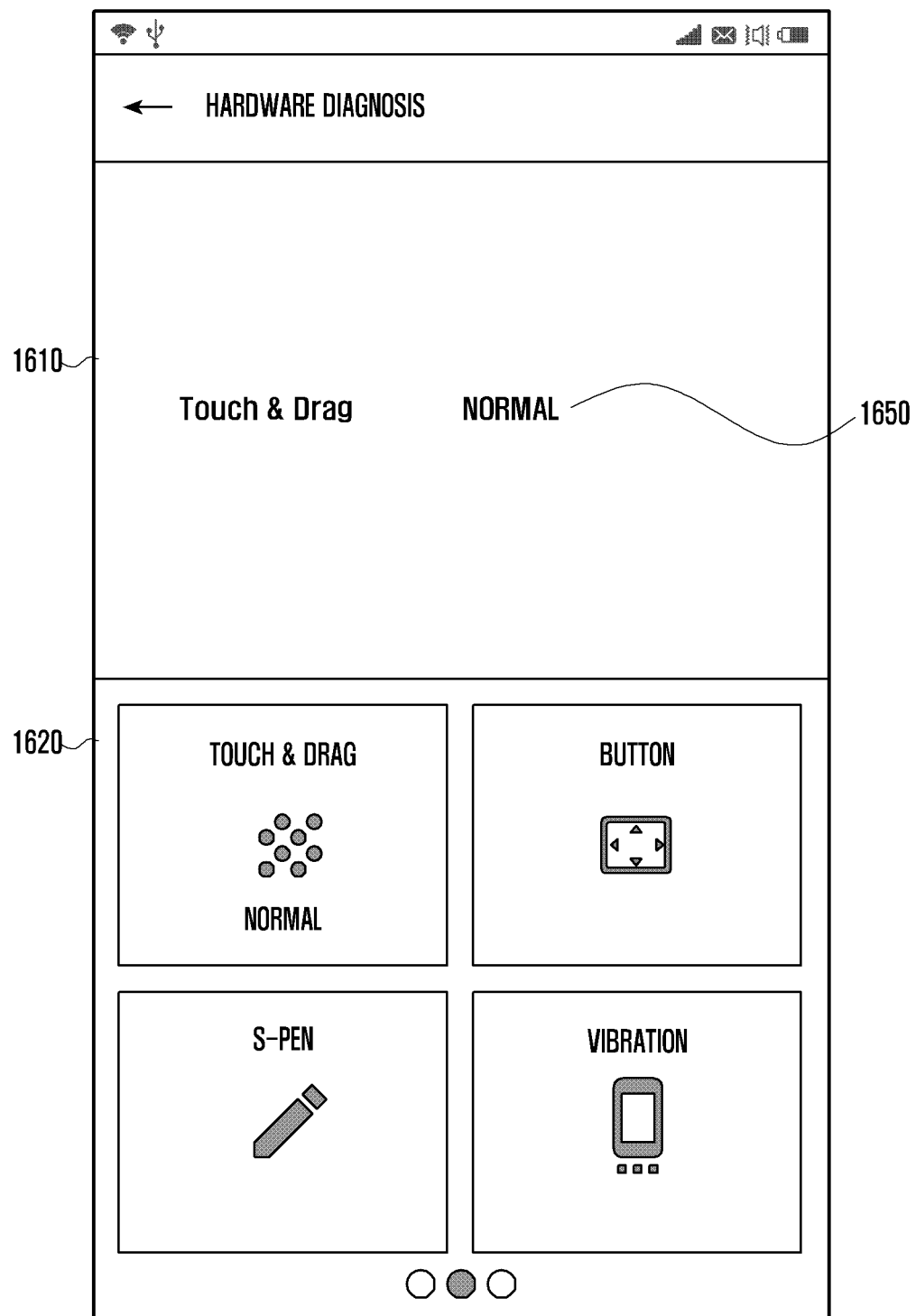

If the touch input is detected on all sections of the grid, the AP 210 may determine that the touch panel 252 is operating normally and control the display 260 to display the information 1650 indicating that the diagnosis result is normal, as illustrated in FIG. 16D.

Figure 16E:
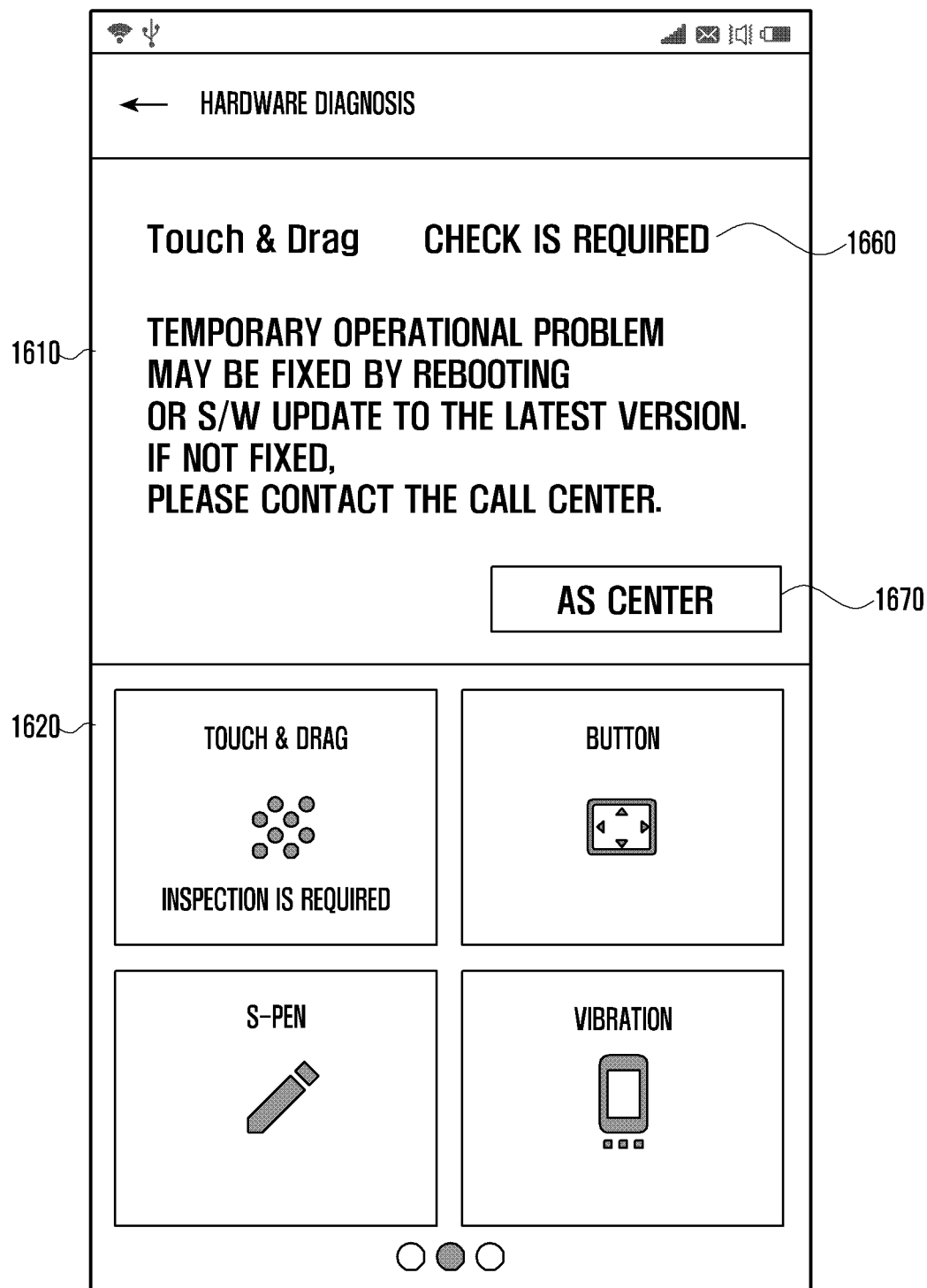

However, if a touch input is not detected at a section, the AP 210 may determine that the touch panel 252 is operating abnormally and control the display 260 to display the information 1660 indicating that the diagnosis result is abnormal, as illustrated in FIG. 16E.

Referring to FIG. 16E, the AP 210 controls the display 260 to display the text link "AS center" 1670 associated with an AS request service.

If no touch input is detected on the touch panel 252 for a predetermined time (e.g., 3 seconds) after the diagnosis on the touch panel 252 has started, the AP 210 may control the display 260 to display the information asking for touch input one more time. Thereafter, if no touch input is detected on the touch panel 252 in the predetermined time (e.g., another 3 seconds) after the request, the AP 210 may control the display 260 to display the information indicating that the diagnosis result is abnormal (e.g., text "check recommendation").

Alternatively, the grid may be replaced with another pattern (e.g., points). For example, the AP 210 may control the display 260 to display a plurality of points, and if touch input is detected at all of the points, determine that the touch panel 252 is operating normally. If no touch input is detected at one of the points, the AP 210 may determine that the touch panel 252 is operating abnormally.

FIGS. 17A to 17H illustrate a user interface for displaying an electronic pen diagnosis operation and diagnosis result according to an embodiment of the present disclosure. Although the user interface of FIGS. 17A to 17H is described below as being displayed by the electronic device illustrated FIG. 2, it is not limited thereto.

Figure 17A:
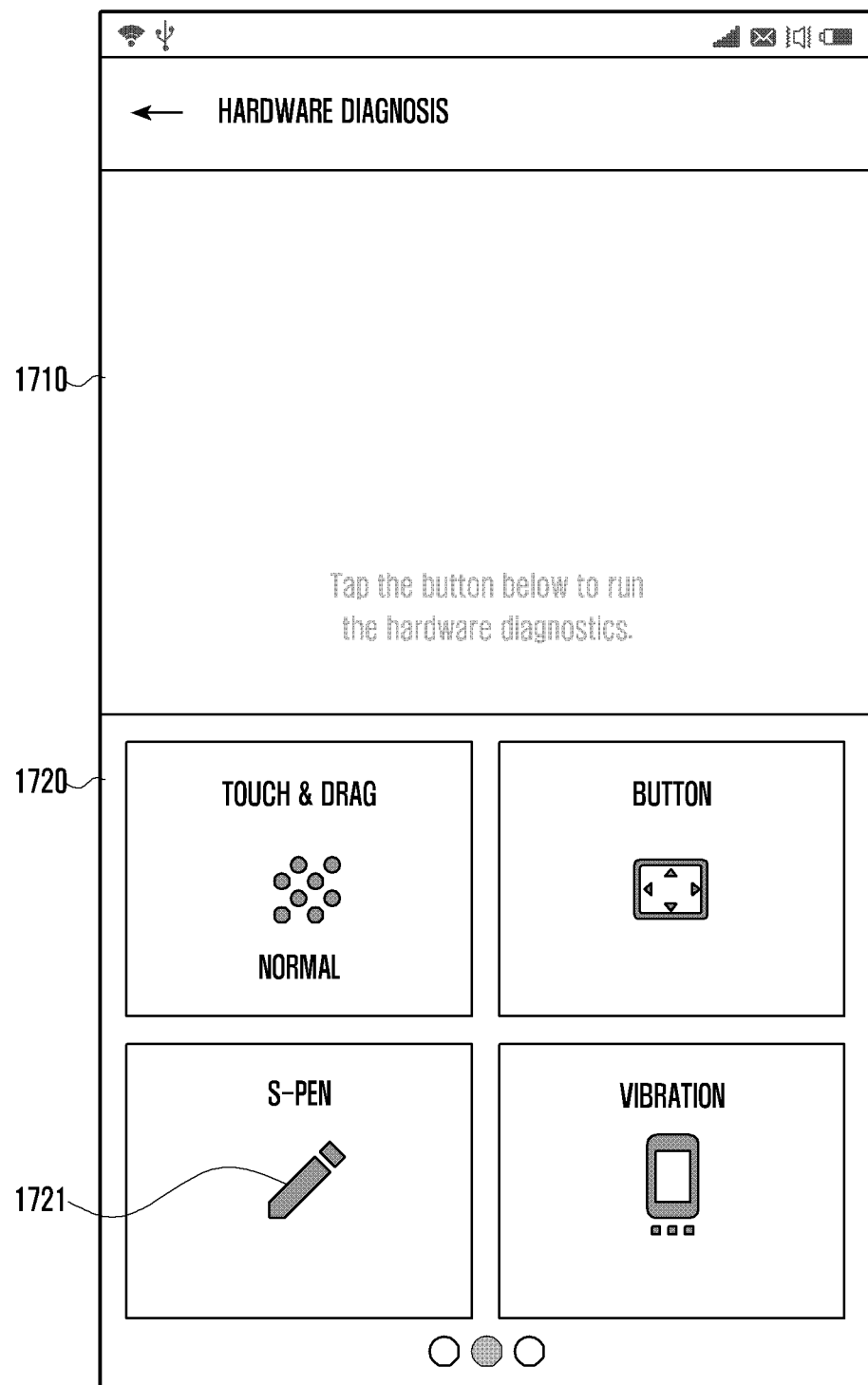
FIGS. 17A to 17H illustrate a user interface for displaying an electronic pen diagnosis operation and diagnosis result according to an embodiment of the present disclosure.

Referring to FIG. 17A, the AP 210 controls the display 260 to display a guidance window 1710 and a diagnosis target selection window 1720. If an S pen icon 1721 is selected in the diagnosis target selection window 1720, the AP 210 controls the display 260 to display an image, as illustrated in FIG. 17B.

Figure 17B:
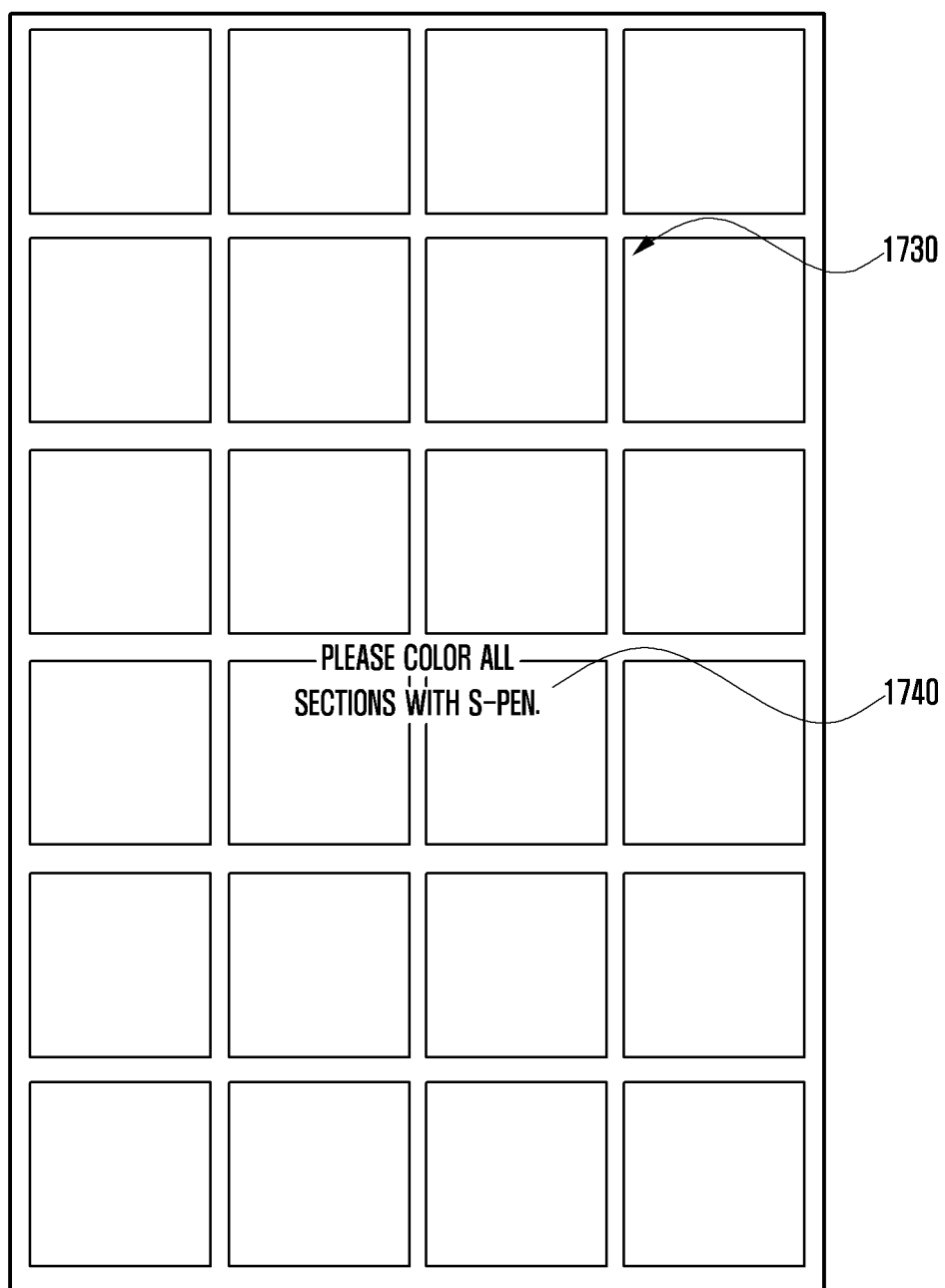

Referring to FIG. 17B, the AP 210 controls the display 260 to display a grid image 1730 for touch input diagnosis and a text 1740 prompting the user to make a touch input.

Figure 17C:
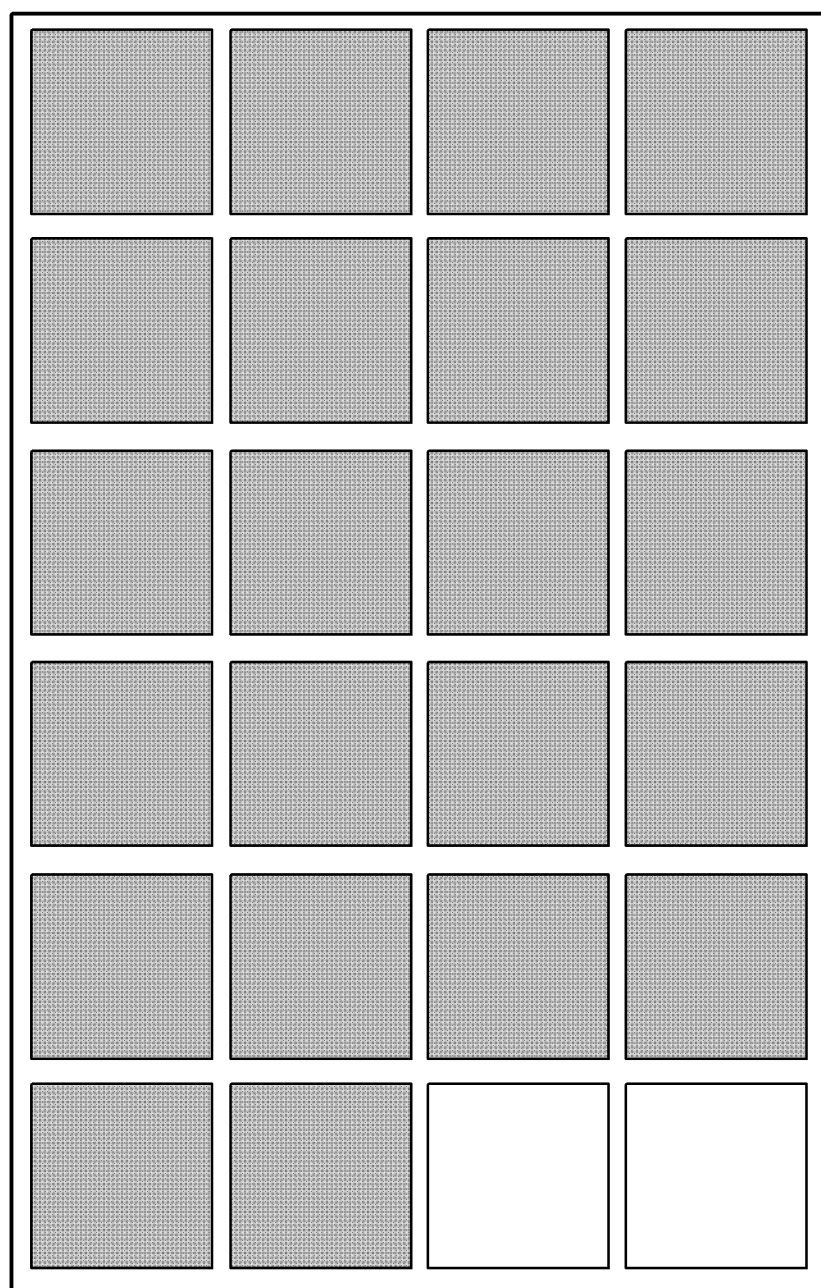

Referring to FIG. 17C, the processor may detect a touch input made by the electronic pen at the individual sections of the grid image 1730. If a touch input is detected, the AP 210 may change the section (e.g., in color) on which the touch input is made. If the touch input is detected at all of the sections, the AP 210 determines that the touch input with the electronic pen is normal. However, if no touch input is detected at a section, the AP 210 may determine that the touch input with the electronic pen is abnormal. If the touch input diagnosis is completed, the AP 210 controls the display 260 to display an image, as illustrated in FIG. 17D.

Figure 17D:
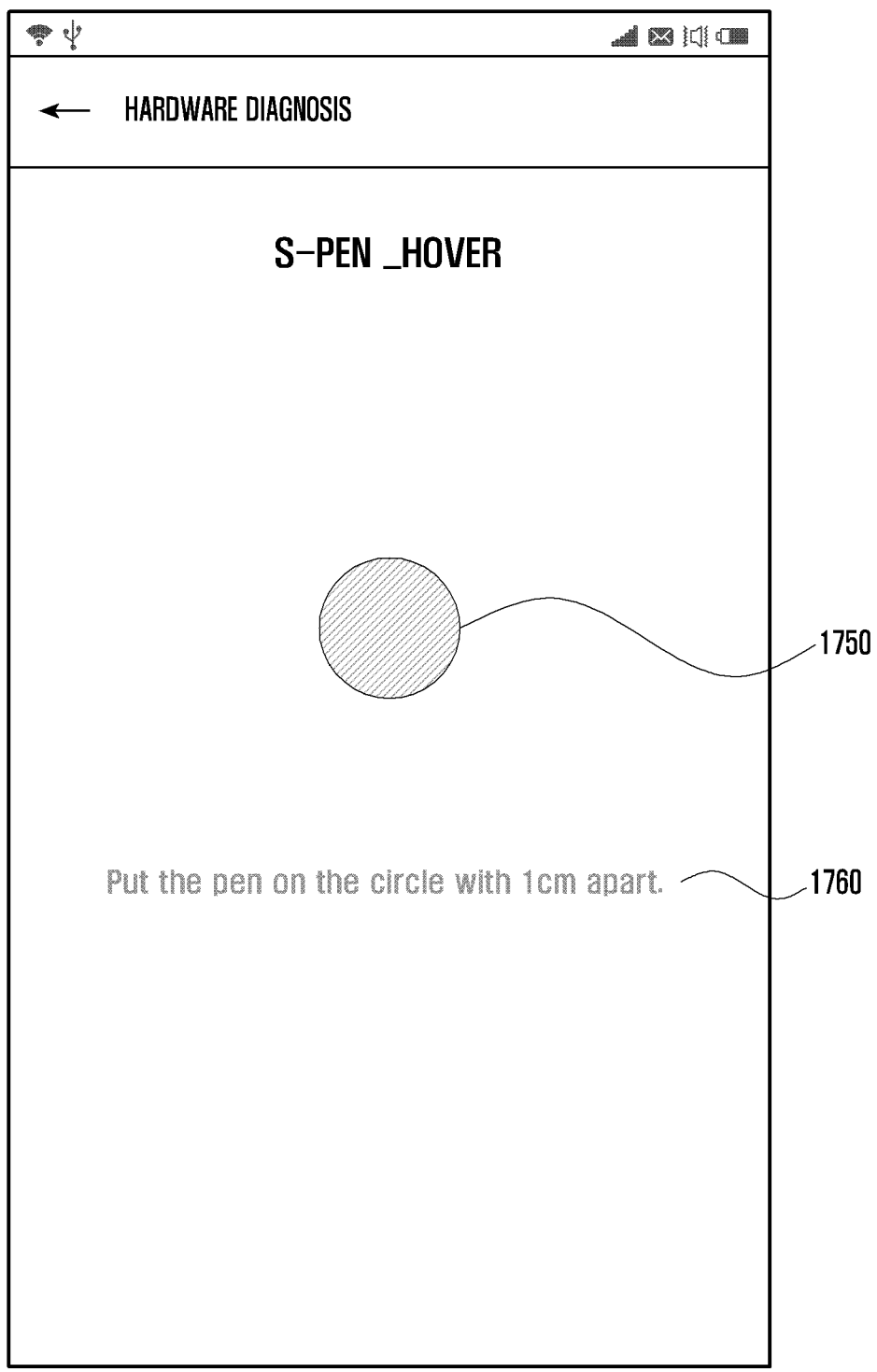

Referring to FIG. 17D, the AP 210 controls the display 260 to display an input zone 1750 for a hovering input (i.e., proximity input) diagnosis and a text 1760 prompting the user to make a hovering input. If no hovering input is detected above the input zone 1750, the AP 210 determines that the hovering input with the electronic pen is abnormal. If a hovering input is detected above the input zone 1750, the AP 210 controls the display 260 to display an image, as illustrated in FIG. 17E.

Figure 17E:
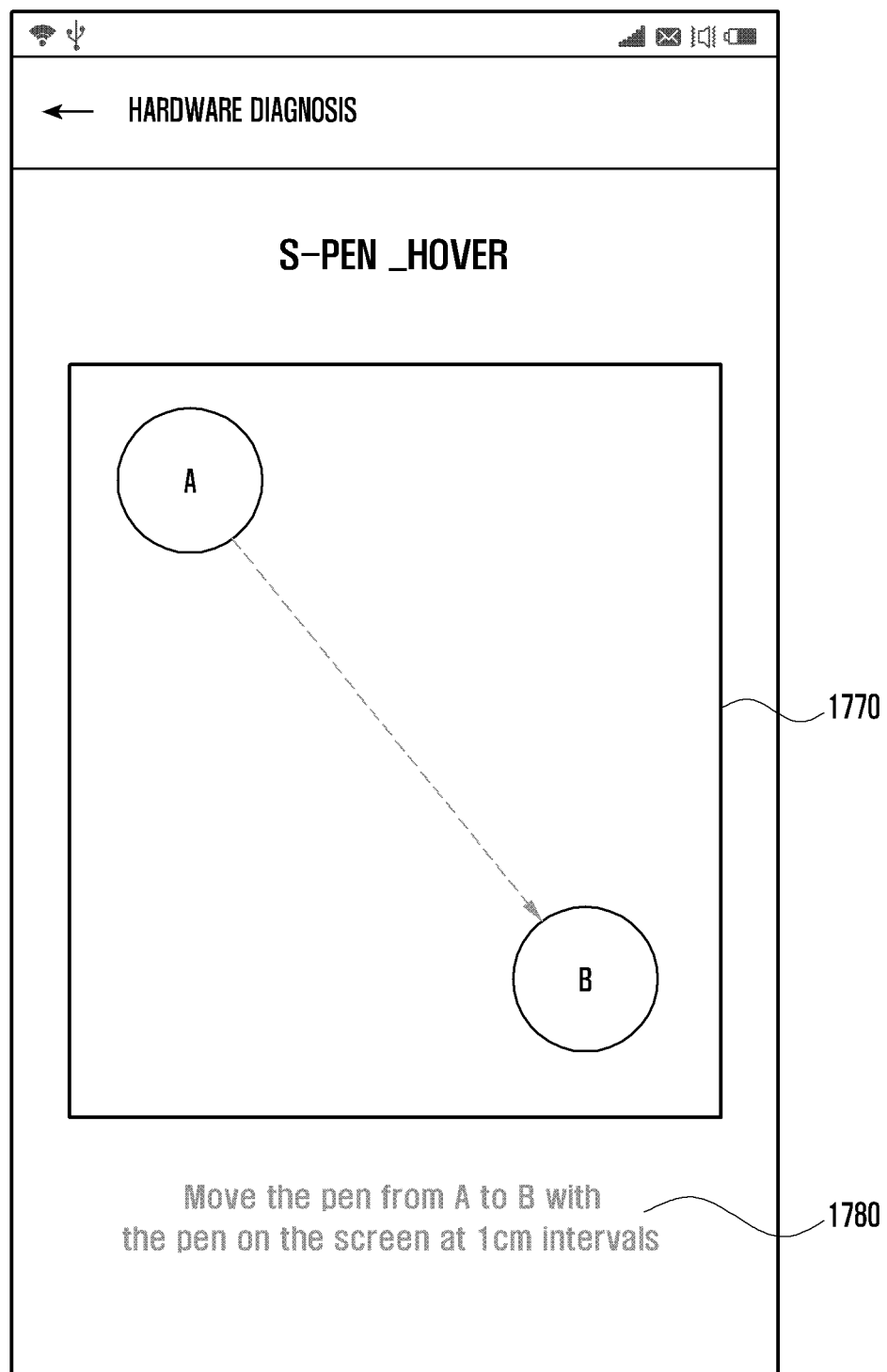

Referring to FIG. 17E, the AP 210 controls the display 260 to display a text 1780 prompting the user to make a hovering input above a drag zone 1770. If a hovering input made with a gesture drawing a straight line from a point A to another point B in the drag zone is detected, the AP 210 determines that the hovering input made with the electronic device is normal.

Figure 17F:
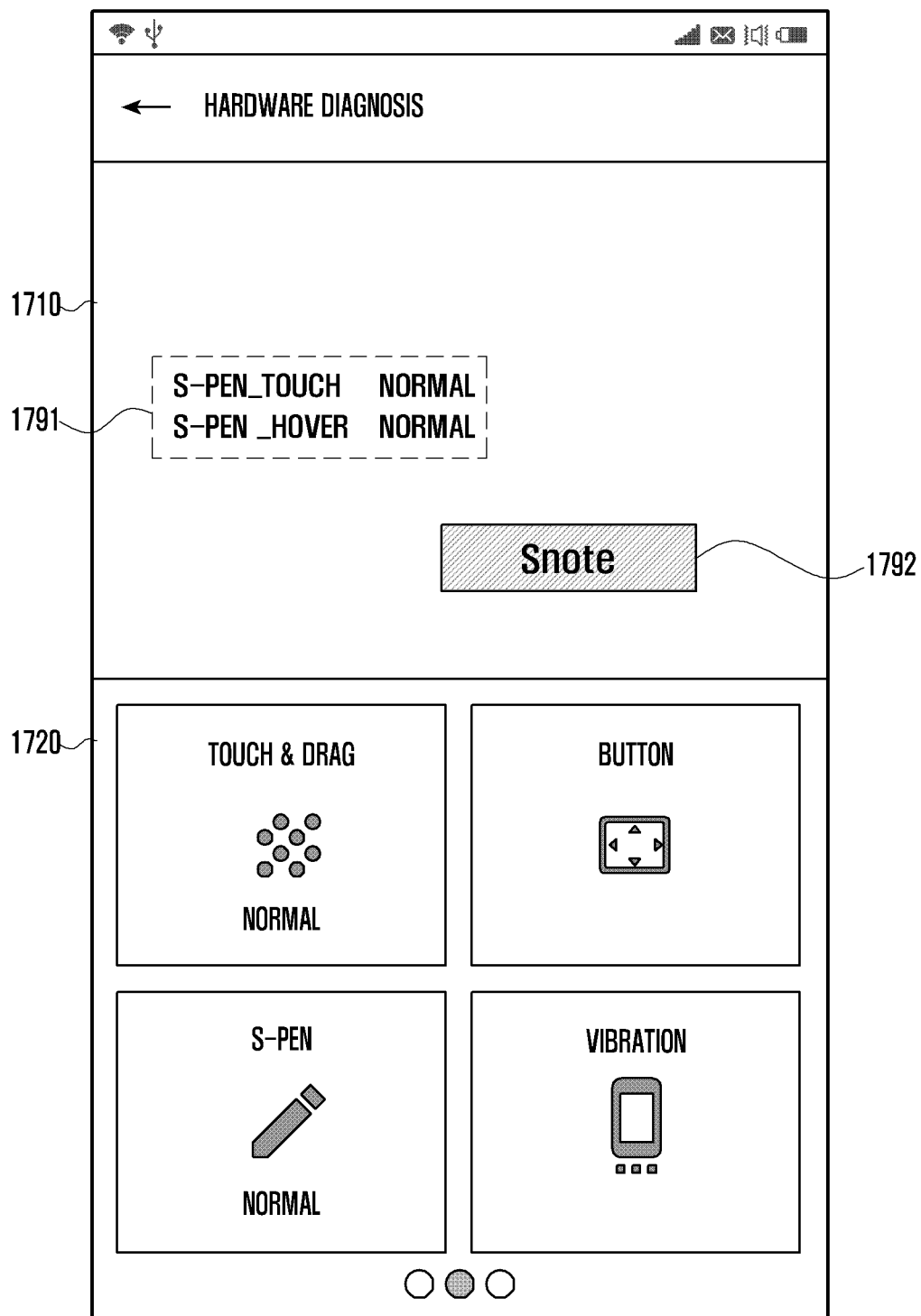

If it is determined that the electronic pen is operating normally, the AP 210 controls the display 260 to display in the guidance window 1710 the information 1791 indicating that the diagnosis result is normal, as illustrated in FIG. 17F.

Referring to FIG. 17F, the AP 210 controls the display 260 to display the text link "Snote" 1792 associated with an electronic pen application.

Figure 17G:
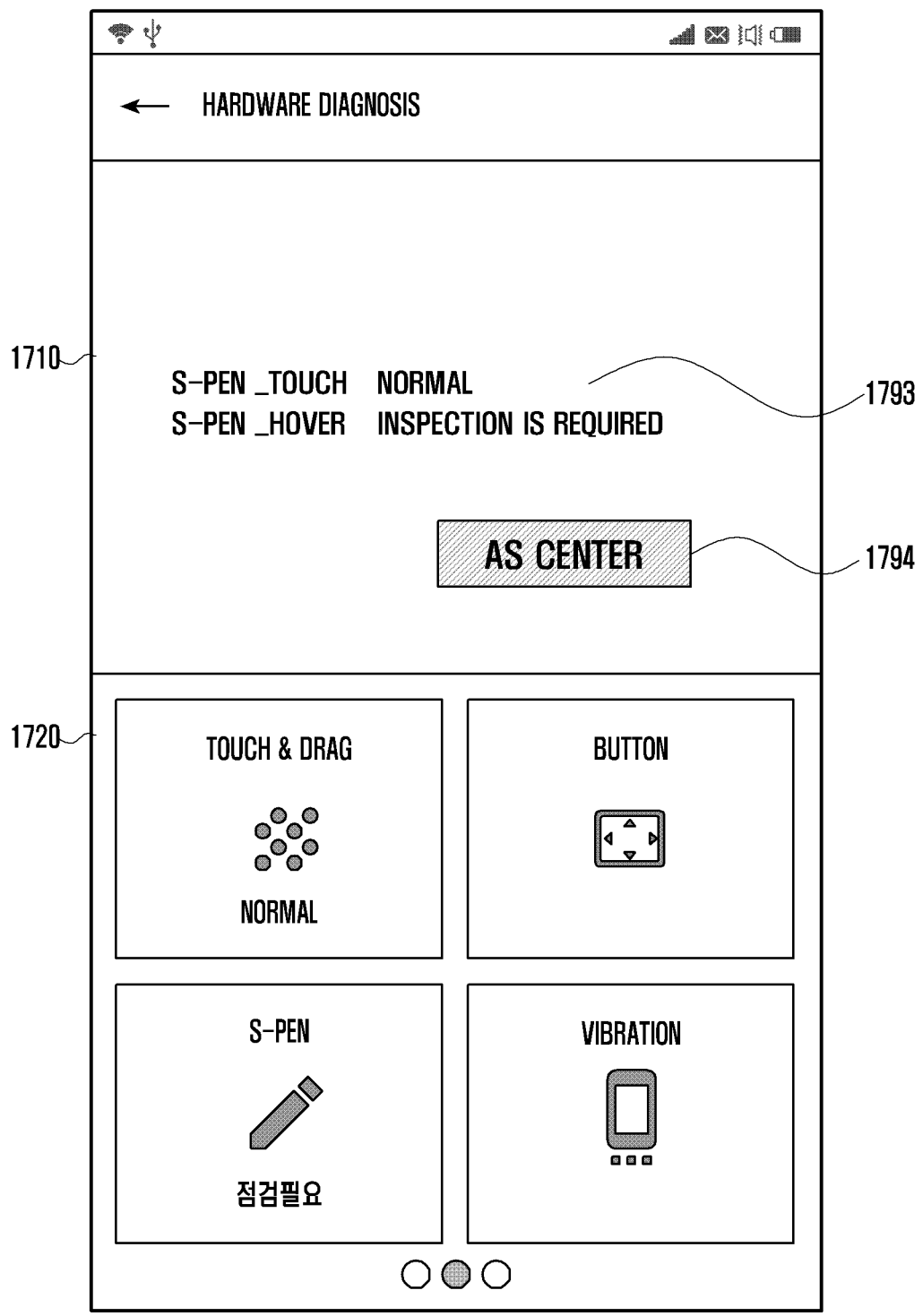

If it is determined that the hover input made with the electronic pen is abnormal, the AP 210 controls the display 260 to display the diagnosis result 1793 indicating that the hovering input made with the electronic pen is abnormal, as illustrated in FIG. 17G.

Referring to FIG. 17G, the AP 210 also controls the display 260 to display the text link "AS center" 1794 associated with the AS request service.

An electronic pen diagnosis may be stopped.

Figure 17H:
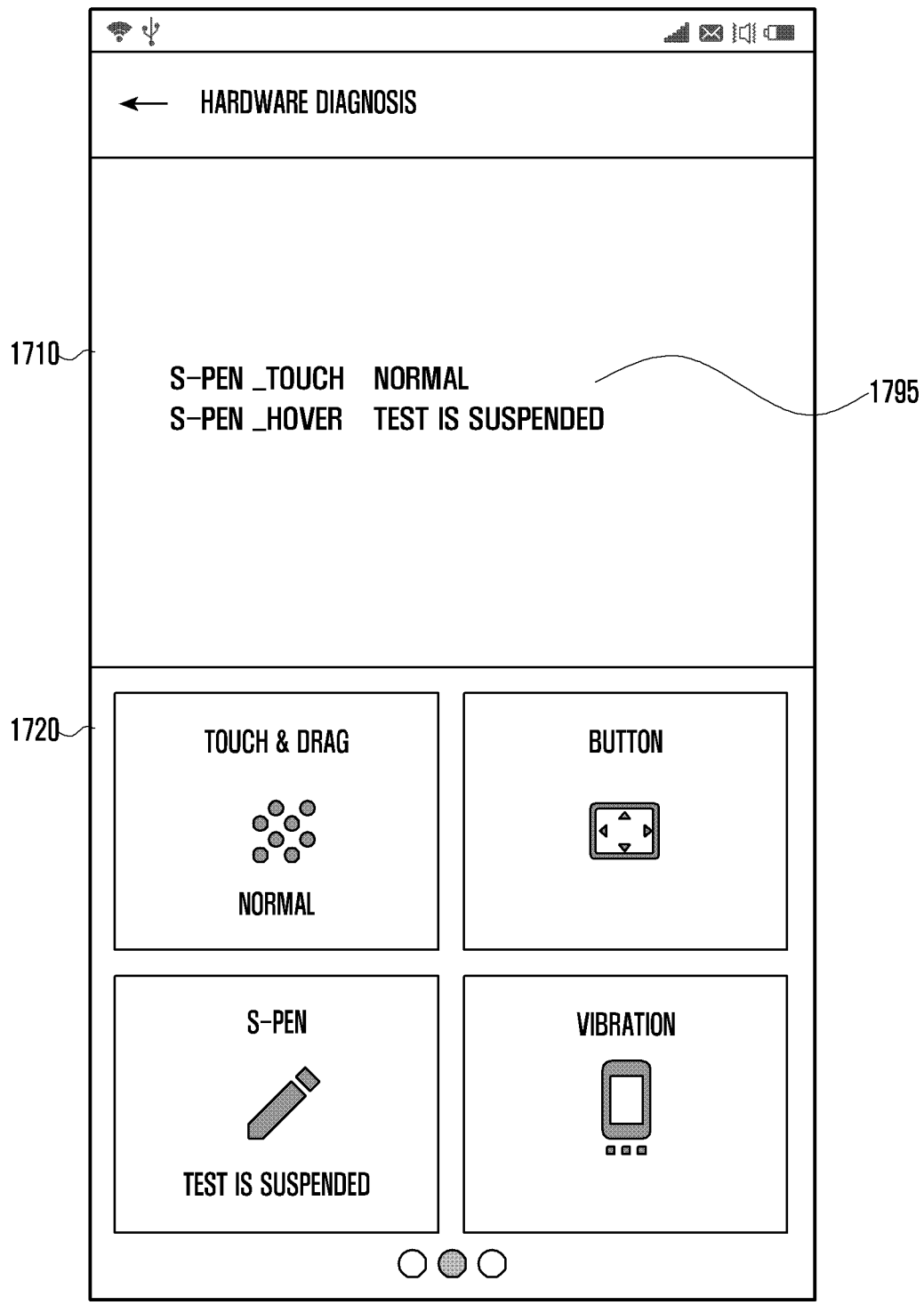

Referring to FIG. 17H, the AP 210 controls the display 260 to display the information indicating that the diagnosis is stopped. If the S pen icon 1721 is selected after the stopping of the diagnosis, the AP 210 may resume the electronic pen diagnosis.

FIGS. 18A to 18I illustrate a user interface for displaying a key (button) diagnosis operation and diagnosis result according to an embodiment of the present disclosure. Although the user interface of FIGS. 18A to 18I is described below as being displayed by the electronic device illustrated FIG. 2, it is not limited thereto.

Figure 18A:
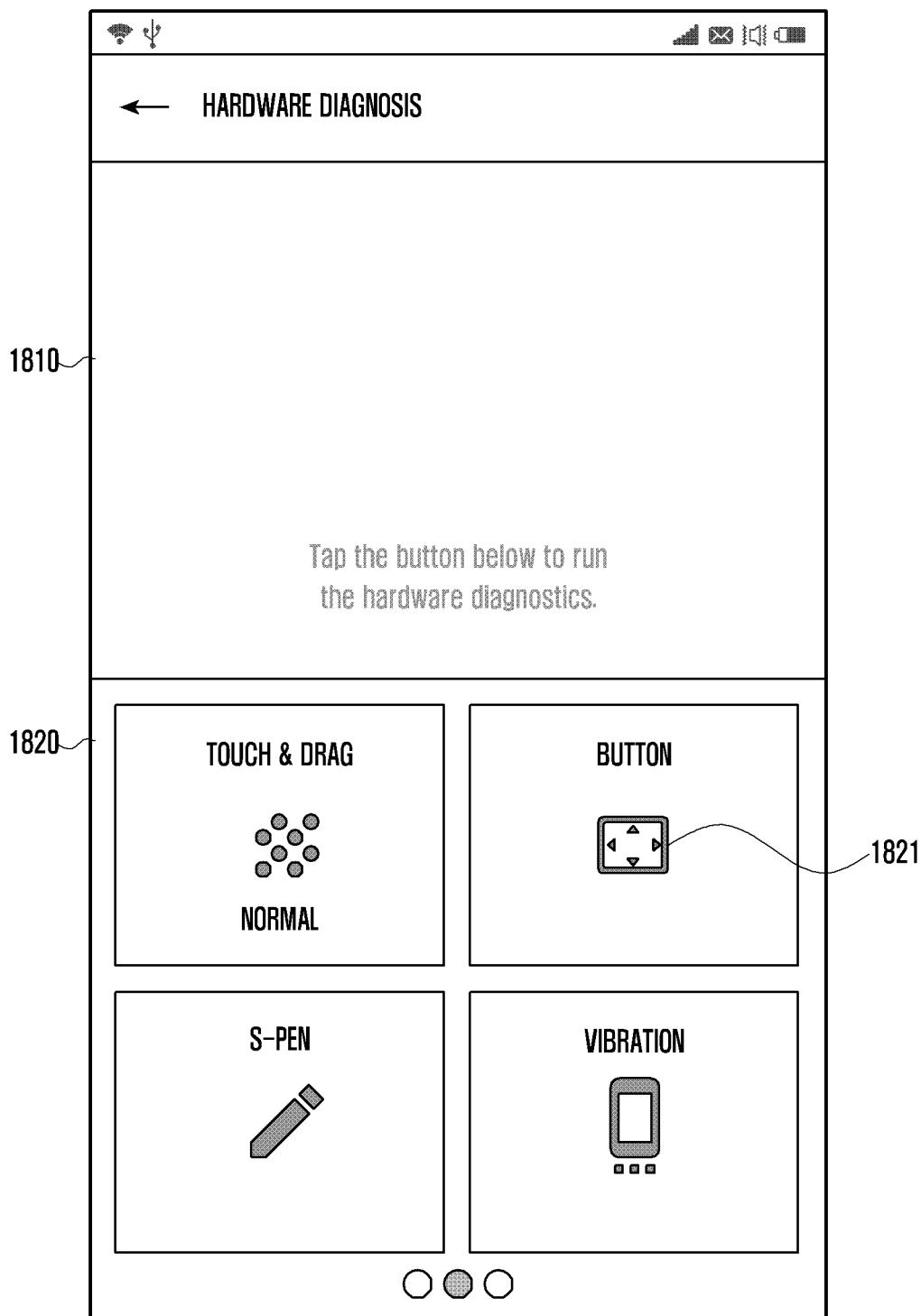
FIGS. 18A to 18I illustrate a user interface for displaying a key (button) diagnosis operation and diagnosis result according to an embodiment of the present disclosure.

Referring to FIG. 18A, the AP 210 controls the display 260 to display a guidance window 1810 and a diagnosis target selection window 1820. If a button icon 1821 is selected in the diagnosis target selection window 1820, the AP 210 starts diagnosis on the keys (buttons) of the electronic device 201.

Figure 18B:
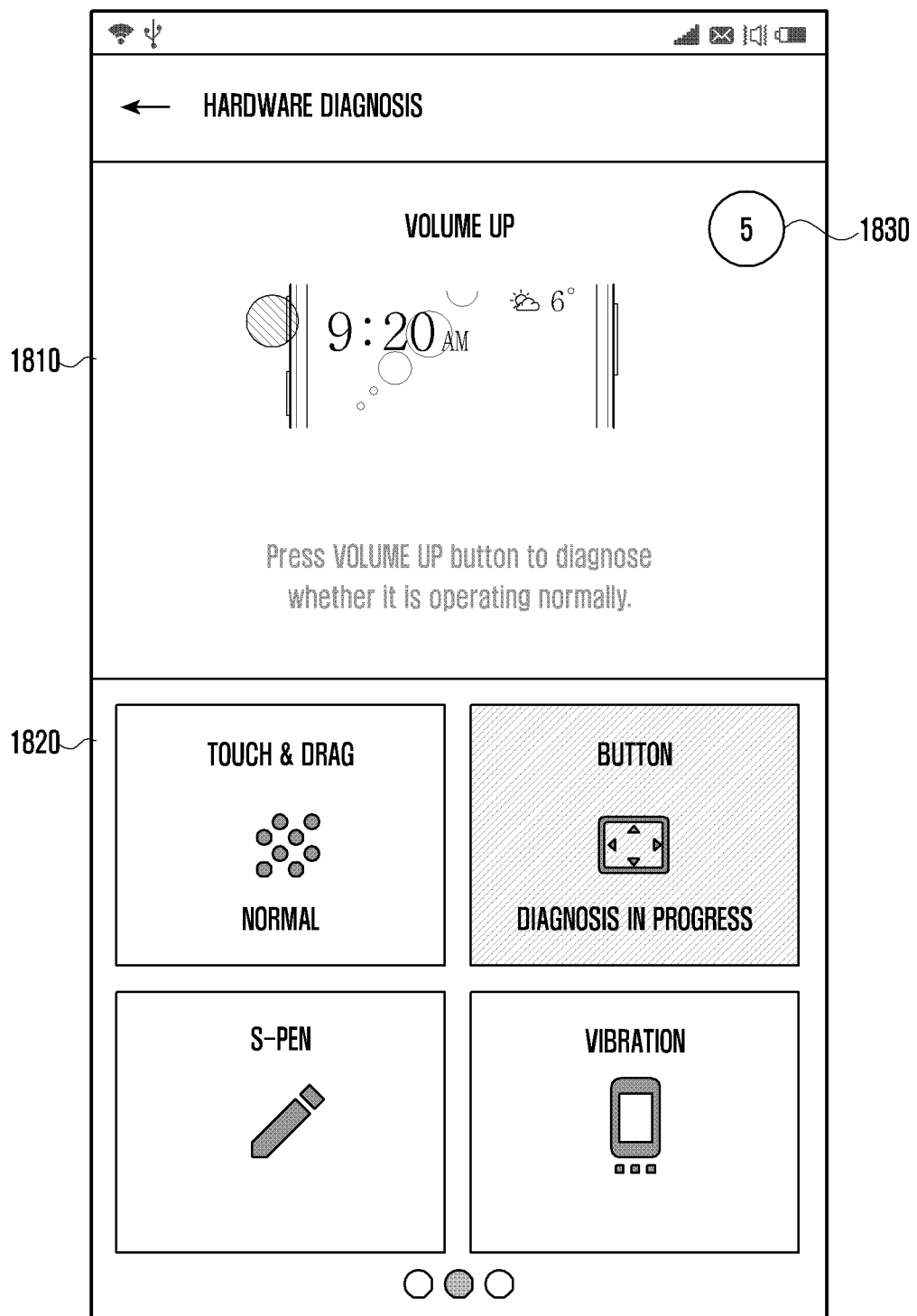
Figure 18C:
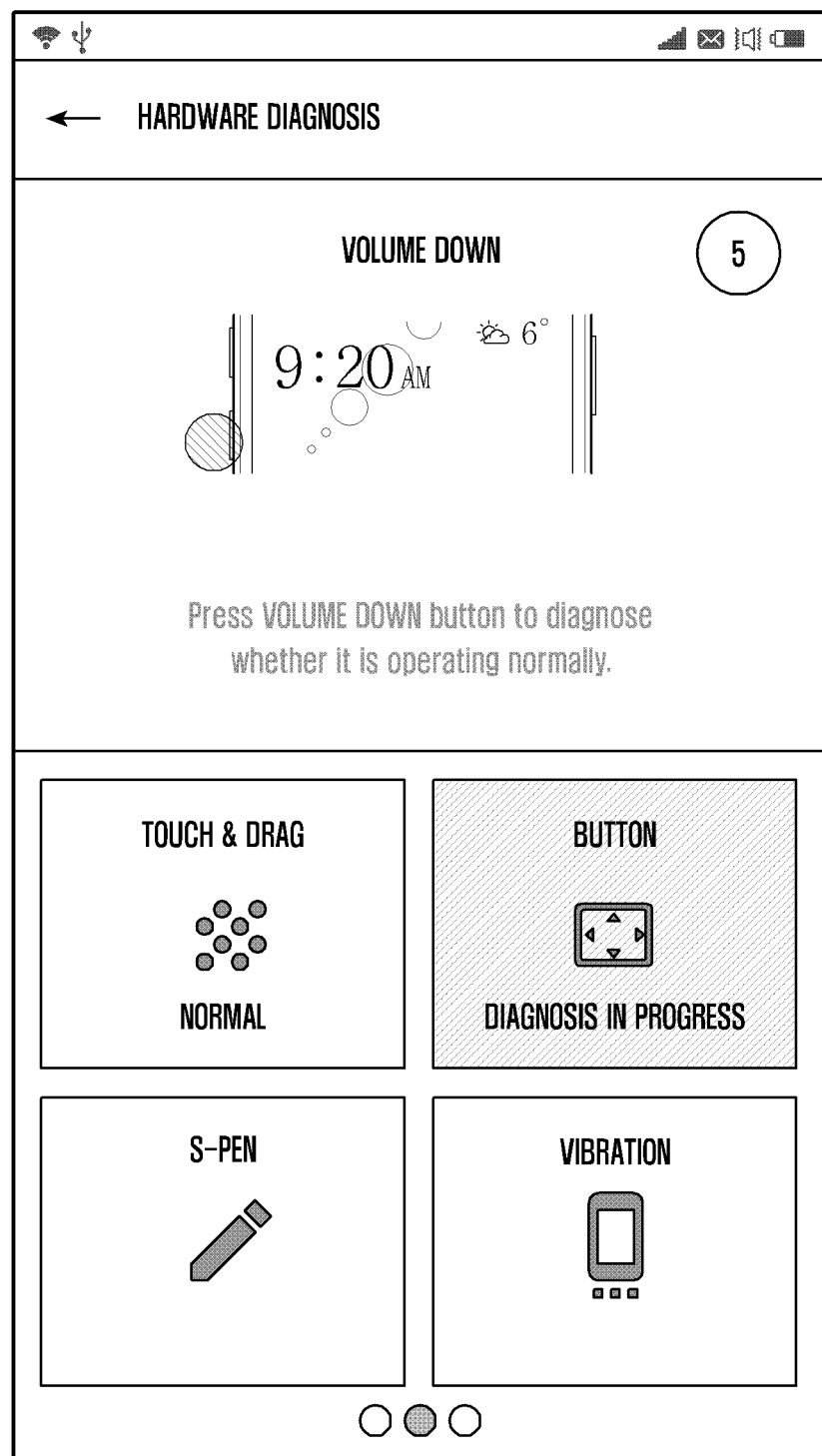
Figure 18D:
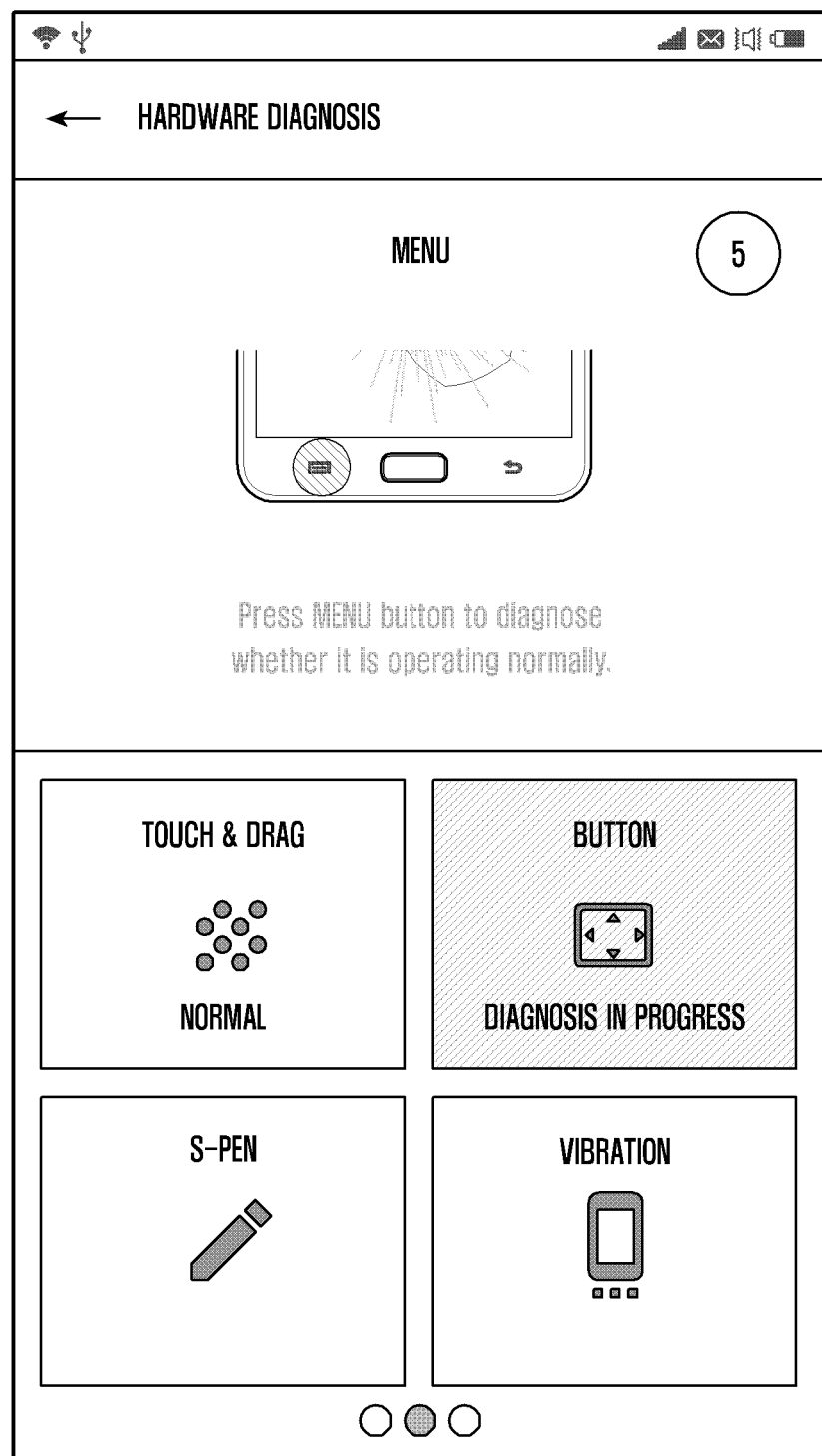
Figure 18E:
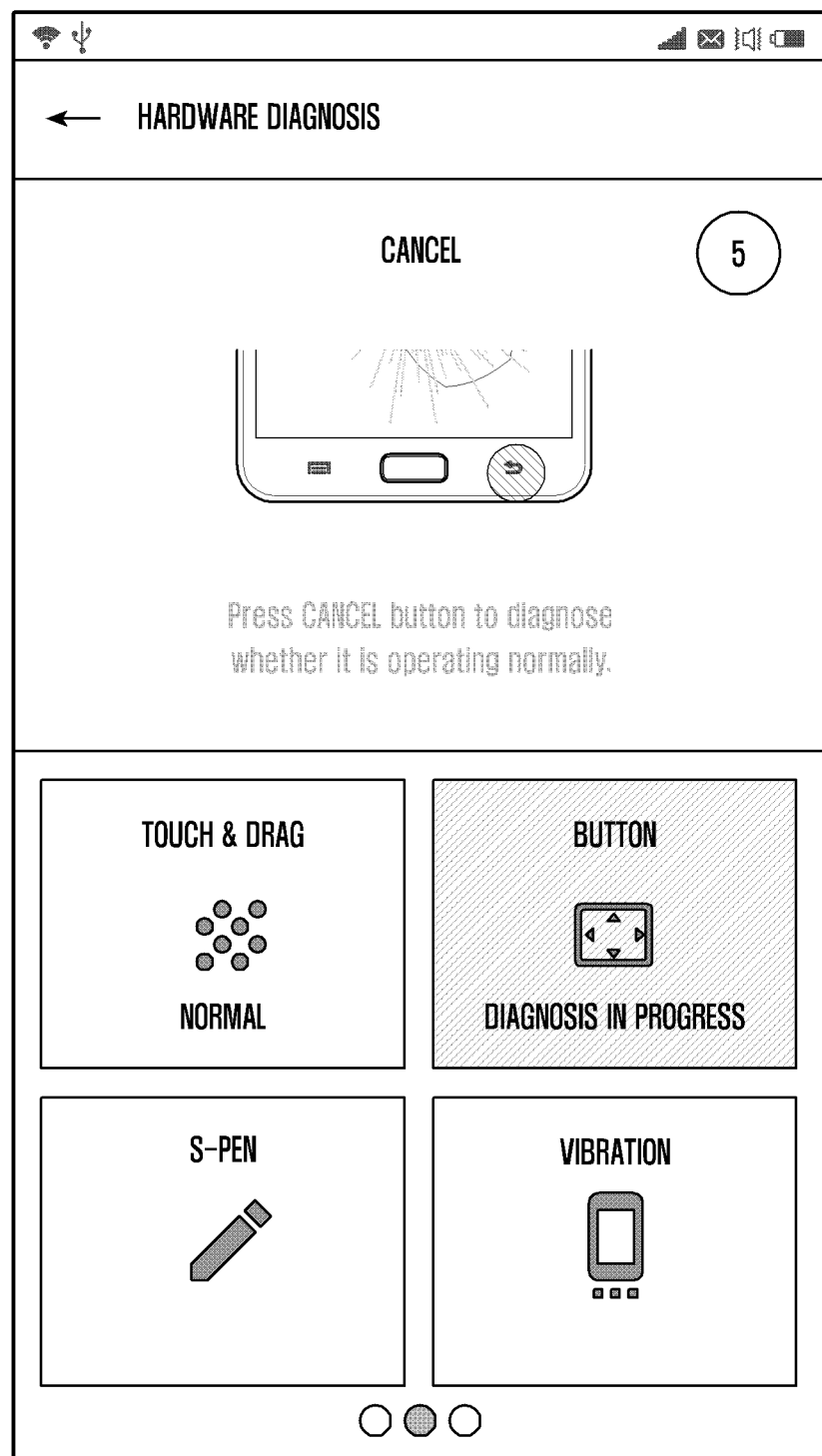
Figure 18F:
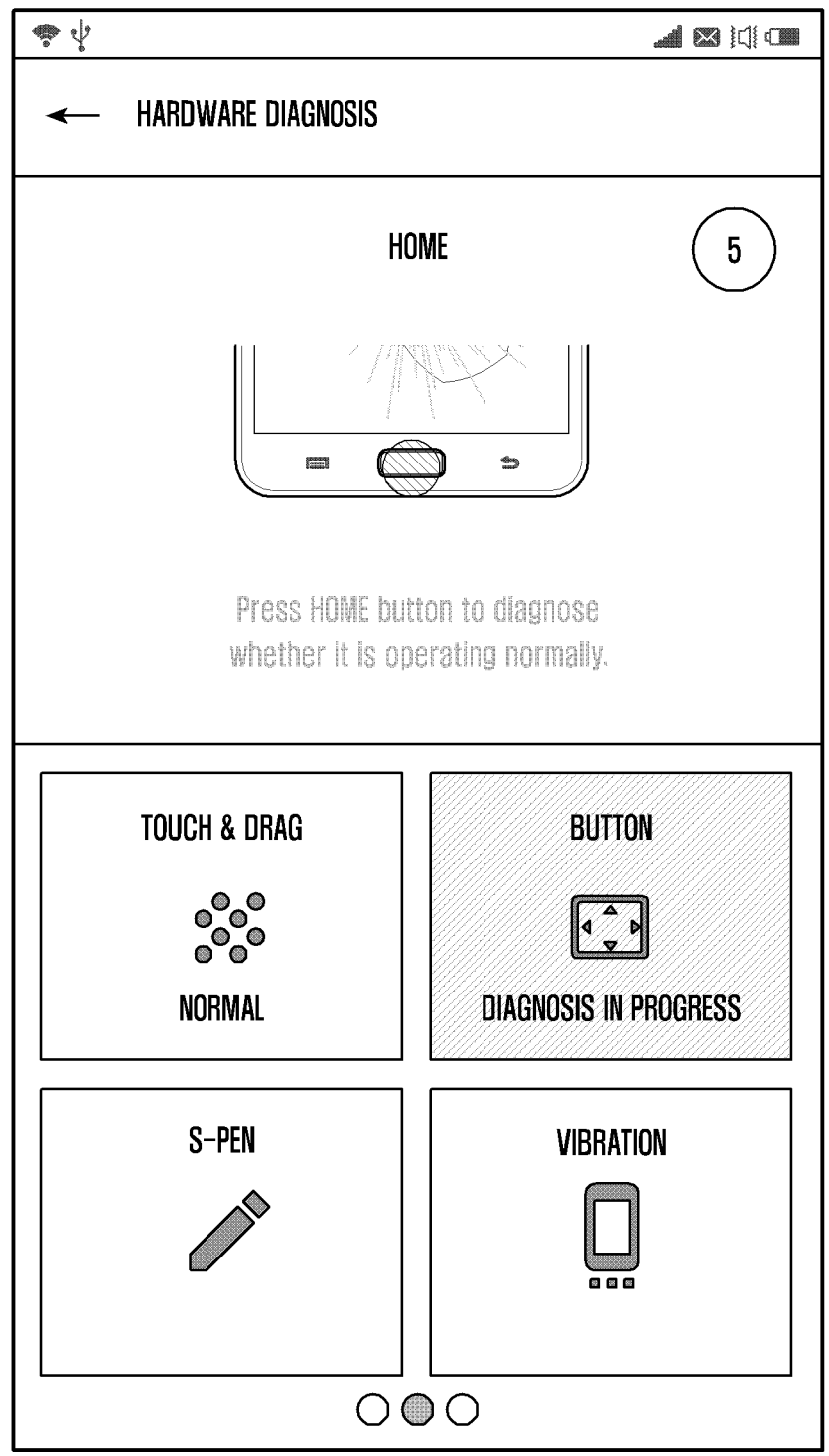
Figure 18G:
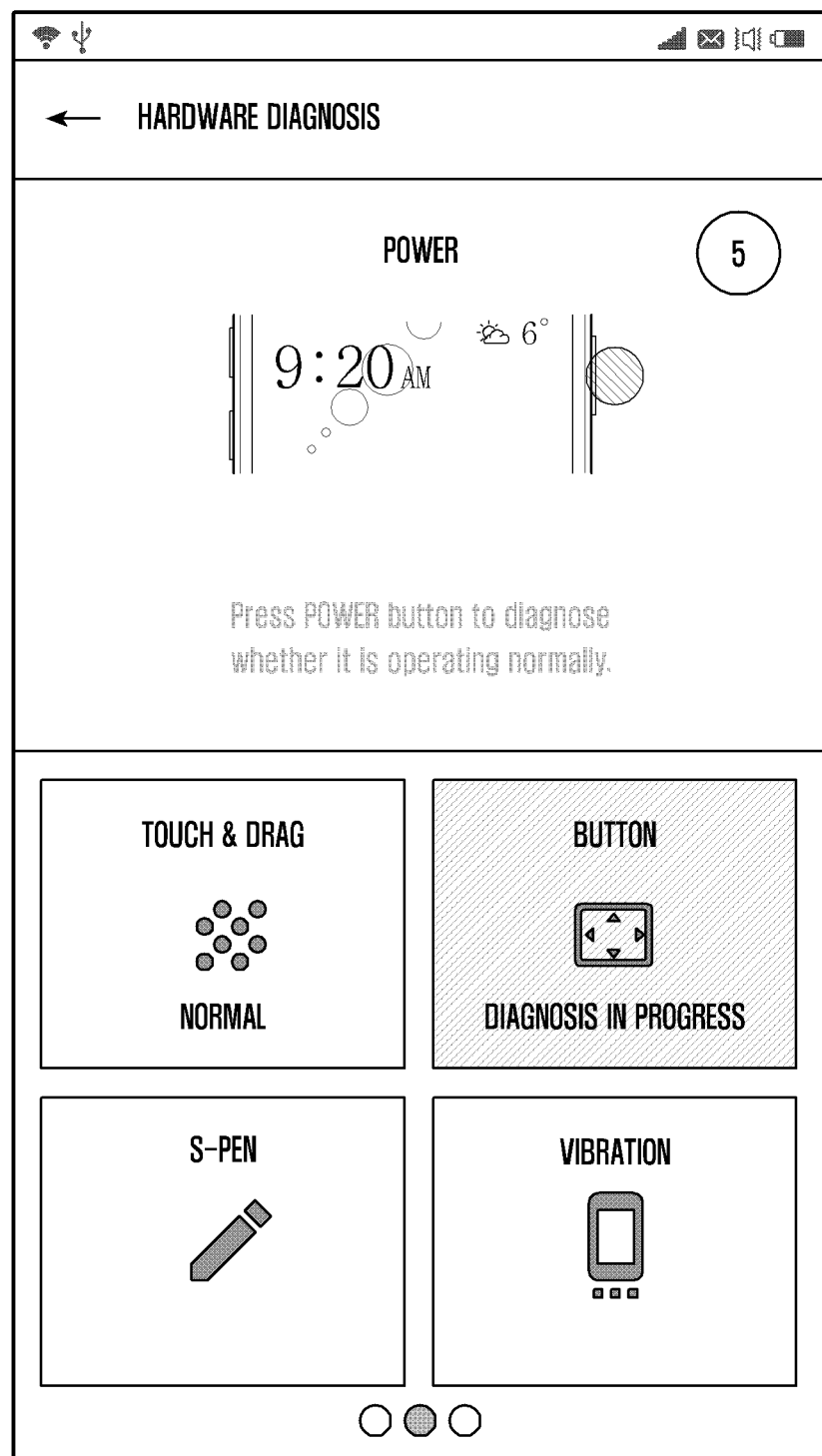

Referring to FIG. 18B, if the button icon 1821 is selected, the AP 210 performs diagnosis on the volume-up button. The volume-up button may be arranged on the right side of the housing as guided in the guidance window 1810, and if a timer 1840 expires (e.g., 5 seconds elapse), the AP 210 may perform diagnosis on the next button.

Referring to FIGS. 18C to 18G, the processor performs diagnosis in the order of a volume-down button, a menu button, a cancel button, a home button, and a power button. If a key input made with a button is detected, the AP 210 determines that the corresponding button is operating normally. If no key input made with a key in a predetermined time (e.g., 5 seconds), the AP 210 controls the display 260 to display a message to prompt the user to push the corresponding button in the guidance window 1810 or determines that the corresponding button is operating abnormally.

Figure 18H:
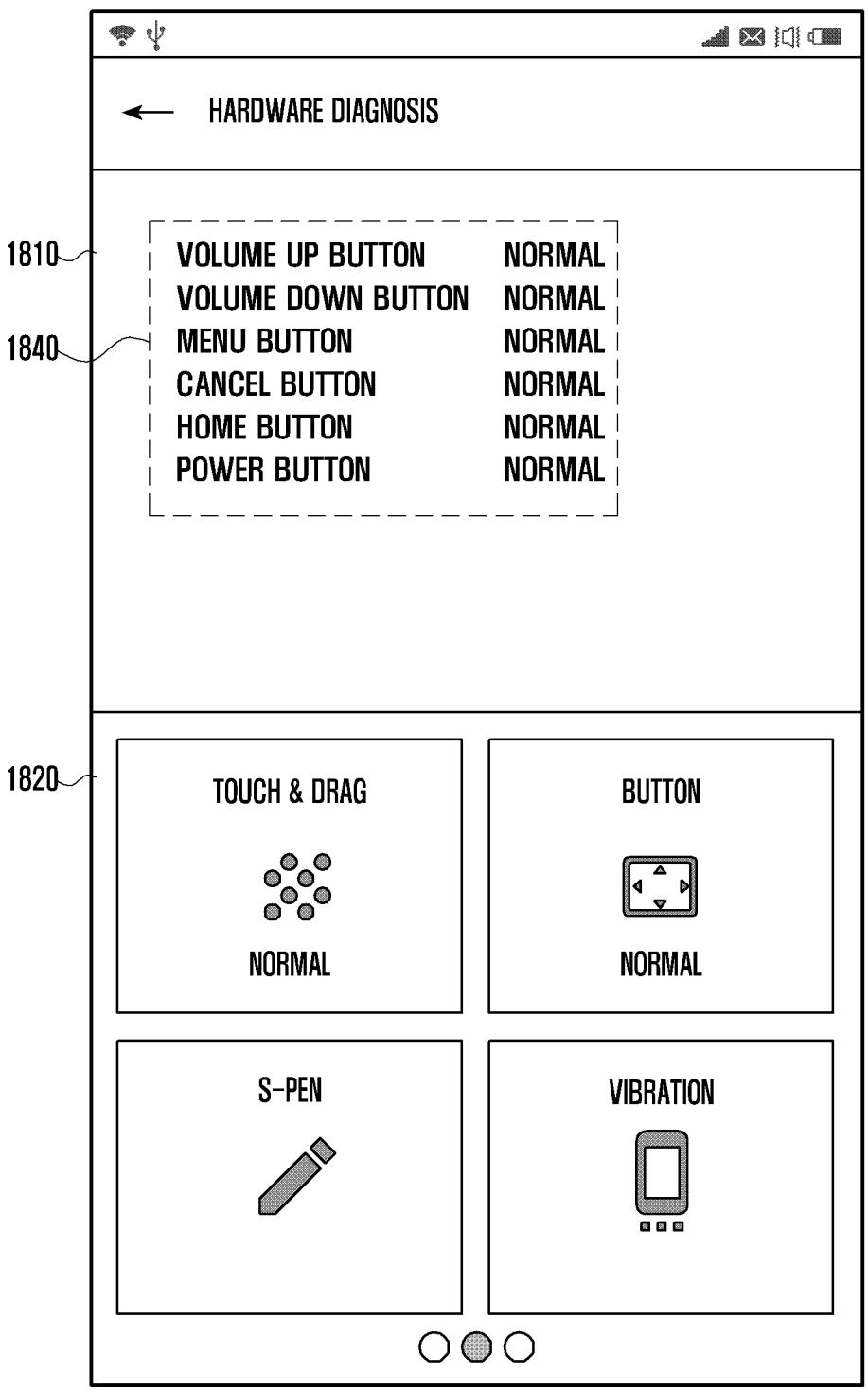

If it is determined that all of the buttons are operating normally, the AP 210 controls the display 260 to display the diagnosis result 1840 indicating that the buttons are operating normally, as illustrated in FIG. 18H.

Figure 18I:
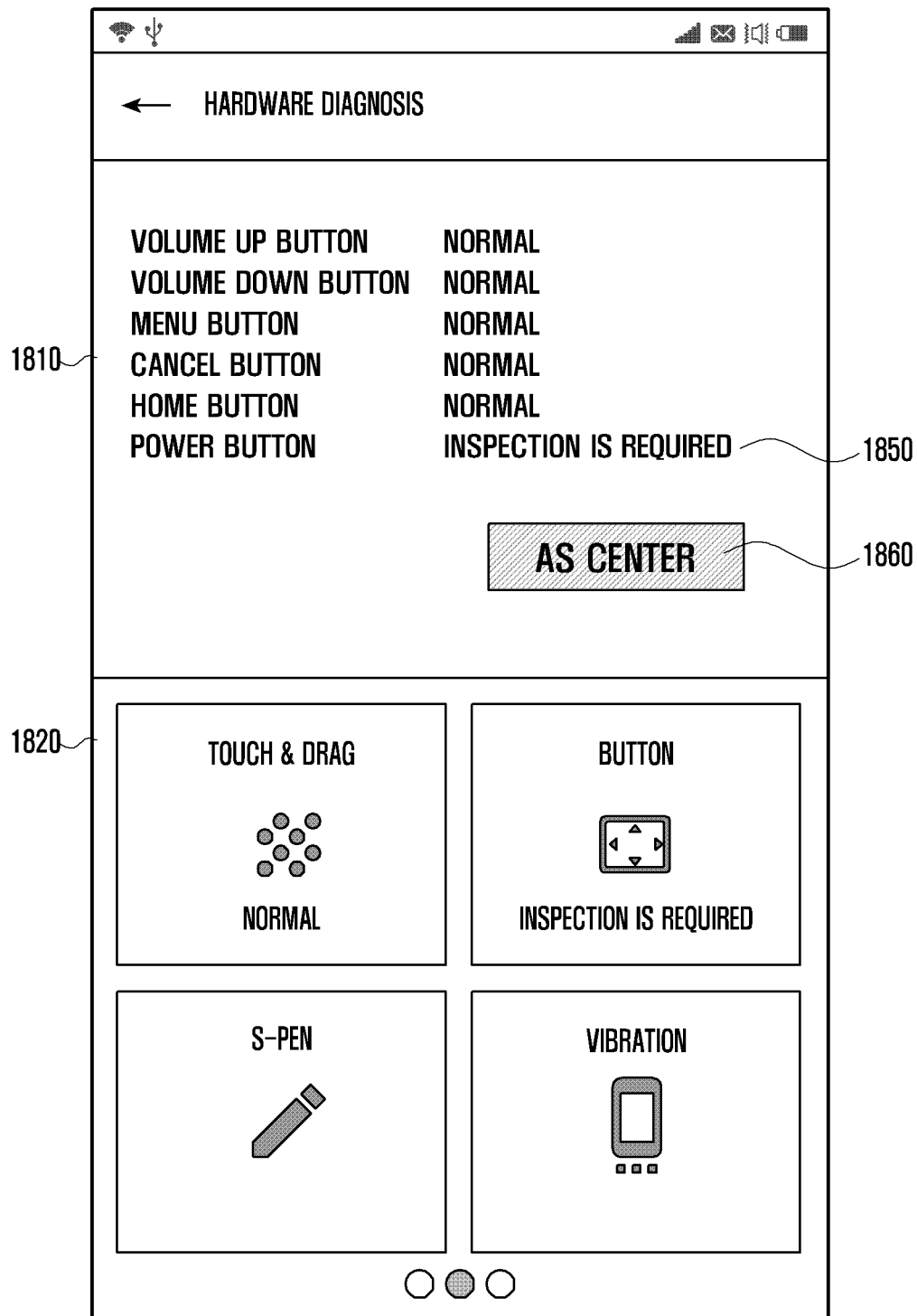

However, if it is determined that at least one of the buttons (e.g., the power button) is operating abnormally, the AP 210 controls the display 260 to display in the guidance window 1810 the text link "AS center" 1860 associated with an AS request service, as illustrated in FIG. 18I.

FIGS. 19A to 19D illustrate a user interface for displaying an SIM card diagnosis operation and diagnosis result according to an embodiment of the present disclosure. Although the user interface of FIGS. 19A to 19D is described below as being displayed by the electronic device illustrated FIG. 2, it is not limited thereto.

Figure 19A:
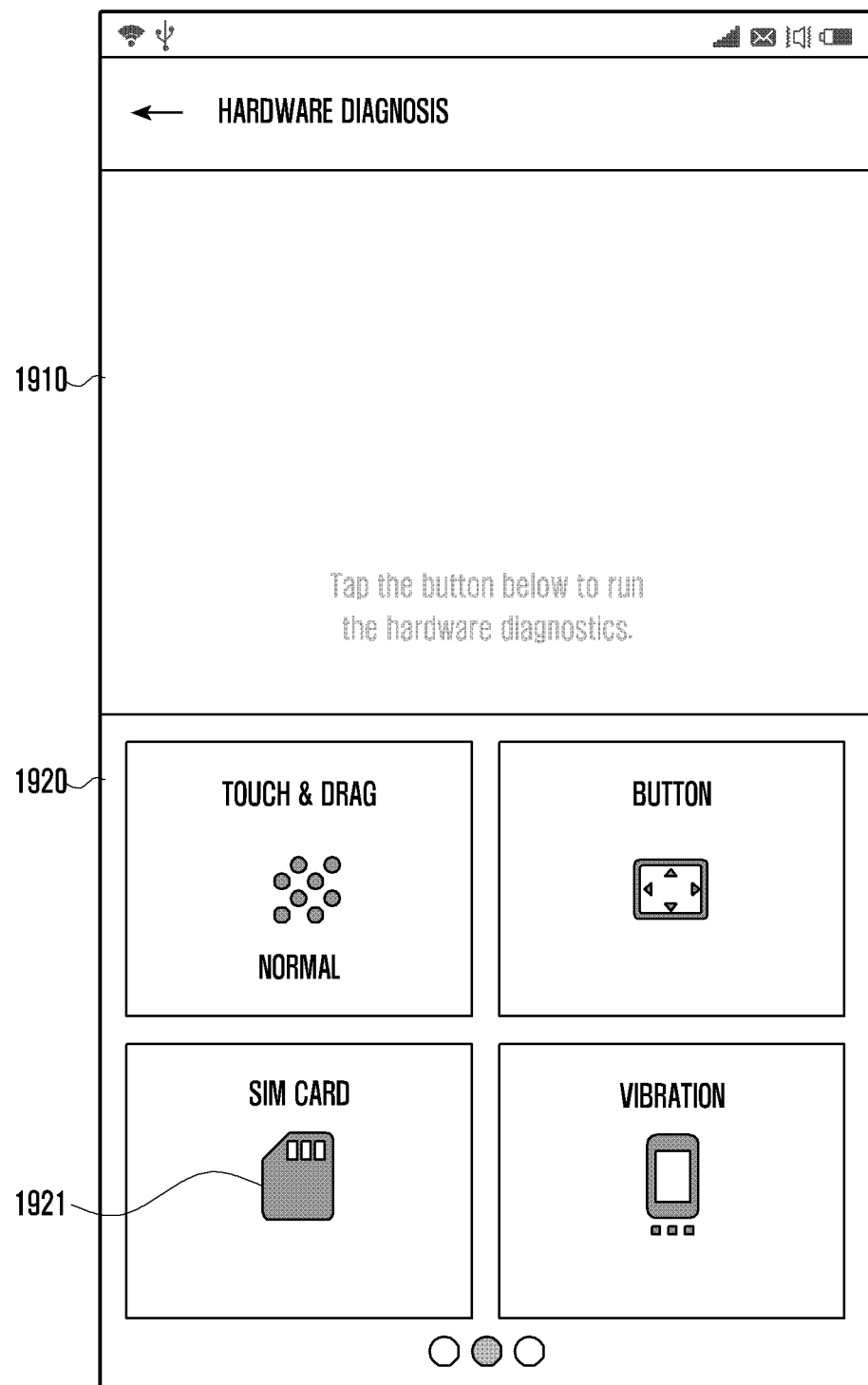
FIGS. 19A to 19D illustrate a user interface for displaying a subscriber identification module (SIM) card diagnosis operation and diagnosis result according to an embodiment of the present disclosure.
Figure 19B:
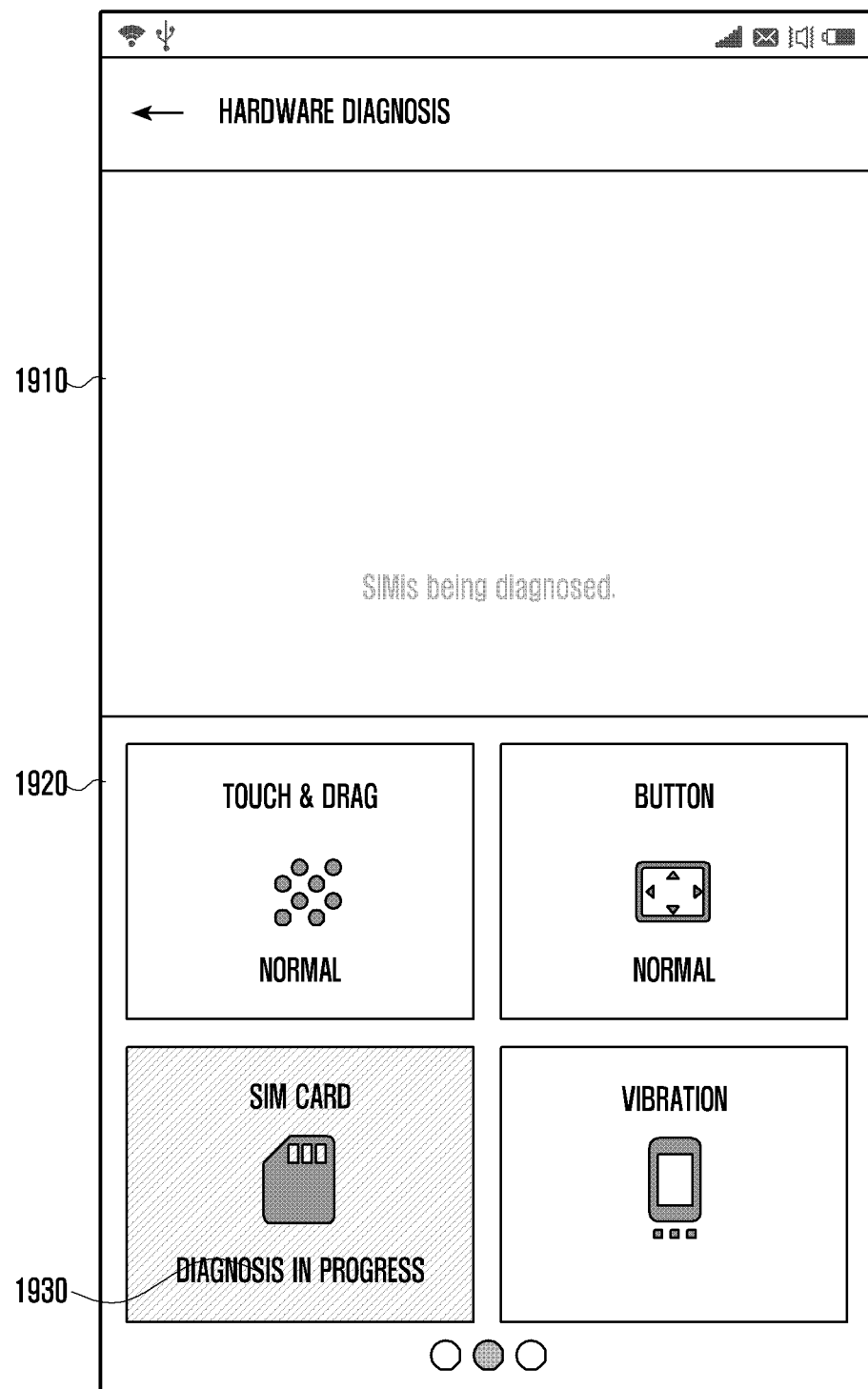

Referring to FIGS. 19A and 19B, the AP 210 controls the display 260 to display a guidance window 1910 and a diagnosis target selection window 1920. If a SIM card icon 1921 is selected in the diagnosis target selection window 1920, the AP 210 starts diagnosis on the SIM 224.

If the diagnosis is started, the information indicating that the diagnosis is in progress is displayed in the guidance window 1910. Information on the diagnosis in progress 1930 may also be displayed below the SIM card icon 1921. If it is determined that the SIM 224 is not inserted in the electronic device 201, the AP 210 may control the display 260 to display information indicating absence of the SIM card.

Figure 19C:
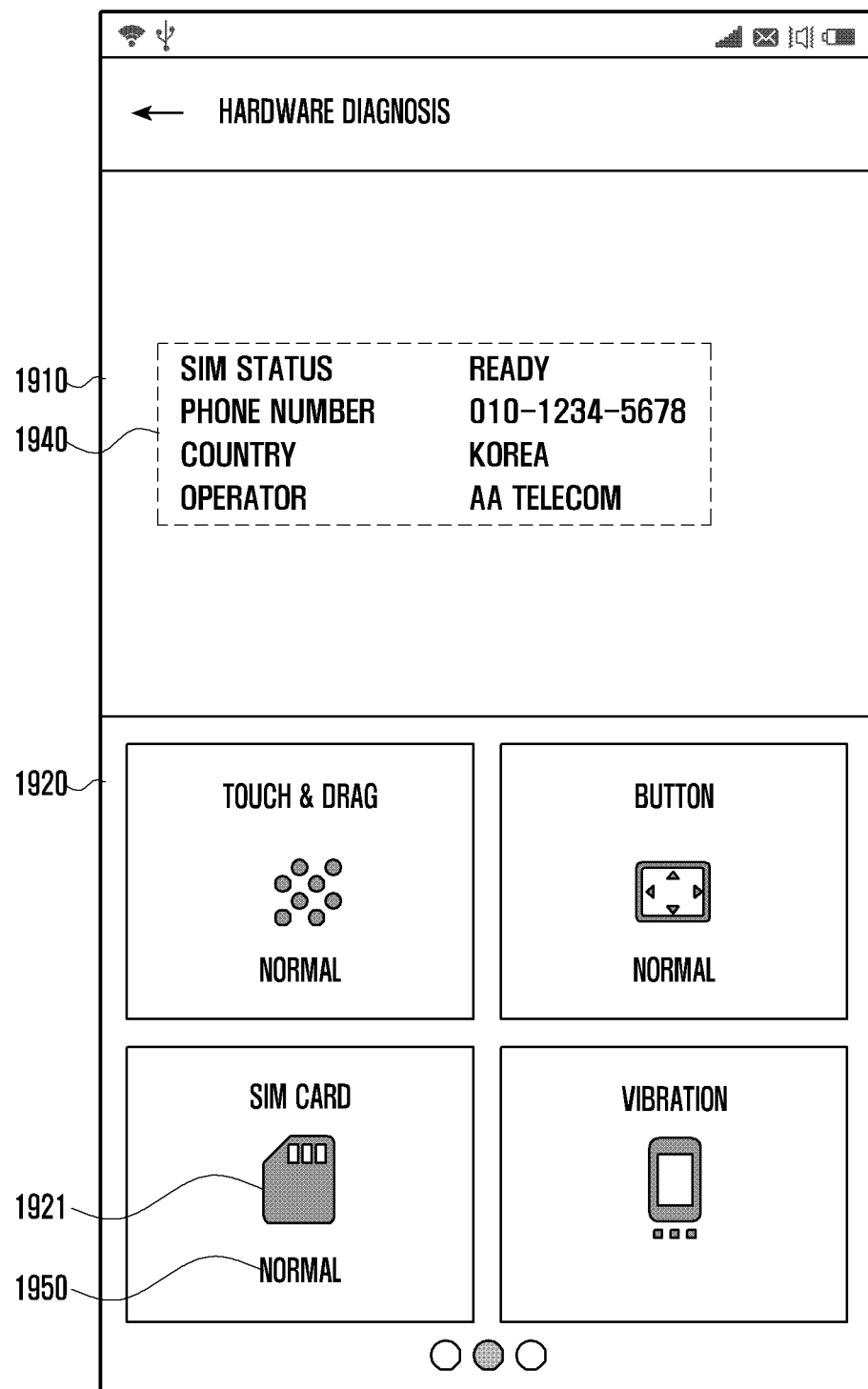

If it is determined that the SIM 224 is operating normally, the AP 210 may control the display 260 to display, in the guidance window 1910, the SIM card information 1940, as illustrated in FIG. 19C.

Referring to FIG. 19C, the AP 210 also controls the display 260 to display the information 1950 indicating that the SIM 224 is operating normally below the SIM card icon 1921.

Figure 19D:
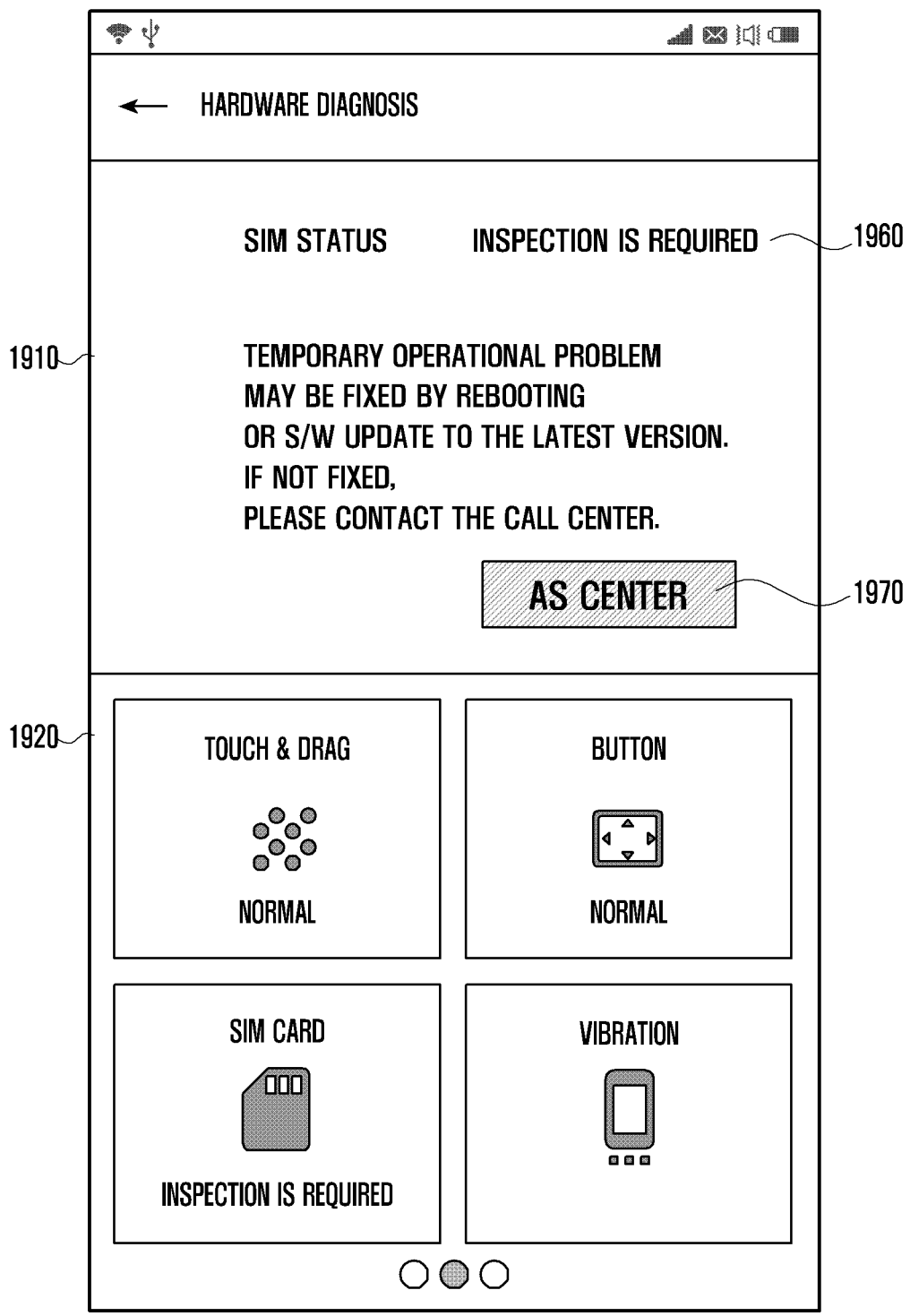

If it is determined that the SIM 224 is operating abnormally, the AP 210 controls the display 260 to display the information 1960 indicating that the SIM 224 is operating abnormally, as illustrated in FIG. 19D. The AP 210 also controls the display 260 to display the text link "AS center" 1970 associated with an AS request service.

FIGS. 20A to 20F illustrate a user interface for displaying a vibration motor diagnosis operation and diagnosis result according to an embodiment of the present disclosure. Although the user interface of FIGS. 20A to 20F is described below as being displayed by the electronic device illustrated FIG. 2, it is not limited thereto.

Figure 20A:
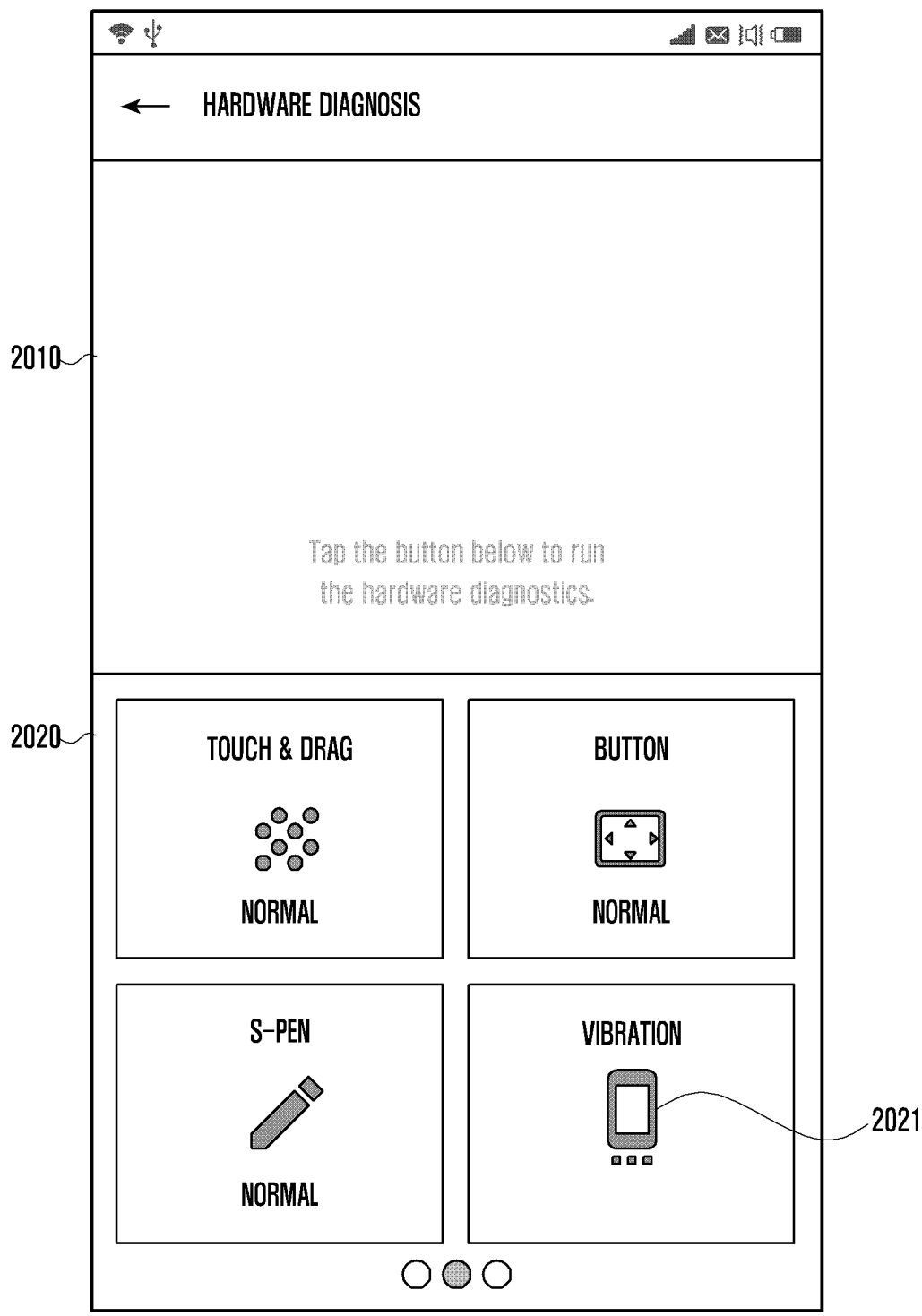
FIGS. 20A to 20F illustrate a user interface for displaying a vibration motor diagnosis operation and diagnosis result according to an embodiment of the present disclosure.
Figure 20B:
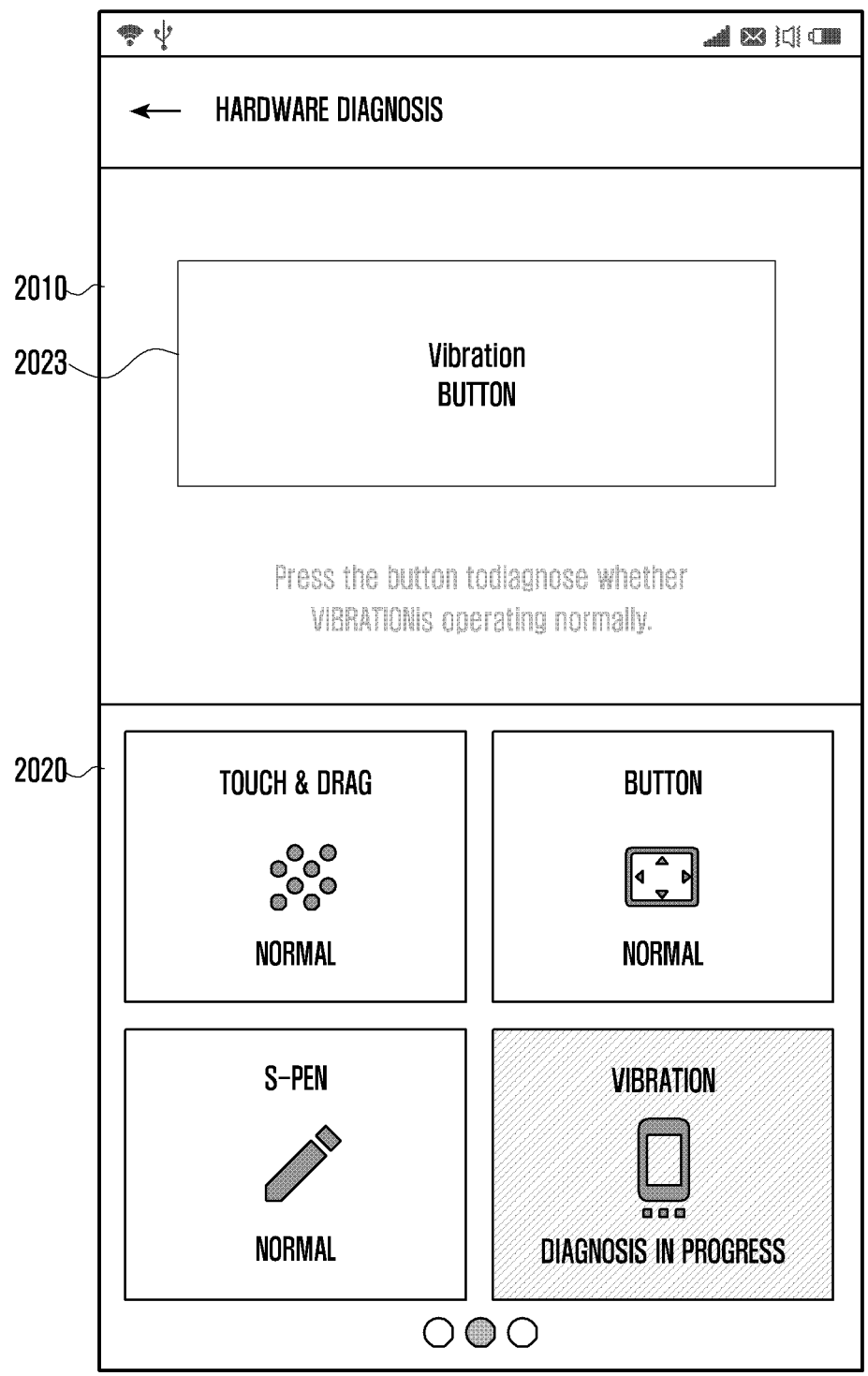
Figure 20C:
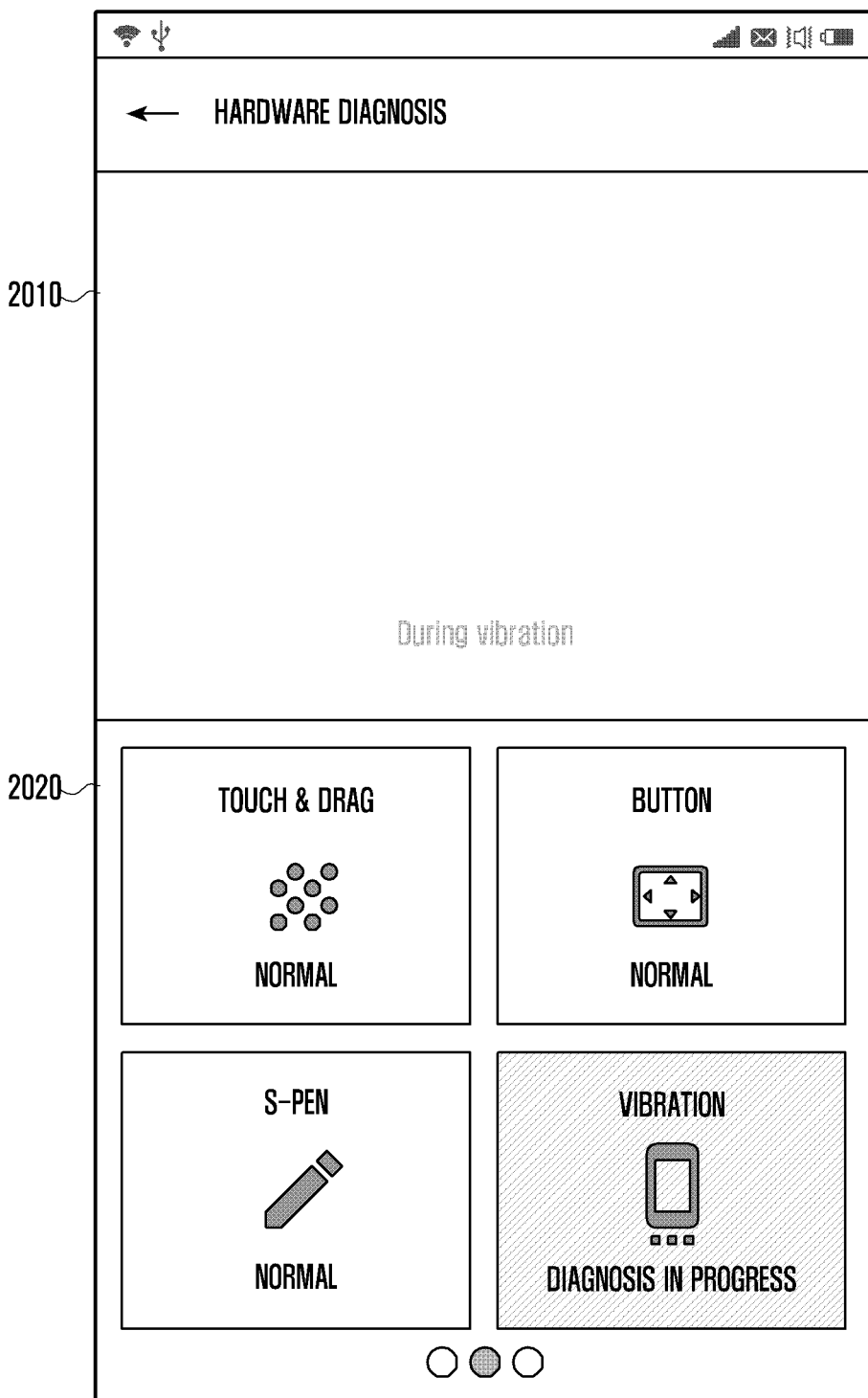

Referring to FIG. 20A, the AP 210 controls the display 260 to display a guidance window 2010 and a diagnosis target selection window 2020. If a vibration icon 2021 is selected in the diagnosis target selection window 2020, the processor starts diagnosis on the motor 298. For example, if the vibration icon 2021 is selected, the AP 210 controls the display 260 to display the vibration button 2023 to the user in the guidance window 2010, as illustrated in FIG. 20B, and if the vibration button 2023 is selected, controls the motor 298 to generate vibration after a given time (e.g., 0.3 seconds). The vibration may be continued for a predetermined time period (e.g., 2 seconds), and information indicating that the vibration is in progress is presented to the user in the guidance window 2010, as illustrated in FIG. 20C.

Figure 20D:
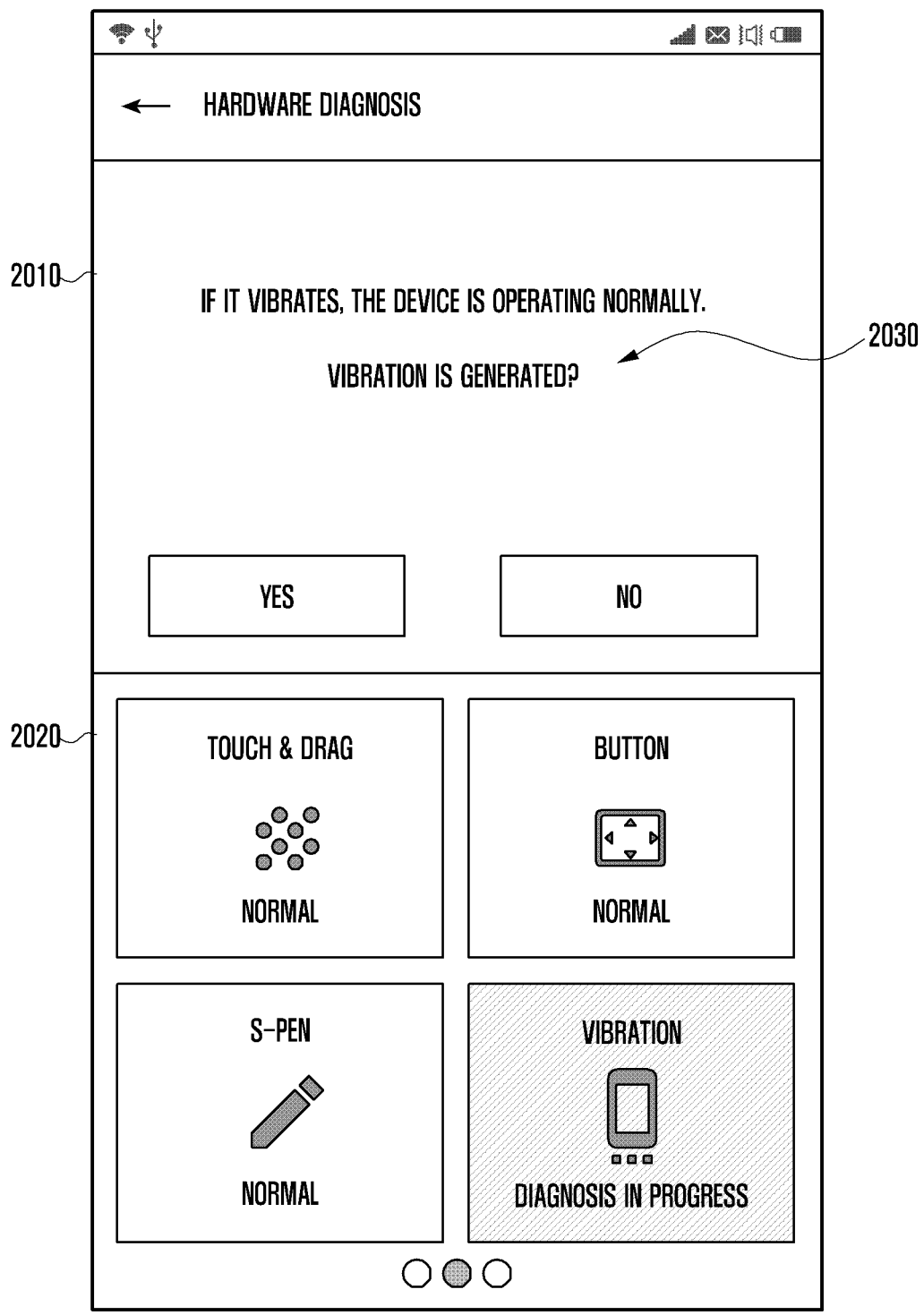

If a predetermined time elapses, the AP 210 controls the motor 298 to stop vibrating and the display unit 260 to display in the guidance window 2010 a popup window 2030, prompting the user to answer whether or not vibration is generated, as illustrated in FIG. 20D.

Figure 20E:
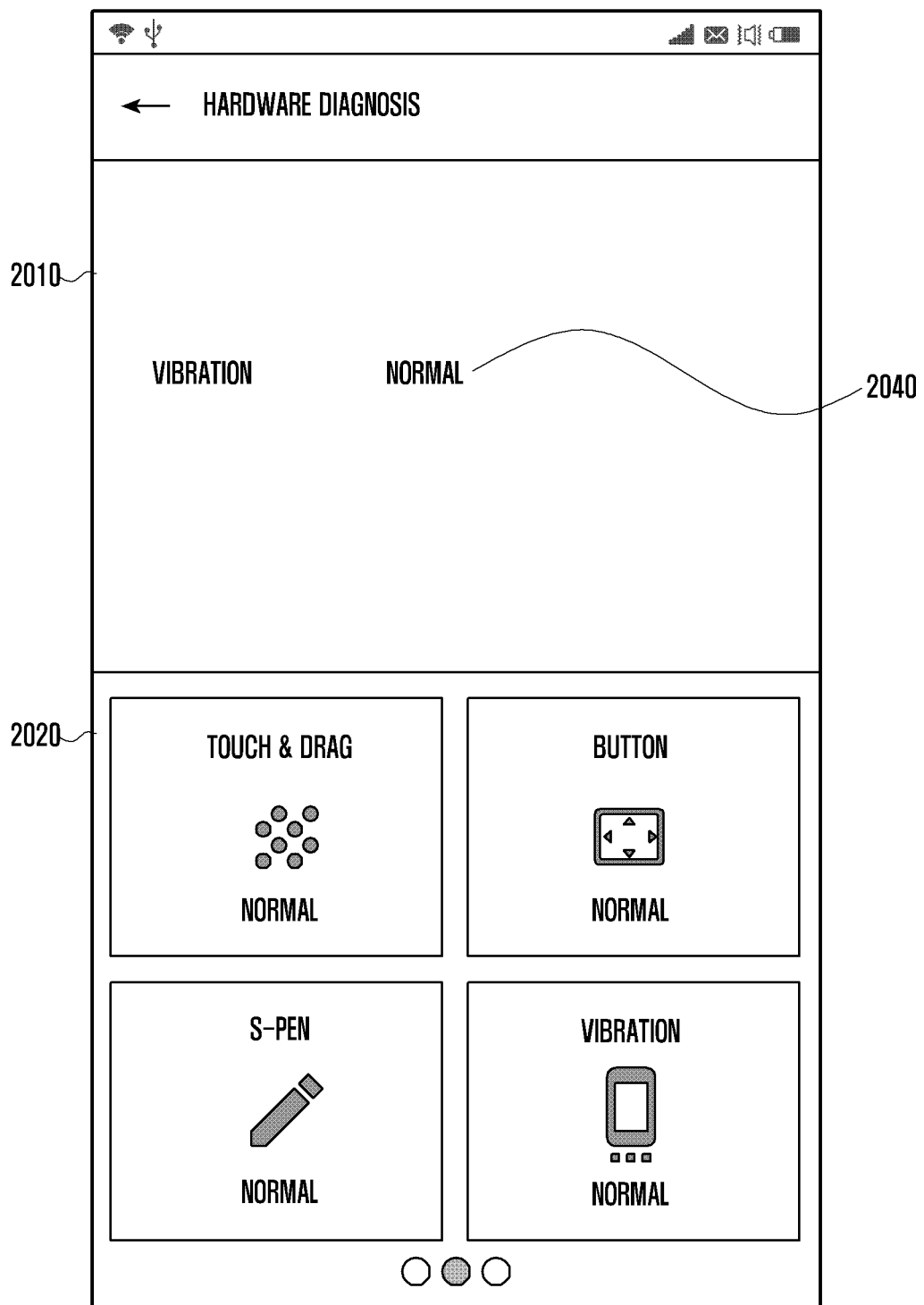

If the user pushes a "Yes" button in the popup window 2030, the processor determines that the motor 298 operates normally and controls the display 260 to display in the guidance window 2010 the information 2040 indicating that the motor 298 is operating normally, as illustrated in FIG. 20E.

Figure 20F:
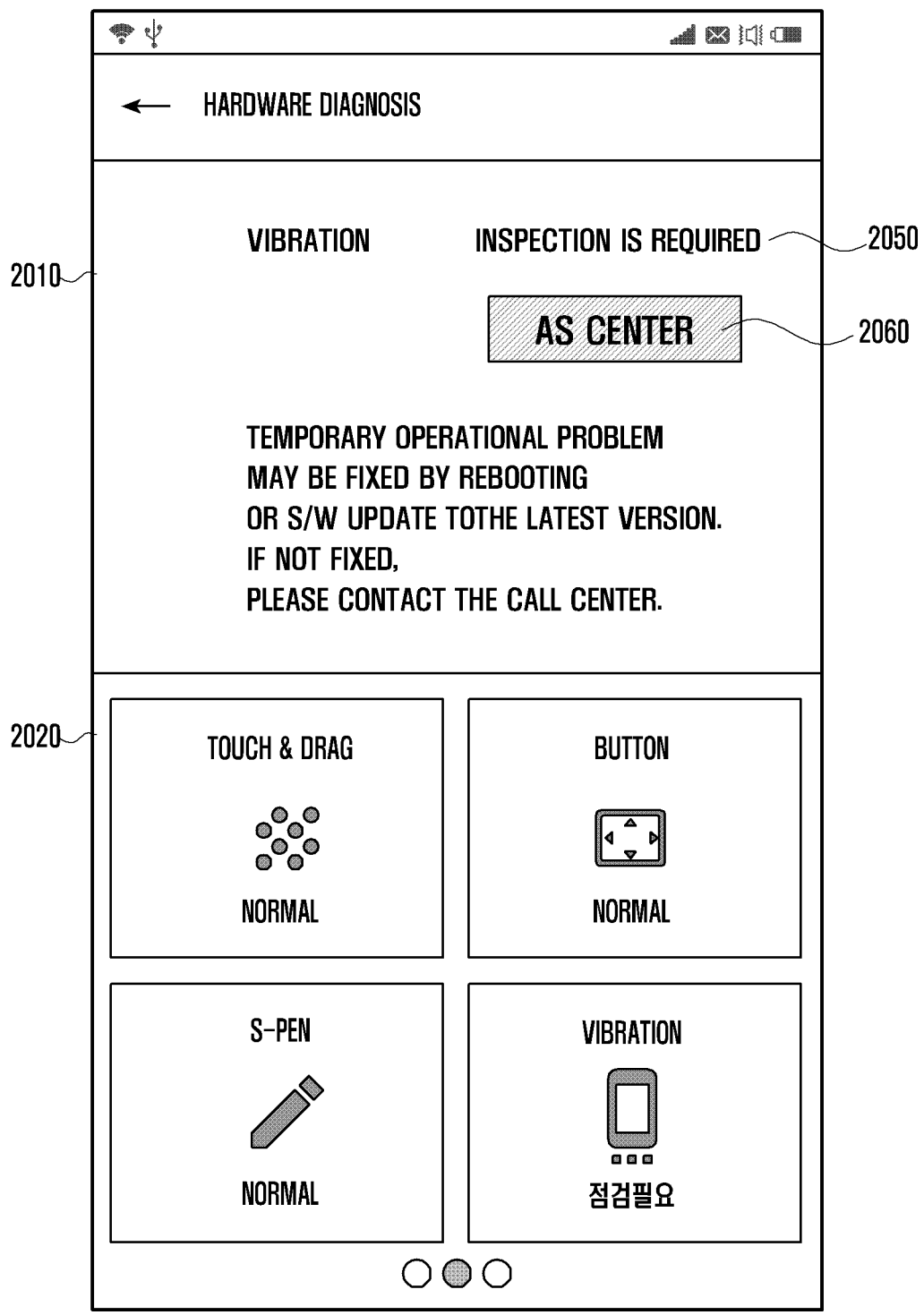

However, if the user pushes a "No" button in the popup window 2030, the processor determines that the motor 298 operates abnormally and controls the display 260 to display the information 2050 indicating that the motor 298 is operating abnormally and the text link "AS center" 2060 associated with an AS request service, as illustrated in FIG. 20F.

FIGS. 21A to 21G are diagrams for explaining a user interface for displaying a microphone diagnosis operation and diagnosis result according to various embodiments of the present disclosure. Although the user interface of FIGS. 21A to 21G is described below as being displayed by the electronic device illustrated FIG. 2, it is not limited thereto.

Figure 21A:
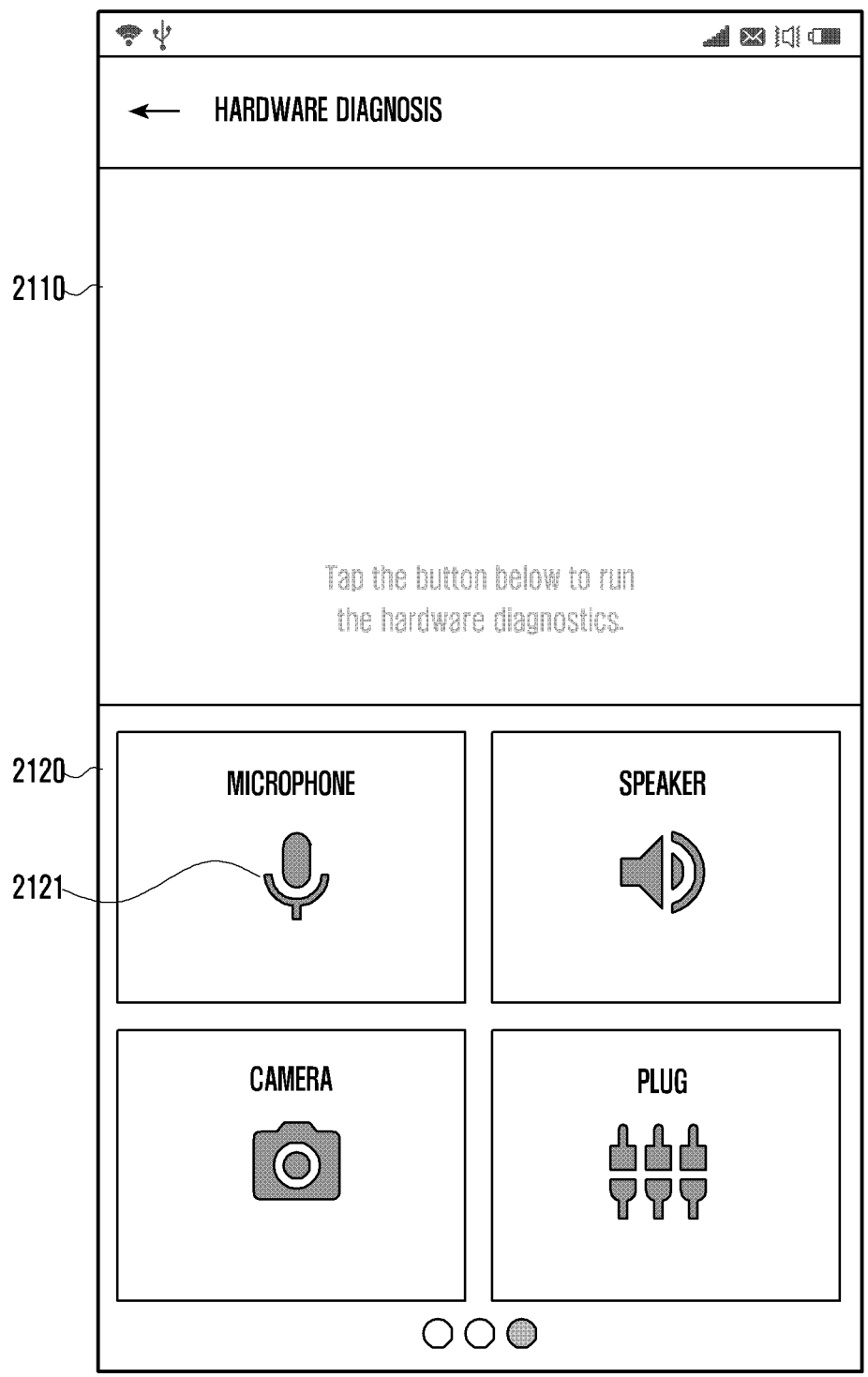
FIGS. 21A to 21G illustrate a user interface for displaying a microphone diagnosis operation and diagnosis result according to an embodiment of the present disclosure.

Referring to FIG. 21A, the AP 210 controls the display 260 to display a guidance window 2110 and a diagnosis target selection window 2120. If a microphone icon 2121 is selected in the diagnosis target selection window 2120, the processor starts diagnosis on the microphone 288.

Figure 21B:
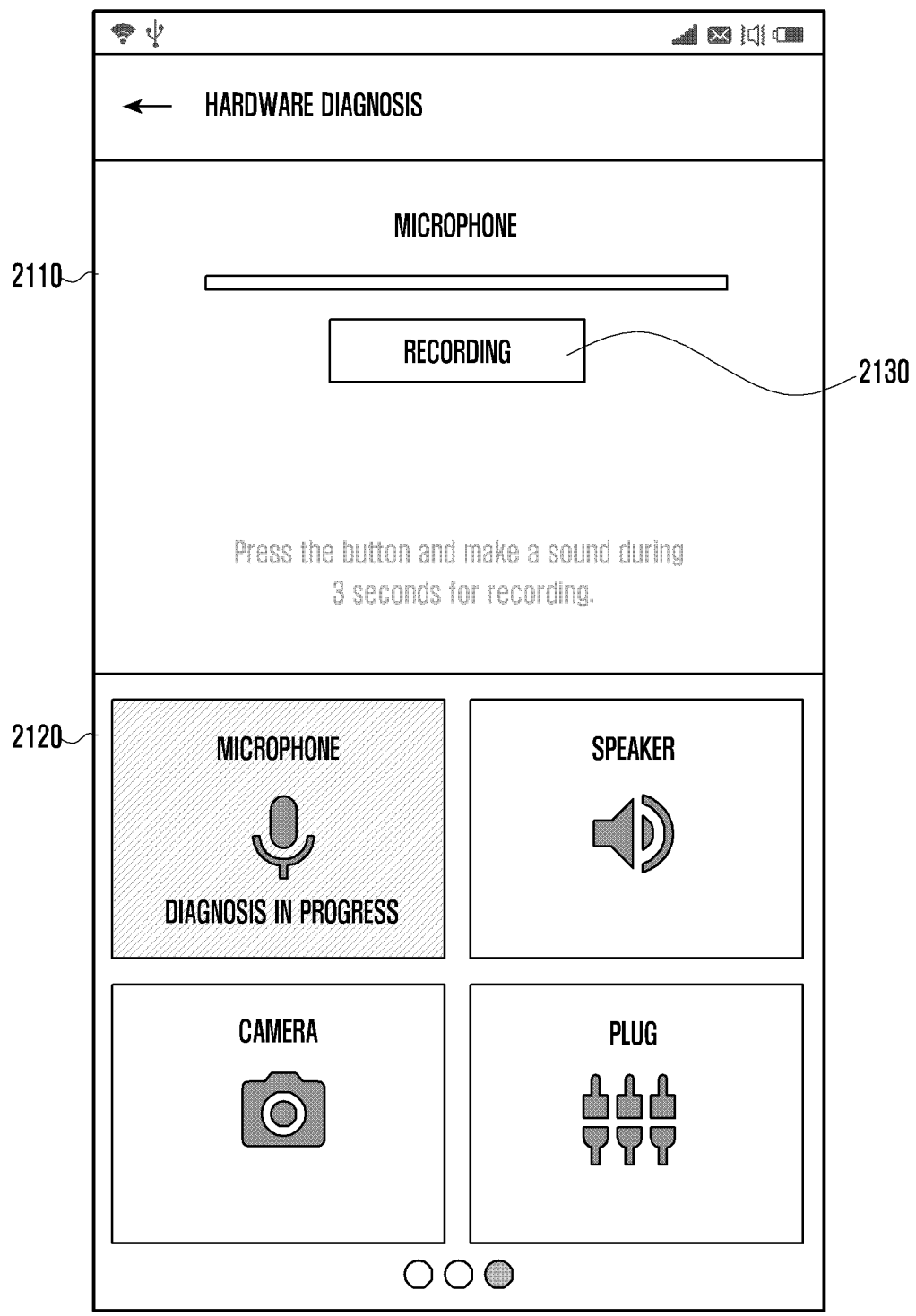
Figure 21C:
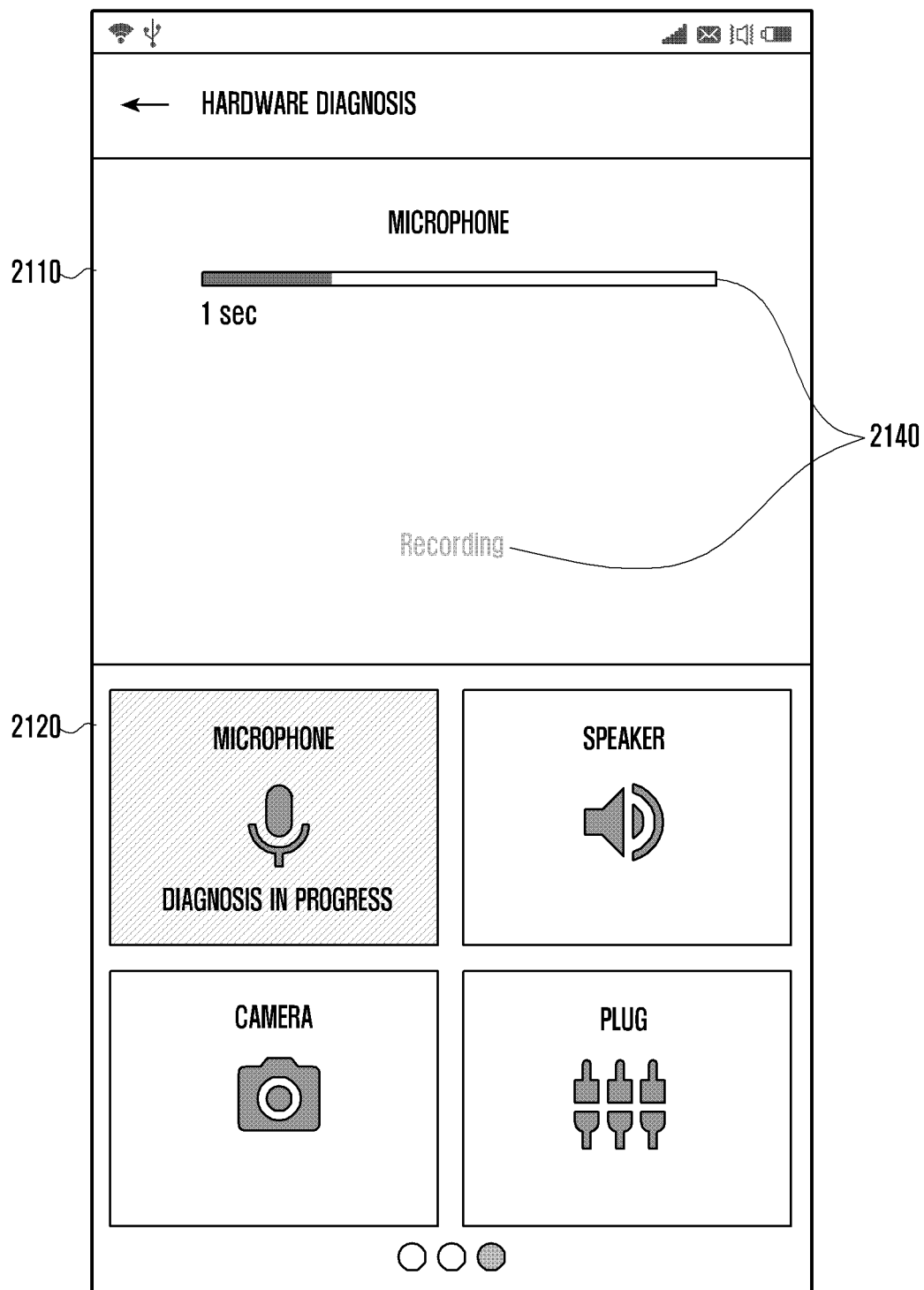

Referring to FIG. 21B, when the microphone icon 2121 is selected, the AP 210 controls the display 260 to display, in the guidance window 2110, a recording button 2130. If the recording button 2130 is selected, the AP 210 records voice data input through the microphone 288 and controls the display 260 to display in the guidance window 2110 the information 2140 indicating that recording is in progress, as illustrated in FIG. 21C.

Figure 21D:
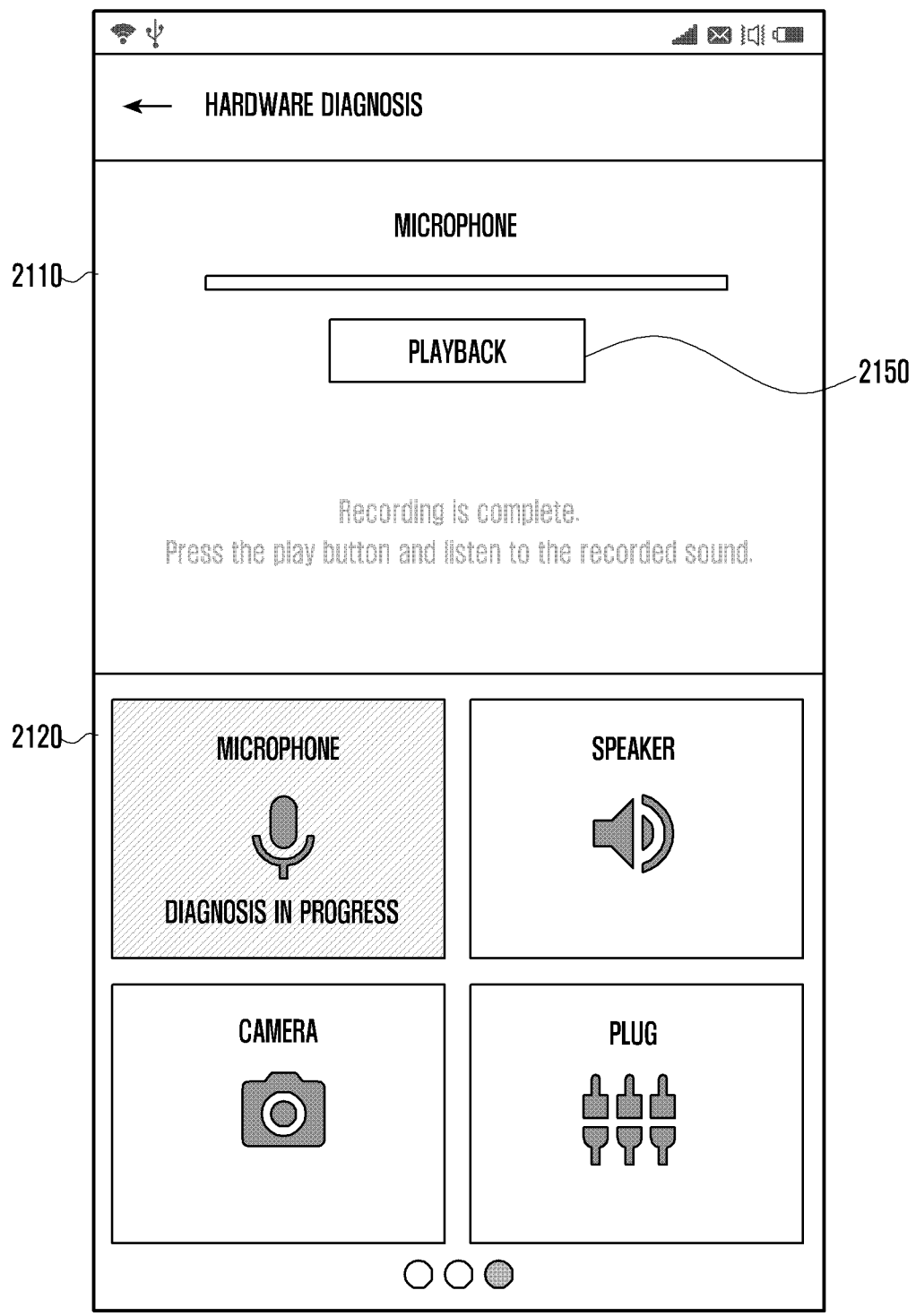

If the voice data recording is completed during a predetermined time period (e.g., 3 seconds), the AP 210 controls the display 260 to display, in the guidance window 2110, a playback button 2150, as illustrated in FIG. 21D. If the playback button 2150 is selected, the processor may output the recorded voice data through the speaker 282.

Figure 21E:
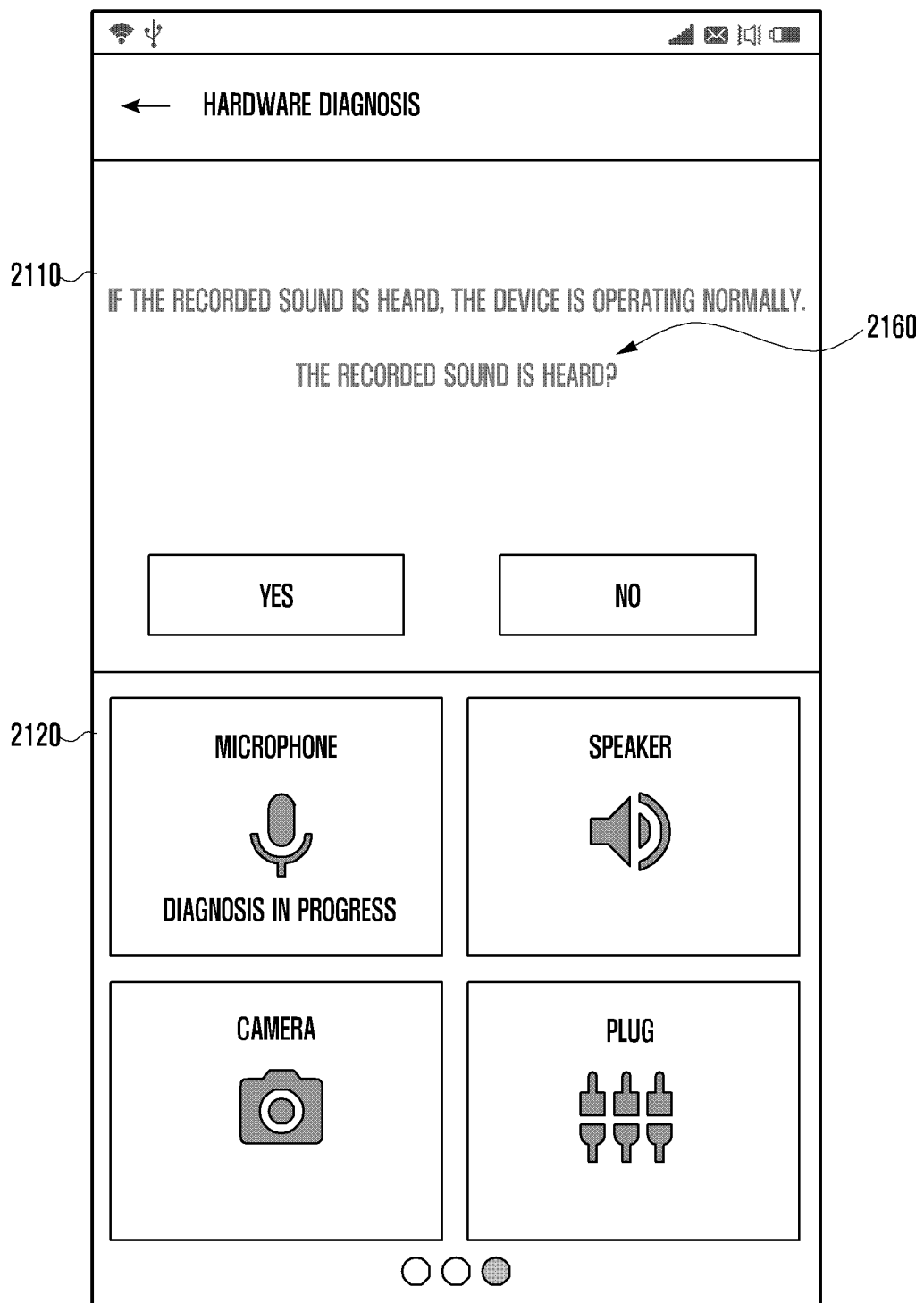

If the recording is completed, the AP 210 controls the display 260 to display, in the guidance window 2110, a message window 2160 asking whether the recording is performed normally, as illustrated in FIG. 21E.

Figure 21F:
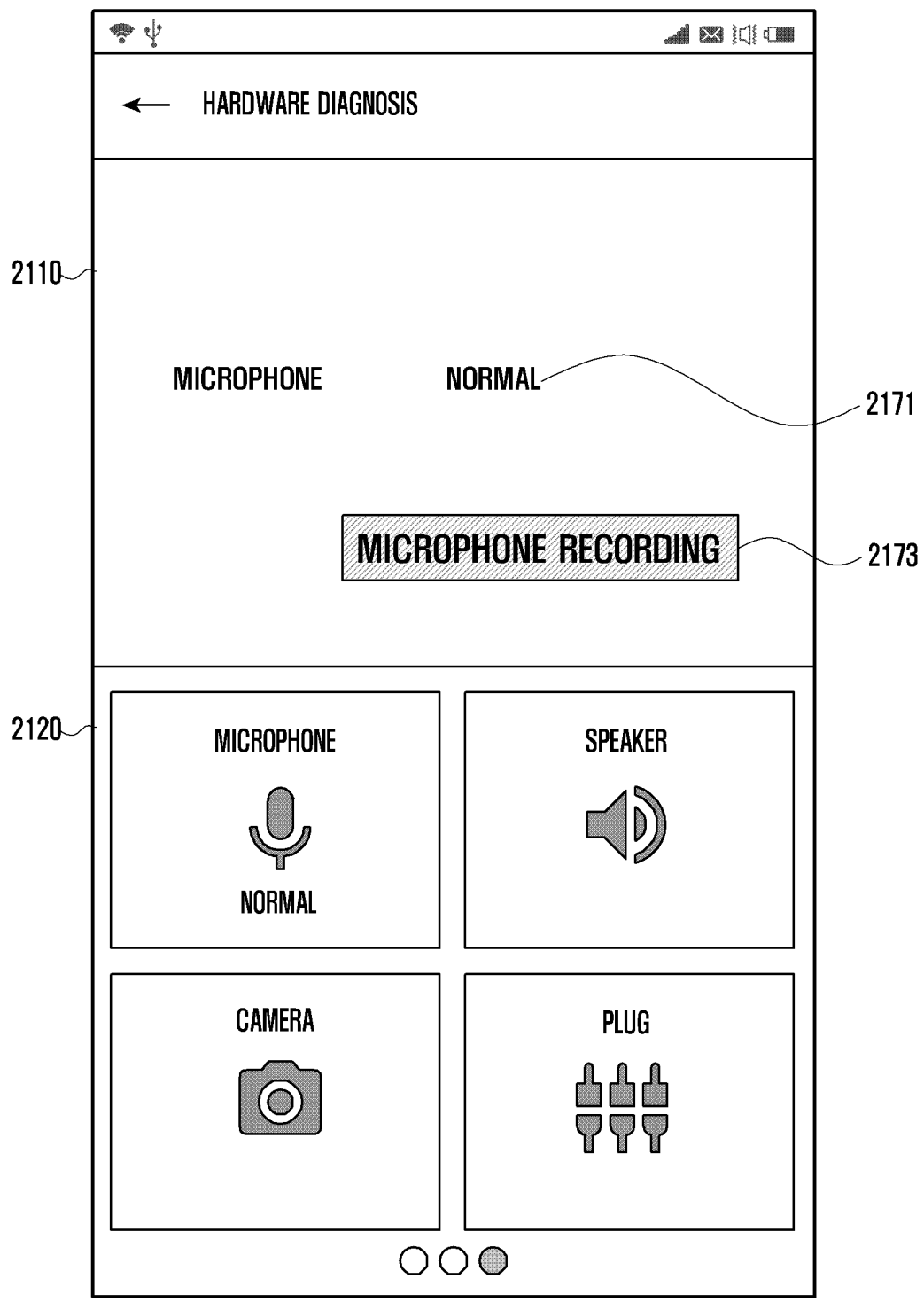

If the user selects the "Yes" button provided in the message window 2160, the AP 210 determines that the microphone 288 is operating normally and controls the display 260 to display, in the guidance window 2110, the information 2171 indicating that the microphone 288 is operating normally and the text link "microphone recording" 2173 in association with the application, as illustrated in FIG. 21F.

Figure 21G:
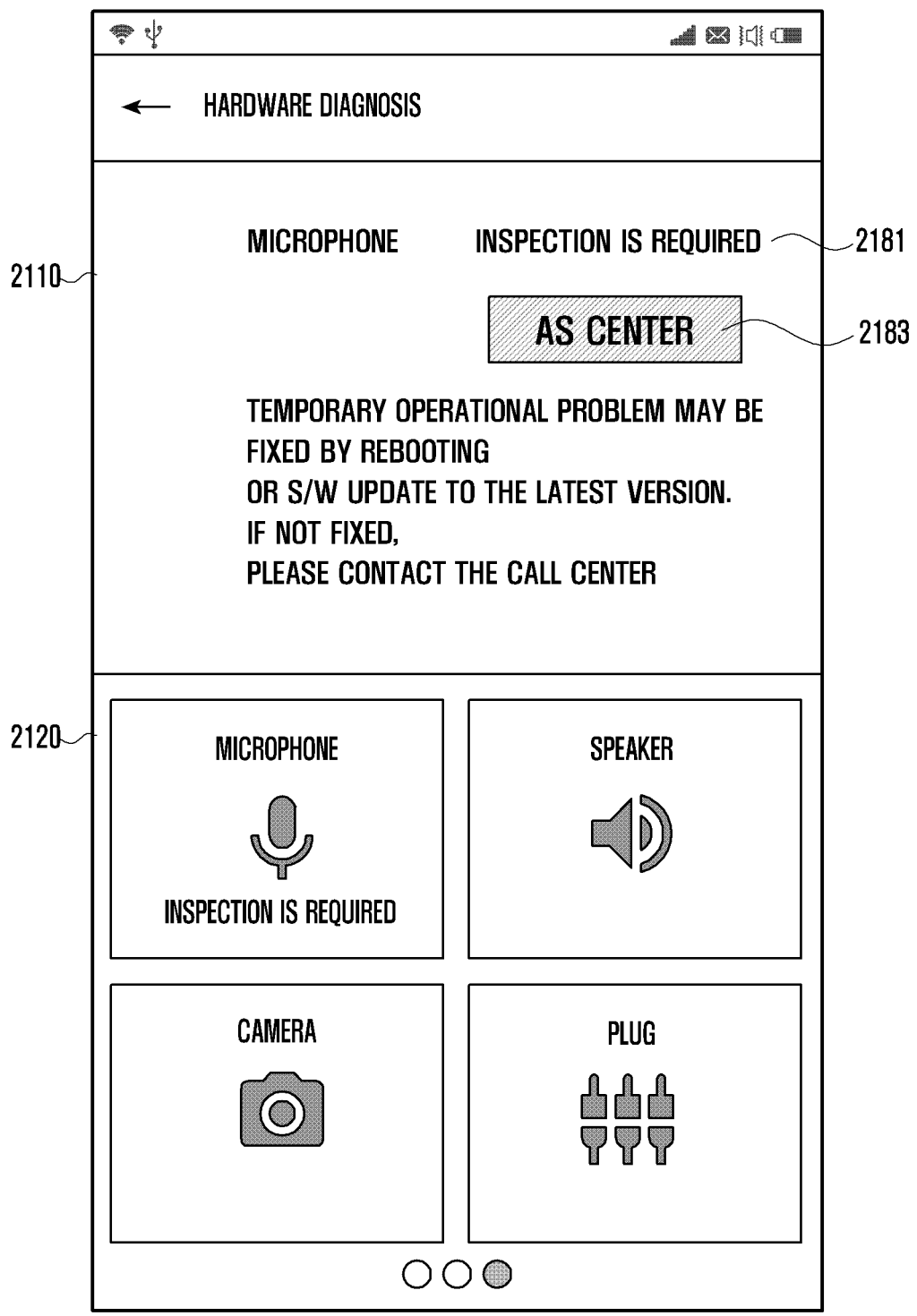

However, if the user selects the "No" button provided in the message window 2160, the AP 210 determines that the microphone 200 is operating abnormally and controls the display 260 to display the information indicating the abnormality and the text link "AS center" 2183 associated with an AS request service, as illustrated in FIG. 21G.

FIGS. 22A to 22F illustrate a user interface for displaying a speaker diagnosis operation and diagnosis result according to an embodiment of the present disclosure. Although the user interface of FIGS. 22A to 22F is described below as being displayed by the electronic device illustrated FIG. 2, it is not limited thereto.

Figure 22A:
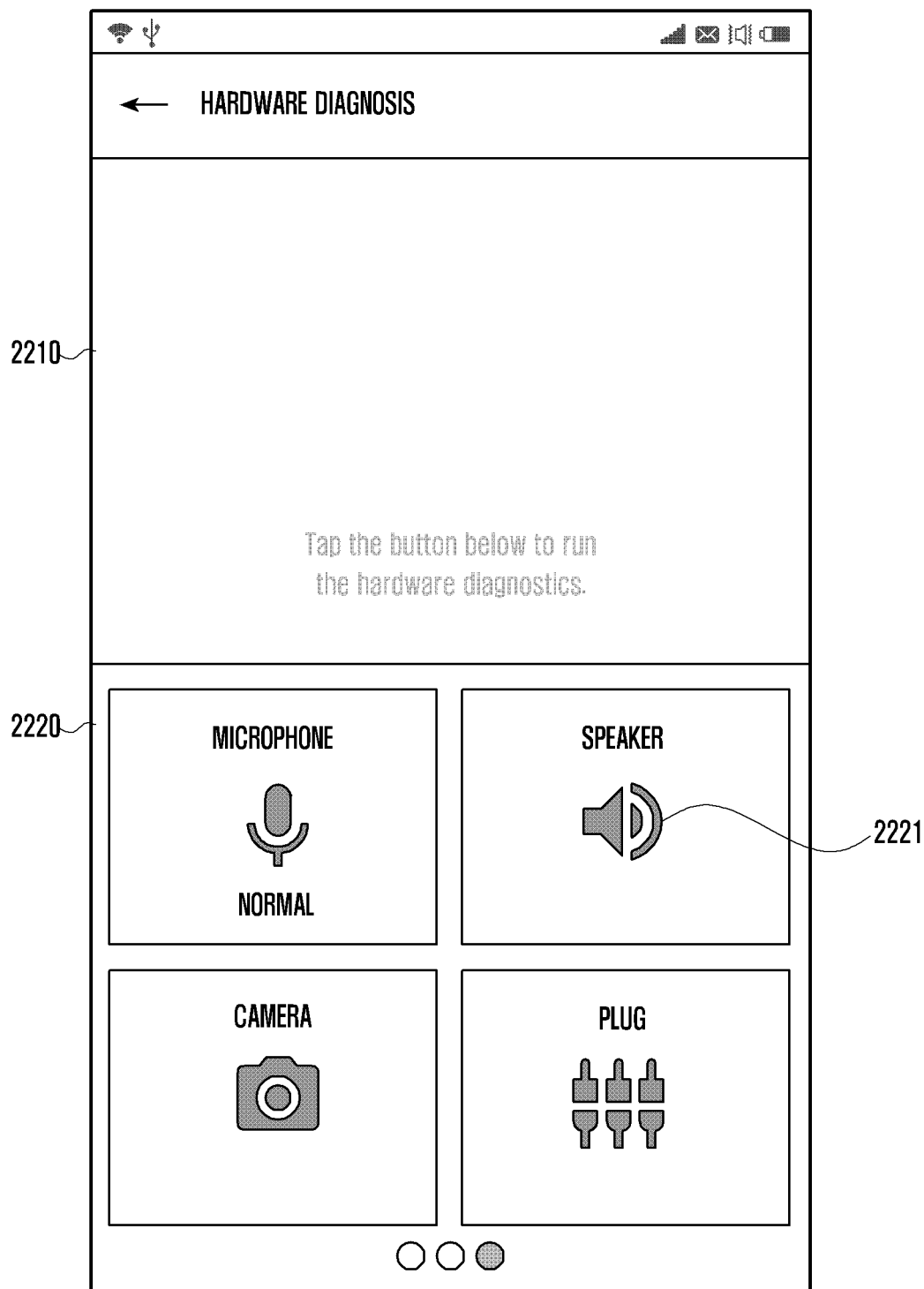
FIGS. 22A to 22F illustrate a user interface for displaying a speaker diagnosis operation and diagnosis result according to an embodiment of the present disclosure.
Figure 22B:
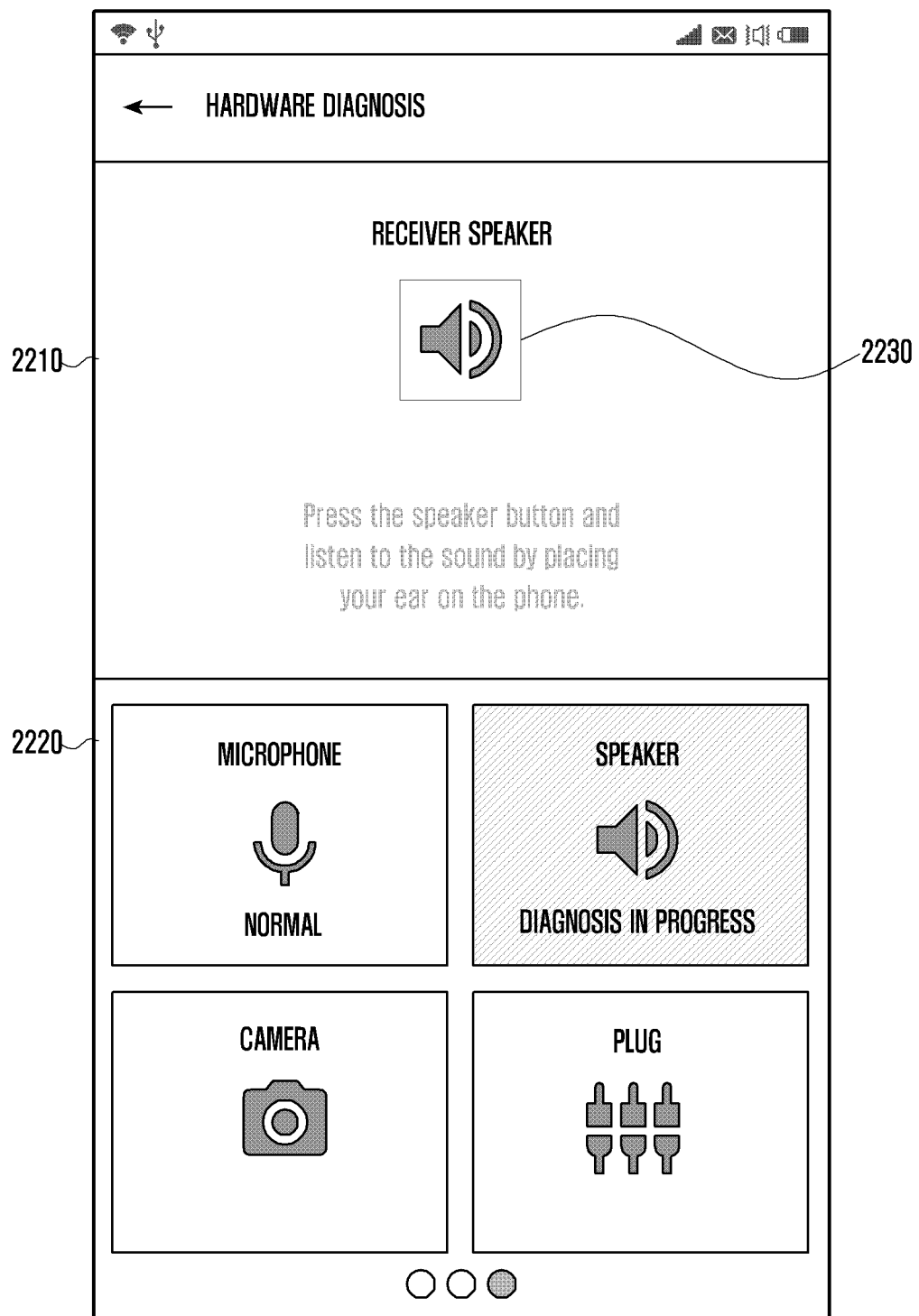

Referring to FIG. 22A, the AP 210 controls the display 260 to display a guidance window 2210 and a diagnosis target selection window 2220. If the speaker icon 2221 is selected in the diagnosis target selection window 2220, the AP 210 starts diagnosis on a receiver speaker (e.g. the receiver 284) and a media speaker (e.g., the speaker 282). For example, if the speaker icon 2221 is selected, the AP 210 controls the display 260 to display, in the guidance window 2210, the first speaker button 2230, as illustrated in FIG. 22B.

Figure 22C:
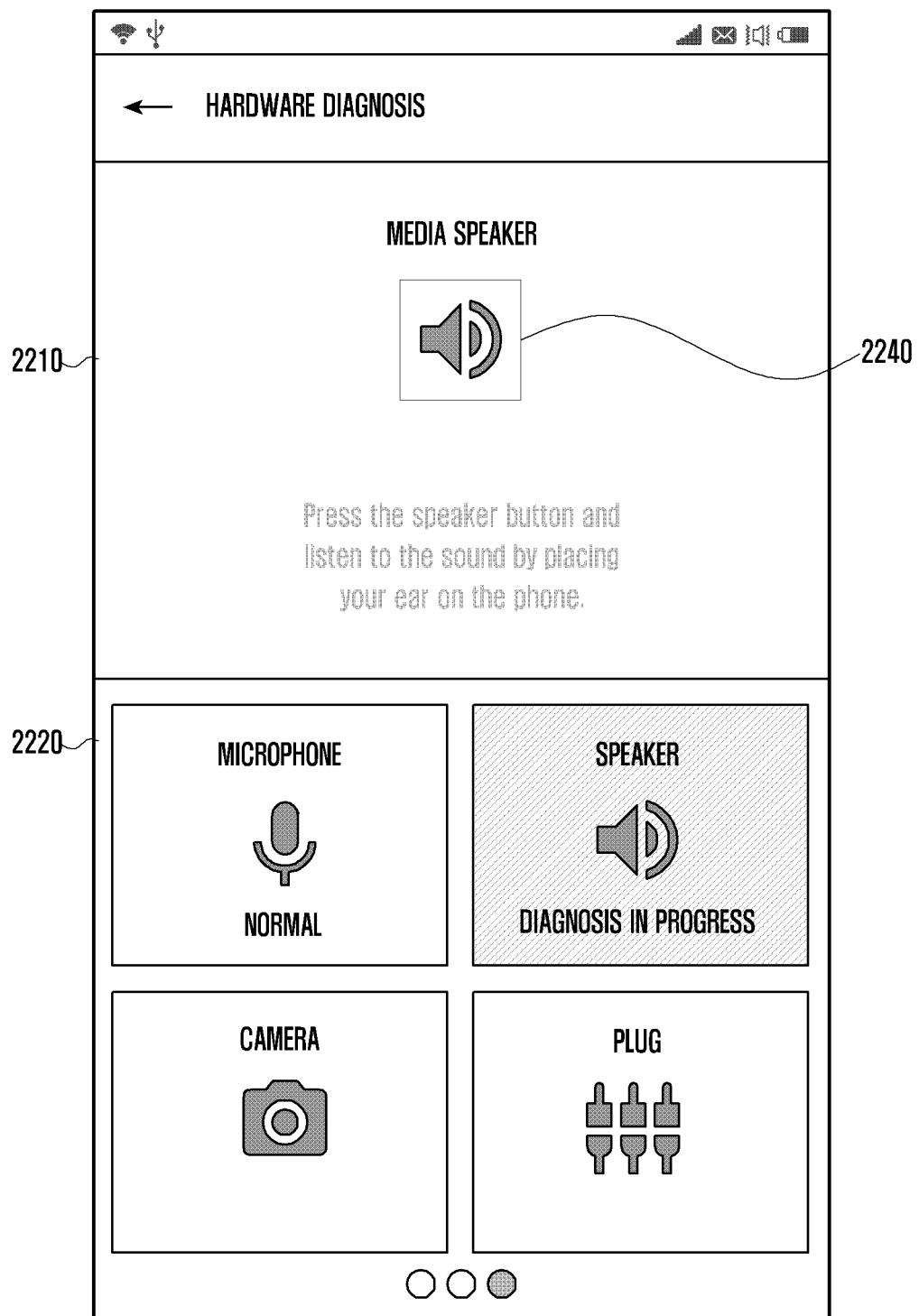

If the first speaker button 2230 is selected, the AP 210 controls the audio module 280 to output audio to the receiver 284, and if the output is completed, controls the display 260 to display, in the guidance window 2210, a second speaker button 2240, as illustrated in FIG. 22C.

Figure 22D:
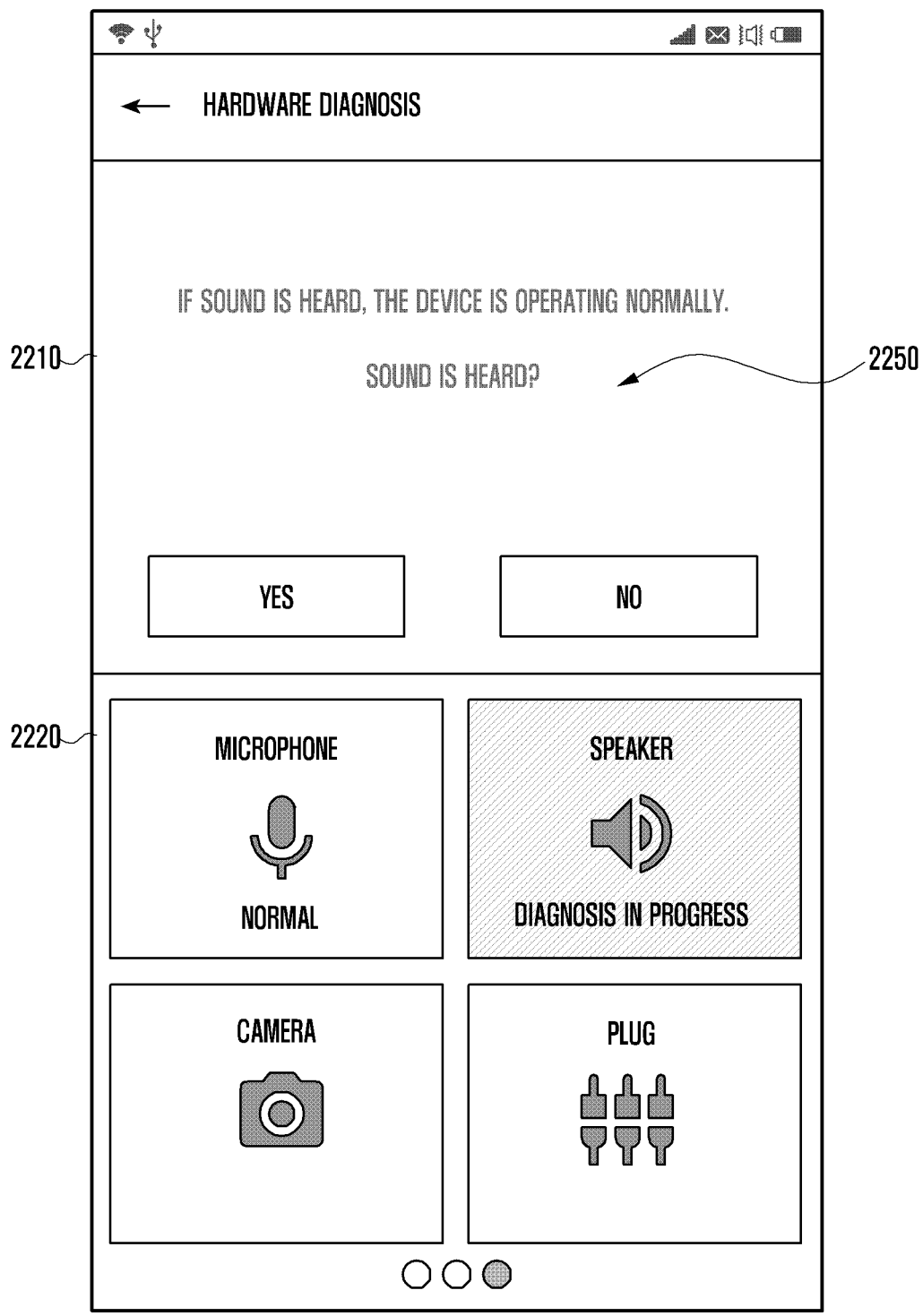

If the second speaker button 2240 is selected, the AP 210 controls the audio module 280 to output audio to the speaker 282, and if the output is completed, controls the display 260 to display, in the guidance window 2210, a message 2250 asking whether the audio is heard normally, as illustrated in FIG. 22D.

Figure 22E:
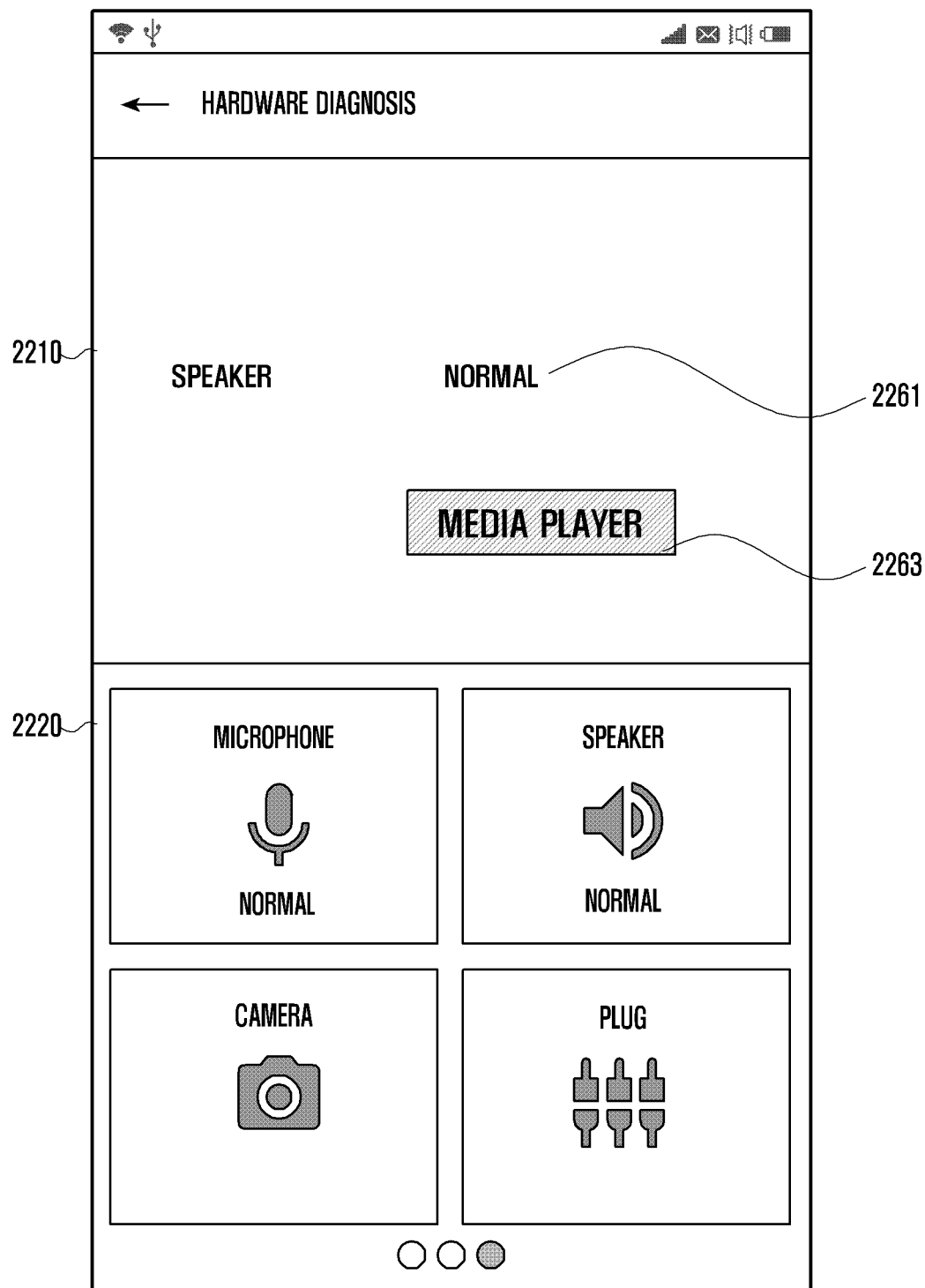

If the user selects the "Yes" button provided along with the message 2250, the AP 210 determines that the receiver speaker and the media speaker are operating normally, and thus, controls the display 260 to display, in the guidance window 2210, the information 2261 indicating that the speakers are operating normally and the text link "media player" 2263 associated with an application, as illustrated in FIG. 22E.

Figure 22F:
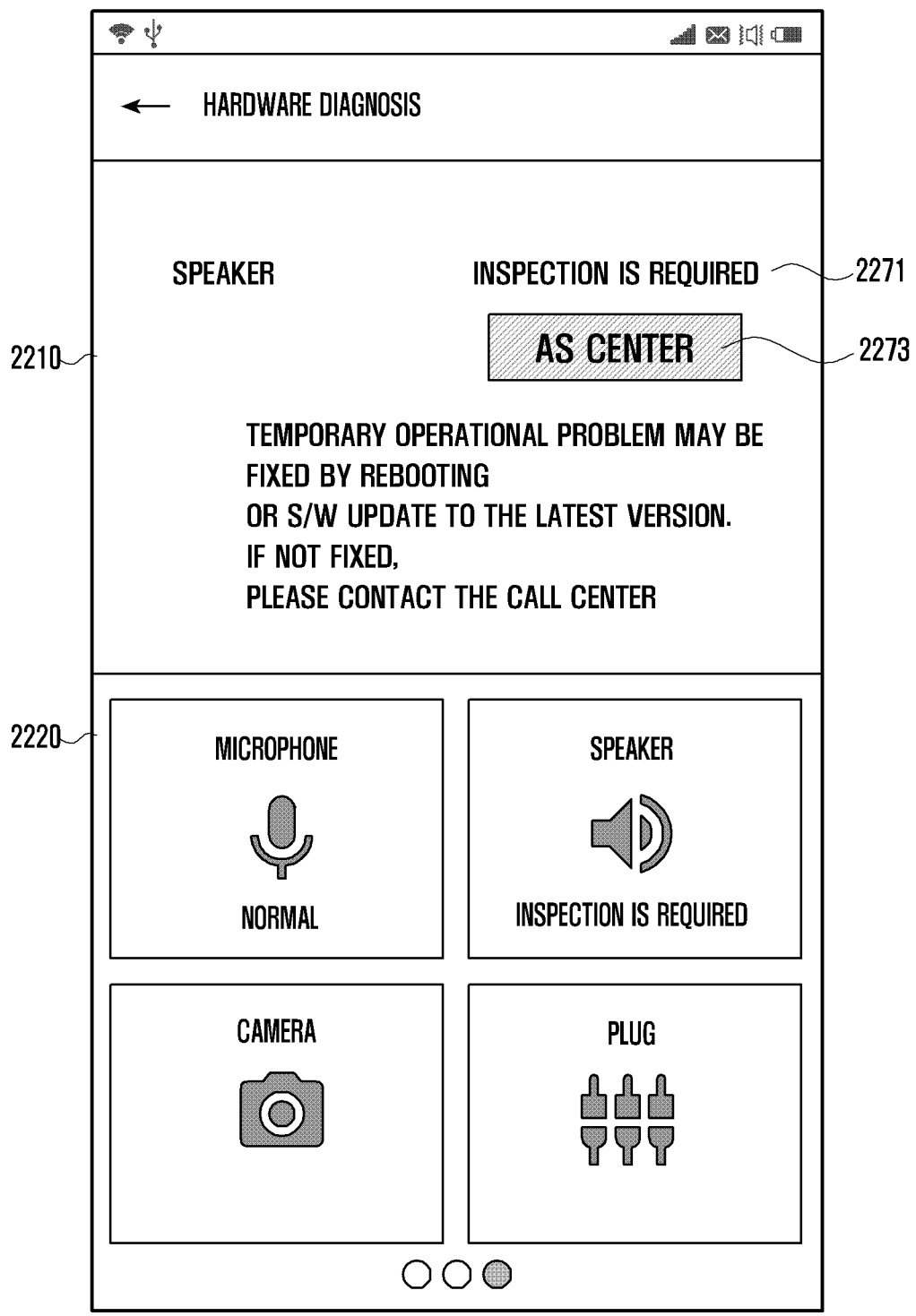

However, if the user selects the "No" button provided along with the message 2250, the AP 210 determines that one of the receiver speaker and the media speaker is operating abnormally, and thus, controls the display 260 to display the information 2271 indicating that the speakers are operating abnormally and the text link "AS center" 2273 associated with an AS request service, as illustrated in FIG. 22F.

FIGS. 23A to 23H illustrate a user interface for displaying a camera diagnosis operation and diagnosis result according to an embodiment of the present disclosure. Although the user interface of FIGS. 23A to 23H is described below as being displayed by the electronic device illustrated FIG. 2, it is not limited thereto.

Figure 23A:
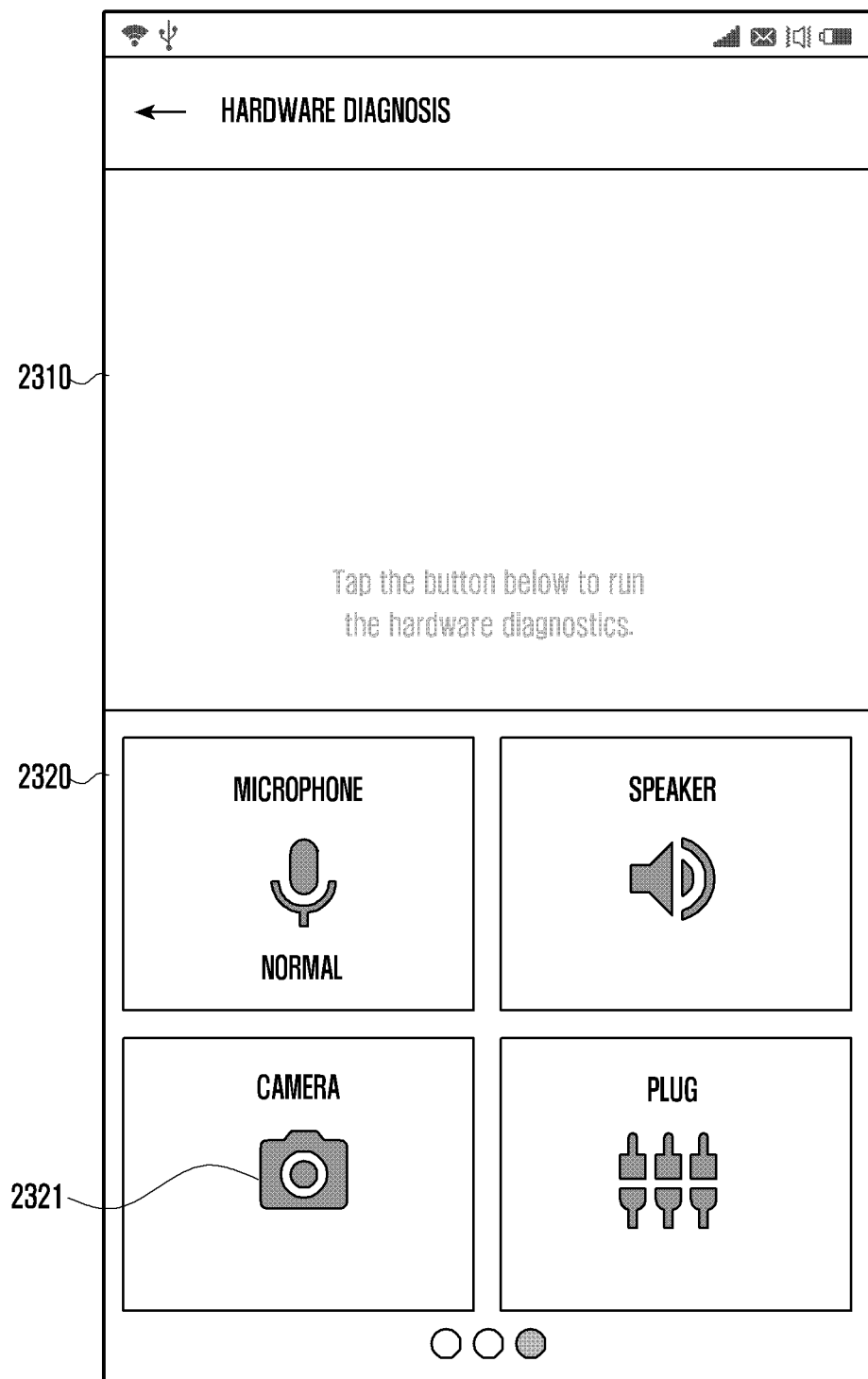
FIGS. 23A to 23H illustrate a user interface for displaying a camera diagnosis operation and diagnosis result according to an embodiment of the present disclosure.

Referring to FIG. 23A, the AP 210 controls the display 260 to display a guidance window 2310 and a diagnosis target selection window 2320. If a camera icon 2321 is selected in the diagnosis target selection window 2320, the AP 210 starts diagnosis on the camera module 291.

Figure 23B:
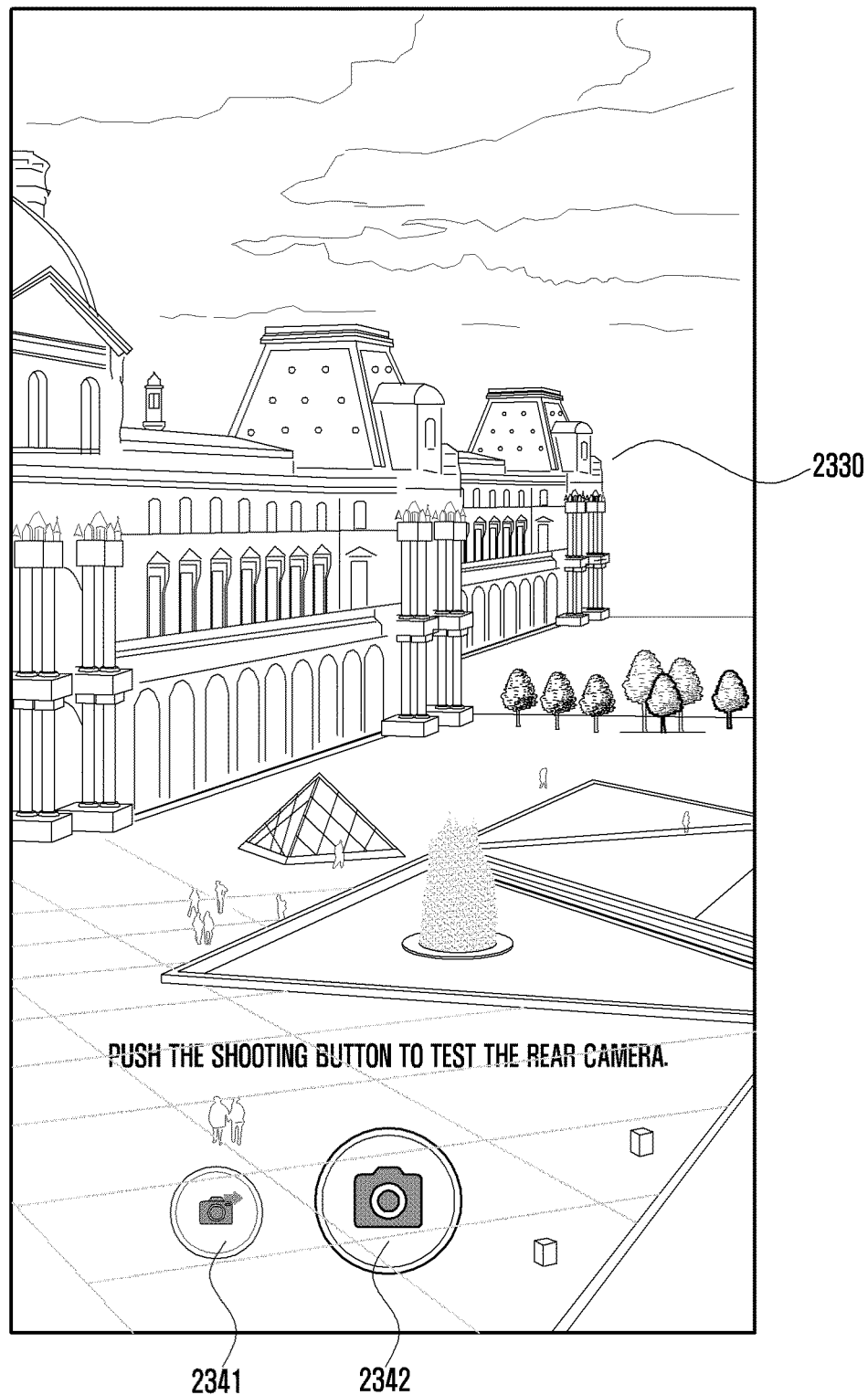

Referring to FIG. 23B, if the camera icon 2321 is selected, the AP 210 controls the display 260 to display an image sensor switching button 2341 and a shooting button 2342 along with the image 2330 taken by the rear image sensor of the camera module 291 (and then processed by the AP 210).

Figure 23C:
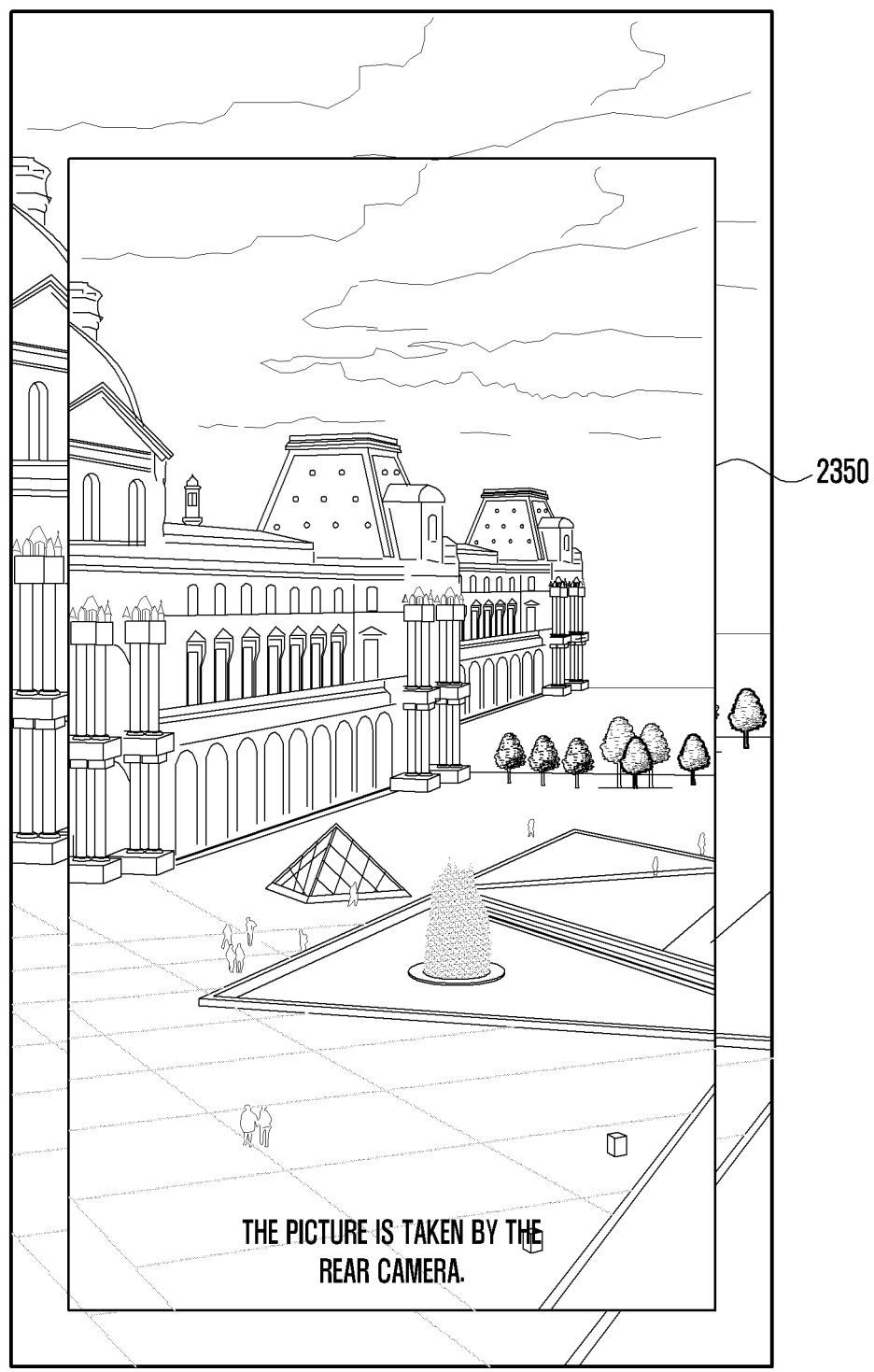

If the shooting button 2342 is selected when the image 2330 is displayed, the AP 210 stores the image taken by the rear image sensor of the camera module 291 (and then processed by the AP 210) in the memory 230 and controls the display 260 to display the image 2350 stored after being taken (and then processed), as illustrated in FIG. 23C.

Figure 23D:
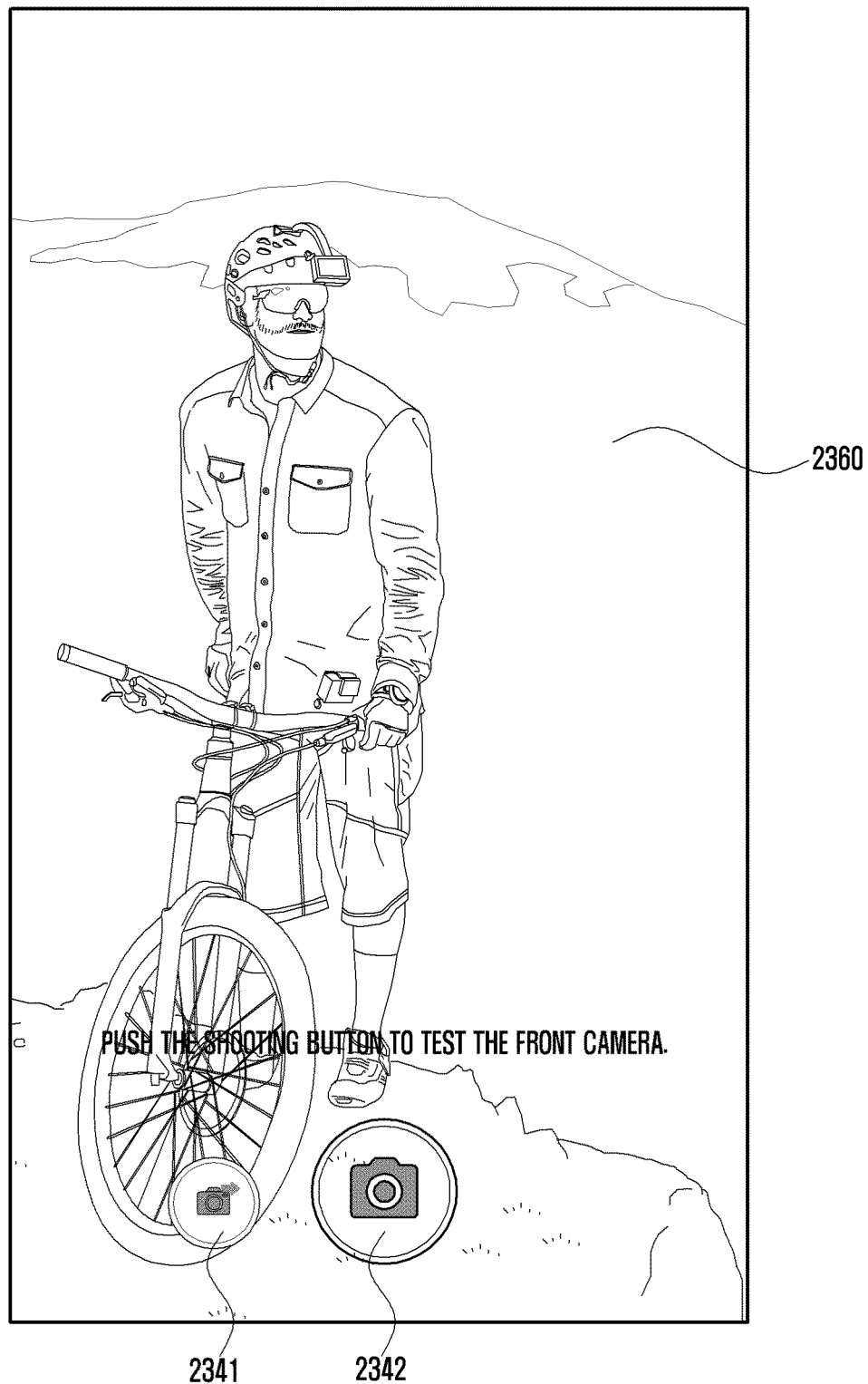

If a touch input is detected on the touch panel 252 or the switching button 2341 is selected a predetermined time (e.g., 3 seconds) after the image 2350 is displayed or when the image 2340 is displayed, the AP 210 controls the display 260 to display the image 2360 taken by the front image sensor (and then processed by the AP 210) along with the switching button 2341 and the shooting button 210, as illustrated in FIG. 23D.

Figure 23E:
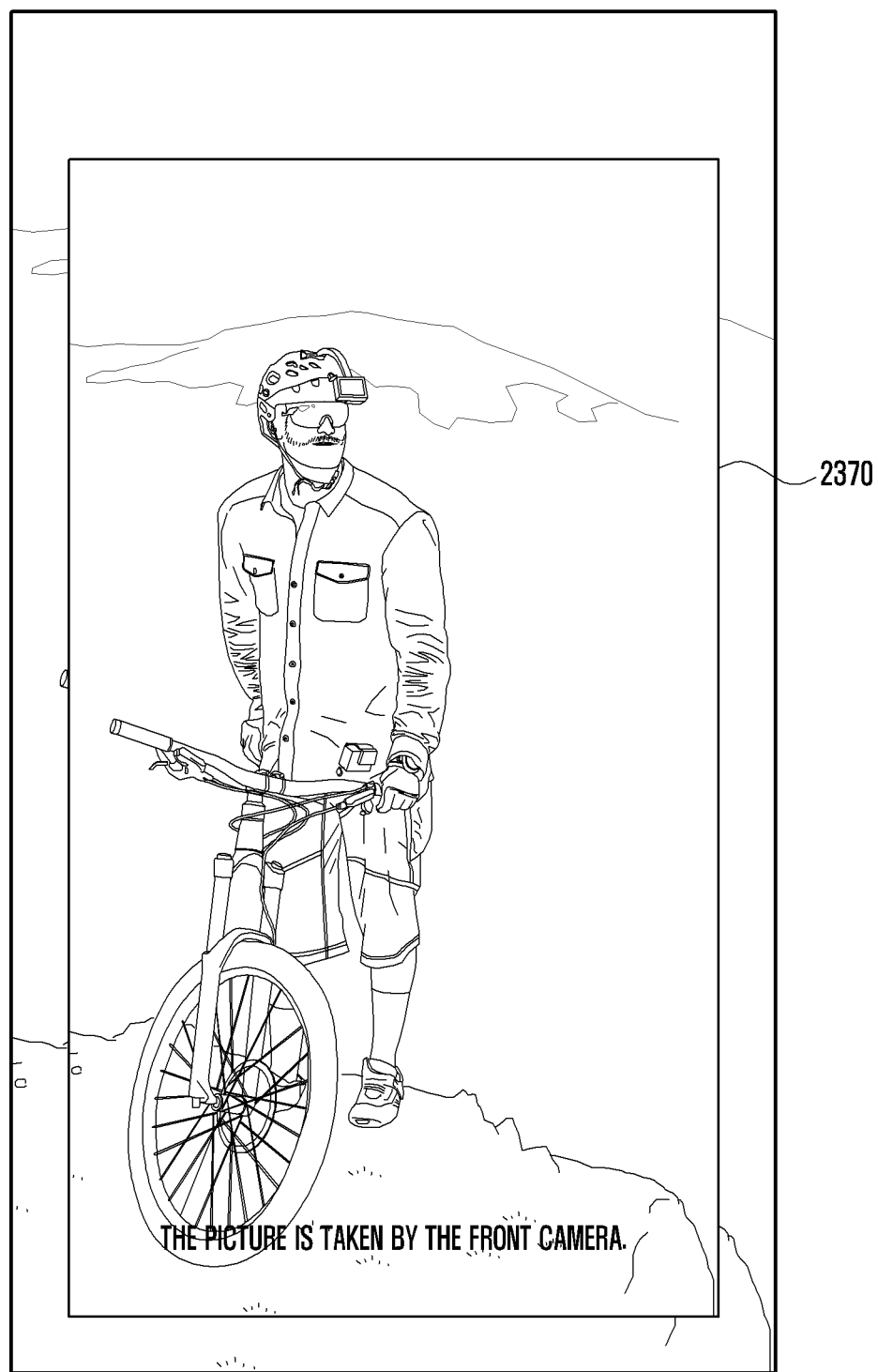

If the shooting button 242 is selected when the image 2360 is displayed, the AP 210 stores the image taken by the front image sensor of the camera module 291 (and then processed by the AP 210) in the memory 230 and controls the display 260 to display the image 2370 stored after being taken (and then processed by the AP 210), as illustrated in FIG. 23E.

Figure 23F:
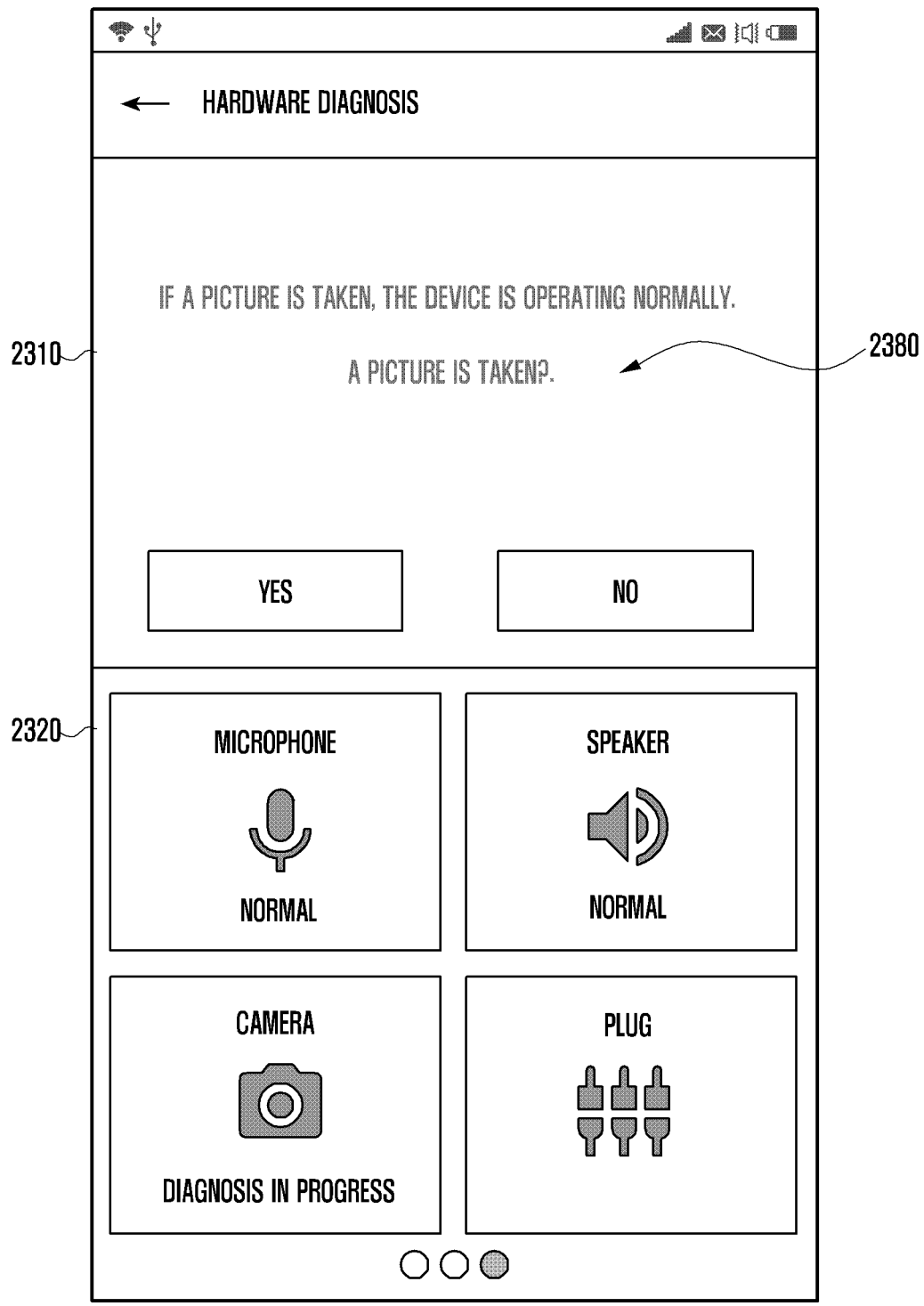

If a predetermined time period (e.g., 2 seconds) elapses or a touch input is detected on the touch panel 252 after an image is taken by the front/rear image sensor, the AP 210 may control the display 260 to display, in the guidance window 2310, a message 2380 asking whether the image is taken normally, as illustrated in FIG. 23F.

Figure 23G:
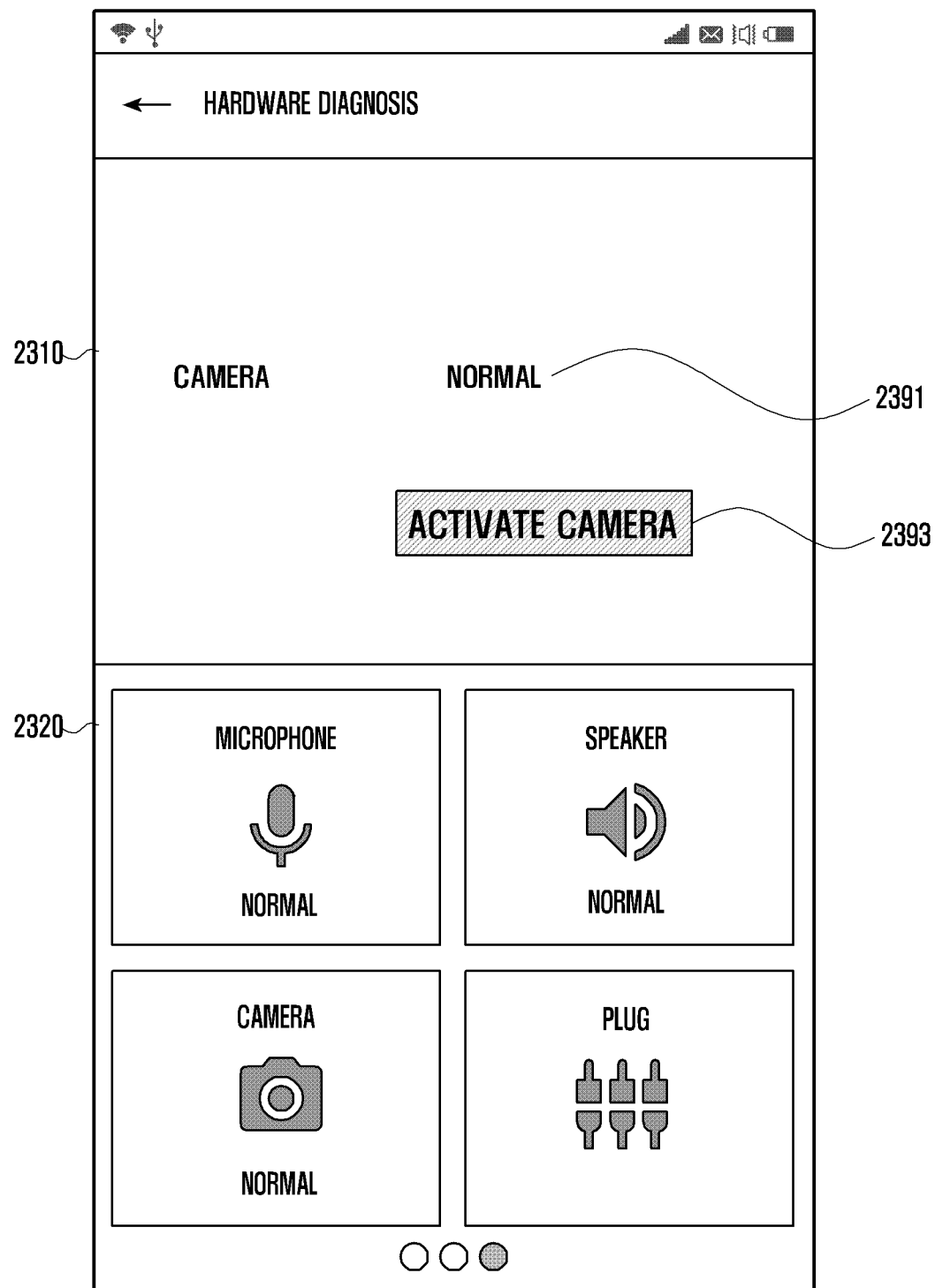

If the user selects the "Yes" button provided with the message 2380, the AP 210 determines that the camera module 291 is operating normally and controls the display 260 to display, in the guidance window 2310, the information 2391 indicating that the camera module 291 is operating normally and the text link "camera execution" 2393 associated with an application, as illustrated in FIG. 23G.

Figure 23H:
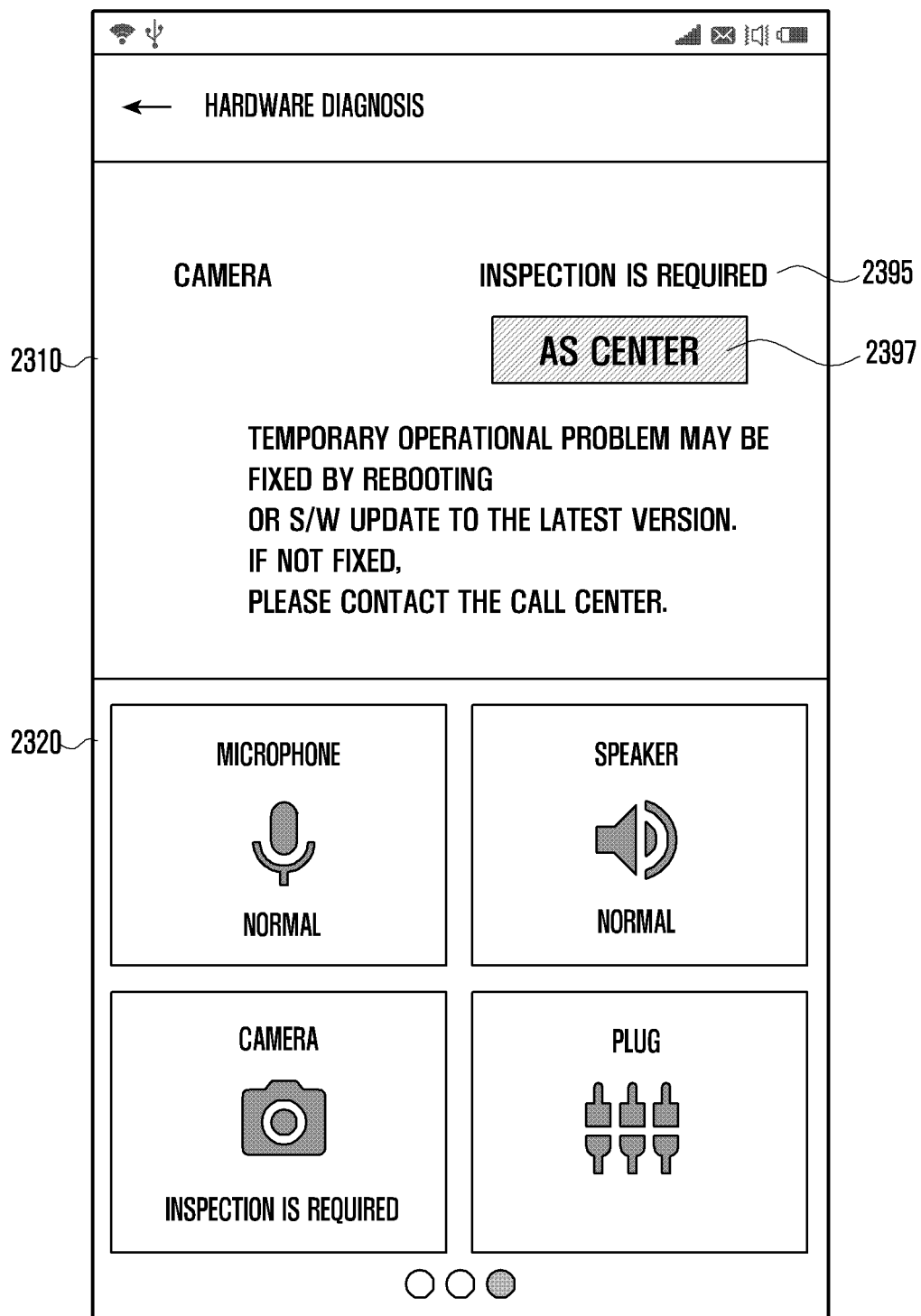

However, if the user selects the "No" button provided with the message 2380, the AP 210 determines that the camera module 291 is operating abnormally and controls the display 260 to display the information 2395 indicating the abnormality and the text link "AS center" 2397 associated with an AS request service, as illustrated in FIG. 23H.

FIGS. 24A to 24G are diagrams for explaining a user interface for displaying a plug diagnosis operation and diagnosis result according to various embodiments of the present disclosure. Although the user interface of FIGS. 24A to 24G is described below as being displayed by the electronic device illustrated FIG. 2, it is not limited thereto.

Figure 24A:
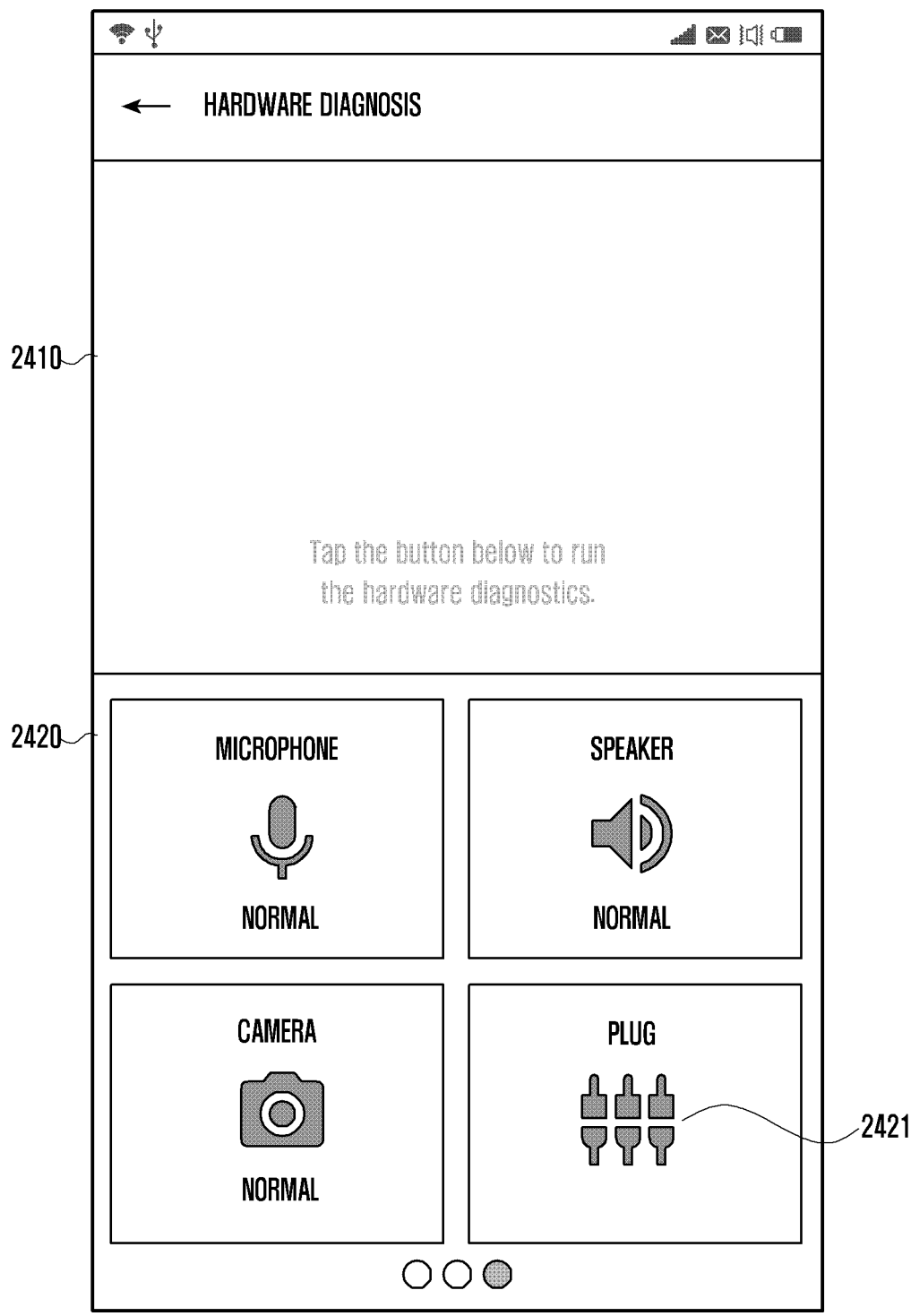
FIGS. 24A to 24G illustrate a user interface for displaying a plug diagnosis operation and diagnosis result according to an embodiment of the present disclosure.
Figure 24B:
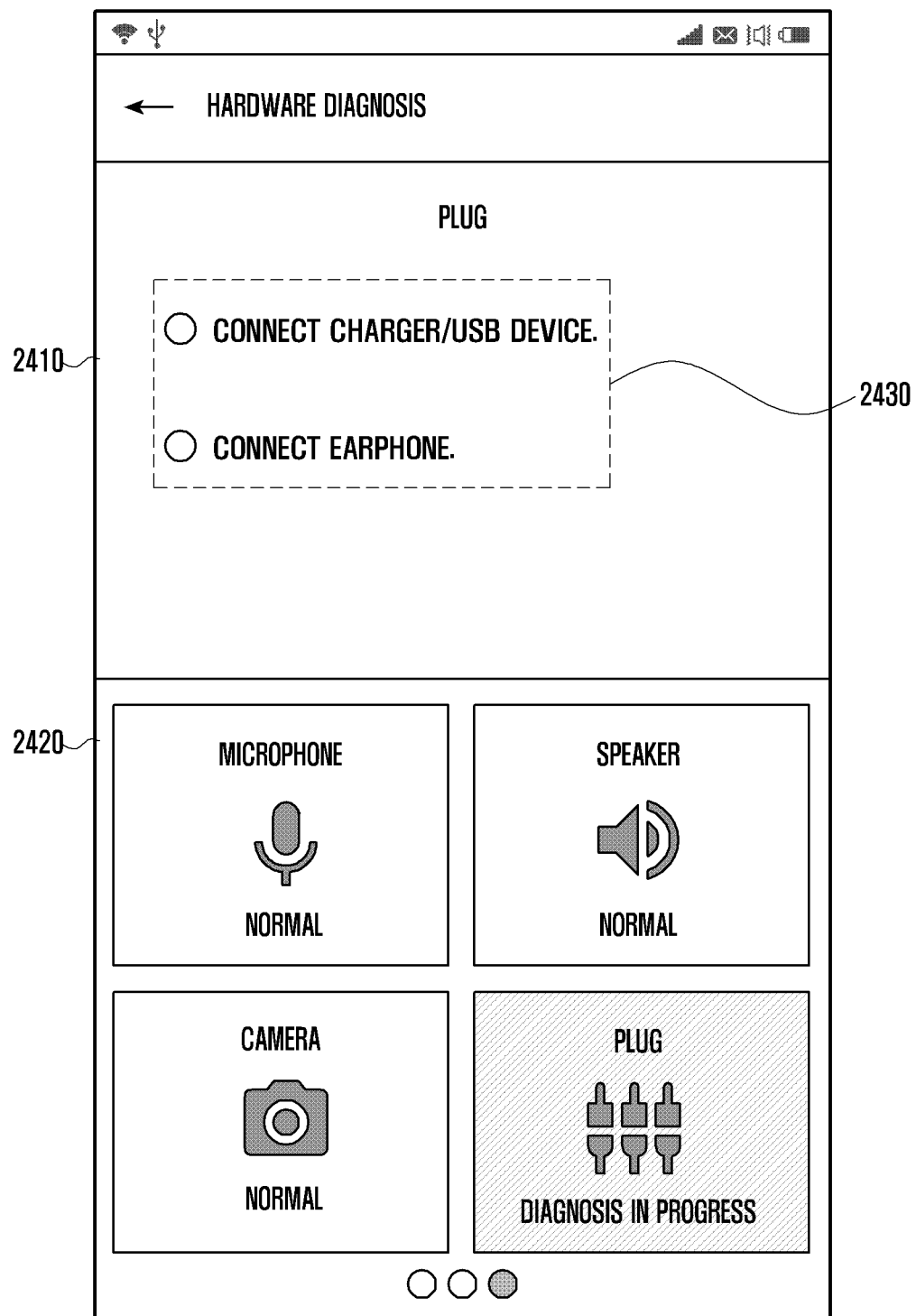

Referring to FIG. 24A, the AP 210 controls the display 260 to display a guidance window 2410 and a diagnosis target selection window 2420. If the plug icon 2421 is selected in the diagnosis target selection window 2420, the processor starts diagnosis on the plug (e.g., the microphone 288 and the USB 274). For example, if the plug icon 2421 is selected, the AP 210 controls the display 260 to display, in the guidance window 2410, a message 2430 prompting the user to connect a plug, as illustrated in FIG. 24B.

Figure 24C:
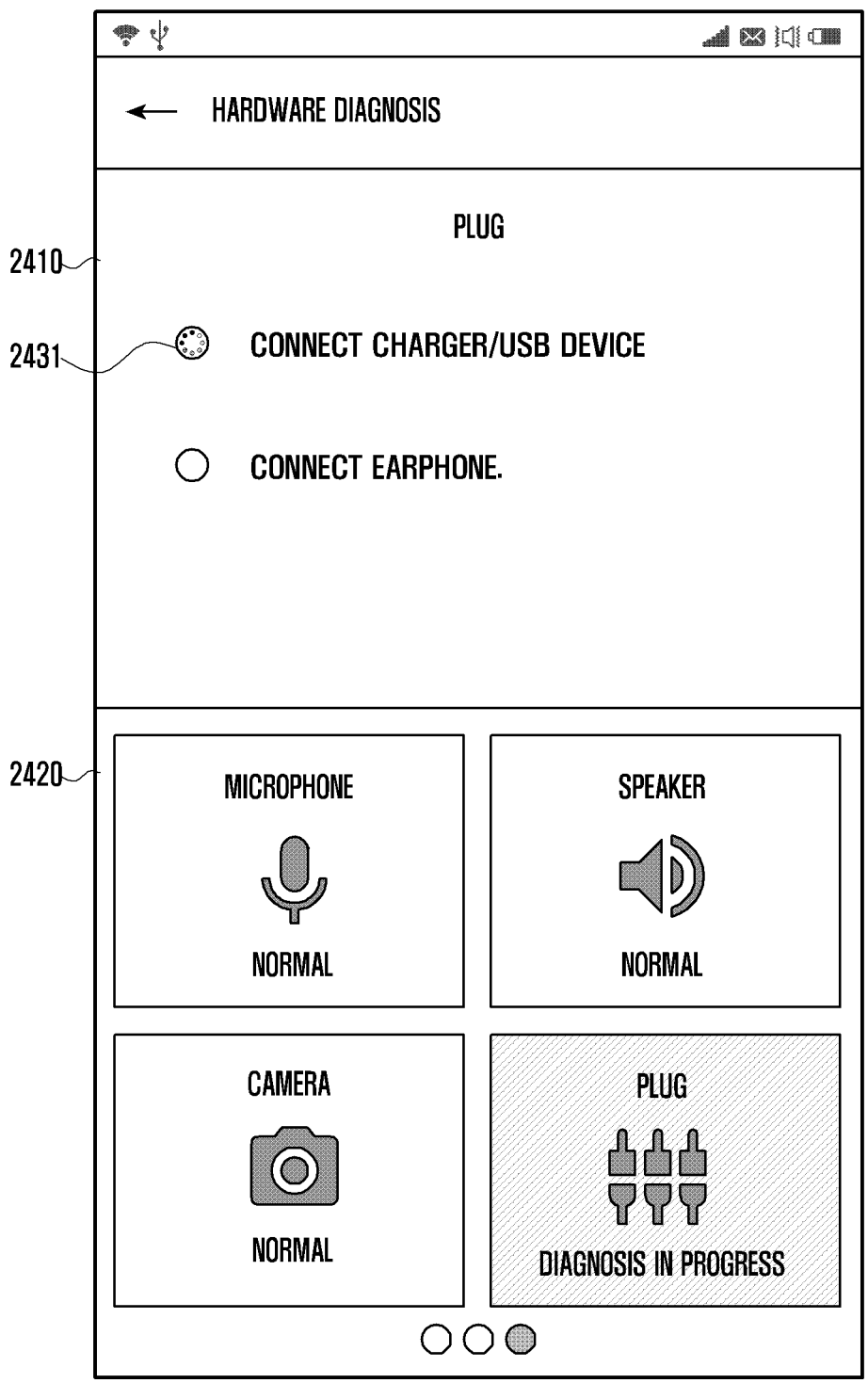

If an external device is connected to the USB 274, the processor controls the display 260 to display, in the guidance window 2410, an icon 2431 indicating external device recognition in progress, as illustrated in FIG. 24C.

Figure 24D:
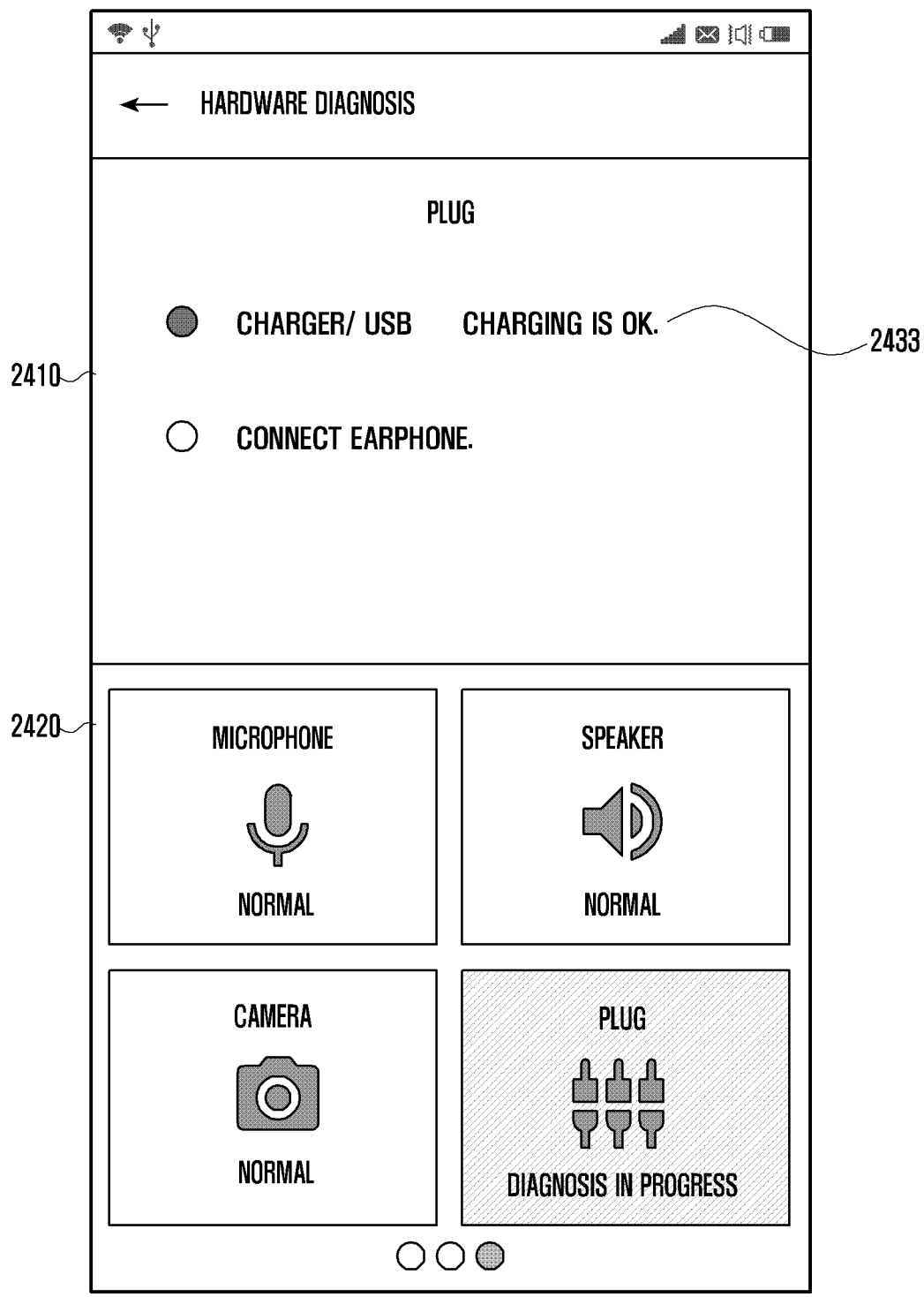

If the external device is recognized as a charger, the AP 210 control the power management module 295 to charge the battery 296. The AP 210 also controls the display 260 to display, in the guidance window 2410 the information 2433 indicating that the USB 274 is operating normally (i.e., USB-based charging is possible), as illustrated in FIG. 24D.

Figure 24E:
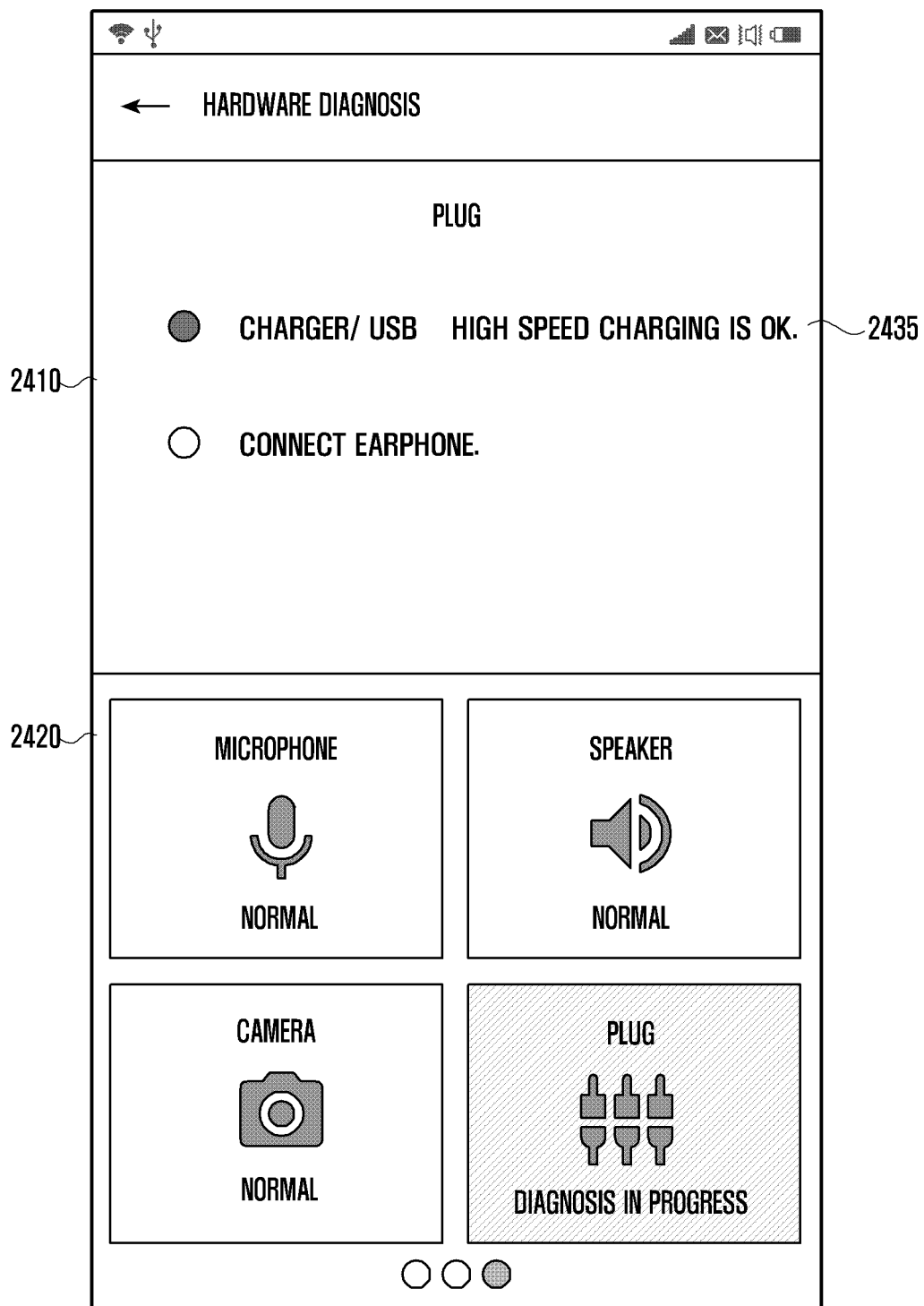

If the external device is recognized as a high-speed charger, the AP 210 controls the display 260 to display, in the guidance window 2410, the information 2435 indicating that high-speed charging is possible, as illustrated in FIG. 24E.

Figure 24F:
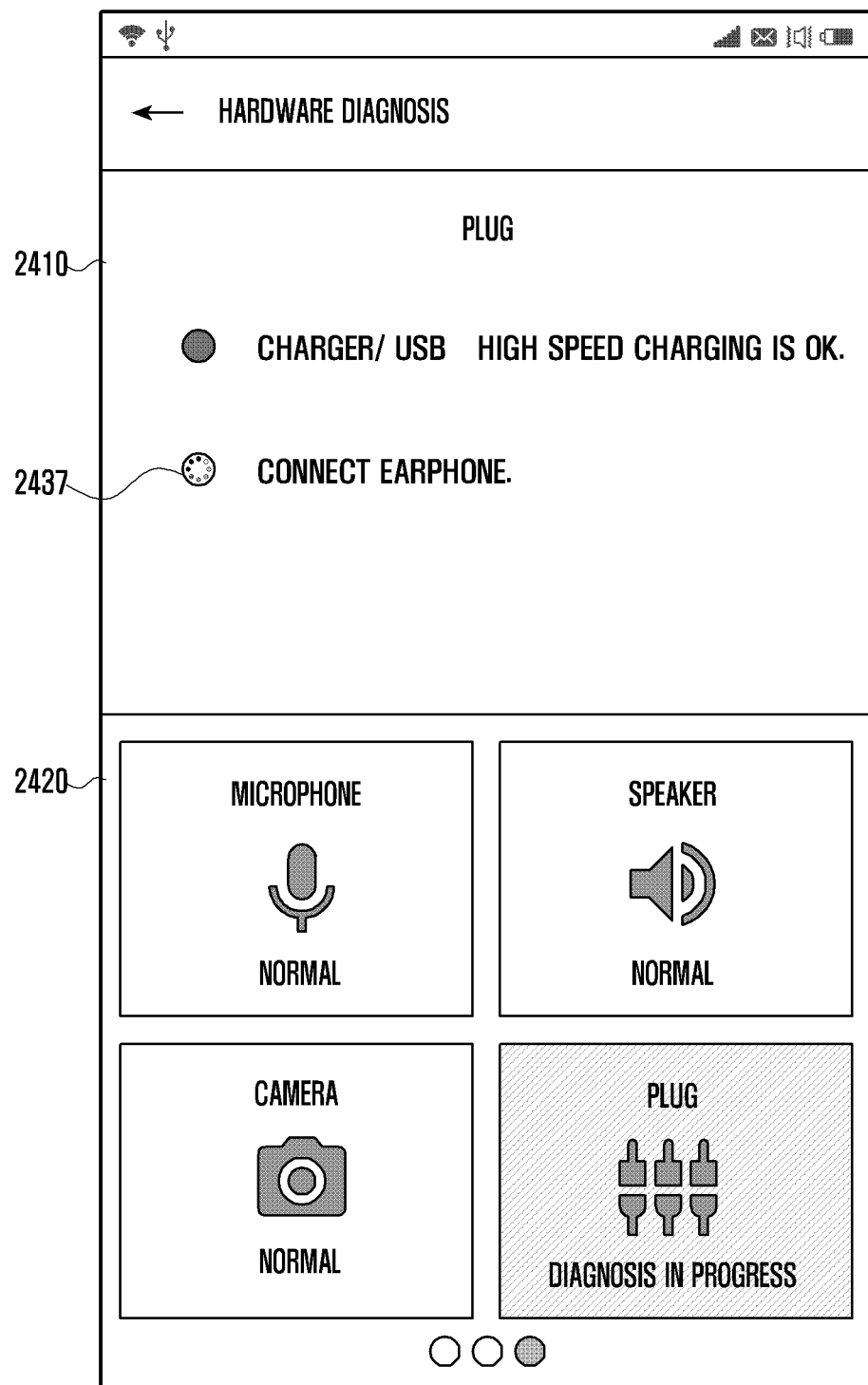
Figure 24G:
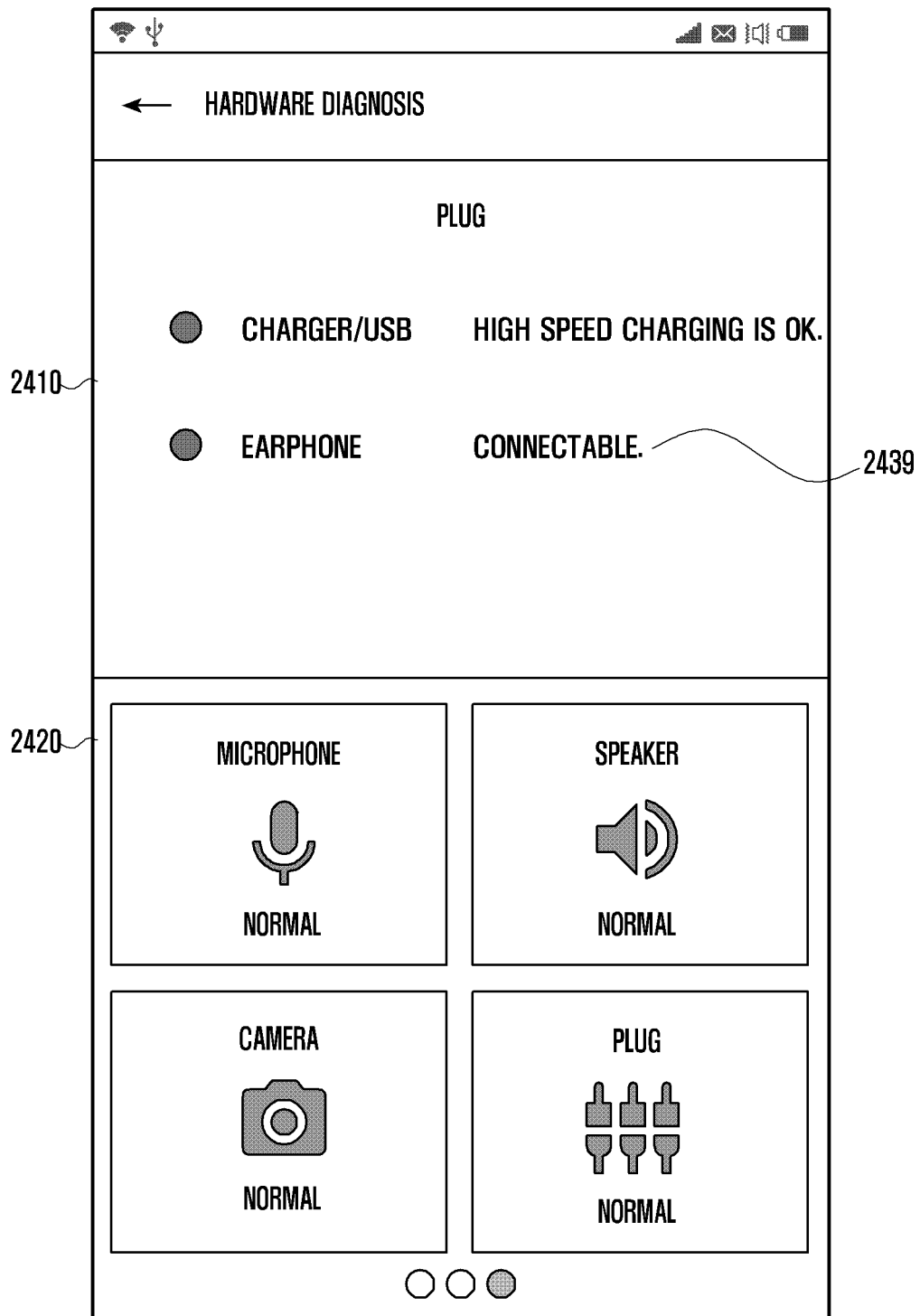

If a plug of an earphone 286 is inserted into a socket, the AP 210 recognizes that the earphone 286 is connected to the audio module 280 and controls the display 260 to display, in the guidance window 2410, the information 2437 indicating that the connection recognition is in progress, as illustrated in FIG. 24F. The AP 210 also controls the display 260 to display, in the guidance window 2410, the information 2439 indicating that the earphone 286 is connected, as illustrated in FIG. 24G.

FIGS. 25A to 25D illustrate a user interface for displaying an application use right restriction process according to an embodiment of the present disclosure. Although the user interface of FIGS. 25A to 25D is described below as being displayed by the electronic device illustrated FIG. 2, it is not limited thereto.

Referring to FIG. 25A to 25D, a related application is executed during the hardware diagnosis. If the application is configured with a usage right, the processor 201 asks the user whether to use the application, and if the user enters an accept, perform hardware diagnosis. If the user enters a reject, the AP 210 may stop the hardware diagnosis.

Figure 25A:
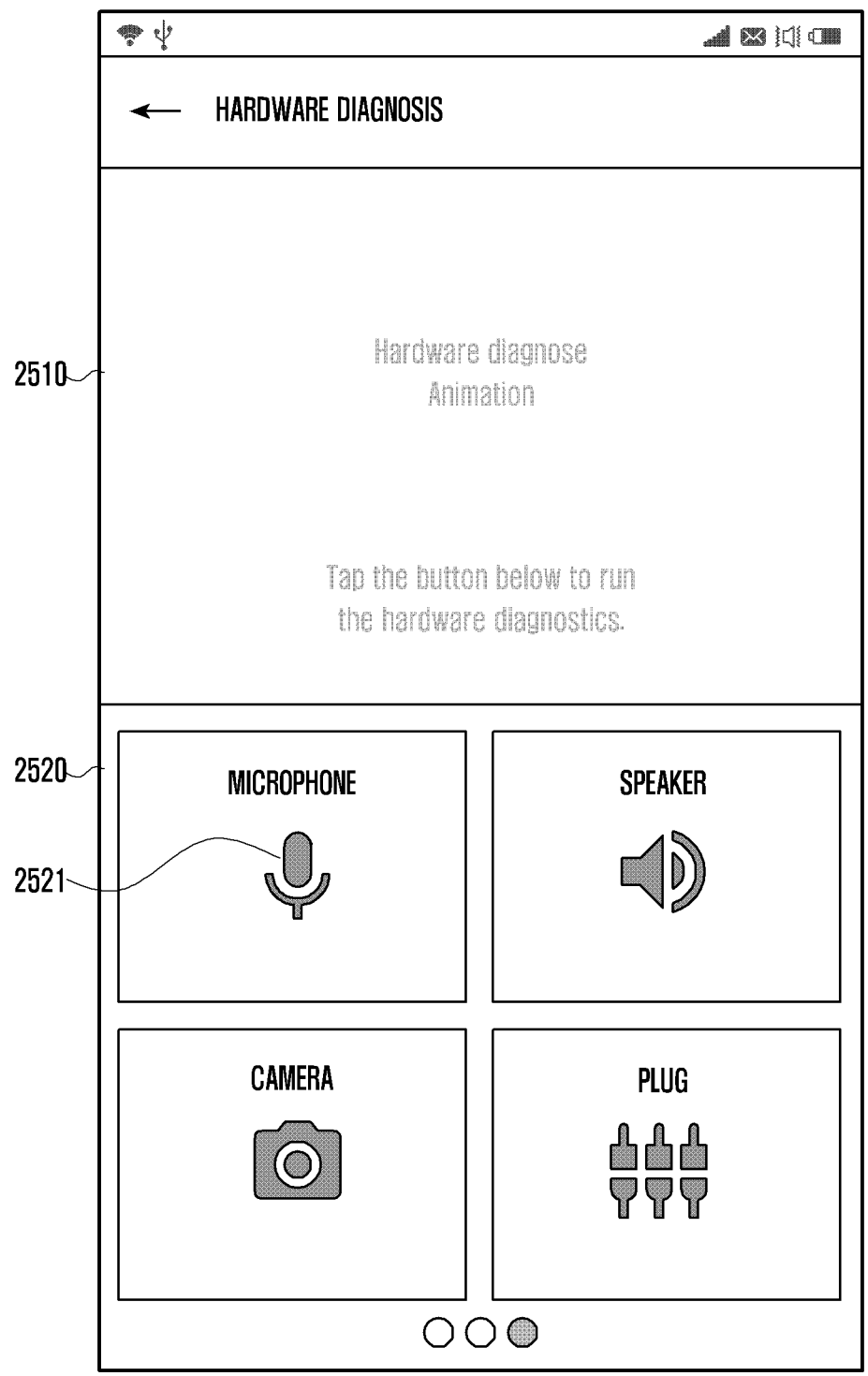
FIGS. 25A to 25D illustrate a user interface for displaying an application use right restriction process according to an embodiment of the present disclosure.
Figure 25B:
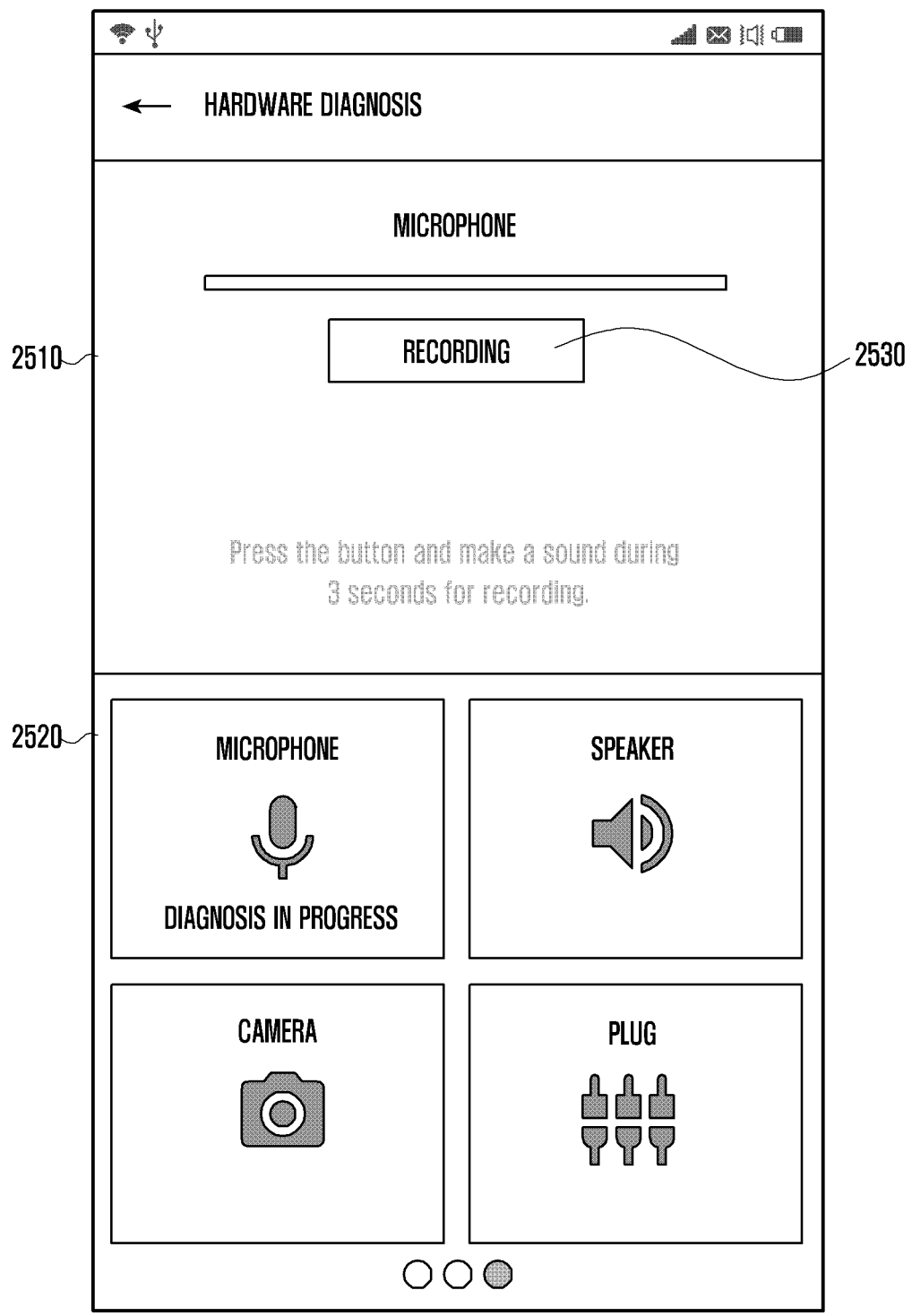
Figure 25C:
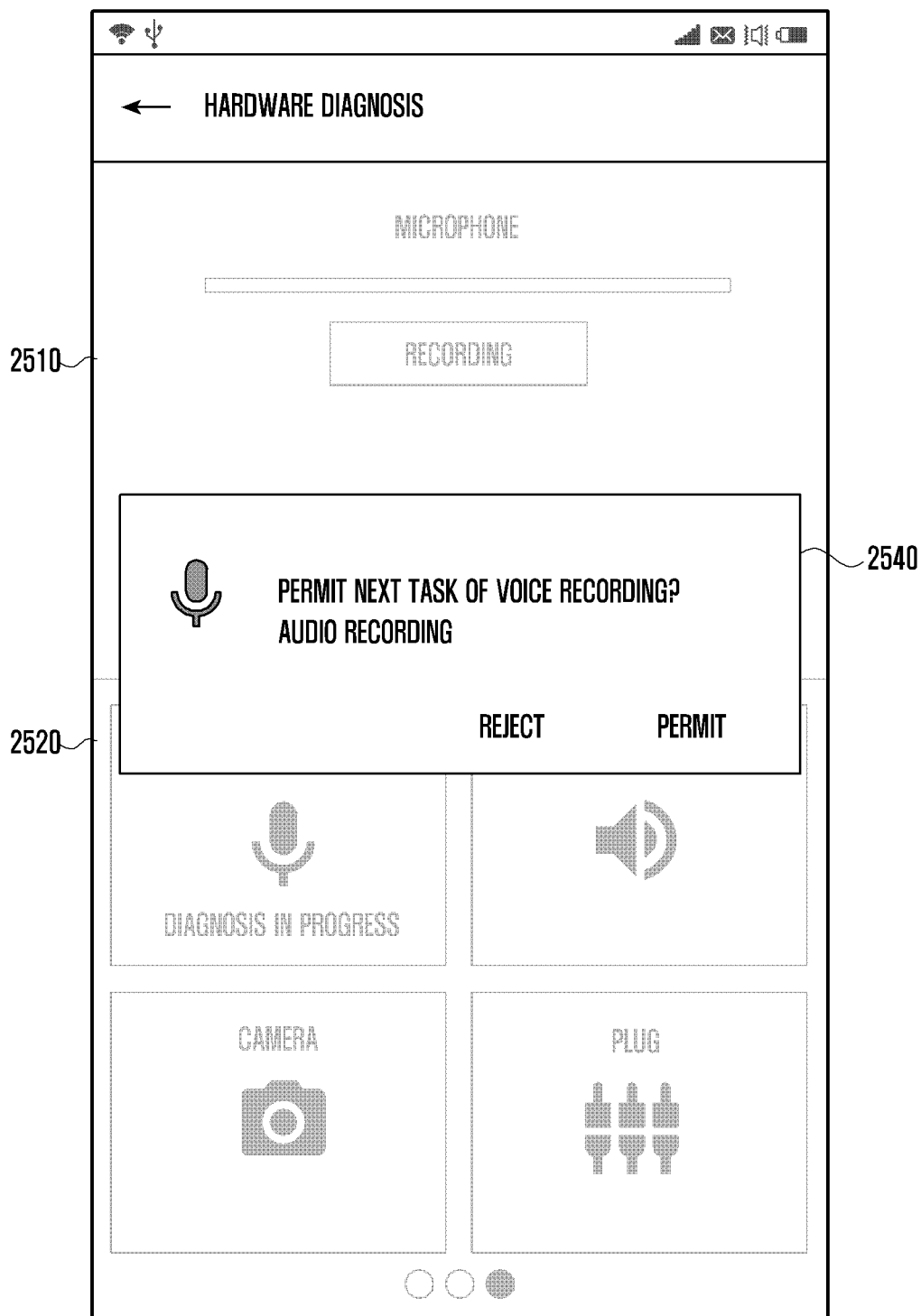

For example, the AP 210 controls the display 260 to display a guidance window 2510 and a diagnosis target selection window 2520. If a microphone icon 2521 is selected in the diagnosis target selection window 2520, the AP 210 controls the display 260 to display, in the guidance window 2510, a recording button 2530, as illustrated in FIG. 25B. If the recording button 2530 is selected, the AP 210 controls the display 260 to display the popup window 2540 asking whether to perform recording, as illustrated in FIG. 25C.

Figure 25D:
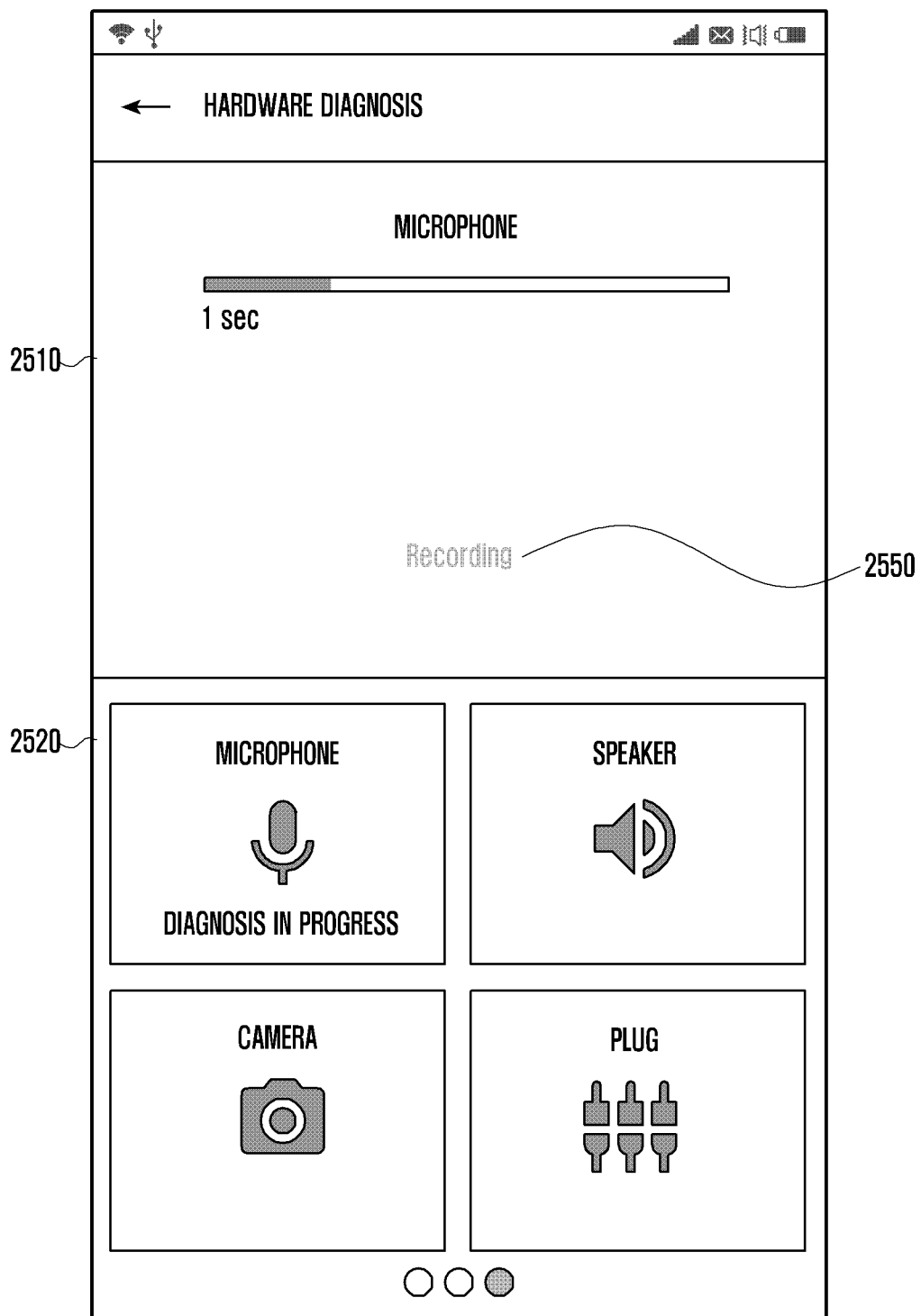

If the user selects an "accept" button provided in the popup window 2540, the AP 210 controls to hide the popup window 2540, performs recording of the voice data input through the microphone 288, and controls the display 260 to display, in the guidance window 2510, the information 2550 indicating that recording is in progress, as illustrated in FIG. 25D.

If the user selects a "reject" button provided in the popup window 2540, the AP 210 controls to hide the popup window 2540.

FIGS. 26A to 26G illustrate a user interface for displaying a temperature/humidity sensor diagnosis operation and diagnosis result according to an embodiment of the present disclosure. Although the user interface of FIGS. 26A to 26G is described below as being displayed by the electronic device illustrated FIG. 2, it is not limited thereto.

Figure 26A:
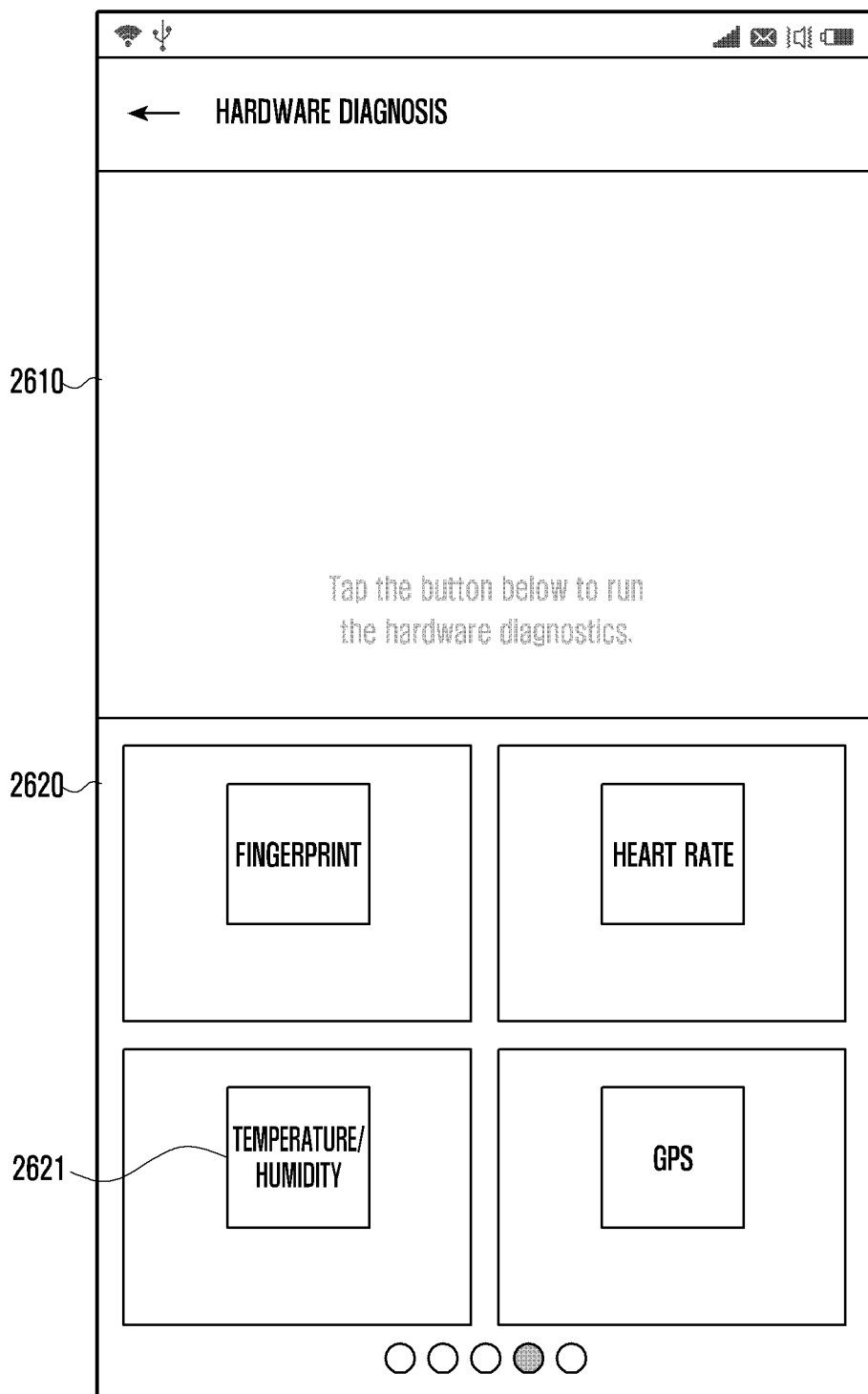
FIGS. 26A to 26G illustrate a user interface for displaying a temperature/humidity sensor diagnosis operation and diagnosis result according to an embodiment of the present disclosure.
Figure 26B:
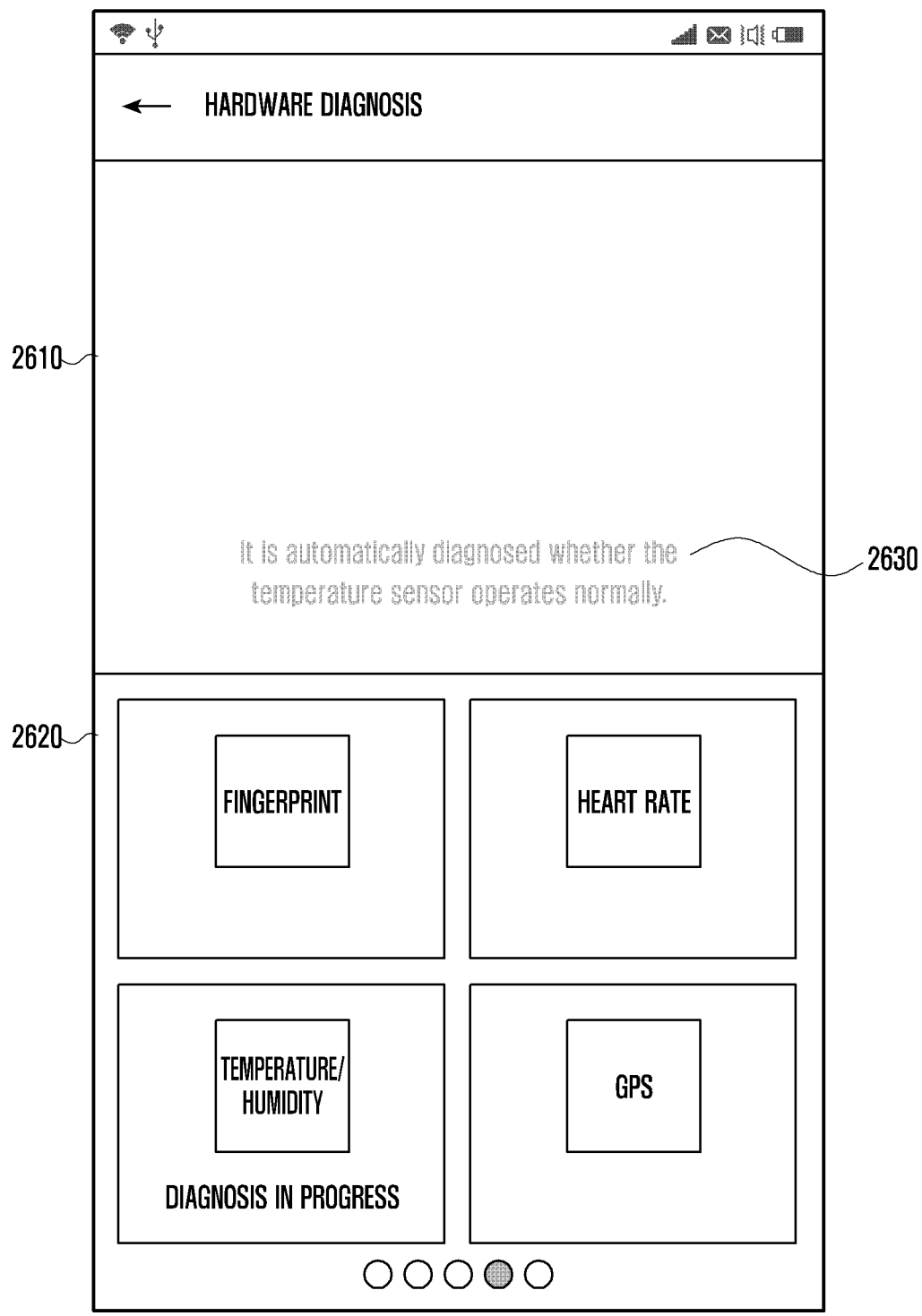

Referring to FIG. 26A, the AP 210 controls the display 260 to display a guidance window 2610 and a diagnosis target selection window 2620. If the temperature/humidity icon 2621 is selected, the AP 210 starts diagnosis on the temperature/humidity sensor 240J. For example, if the temperature/humidity icon 2621 is selected, the AP 210 perform diagnosis on the temperature and controls the display 260 to display, in the guidance window 2610, the information 2630 indicating that the temperature sensor diagnosis is in progress, as illustrated in FIG. 26B.

Figure 26C:
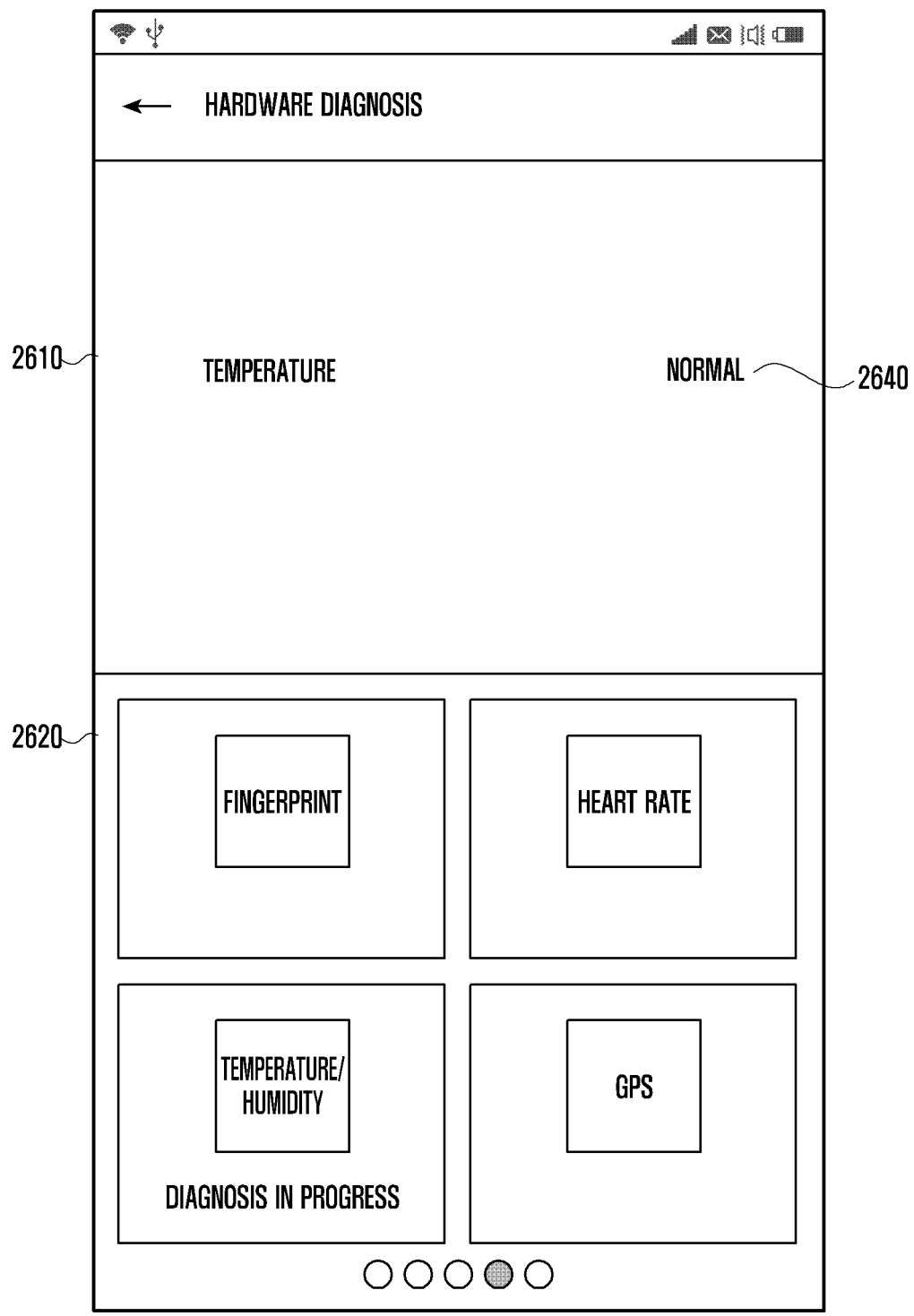

If it is determined that the temperature sensor is operating normally, the AP 210 controls the display 260 to display, in the guidance window 2610, the information 2640 indicating that the temperature sensor is operating normally, as illustrated in FIG. 26C.

Figure 26D:
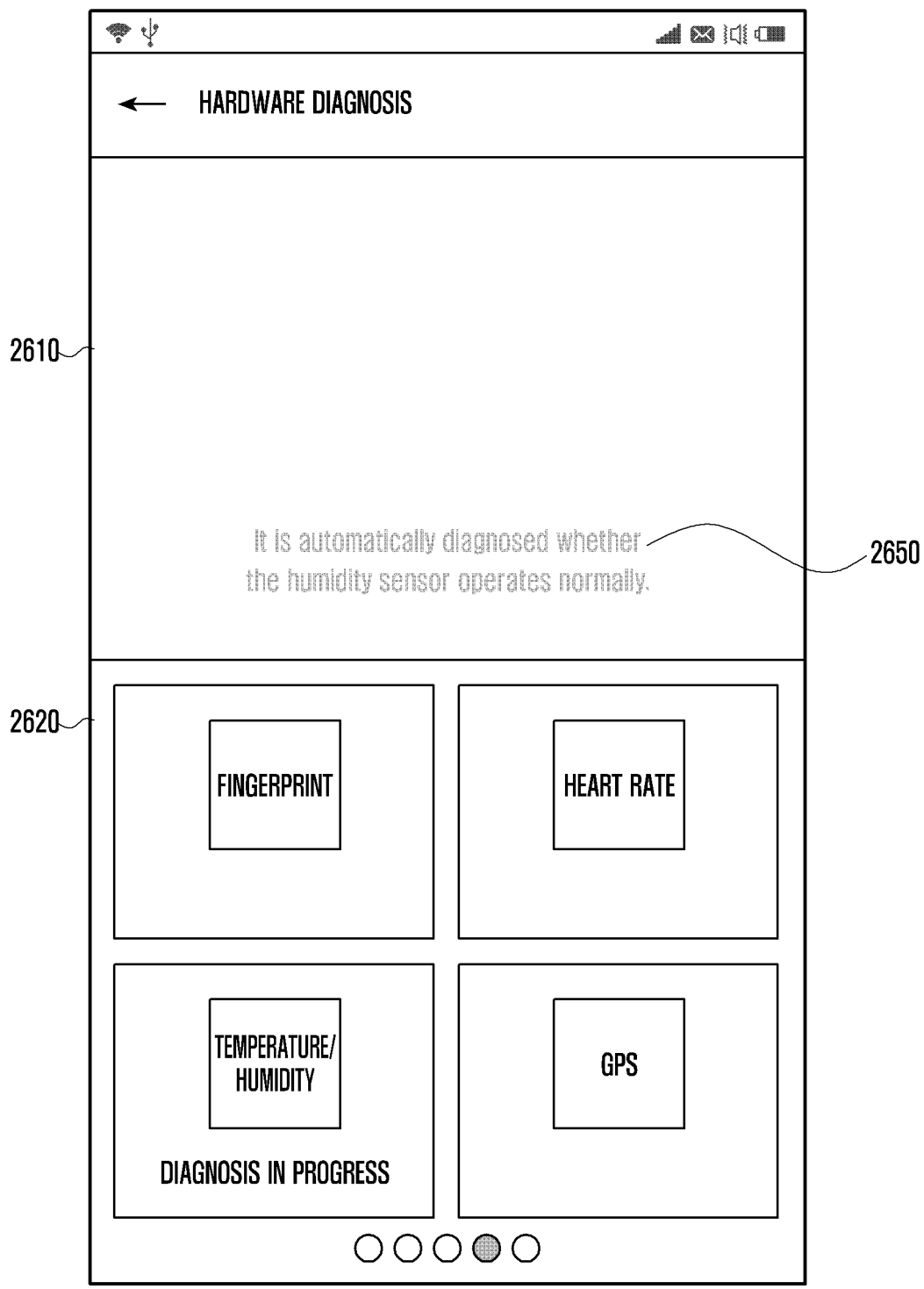

If the temperature sensor diagnosis is completed, the AP 210 perform diagnosis on the humidity sensor and controls the display 260 to display, in the guidance window 2610, the information 2650 indicating that the humidity sensor diagnosis is in progress, as illustrated in FIG. 26D.

Figure 26E:
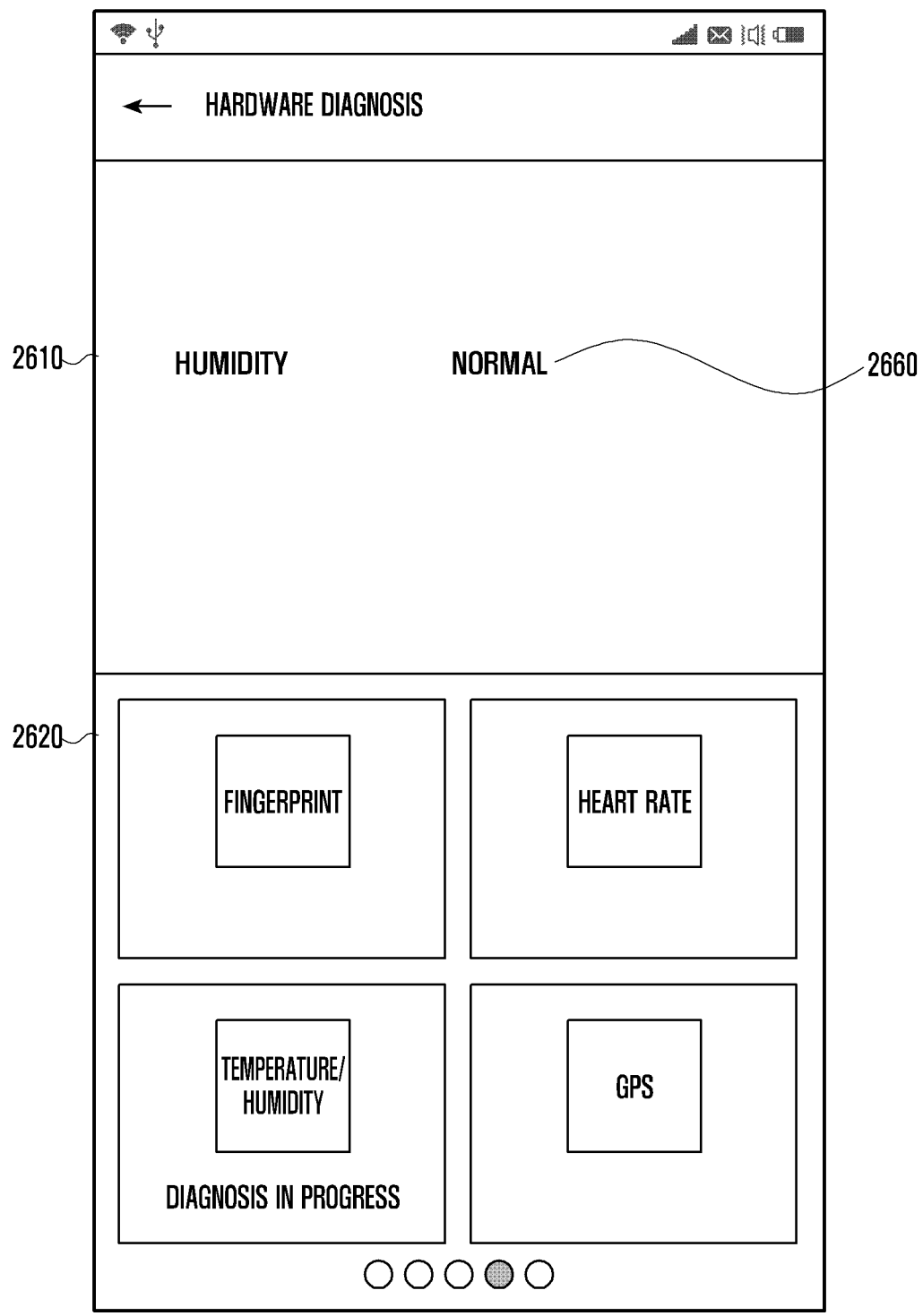

If it is determined that the humidity sensor is operating normally, the AP 210 controls the display 260 to display, in the guidance window 2610, the information 2660 indicating that the humidity sensor is operating normally, as illustrated in FIG. 26E.

If the diagnosis on the temperature/humidity sensor 240J is completed, the diagnosis results and a related link are displayed on the display 260.

Figure 26F:
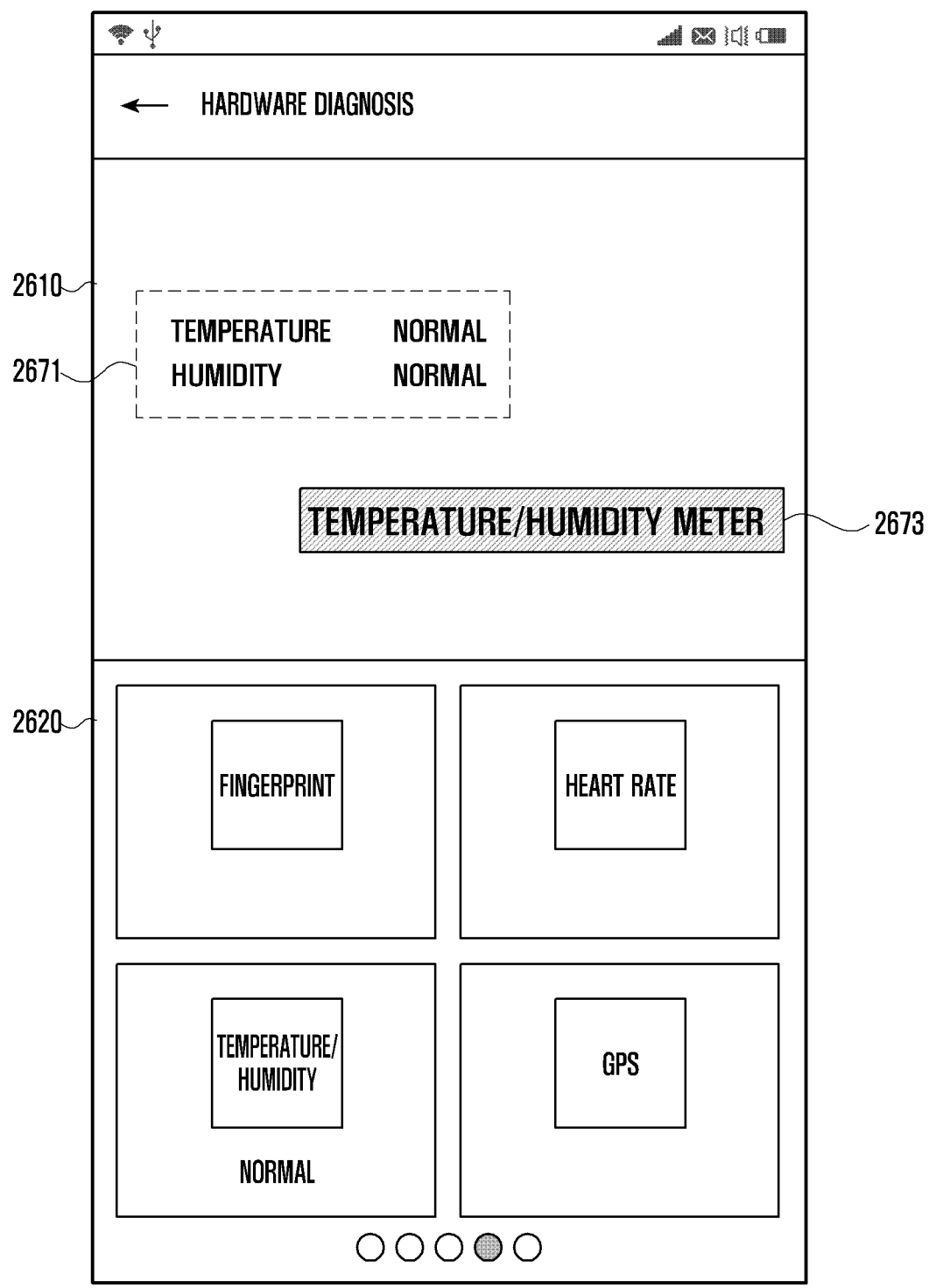

For example, if it is determined that the temperature/humidity sensor 240J is operating normally, the AP 210 controls the display 260 to display, in the guidance window 2610, the information 2671 indicating that the temperature/humidity sensor 240J is operating normally and the text link "temperature/humidity sensor" 2673 associated with an application, as illustrated in FIG. 26F.

Figure 26G:
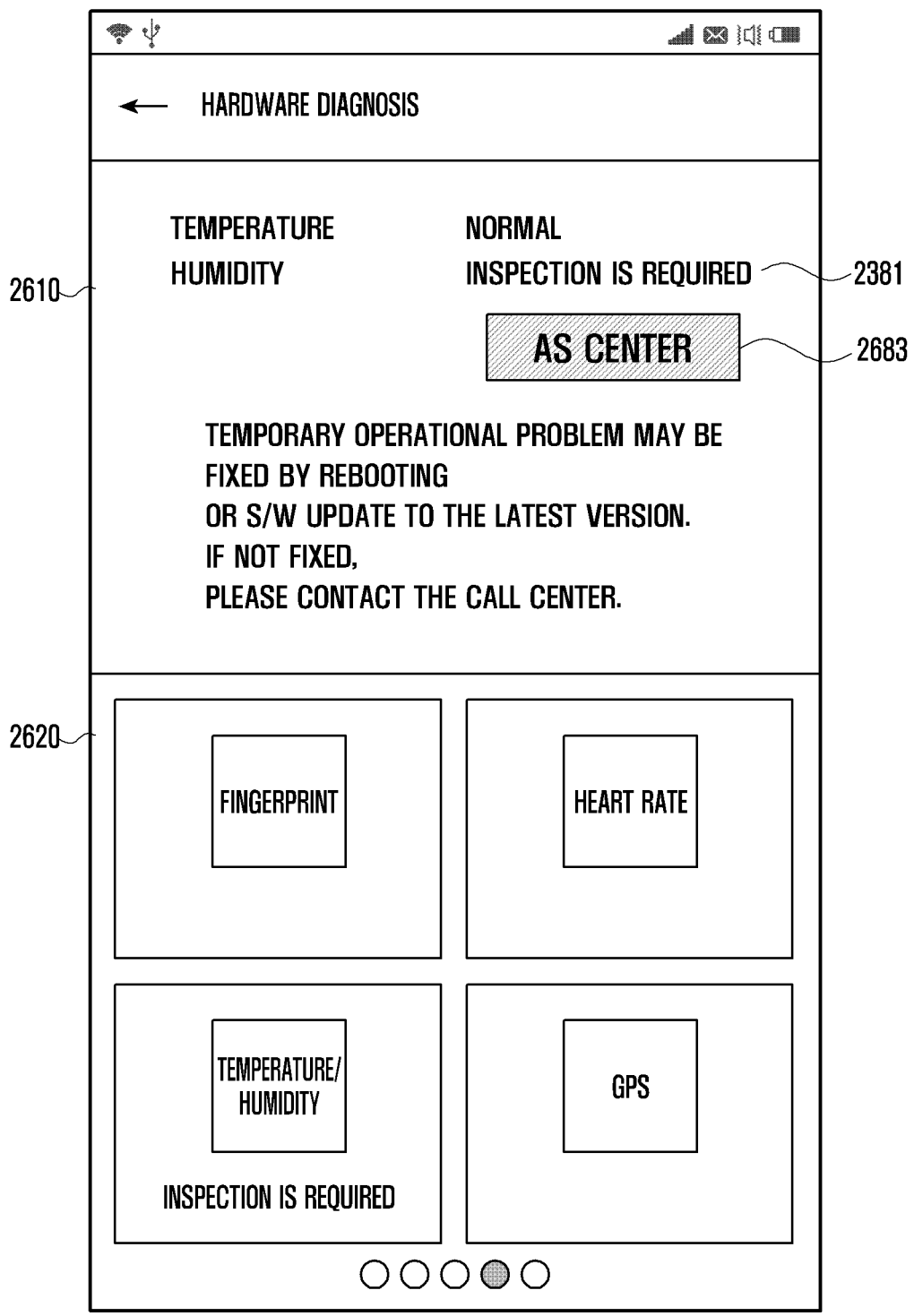

However, if it is determined that at least one of the temperature sensor or the humidity sensor is operating abnormally, the AP 210 controls the display 260 to display the information 2681 indicating the respective diagnosis results of the temperature and humidity sensors (e.g., temperature sensor: normal and humidity sensor: check recommendation) and the text link "AS center" 2683 associated with an AS request service, as illustrated in FIG. 26G.

FIGS. 27A to 27E illustrate a user interface for displaying a GPS module diagnosis operation and diagnosis result according to an embodiment of the present disclosure. Although the user interface of FIGS. 27A to 27E is described below as being displayed by the electronic device illustrated FIG. 2, it is not limited thereto.

Figure 27A:
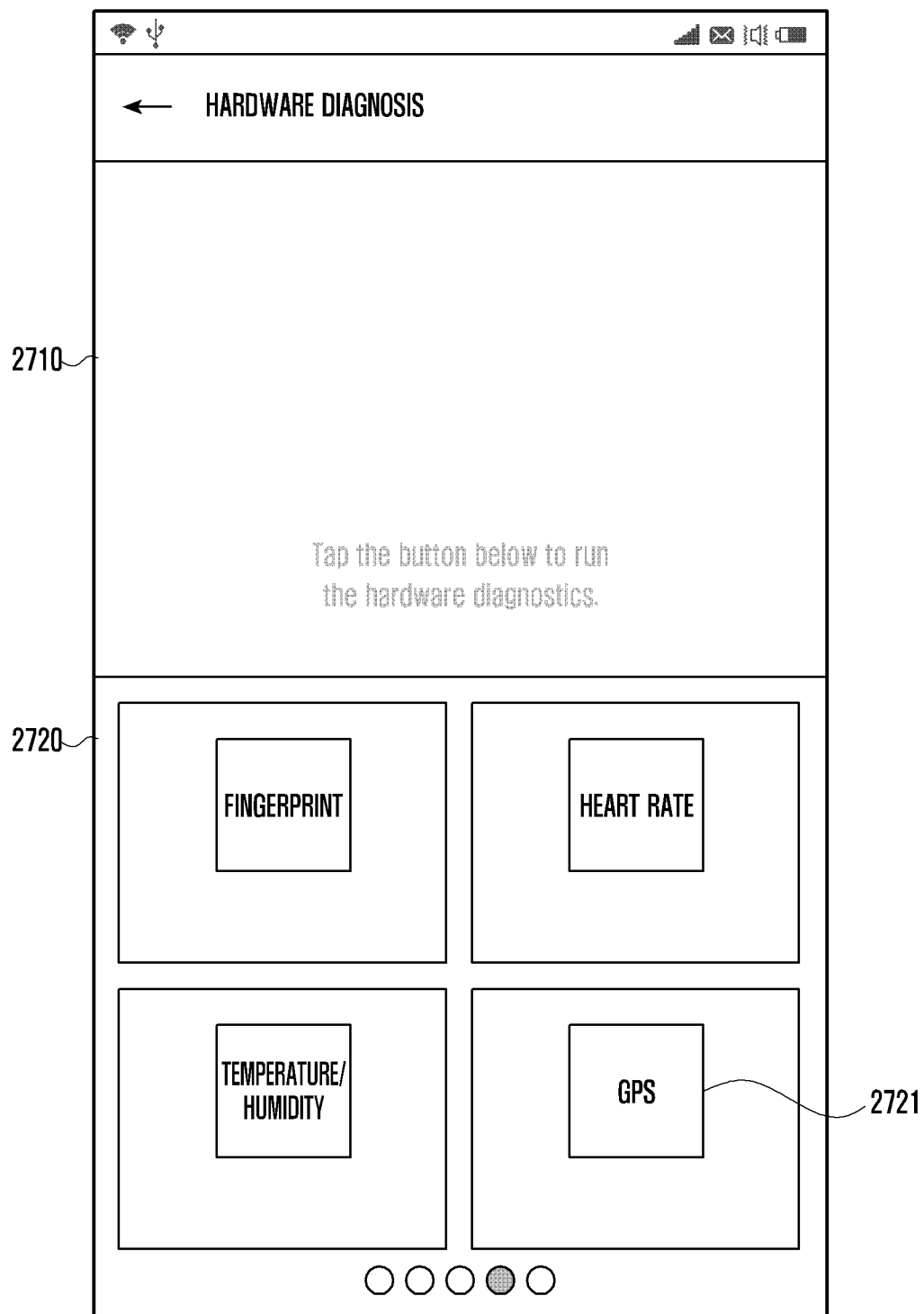
FIGS. 27A to 27E illustrate a user interface for displaying a global navigation satellite system (GNSS) module diagnosis operation and diagnosis result according to an embodiment of the present disclosure.
Figure 27B:
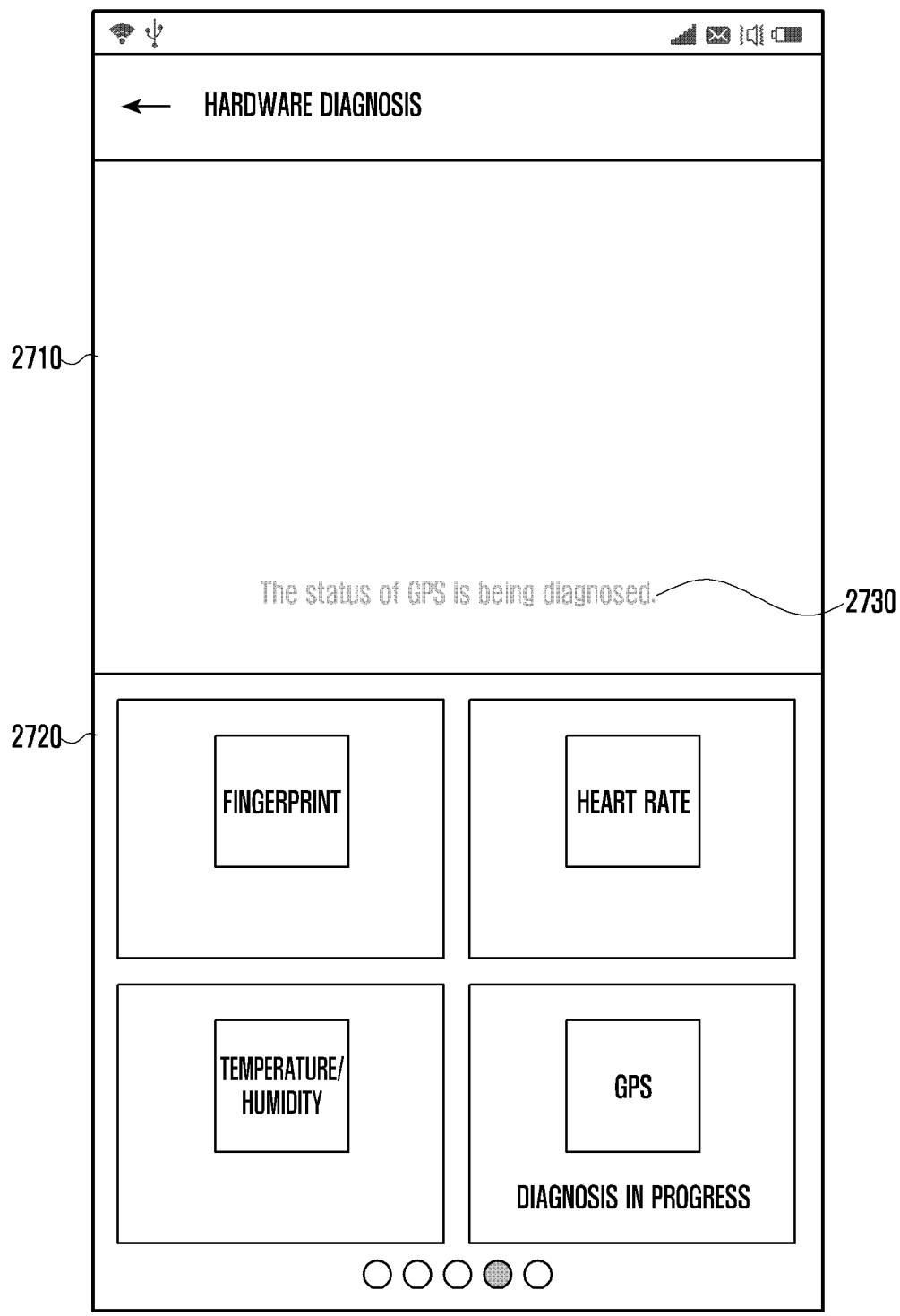

Referring to FIG. 27A, the AP 210 controls the display unit 260 to display a guidance window 2710 and a diagnosis target selection window 2720. If a GPS icon 2721 is selected in the diagnosis target selection window 2720, the processor starts diagnosis on the GPS module 227. For example, if the GPS icon 2721 is selected, the processor performs diagnosis on the GPS module 227 and controls the display 260 to display, in the guidance window 2710, the information 2730 indicating that the GNSS module diagnosis is in progress, as illustrated in FIG. 27B.

Figure 27C:
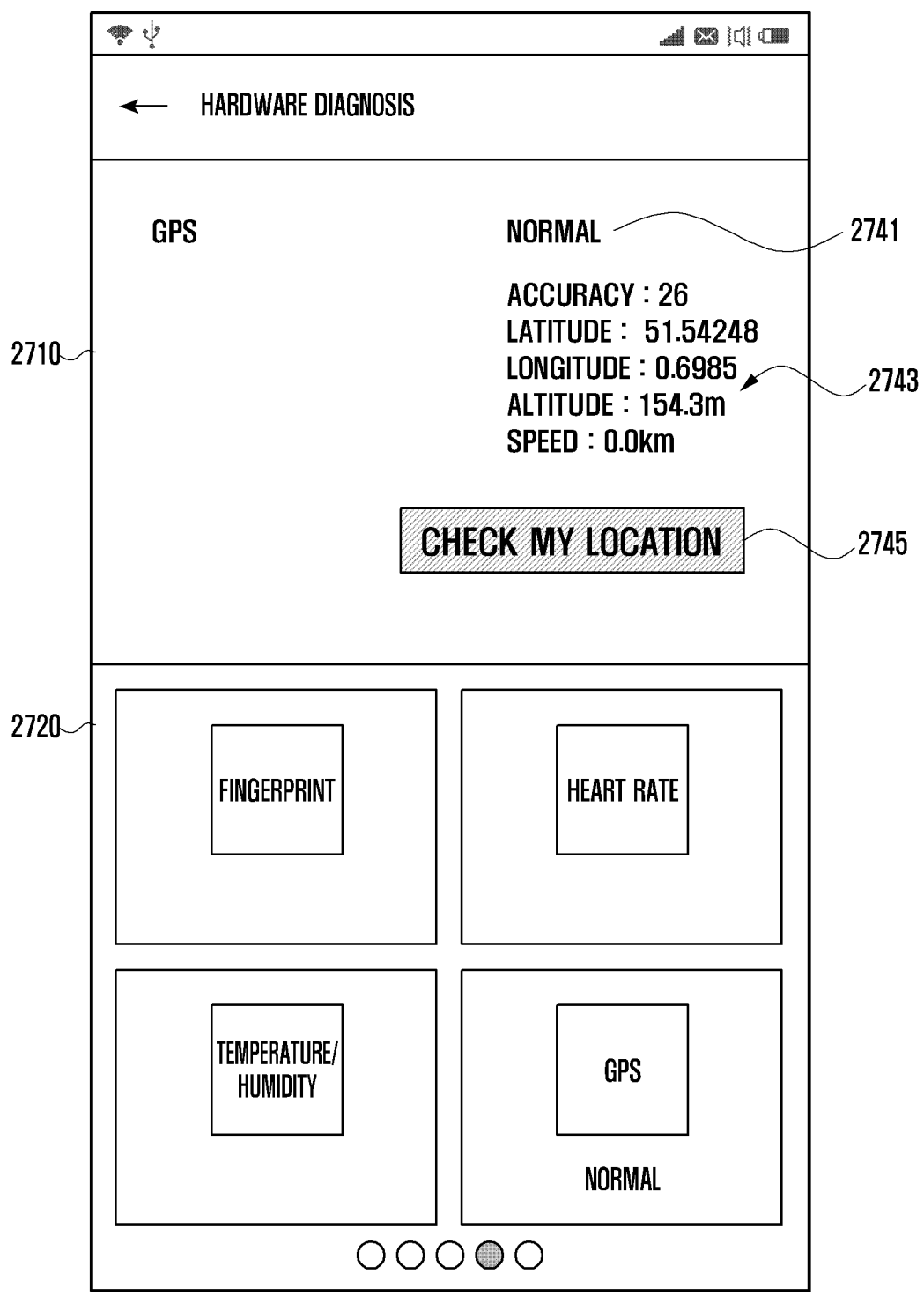

If it is determined that the GPS module 227 is operating normally (e.g., if a GPS signal is received from the GPS module 227), the AP 210 controls the display 260 to display, in the guidance window 2710, the information 2741 indicating that the GNSS module 227 is operating normally, the location information 2743 calculated based on the GPS signal, and the text link "my location check" 2745 associated with a related application, as illustrated in FIG. 27C.

Figure 27D:
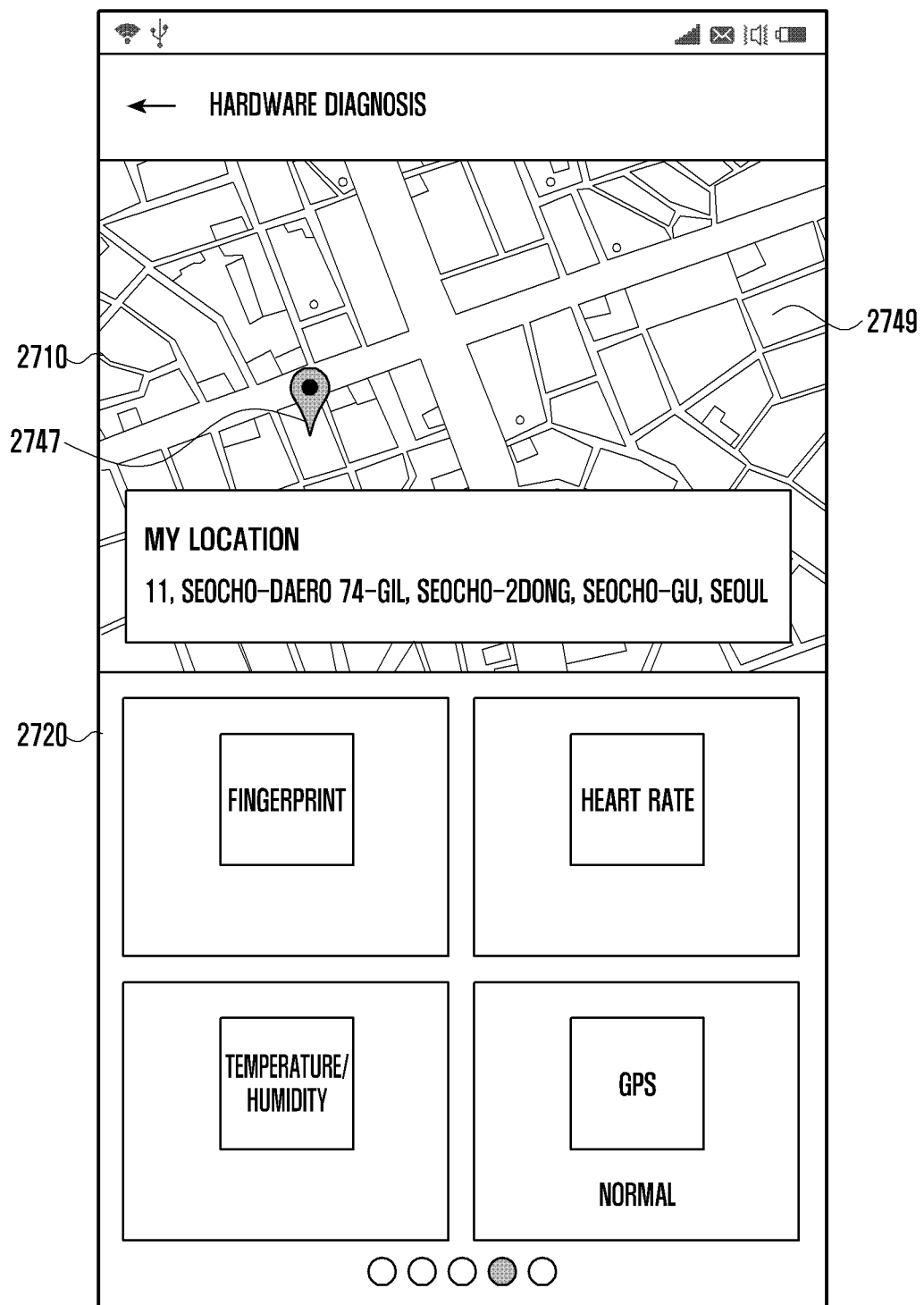

If the text link 2745 is selected, the AP 210 executes a map application and controls the display 260 to mark the location 2747 on the map 2749, as illustrated in FIG. 27D.

Figure 27E:
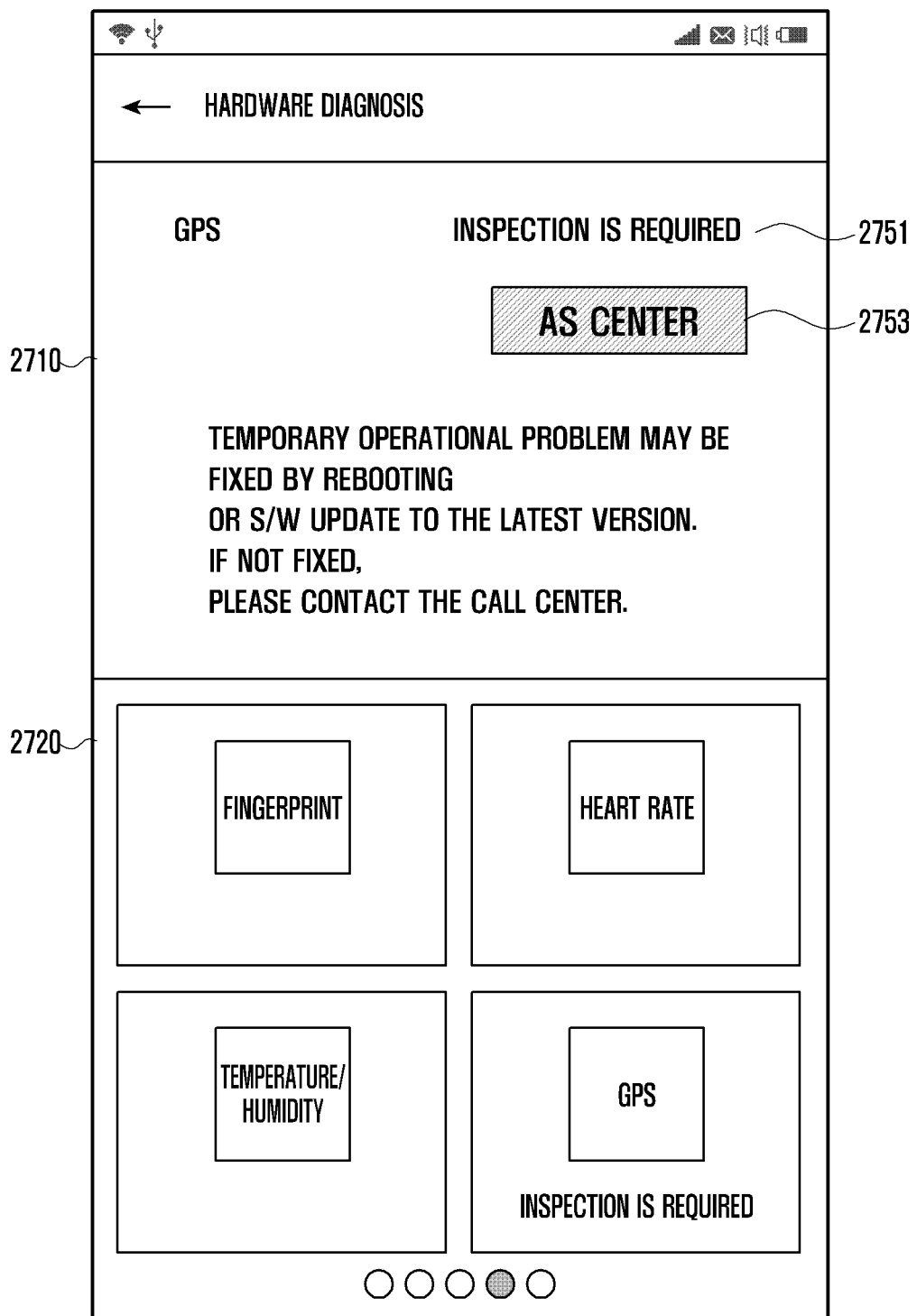

If it is determined that the GPS module 227 is operating abnormally (e.g., no GPS signal is received from the GPS module 227 for a predetermined time), the AP 210 controls the display 260 to display the information 2751 indicating that the GPS module 227 is operating abnormally and the text link "AS center" 2753 associated with an AS request service, as illustrated in FIG. 27E.

FIGS. 28A to 28E illustrated a user interface for displaying a wireless charging module diagnosis operation and diagnosis result according to an embodiment of the present disclosure. Although the user interface of FIGS. 28A to 28E is described below as being displayed by the electronic device illustrated FIG. 2, it is not limited thereto.

Figure 28A:
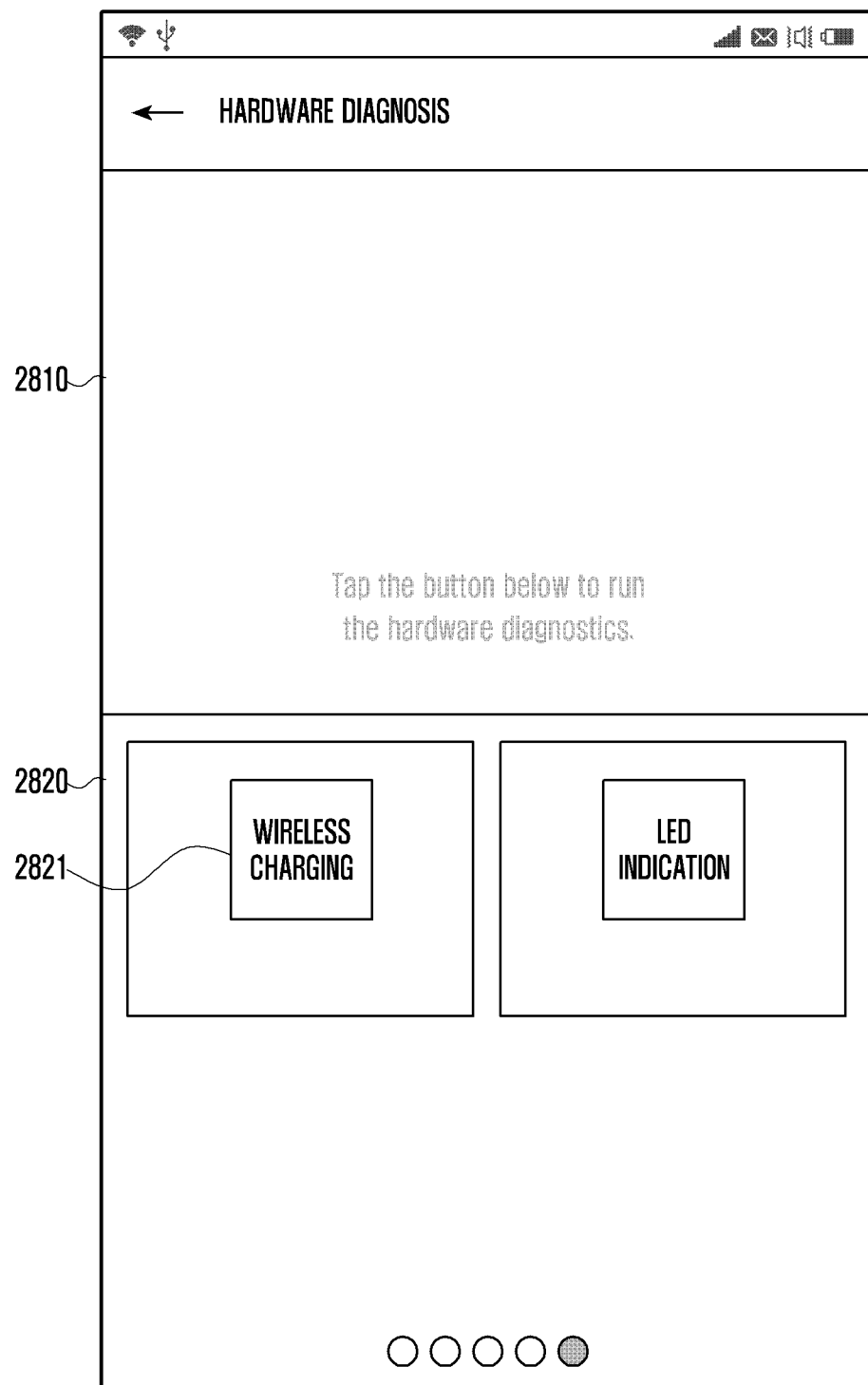
FIGS. 28A to 28E illustrate a user interface for displaying a wireless charging module diagnosis operation and diagnosis result according to an embodiment of the present disclosure.
Figure 28B:
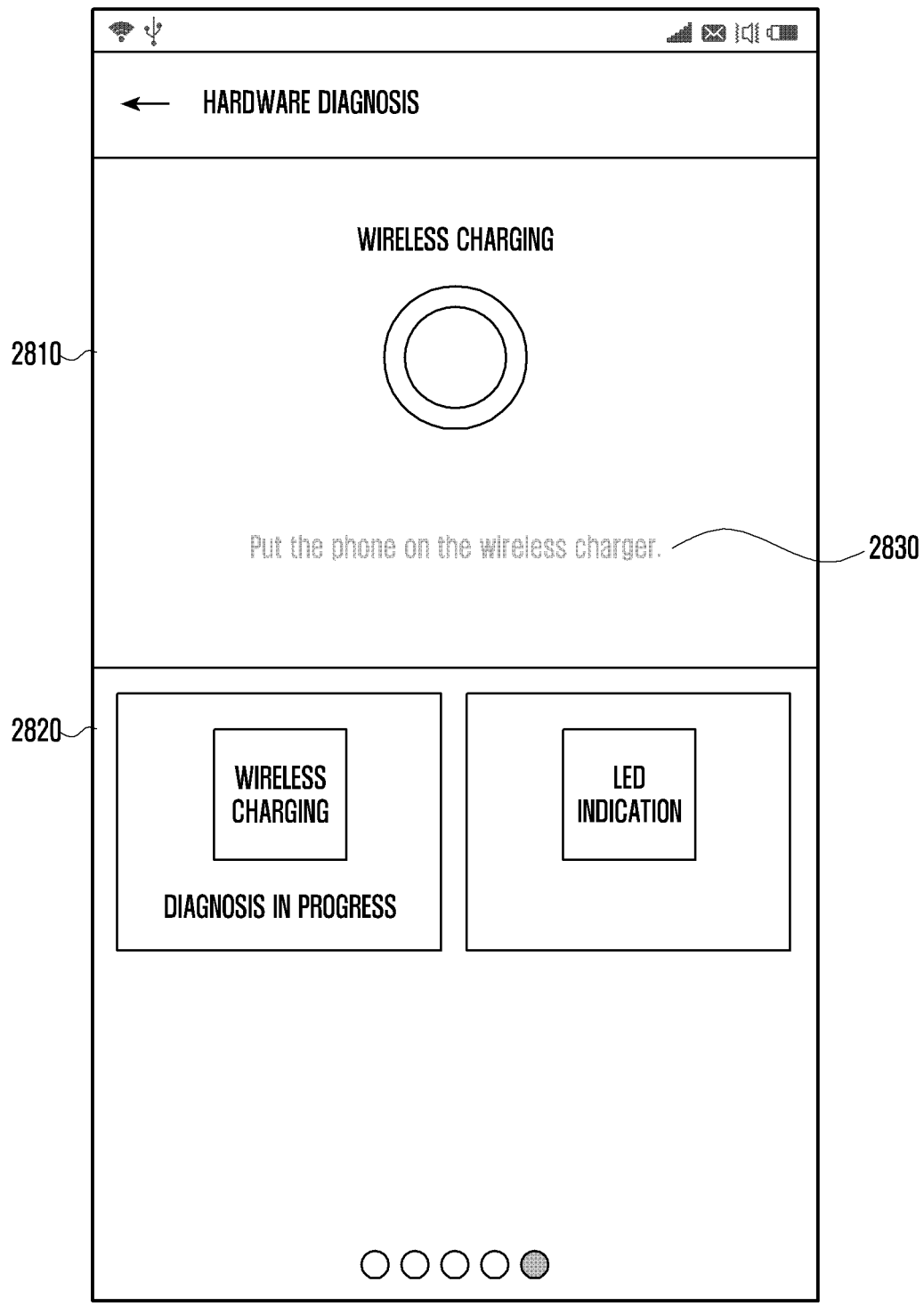

Referring to FIG. 28A, the processor controls the display unit 260 to display a guidance window 2810 and a diagnosis target selection window 2820. If the wireless charger icon 2821 is selected in the diagnosis target selection window 2820, the AP 210 starts diagnosis on the wireless charging module of the power management module 295. For example, if the wireless charger icon 2821 is selected, the AP 210 performs diagnosis on the wireless charging module and controls the display 260 to display, in the guidance window 2810, the information 2830 indicating wireless charging request, as illustrated in FIG. 28B.

Figure 28C:
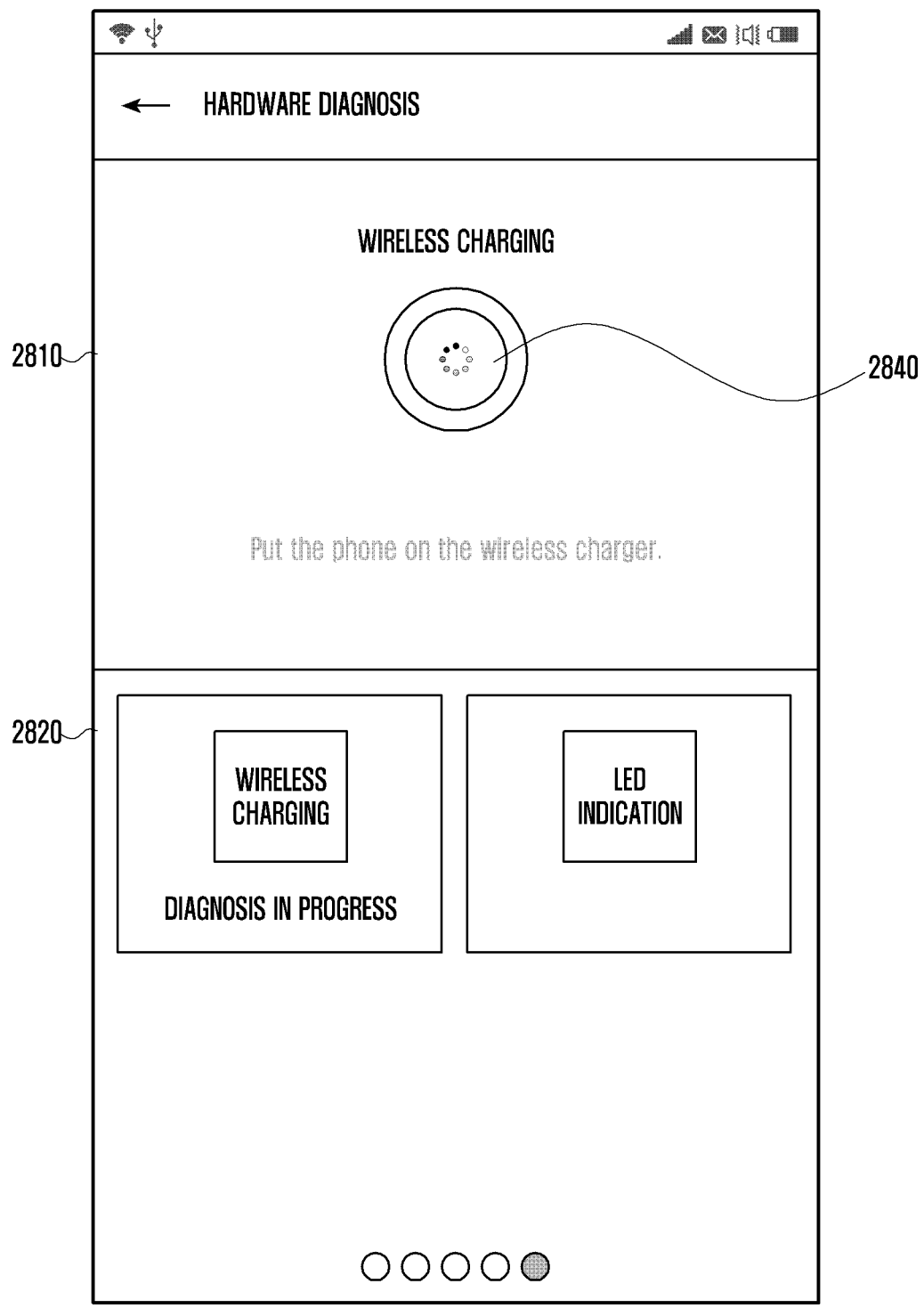

The AP 210 recognizes the wireless charger by using the wireless charging module and controls the display 260 to display, in the guidance window 2810, the information 2840 indicating that the wireless charger recognition is in progress, as illustrated in FIG. 28C.

Figure 28D:
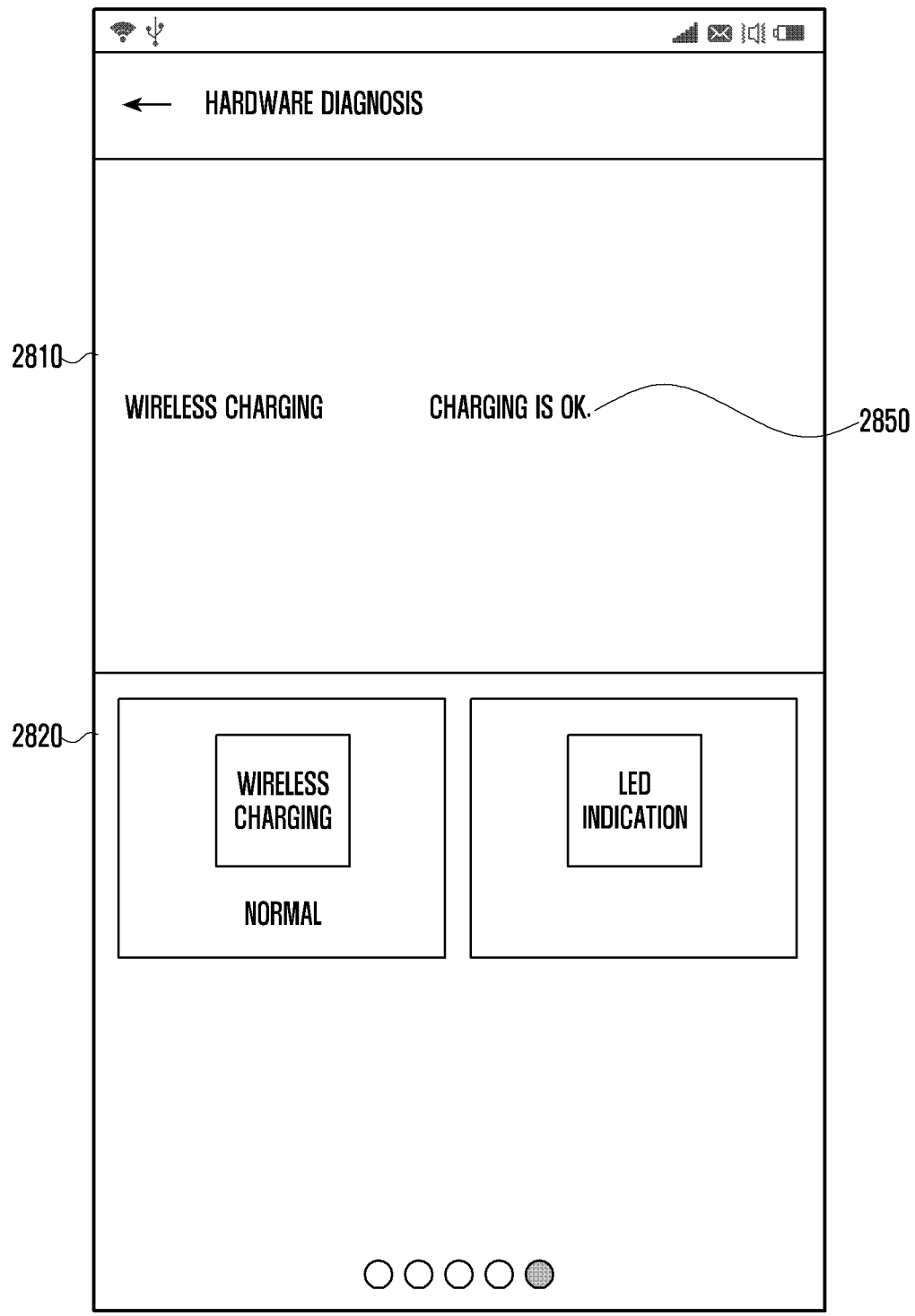

The AP 210 also controls the display 260 to display, in the guidance window 2810, the information 2850 indicating that the wireless charging module is operating normally (i.e., wireless charging is possible), as illustrated in FIG. 28D.

If the wireless charter is not recognized in a predetermined time period, the AP 210 outputs a message (e.g., text message or sound) requesting the user to perform wireless charging or determine that the wireless charging module is operating abnormally.

Figure 28E:
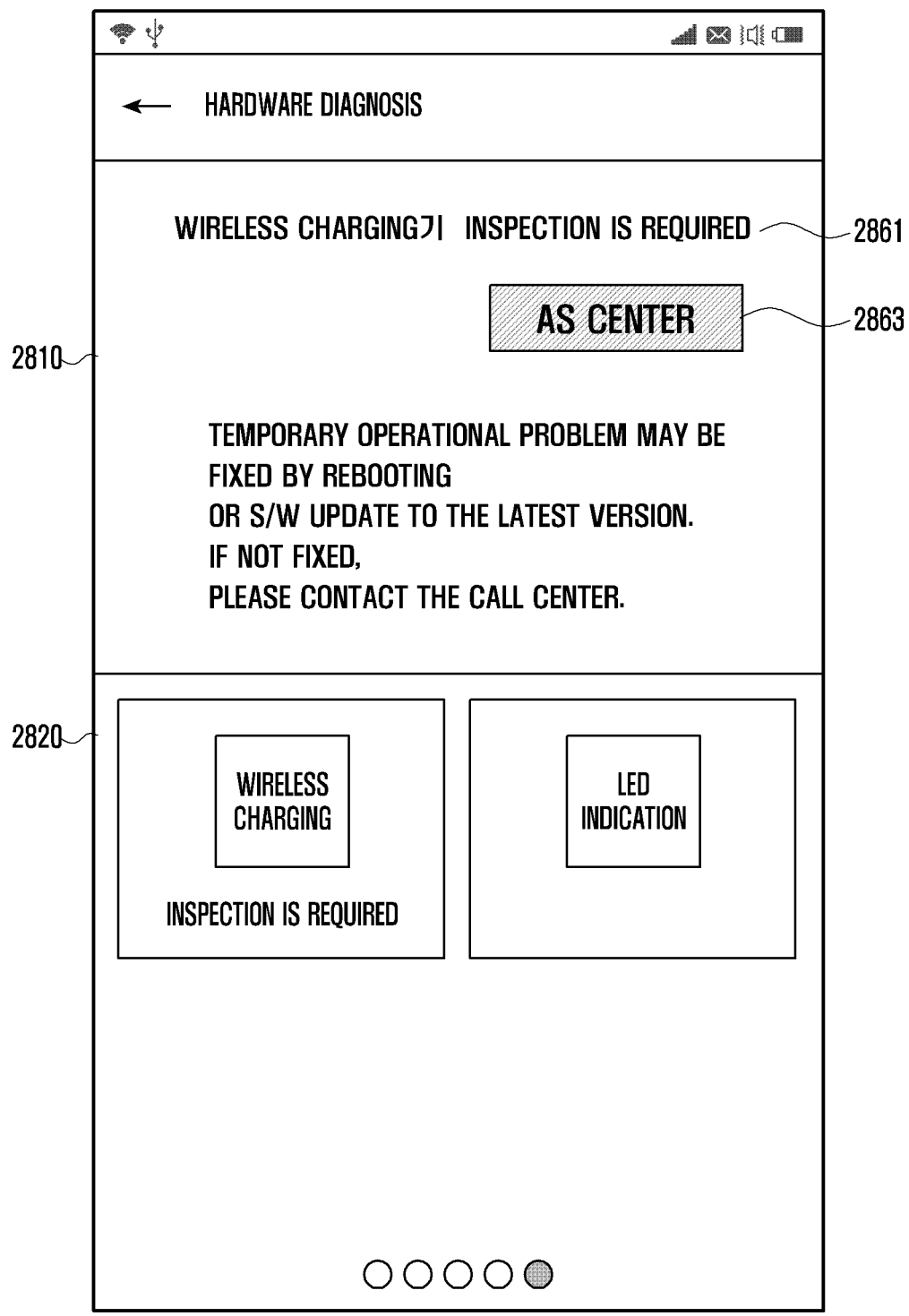

If the wireless charging module is operating abnormally, the AP 210 controls the display 260 to display the information 2861 indicating that the wireless charging module is operating abnormally and the text link "AS center" 2863 associated with an AS request service, as illustrated in FIG. 28E.

As described above, the process execution method and apparatus of the present disclosure is advantageous in terms of facilitating use of services (e.g., AS request, application execution, and user information input) by performing hardware diagnosis and executing a service based on the hardware diagnosis result.

While the present disclosure has been shown and described with reference to certain embodiments thereof, it will be understood by those skilled in the art that various changes in form and details may be made therein without departing from the scope of the present disclosure. Therefore, the scope of the present disclosure should not be defined as being limited to the embodiments, but should be defined by the appended claims and equivalents thereof.

What is claimed is:

1. An electronic device, comprising:
a plurality of hardware components;
a display configured to display information on at least one component of the plurality of hardware components; and
a processor configured to:
 diagnose a hardware component selected as a diagnosis target among the plurality of hardware components, and
 display information related to a result of the diagnosis and a link for providing a service related to the diagnosis target,
wherein the displayed information indicates that the diagnosis target is operating normally or abnormally,
wherein the link is to an application configured to provide the service related to the diagnosis target, when the diagnosis target is determined to be operating normally, and
wherein the link is to an after service (AS) request service, when the diagnosis target is determined to be operating abnormally,
wherein the processor is further configured to transmit, in response to selection of the link to the AS request service, AS request information to an external device, and
wherein the AS request information includes at least one of:
 information related to the diagnosis target, and
 user information.

2. The electronic device of claim 1, wherein the processor is further configured to receive, from the external device, AS request completion information including an AS center location and a reservation time.

3. The electronic device of claim 1 wherein when the diagnosis target is determined to be operating normally and the application is not installed in the electronic device, the service is a download service.

4. The electronic device of claim 3, wherein the processor is further configured to download, in response to selection of the link, the application from the external device.

5. The electronic device of claim 1, wherein the processor is further configured to execute, in response to selection of the link, an application configured to provide a service related to the diagnosis target.

6. The electronic device of claim 1, wherein the processor is further configured to:
determine, when the diagnosis target is operating normally, whether user information for executing a service associated with the diagnosis target is present in the electronic device, and
connect the link to a user registration service, when the user information is not present in the electronic device.

7. The electronic device of claim 6, wherein, when the diagnosis target is a fingerprint sensor, the link is to a fingerprint registration service.

8. The electronic device of claim 1, wherein the plurality of hardware components comprise at least one of:
a sensor module;
a battery;
a short-range communication module;
a touch panel;
an electronic pen;
a key;
a user identity module;
a vibration motor;
a speaker;
a camera;
an earphone;
a Universal Serial Bus (USB) port;
a Global Navigation Satellite System (GNSS) module; and
a wireless charging module.

9. The electronic device of claim 8, wherein the sensor module comprises at least one of:
- a biometric sensor configured to acquire biometric information; and
- a physical quantity sensor configured to measure a physical quantity.

10. The electronic device of claim 9, wherein the biometric information comprises at least one of:
- a fingerprint;
- a heart rate;
- a temperature; and
- a blood pressure.

11. The electronic device of claim 1, wherein the processor is further configured to:
- display at least one icon representing at least one component of the plurality of hardware components;
- receive a selection of an icon among the displayed at least one icon; and
- diagnose a hardware component corresponding to the selected icon.

12. The electronic device of claim 1, wherein the processor is further configured to diagnose the plurality of hardware components in series and display the diagnosis result.

13. The electronic device of claim 1, wherein the processor is further configured to diagnose at least one of a touch input and a hovering input made by an electronic pen.

14. The electronic device of claim 1, wherein the processor is further configured to:
- display a guidance window for user guided diagnosis of the at least one hardware component of the plurality of hardware components; and
- display a selection window for the user to select the diagnosis target, and
- wherein the selection window includes at least one icon representing the at least one hardware component of the plurality of hardware components.

15. The electronic device of claim 14, wherein the processor is further configured to:
- diagnose a hardware component corresponding to a selected one of the at least one icon; and
- display, in response to a user input in the selection window, at least one other icon.

16. A method for operating an electronic device equipped with a plurality of hardware components, the method comprising:
- diagnosing a hardware component selected as a diagnosis target among the plurality of hardware components;
- displaying information related to a result of the diagnosis and a link for providing a service related to the diagnosis target,
- wherein the displayed information indicates that the diagnosis target is operating normally or abnormally,
- wherein the link is to an application configured to provide the service related to the diagnosis target, when the diagnosis target is determined to be operating normally, and
- wherein the link is to an after service (AS) request service, when the diagnosis target is determined to be operating abnormally; and
- transmitting, in response to selection of the link to the AS request service, AS request information to an external device,
- wherein the AS request information includes at least one of:
  - information related to the diagnosis target, and
  - user information.

17. The method of claim 16, further comprising:
- determining, when the diagnosis target is operating normally, whether an application for providing a service related to the diagnosis target is present in the electronic device; and
- providing a service for downloading the application, in response to selection of the link, when the application is not present in the electronic device.

18. The method of claim 16, further comprising:
- determining, when the diagnosis target is operating normally, whether user information for executing a service related to the diagnosis target is present in the electronic device and
- providing, when the user information is not present in the electronic device, a user registration service, in response to selection of the link.

* * * * *